US012565494B2

(12) United States Patent
Beshore et al.

(10) Patent No.: US 12,565,494 B2
(45) **Date of Patent: *Mar. 3, 2026**

(54) INHIBITORS OF HUMAN RESPIRATORY SYNCYTIAL VIRUS AND METAPNEUMOVIRUS

(71) Applicant: Merck Sharp & Dohme LLC, Rahway, NJ (US)

(72) Inventors: Douglas C. Beshore, Lower Gywnedd, PA (US); Brett R. Ambler, Blue Bell, PA (US); Kira A. Armacost, Doylestown, PA (US); Christopher James Bungard, Lansdale, PA (US); Danielle M. Hurzy, Garnet Valley, PA (US); Peter J. Manley, Harleysville, PA (US); Kelly-Ann S. Schlegel, Fleetwood, PA (US); Linda M. Suen-Lai, Malvern, PA (US); Mahdieh Yazdani, Blue Bell, PA (US)

(73) Assignee: Merck Sharp & Dohme LLC

( * ) Notice: Subject to any disclaimer, the term of this patent is extended or adjusted under 35 U.S.C. 154(b) by 477 days.

This patent is subject to a terminal disclaimer.

(21) Appl. No.: 18/315,720

(22) Filed: May 11, 2023

(65) Prior Publication Data

US 2023/0365551 A1 Nov. 16, 2023

Related U.S. Application Data

(60) Provisional application No. 63/495,307, filed on Apr. 11, 2023, provisional application No. 63/341,910, filed on May 13, 2022.

(51) Int. Cl.
*C07D 417/14* (2006.01)
*A61P 31/14* (2006.01)
*C07D 413/14* (2006.01)

(52) U.S. Cl.
CPC ............ *C07D 417/14* (2013.01); *A61P 31/14* (2018.01); *C07D 413/14* (2013.01)

(58) Field of Classification Search
CPC ...... C07D 417/14; C07D 413/14; A61P 31/14
See application file for complete search history.

(56) References Cited

U.S. PATENT DOCUMENTS 9,527,830 B2 * 12/2016 Walsh et al.

FOREIGN PATENT DOCUMENTS

WO WO 2012/125661 A1 * 9/2012
WO 2016149271 A1 9/2016
WO WO 2021/216665 A1 * 10/2021

OTHER PUBLICATIONS

Aitipamula, S., et al, "Polymorphs, Salts, and Cocrystals: What's In A Name", Crystal Growth and Design, 2012, pp. 2147-2152, vol. 12.
Biacchesi, Ste'phane et al., Frequent Frameshift and Point Mutations in the SH Gene of Human Metapneumovirus Passaged In Vitro, Journal of Virology, 2007, 6057-6067, 81(11).
Fearns, Rachel et al., New antiviral approaches for respiratory syncytial virus and other mononegaviruses: Inhibiting the RNA polymerase, Antiviral Research, 2016, 63-76, 134.
Kesisoglou, F., et al, "Nanosizing—Oral Formulation Developement And Biopharmaceutical Evaluation", Adv. Drug Delivery, 2007, pp. 631-644, vol. 59, No. 7.
Kim, Hyun Wha et al., Respiratory Syncytial Virus Disease in Infants Despite Prior Administration of Antigenic Inactivated Vaccine, American Journal of Epidemiology, 1969, 422-434, 89(4).
Serajuddin, A., et al.,, "Solid Dispersion of Poorly Water-Soluble Drugs: Early Promises, Subsequent Problems, and Recent Breakthroughs", J. Pharm Sci., 1999, pp. 1058-1066, vol. 88, No. 10.
Wen, Zhiyun et al., Development and application of a higher throughput RSV plaque assay by immunofluorescent imaging, Journal of Virological Methods, 2019, 88-95, 263.

* cited by examiner

*Primary Examiner* — Kortney L. Klinkel
*Assistant Examiner* — Jackson J Hernandez
(74) *Attorney, Agent, or Firm* — Eric Greenwald; John C. Todaro

(57) ABSTRACT

The present disclosure is directed to compounds of Formula I

I

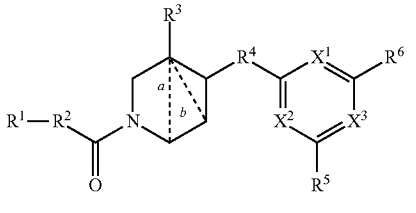

or a pharmaceutically acceptable salt thereof, and their use for the treatment of hRSV and hMPV.

22 Claims, No Drawings

INHIBITORS OF HUMAN RESPIRATORY SYNCYTIAL VIRUS AND METAPNEUMOVIRUS

CROSS REFERENCE TO RELATED APPLICATIONS

The present application is a U.S. Non-Provisional application which claims priority from and the benefit of U.S. Provisional Application Nos. 63/341,910 filed May 13, 2022, and 63/495,307 filed Apr. 11, 2023, which are hereby incorporated by reference in their entireties.

FIELD OF THE INVENTION

The present invention relates to therapeutic compounds useful for the inhibition of respiratory syncytial virus replication and metapneumovirus replication. The therapeutic compounds may be used in the treatment or prevention of respiratory syncytial virus infection and metapneumovirus infection.

BACKGROUND OF THE INVENTION

Paramyxoviruses are enveloped negative-strand RNA viruses that are significant human and animal pathogens. Human Respiratory Syncytial Virus (hRSV, RSV) belongs to the family Paramyxoviridae, subfamily Pneumovirinae. Two subtypes, type A and type B, have been identified and are a major cause of severe and sometimes even fatal respiratory infections in children less than 6 months of age. Adults with underlying diseases, such as COPD, asthma, cancer, immunocompromised status, including HIV or post transplantation, are also at risk of developing severe RSV infections. Fifteen percent of annual hospitalizations in adults over 50 years of age are due to acute respiratory infections caused by RSV. In the United States, RSV causes more than 100,000 hospitalizations annually and is estimated to cause 160,000 deaths globally each year. Other viral family members, including Human Metapneumovirus (hMPV) and Human Parainfluenza Virus (hPIV), are also responsible for acute respiratory illness similar to hRSV.

The RSV genome is a single-stranded negative-sense RNA molecule of approximately 15 kb, which encodes for 11 proteins. Two of these proteins are the main surface glycoproteins of the virion. These are the attachment (G) protein, which mediates virus binding to cells, and the fusion (F) protein, which promotes both fusion of the viral and cell membranes at the initial stages of the infectious cycle and fusion of the membrane of infected cells with those of adjacent cells to form characteristic syncytia. Four of the polypeptides, together with the viral RNA genome, form the RSV ribonucleoprotein (RNP) complex. These proteins are the nucleocapsid (N) protein, phosphoprotein (P), RNA polymerase (L) protein, and transcription factor M2-1, which are also each required for the transcription and replication of the viral genome and the subject of drug discovery research.

After hRSV, hMPV is the second most common cause of lower respiratory infection in young children. hMPV is responsible for 5-40% of respiratory tract infections in hospitalized and outpatient children. In healthy adults, hMPV generally results in mild respiratory tract infections; However, adults 70 years old and older, immunocompromised individuals and, people with comorbidities such as asthma and chronic obstructive pulmonary disease (COPD) are at higher risk for more serious disease and hospitalization as a result of hMPV infection. The hMPV genome is approximately 13 kb and the organization is similar to hRSV. hMPV genome RNA replication and mRNA transcription relies on the hMPV L-protein polymerase, which is highly homologous with the hRSV L-protein polymerase.

Currently there are few options available for prophylaxis and treatment of RSV infections. There is no marketed vaccine for RSV. A clinical trial with a formalin-inactivated virus was associated with increased disease severity in infants upon infection with RSV (see Kim et al., *American Journal of Epidemiology,* 89:422-434 (1969)). The monoclonal antibody palivizumab (Synagis®) is approved for prophylactic use but has limited efficacy and its use is limited to high-risk infants as a result of high cost. Ribavarin (ViraZole®), a guanosine nucleoside analog broad-spectrum antiviral is approved as an inhaled treatment for RSV infection in infants, but clear efficacy data is lacking (Fearns et al., 2016 *Antiviral Research,* 134:63-76). In addition, the teratogenic potential of ribavirin raises significant risks for caregivers. The standard of care currently for RSV-infected patients is palliative and includes supplemental oxygen and intravenous fluids.

There continues to be a need for anti-viral agents with pharmacokinetic properties suitable for a significant number of patients in the affected population. The present invention provides novel replication inhibitors of hRSV and hMPV useful for the inhibition of respiratory syncytial virus replication and metapneumovirus replication for addressing this need.

SUMMARY OF THE INVENTION

The present disclosure is directed to compounds of Formula I and embodiments thereof for use as anti-viral agents for inhibition of the replication of hRSV and hMPV and the treatment and/or prophylaxis of hRSV and hMPV infection. Compositions and methods of use comprising the compounds of this disclosure are also provided.

DETAILED DESCRIPTION OF THE INVENTION

The present disclosure is directed to compounds of Formula I

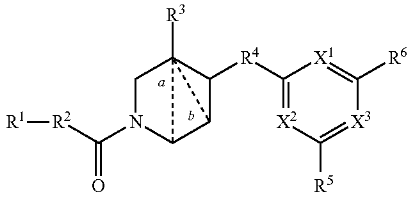

or a pharmaceutically acceptable salt thereof, wherein:

$R^1$ is a 5-member aromatic heterocyclyl ring comprised of:

(1) two carbon atoms and (ii) two of N and one of NH or (i) three of N, (2) three carbon atoms and (i) two of N, (ii) N and NH, or (iii) N and one of S or O, or (3) four carbon atoms and one of S or O, wherein the heterocyclyl ring is unsubstituted or substituted with 1 or 4 substituents, as valence will allow, independently selected at each occurrence from halo and $C_{1-6}$alkyl;

$R^2$ is 5-member aromatic heterocyclyl ring comprised of:
(1) three carbon atoms and (i) two of N, (ii) N and NH, or (iii) N and one of S or O, or
(2) two carbon atoms and (i) three of N, (ii) two of N and one of NH or (iii) two of N and one of S or O,
wherein the heterocyclyl ring is unsubstituted or substituted with 1, 2 or 3 substituents, as valence will allow, independently selected at each occurrence from:
(a) halo,
(b) —$NH_2$,
(c) —$C_{3-6}$cycloalkyl,
(d) —$C_{1-6}$alkyl unsubstituted or substituted with 1 to 6 substituents independently selected at each occurrence from halo, —OH and —$NH_2$, and
(e) —$OC_{1-6}$alkyl unsubstituted or substituted with 1 to 6 substituents independently selected at each occurrence from halo, —OH and —$NH_2$;

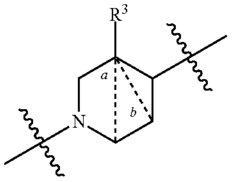

represents a bicyclic ring that is:

(i)

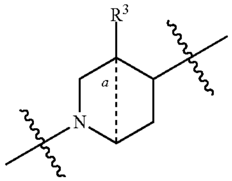

or 2-azabicyclo[2.2.0]hexane (ii)

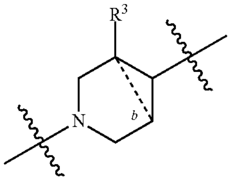

;

3-azabicyclo[3.1.0]hexane $R^3$ is —H, halo or —$C_{1-6}$alkyl;
$R^4$ is —O— or —NH—;
One of $X^1$, $X^2$ and $X^3$ is N and the others are each CH;
$R^5$ is selected from:
(1) —$C_{1-6}$alkyl unsubstituted or substituted with 1 to 6 substituents independently selected at each occurrence from halo, —OH, —$NR^XR^Y$ and —C(O)$NR^XR^Y$,
(2) —C(O)$NR^XR^Y$,
(3)

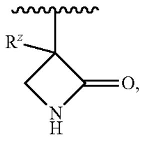

-continued

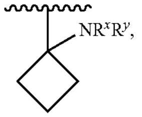

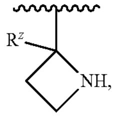

and
(4)

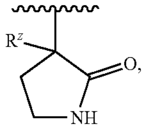

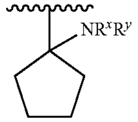

and

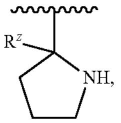

wherein $R^X$ and $R^Y$ are independently selected from —H, —$C_{1-6}$alkyl, and $R^Z$ is —$C_{1-6}$alkyl; and
$R^6$ is selected from:
(1) phenyl, unsubstituted or substituted with 1 to 5 substituents independently selected at each occurrence from:
(a) halo,
(b) —CN,
(c) —$C_{1-6}$alkyl unsubstituted or substituted with 1 to 6 substituents independently selected at each occurrence from halo and —OH;
(d) —$OC_{1-6}$alkyl unsubstituted or substituted with 1 to 6 substituents independently selected at each occurrence from halo and —OH, and
(e) —$C_{3-6}$cycloalkyl unsubstituted or substituted with 1 to 5 substituents independently selected at each occurrence from halo, —OH, —$C_{1-6}$alkyl and —$OC_{1-6}$alkyl;
(2) pyridinyl, unsubstituted or substituted with 1 to 5 substituents independently selected at each occurrence from (i) halo, (ii) CN and (iii) —$C_{1-6}$alkyl unsubstituted or substituted with 1 to 6 of —F and/or —Cl;
(3)

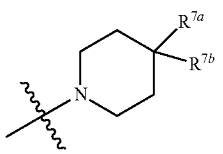

wherein $R^{7a}$ and $R^{7b}$ are each selected from —H, —$C_{1-6}$alkyl wherein $R^{7a}$ and $R^{7b}$ are each selected from —H, —$C_{1-6}$alkyl unsubstituted or substituted with 1 to 6 of —F and/or —Cl;

(4)

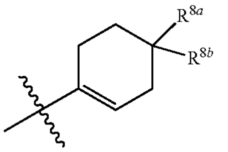

and

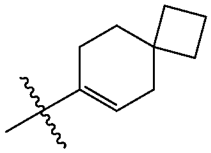

wherein $R^{8a}$ and $R^{8b}$ are each selected from —H, —$C_{1-3}$alkyl and —$CF_3$;

(5) A bicyclic ring system selected from:

(a)

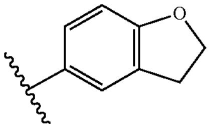

, (b)

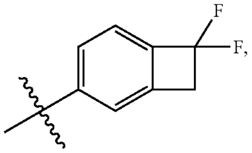

(c)

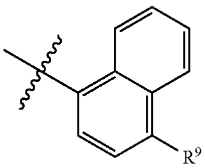

(d)

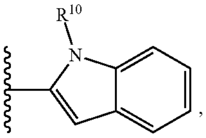

, (e)

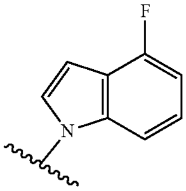

and (f)

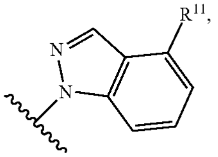

wherein $R^9$, $R^{10}$ and $R^{11}$ are independently selected at each occurrence from —H, —$C_{1-6}$alkyl, —$CF_3$ and 1, 2 or 3 of halo.

(6) —$C_{3-6}$cycloalkyl unsubstituted or substituted with 1 to 5 substituents independently selected at each occurrence from halo, —OH, —$C_{1-6}$alkyl, and —$OC_{1-6}$alkyl; and (7) pyrazolyl, unsubstituted or substituted with one or more substituents independently selected at each occurrence from:

(a) 1 to 3 of halo, (b) CN, (c) —$C_{1-6}$alkyl unsubstituted or substituted with 1 to 6 substituents independently selected at each occurrence from halo, —OH, and —$OC_{1-6}$alkyl;

(d) —$OC_{1-6}$alkyl unsubstituted or substituted with 1 to 6 substituents independently selected at each occurrence from halo, —OH and $OC_{1-6}$alkyl, and (e) —$C_{3-6}$cycloalkyl unsubstituted or substituted with 1 to 5 substituents independently selected at each occurrence from halo, —OH and —$OC_{1-6}$alkyl; and (8)

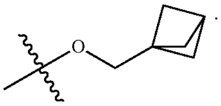 [SMILES: *OCC12CC(C1)C2]

.

In Embodiment 1 of this disclosure are compounds of Formula I, or a pharmaceutically acceptable salt thereof, wherein $R^1$ is 5-member aromatic heterocyclyl ring selected from: thiazolyl, imidazolyl, oxazolyl, isoxazolyl, triazolyl, pyrazolyl, thiophenyl and furanyl, wherein each ring is unsubstituted or substituted with 1 to 4 substituents, as valence will allow, independently selected at each occurrence from halo and $C_{1-6}$alkyl. In a first class of Embodiment 1, $R^1$ is selected from:

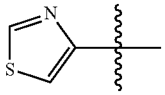

,

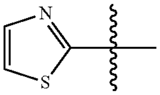

,

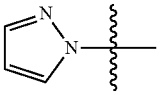

,

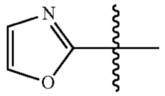

,

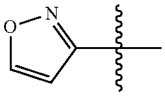

,

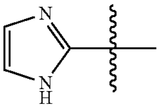

,

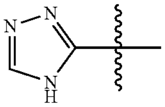

,

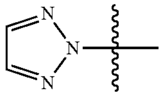

,

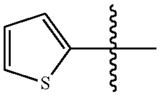

and

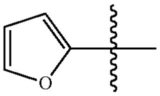

, wherein the heterocyclyl ring is unsubstituted or substituted with 1, 2, 3 or 4 substituents, as valence will allow, independently selected at each occurrence from halo and $C_{1-6}$alkyl. In a second class thereof, the substituents are selected at each occurrence from —F, —Cl and $C_{1-3}$alkyl. In a third class thereof, the heterocyclyl ring is unsubstituted or substituted with 1, 2, 3 or 4 substituents, as valence will allow, selected at each occurrence from —F, —Cl and $C_{1-3}$alkyl (e.g., methyl).

In Embodiment 2 of this disclosure are compounds of Formula I and Embodiment 1, or a pharmaceutically acceptable salt thereof, wherein $R^2$ is 5-member aromatic heterocyclyl ring selected from: thiadiazolyl, triazolyl, pyrazolyl, thiazolyl and isothiazolyl, wherein each is unsubstituted or substituted with 1, 2 or 3 substituents, as valence will allow, selected from (i) halo (e.g., —F and —Cl), (ii) —$NH_2$, (iii) $C_{1-3}$alkyl unsubstituted or substituted with 1 to 5 substituents selected from halo (e.g., —F and —Cl), —OH and $C_{3-6}$cycloalkyl (e.g., cylopropyl).

In a class of Embodiment 2, $R^2$ is selected from:

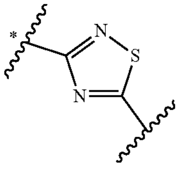
,
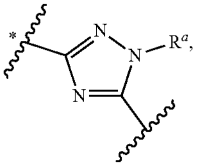
,

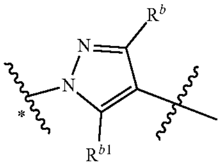
,
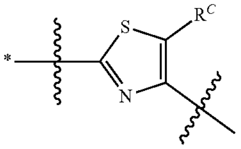
,

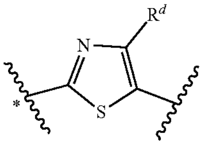
,
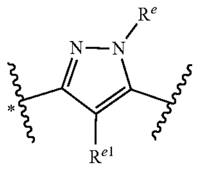
and

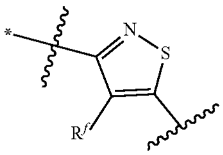

wherein * is the point of attachment to $R^1$, and each of $R^a$, $R^b$, $R^{b1}$, $R^c$, $R^d$, $R^e$, $R^{e1}$, and $R^f$ is independently selected from:

(a) —H, (b) halo, (c) —$NH_2$, (d) —$C_{3-6}$cycloalkyl, (e) —$C_{1-6}$alkyl unsubstituted or substituted with 1 to 6 substituents independently selected at each occurrence from halo, —OH and —$NH_2$, and (f) —$OC_{1-6}$alkyl unsubstituted or substituted with 1 to 6 substituents independently selected at each occurrence from halo, —OH and —$NH_2$.

The above-listed structure

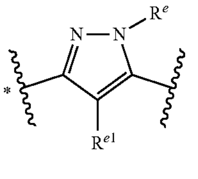

may otherwise be illustrated in the present disclosure as the structure

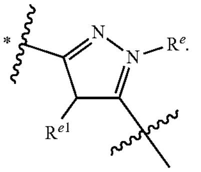

In a second class of Embodiment 2, each of $R^a$, $R^b$, $R^{b1}$, $R^c$, $R^d$, $R^e$, $R^{e1}$, and $R^f$ is independently selected from: (a) —H, (b) halo (e.g. —F and —Cl), (c) —$NH_2$, (d) —$C_{3-6}$cycloalkyl (e.g., cyclopropyl), (e) —$C_{1-3}$alkyl unsubstituted or substituted with 1, 2 or 3 substituents independently selected at each occurrence from halo (e.g. —F and —Cl), —OH, and —$NH_2$, and (f) —$OC_{1-3}$alkyl unsubstituted or substituted with 1, 2 or 3 substituents independently selected at each occurrence from halo (e.g. —F and —Cl), —OH, and —$NH_2$.

In Embodiment 3A of this disclosure are compounds of Formula I, and each of Embodiments 1 and 2, and classes thereof, or a pharmaceutically acceptable salt thereof wherein:

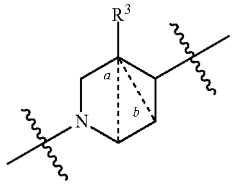
is
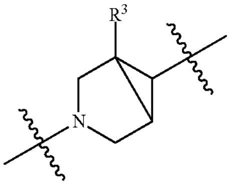
.

In Embodiment 3B of this disclosure are compounds of Formula I, and each of Embodiments 1 and 2, and classes thereof, or a pharmaceutically acceptable salt thereof wherein:

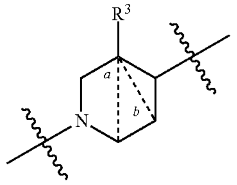
is
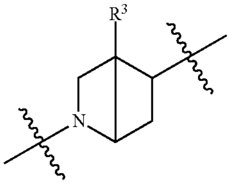
.

In Embodiment 4 of this disclosure are compounds of Formula I, and each of Embodiments 1, 2, 3A and 3B, and classes thereof, or a pharmaceutically acceptable salt thereof, wherein $R^3$ is selected from —H, halo or —$C_{1-3}$ alkyl. In a first class thereof, $R^3$ is —H, —F, —Cl or —$C_{1-3}$alkyl. In a first class thereof, $R^3$ is —H, —F, —Cl or —$CH_3$.

In Embodiment 5A of this disclosure are compounds of Formula I, and each of Embodiments 1, 2, 3A, 3B and 4, and classes thereof, or a pharmaceutically acceptable salt thereof, wherein $R^4$ is —O—.

In Embodiment 5B of this disclosure are compounds of Formula I, and each of Embodiments 1, 2, 3A, 3B and 4, and classes thereof, or a pharmaceutically acceptable salt thereof, wherein $R^4$ is —NH—.

In Embodiment 6 of this disclosure are compounds of Formula I, and each of Embodiments 1, 2, 3A, 3B, 4, 5A and 5B and classes thereof, or a pharmaceutically acceptable salt thereof, wherein $X^1$ is N and $X^2$ and $X^3$ are each CH; or $X^2$ is N and $X^1$ and $X^3$ are each CH; or $X^3$ is N and $X^1$ and $X^2$ are each CH.

In Embodiment 7 of this disclosure are compounds of Formula I, and each of Embodiments 1, 2, 3A, 3B, 4, 5A, 5B and 6, and classes thereof, or a pharmaceutically acceptable salt thereof, wherein $R^5$ is selected from:

(1) —$C_{1-6}$alkyl (e.g., —$C_{1-3}$alkyl or —$CH_3$) unsubstituted or substituted with 1 to 6 substituents independently selected at each occurrence from halo, —OH, —$NH_2$ and —C(O)$NH_2$, (2) —C(O)$NH_2$, (3)

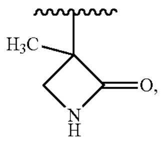

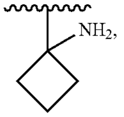

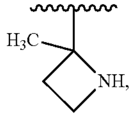

and (4)

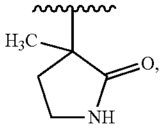

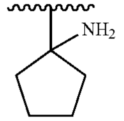

and

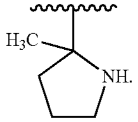

In sub-embodiments of Embodiment 7, R5 is a —$C_{1-6}$ alkyl (e.g., —$C_{1-3}$alkyl or —$CH_3$) substituted with —$NH_2$.

In Embodiment 8 of this disclosure are compounds of Formula I, and each of Embodiments 1, 2, 3A, 3B, 4, 5A, 5B, 6 and 7, and classes thereof, or a pharmaceutically acceptable salt thereof, wherein $R^6$ is selected from:

(1) phenyl, unsubstituted or substituted with 1 to 5 substituents independently selected at each occurrence from:

(a) —F and —Cl, (b) —CN, (c) —$C_{1-3}$alkyl unsubstituted or substituted with 1 to 4 substituents independently selected at each occurrence from —F, —Cl, and —OH, (d) —$OC_{1-3}$alkyl unsubstituted or substituted with 1 to 4 substituents independently selected at each occurrence from —F, —Cl, and —OH, and (e) —$C_{3-6}$cycloalkyl (e.g., cyclopropyl), unsubstituted or substituted with 1 to 3 substituents independently selected at each occurrence from —F, —Cl, —OH, —$C_{1-3}$alkyl and —$OC_{1-3}$alkyl;

(2) pyridinyl, unsubstituted or substituted with 1, 2 or 3 substituents independently selected at each occurrence from (i) —F and —Cl, (ii) CN and (iii) —$C_{1-3}$alkyl unsubstituted or substituted with 1 to 6 of —F and/or —Cl, e.g., —$CH_2F$, —$CHF_2$, —$CF_3$ and —$C(CH_3)F_2$;

(3)

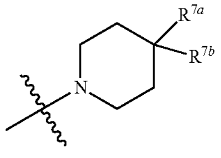

wherein $R^{7a}$ and $R^{7b}$ are each selected from —H and —$C_{1-3}$alkyl unsubstituted or substituted with 1 to 6 of —F and/or —Cl, e.g., —$CH_2F$, —$CHF_2$, —$CF_3$ and —$C(CH_3)F_2$;

(4)

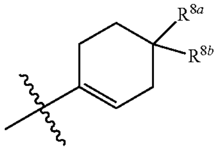

and

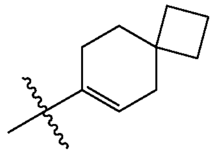

wherein $R^{8a}$ and $R^{8b}$ are each selected from —H, —$C_{1-3}$ alkyl unsubstituted or substituted with 1 to 6 of —F and/or —Cl, e.g., —$CH_2F$, —$CHF_2$, —$CF_3$ and —$C(CH_3)F_2$;

(5) A bicyclic ring system selected from:

(a)

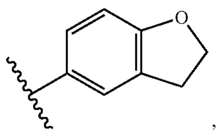

, (b)

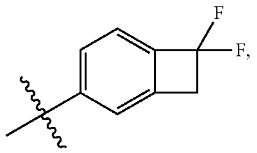

(c)

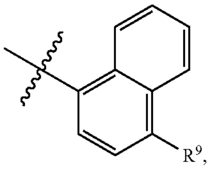

-continued (d)

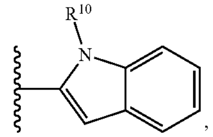

(e)

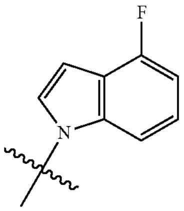

and (f)

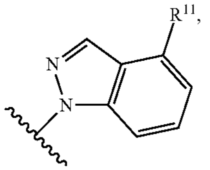

wherein $R^9$, $R^{10}$ and $R^{11}$ are independently selected at each occurrence from —H, 1, 2 or 3 of halo, and —$C_{1-3}$alkyl unsubstituted or substituted with 1 to 6 of —F and/or —Cl;

(6) —$C_{3-6}$cycloalkyl (e.g., cyclopropyl) unsubstituted or substituted with 1 to 5 substituents independently selected at each occurrence from halo, —OH, —$C_{1-6}$ alkyl, and —$OC_{1-6}$alkyl;

(7) pyrazolyl, e.g.,

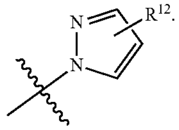

wherein $R^{12}$ is selected from (a) —H, (b) halo, (c) CN, (d) —$C_{1-3}$alkyl unsubstituted or substituted with 1 to 6 of —F and/or —Cl and (e) —$C_{3-6}$cycloalkyl (e.g., cyclopropyl); and (8)

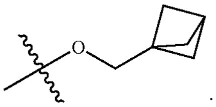 [SMILES: *OCC12CC(C1)C2]

Reference to the compounds of Formula I herein encompasses the compounds of Formula I, Ia, Ib and Ic, and all embodiments, classes and sub-classes thereof and includes the compounds of the Examples herein. The compounds of Formula I encompass neutral compounds or salts thereof when such salts are possible, including pharmaceutically acceptable salts.

The term "e.g." means "for example." When the terms "e.g.," or "for example" are used herein, the example(s) recited are intended to be illustrative and are not intended to be an exhaustive list of all relevant examples.

As used herein, "alkyl" refers to both branched- and straight-chain saturated aliphatic hydrocarbon groups having the specified number of carbon atoms in a specified range. For example the term "$C_{1-6}$alkyl" means linear or branched chain alkyl groups, including all possible isomers, having 1, 2, 3, 4, 5 or 6 carbon atoms, and includes each of the hexyl ("$C_6$alkyl") and pentyl ("$C_5$alkyl") isomers as well as n-, iso-, sec- and tert-butyl (butyl, i-butyl, s-butyl, t-butyl, collectively "$C_4$alkyl"; Bu=butyl), n- and i-propyl (propyl, i-propyl, collectively "$C_3$alkyl"; Pr=propyl), ethyl (Et) and methyl (Me). "$C_{1-3}$alkyl" has 1, 2 or 3 carbon atoms and includes each of n-propyl, i-propyl, ethyl and methyl.

"Cycloalkyl" refers to a cyclized alkyl ring having the indicated number of carbon atoms in a specified range. Thus, for example, "$C_{3-6}$cycloalkyl" includes each of cyclopropyl, cyclobutyl, cyclopentyl and cyclohexyl, and "$C_{3-4}$cycloalkyl" includes each of cyclopropyl and cyclobutyl.

"Halo" or "halogen" refers to chloro, fluoro, bromo or iodo. Chloro, fluoro and bromo are a class of halogens of interest, and more particularly fluoro and chloro.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present disclosure are limited to stable compounds embraced by Formula I and its embodiments. For example, certain moieties as defined in Formula I may be unsubstituted or substituted, and the latter is intended to encompass substitution patterns (i.e., number and kind of substituents) that are chemically possible for the moiety and that result in a stable compound.

This disclosure includes individual diastereomers, particularly epimers, i.e., compounds having the same chemical formula but which differ in the spatial arrangement around a single atom. This disclosure also includes mixtures of diastereomers, particularly mixtures of epimers, in all ratios. This disclosure encompasses compounds of Formula I having either the (R) or (S) stereo-configuration at an asymmetric center and at any additional asymmetric centers that may be present in a compound of Formula I, as well as stereo-isomeric mixtures thereof. Embodiments of this disclosure also include a mixture of enantiomers enriched with 51% or more of one of the enantiomers, including for example 60% or more, 70% or more, 80% or more, or 90% or more of one enantiomer. A single epimer is preferred. An individual or single enantiomer refers to an enantiomer obtained by chiral synthesis and/or using generally known separation and purification techniques, and which may be 100% of one enantiomer or may contain small amounts (e.g., 10% or less) of the opposite enantiomer. Thus, individual enantiomers are a subject of this disclosure in pure form, both as levorotatory and as dextrorotatory antipodes, in the form of racemates and in the form of mixtures of the two enantiomers in all ratios. In the case of a cis/trans isomerism this disclosure includes both the cis form and the trans form as well as mixtures of these forms in all ratios.

The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. The present disclosure includes all such isomers, as well as salts, solvates (which includes hydrates), and solvated salts of such racemates, enantiomers, diastereomers and tautomers and mixtures thereof.

As would be recognized by one of ordinary skill in the art, certain compounds of the present disclosure may be able to exist as tautomers. All tautomeric forms of such compounds, whether isolated individually or in mixtures, are within the scope of the present disclosure. For example, in instances where an oxo (═O) substituent is permitted on an aromatic heterocyclic ring (also referred to as a heteroaromatic ring) and keto-enol tautomerism is possible, it is understood that the substituent might in fact be present, in whole or in part, in the —OH form.

The atoms in a compound of Formula I may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds of Formula I; for example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of Formula I can be prepared without undue experimentation by conventional techniques well known to those skilled in the art or by processes analogous to those described in the Schemes and Examples herein using appropriate isotopically-enriched reagents and/or intermediates.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). When the compounds of Formula I contain one or more acidic groups or basic groups, the invention includes the corresponding pharmaceutically acceptable salts.

The compounds of Formula I, and pharmaceutically acceptable salts thereof, which contain one or more basic groups, i.e., groups which can be protonated, can be used according to the invention in the form of their acid addition salts with inorganic or organic acids as, for example but not limited to, salts with hydrogen chloride, hydrogen fluoride, hydrogen bromide, trifluoroacetic acid (trifluoroacetate), phosphoric acid, sulfuric acid, nitric acid, benzenesulfonic acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. In some embodiments, one or more $NH_2$ groups (e.g., a single $NH_2$ group, or two $NH_2$ groups) of any of the compounds of Formula I is protonated in a salt form. In some embodiments, one or more $NH_2$ groups (e.g., a single $NH_2$ group) of any of the compounds of Formula I is protonated in a salt form with trifluoroacetic acid (trifluoroacetate). In some embodiments, one or more $NH_2$ groups (e.g., a single $NH_2$ group) of any of the compounds of Formula I is protonated in a salt form with hydrogen chloride. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present disclosure also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

The instant disclosure encompasses any composition comprised of a compound of Formula I or a compound that is a salt thereof, including for example but not limited to, a composition comprised of said compound associated together with one or more additional molecular and/or ionic component(s) which may be referred to as a "co-crystal." The term "co-crystal" as used herein refers to a solid phase (which may or may not be crystalline) wherein two or more different molecular and/or ionic components (generally in a stoichiometric ratio) are held together by non-ionic interactions including but not limited to hydrogen-bonding, dipole-dipole interactions, dipole-quadrupole interactions or dispersion forces (van der Waals). There is no proton transfer between the dissimilar components and the solid phase is neither a simple salt nor a solvate. A discussion of co-crystals can be found, e.g., in S. Aitipamula et al., *Crystal Growth and Design,* 2012, 12(5), pp. 2147-2152.

Furthermore, compounds of the present disclosure may exist in amorphous form and/or one or more crystalline forms, and as such all amorphous and crystalline forms and mixtures thereof of the compounds of Formula I and salts thereof are intended to be included within the scope of the present disclosure. In addition, some of the compounds of the instant disclosure may form solvates with water (i.e., a hydrate) or common organic solvents. Such solvates and hydrates, particularly the pharmaceutically acceptable solvates and hydrates, of the compounds of this disclosure are likewise encompassed within the scope of the compounds defined by Formula I and the pharmaceutically acceptable salts thereof, along with un-solvated and anhydrous forms of such compounds.

Accordingly, the compounds of Formula I or salts thereof including pharmaceutically acceptable salts thereof, embodiments thereof and specific compounds described and claimed herein, encompass all possible stereoisomers, tautomers, physical forms (e.g., amorphous and crystalline forms), co-crystal forms, solvate and hydrate forms, and any combination of the foregoing forms where such forms are possible.

Another embodiment of the present disclosure is a compound of Formula I wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as, high performance liquid chromatography, and/or mass spectrometry or NMR techniques. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual stereoisomer.

The compounds of Formula I herein, and pharmaceutically acceptable salts thereof, are useful for the inhibition of respiratory syncytial virus replication and metapneumovirus replication. Thus, the compounds of Formula I and pharmaceutically acceptable salts thereof are useful for:

(i) A method for the treatment of respiratory syncytial virus infection in a human subject in need thereof which comprises administering to the human subject an effective amount of the compound according to Formula I, or a pharmaceutically acceptable salt thereof;

(ii) A method for the prophylaxis of respiratory syncytial virus infection in a human subject in need thereof which comprises administering to the human subject an effective amount of the compound according to Formula I, or a pharmaceutically acceptable salt thereof;

(iii) A method for the treatment of metapneumovirus infection in a human subject in need thereof which comprises administering to the human subject an effective amount of the compound according to Formula I, or a pharmaceutically acceptable salt thereof; and/or (iv) A method for the prophylaxis of metapneumovirus infection in a human subject in need thereof which comprises administering to the human subject an effective amount of the compound according to Formula I, or a pharmaceutically acceptable salt thereof.

Additional embodiments of the present disclosure include the following:

(a) A pharmaceutical composition comprising an effective amount of a compound of Formula I or a pharmaceutically acceptable salt thereof, and a pharmaceutically acceptable carrier, and (b) A pharmaceutical composition which comprises the product prepared by combining (e.g., mixing) an effective amount of a compound of Formula I or a pharmaceutically acceptable salt thereof, and a pharmaceutically acceptable carrier.

Additional embodiments of the present disclosure include each of the pharmaceutical compositions, methods and uses set forth in the preceding paragraphs, wherein the compound of Formula I or its salt employed therein in substantially pure. With respect to a pharmaceutical composition comprising a compound of Formula I or its salt and a pharmaceutically acceptable carrier and optionally one or more excipients, it is understood that the term “substantially pure” is in reference to a compound of Formula I or its salt per se.

The term “administration” and variants thereof (e.g., “administering” a compound) in reference to a compound of Formula I means providing the compound to the individual in need of treatment or prophylaxis and includes both self-administration and administration to the patient by another person or any other means.

As used herein, the term “composition” is intended to encompass a product comprising the specified ingredients, as well as any product which results from combining the specified ingredients. Ingredients suitable for inclusion in a pharmaceutical composition are pharmaceutically acceptable ingredients, which means the ingredients must be compatible with each other and not deleterious to the recipient thereof.

As used herein, the term “subject” refers to an animal, such as a human, that is the object of treatment, observation or experiment. In various embodiments of the present disclosure, a “subject” encompasses a mammalian animal. In some embodiments, the subject encompasses a domesticated or companion animal, or an experimental animal model. In some embodiments, the subject is a rodent, such as a mouse or rat. In some embodiments, the subject is a primate. In some embodiments, the subject is a non-human primate, such as a macaque. In some embodiments, the subject is a human.

The term “human subject” or “patient” as used herein refers to a human (or “person”) who has been the object of treatment, observation or experiment. Patients to be treated with an RSV inhibitor (RSV-i) and/or an MPV inhibitor (MPV-i) agent include but are not limited to, patients who have been infected with RSV and/or MPV. Patients to be treated with an RSV-i and/or an MPV-i agent also include, but are not limited to, those using an RSV-i and/or an MPV-i agent for prophylaxis of RSV and/or MPV infection or for post-exposure prophylaxis after being potentially exposed to RSV and/or MPV to prevent or reduce the severity of symptoms of virus-associated disease or condition; or prevent the patient from becoming infected.

“Prophylaxis” includes each of pre-exposure prophylaxis (PrEP), i.e., using a compound of Formula I or a pharmaceutically acceptable salt thereof to prevent hRSV and/or hMPV infection in a person who is not infected with hRSV and/or hMPV, and post-exposure prophylaxis (PEP), i.e., using a compound of Formula I or a pharmaceutically acceptable salt thereof after being exposed or potentially exposed to hRSV and/or hMPV to prevent or reduce the severity of symptoms of virus-associated disease or condition; or to prevent the person from becoming infected with hRSV and/or hMPV.

The term “effective amount” as used herein means the amount of active compound or pharmaceutical agent that elicits the biological or medicinal response in a tissue, system, animal or human that is being sought by a researcher, veterinarian, medical doctor or other clinician. In one embodiment, the effective amount is a “therapeutically effective amount” for the alleviation of the symptoms of the disease or condition being treated. In another embodiment, the effective amount is a “prophylactically effective amount” for prophylaxis of the symptoms of the disease or condition being prevented.

When the active compound (i.e., active ingredient) is administered as the salt, references to the amount of active ingredient are to the free form (i.e., the non-salt form) of the compound.

In the methods of the present invention, the compounds of this invention, or salts thereof, can be administered by means that produce contact of the active agent with the agent’s site of action. They can be administered by conventional means available for use in conjunction with pharmaceuticals, either as individual therapeutic agents or with other therapeutic agents the patient may be in need of. The compound can be administered itself, but typically is administered with a pharmaceutical carrier selected on the basis of the chosen route of administration and standard pharmaceutical practice. The compounds of the invention can, for example, be administered orally (e.g., via tablet or capsule), parenterally (including subcutaneous injection; intravenous, intramuscular or intrasternal injection; or infusion techniques), by inhalation spray, or rectally, in the form of a unit dosage of a pharmaceutical composition containing an effective amount of the compound and conventional non-toxic pharmaceutically acceptable carriers, adjuvants and vehicles. The compound could also be administered via an implantable drug delivery device adapted to provide an effective amount of the compound or a pharmaceutical composition of the compound over an extended period of time.

The term "administration" and variants thereof (e.g., "administering" a compound) in reference to a compound of Formula I means providing the compound to the individual in need of treatment or prophylaxis and includes both self-administration and administration to the patient by another person or any other means.

As used herein, the term "composition" is intended to encompass a product comprising the specified ingredients, as well as any product which results from combining the specified ingredients. Ingredients suitable for inclusion in a pharmaceutical composition are pharmaceutically acceptable ingredients, which means the ingredients must be compatible with each other and not deleterious to the recipient thereof.

The term "subject" or "patient" as used herein refers to a human (or "person") who has been the object of treatment, observation or experiment. Examples of patients to be treated with the anti-viral agents described herein include, but are not limited to, patients who have been infected with hRSV or hMPV as well as those using the anti-viral agent for prophylaxis of hRSV and hMPV infection.

"Prophylaxis" includes each of pre-exposure prophylaxis (PrEP), i.e., using a compound of Formula I or a pharmaceutically acceptable salt thereof to prevent hRSV or hMPV infection in a person who is not infected with hRSV or hMPV, and post-exposure prophylaxis (PEP), i.e., using a compound of Formula I or a pharmaceutically acceptable salt thereof after being potentially exposed to hRSV or hMPV to prevent or reduce the severity of symptoms of virus-associated disease; or prevent the person from becoming infected with hRSV or hMPV.

The term "effective amount" as used herein means an amount of a compound sufficient to elicit exert a therapeutic effect, and/or a exert a prophylactic effect after administration. One embodiment of "effective amount" is a "therapeutically effective amount" which is an amount of a compound that is effective for treating hRSV or hMPV infection Another embodiment of "effective amount" is a "prophylactically effective amount" which is an amount of the compound that is effective for prophylaxis of hRSV or hMPV infection.

Formulations

Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Liquid preparations suitable for oral administration (e.g., suspensions, syrups, elixirs and the like) can be prepared according to techniques known in the art and can employ any of the usual media such as water, glycols, oils, alcohols and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Implantable compositions can be prepared according to methods known in the art wherein the carrier comprises the active chemical ingredient with polymers and suitable excipients, or utilizing an implantable device for drug delivery. Further description of methods suitable for use in preparing pharmaceutical compositions for use in the present disclosure and of ingredients suitable for use in said compositions is provided in Remington—The Science and Practice of Pharmacy, 22nd Edition, published by Pharmaceutical Press and Philadelphia College of Pharmacy at University of the Sciences, 2012, ISBN 978 0 85711-062-6 and prior editions.

Formulations of compounds of Formula I that result in drug supersaturation and/or rapid dissolution may be utilized to facilitate oral drug absorption. Formulation approaches to cause drug supersaturation and/or rapid dissolution include, but are not limited to, nanoparticulate systems, amorphous systems, solid solutions, solid dispersions, and lipid systems. Such formulation approaches and techniques for preparing them are known in the art. For example, solid dispersions can be prepared using excipients and processes as described in reviews (e.g., A. T. M. Serajuddin, *J Pharm Sci,* 88:10, pp. 1058-1066 (1999)). Nanoparticulate systems based on both attrition and direct synthesis have also been described in reviews such as Wu et al. (F. Kesisoglou, S. Panmai, Y. Wu, *Advanced Drug Delivery Reviews,* 59:7 pp. 631-644 (2007)).

The compounds of Formula I may be administered in a dosage range of, e.g., 1 to 20 mg/kg, or 1 to 10 mg/kg, or about 5 mg/kg of mammal (e.g., human) body weight per day, or at other time intervals as appropriate, in a single dose or in divided doses. The compounds of Formula I may be administered in a dosage range of 0.001 to 2000 mg. per day in a single dose or in divided doses. Examples of dosage ranges are 0.01 to 1500 mg per day, or 0.1 to 1000 mg per day, administered orally or via other routes of administration in a single dose or in divided doses.

For oral (e.g., tablets or capsules) or other routes of administration, the dosage units may about 100 mg to 1500 mg of the active ingredient, for example but not limited to 0.1 mg to about 1500 mg of the active ingredient, for example but not limited to 0.1, 0.25, 0.5, 1, 2, 2.5, 5, 10, 15, 20, 25, 40, 50, 75, 100, 125, 150, 175, 200, 225, 250, 500, 1000, 1250, or 1500 milligrams of the active ingredient for the symptomatic adjustment of the dosage to the patient to be treated. Furthermore, the compound may be formulated in oral formulations for immediate or modified release such as extended or controlled release. When the compound of Formula I is administered as a salt, reference to an amount of the compound in milligrams or grams is based on the free form (i.e., the non-salt form) of the compound.

Daily administration can be via any suitable route of administration but is preferably via oral administration and can be a single dose or more than one dose at staggered times (divided daily doses) within each 24-hour period. Each dose may be administered using one or multiple dosage units as appropriate.

The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, the effect of other drugs the patient is taking while using and RSP-i or an MPV-i compound described herein, the severity of the particular condition, and the host undergoing therapy. In some cases, depending on the potency of the compound or the individual response, it may be necessary to deviate upwards or downwards from the given dose. The amount and frequency of administration will be regulated according to the judgment of the attending clinician considering such factors.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals.

The following acronyms and abbreviations have the indicated meanings: Ad-BippyPhos is 5-[di(1-adamantyl)phosphino]-1',3',5'-triphenyl-1'H-[1,4']bipyrazole; (Ad-BippyPhos)$_2$PdCl$_2$ is bis[5-(di(1-adamantyl)phosphino)-1',3',5'-triphenyl-1'H-[1,4']bipyrazole]palladium(II) dichloride; aq. Is aqueous; BINAP is 2,2'-bis(diphenylphosphino)-1,1'-binaphthalene; CPME is cyclopentyl methyl ether; CV is column volume(s); d is day(s); DCM is dichloromethane; DEA is N,N-diethylamine; DIPEA is N,N-diisopropyl-N-ethylamine; DMA is N,N-dimethylacetamide; DME is dimethoxyethane; DMF is N,N-dimethylformamide; DMSO is dimethyl sulfoxide; Et is ethyl; $Et_2O$ is diethyl ether; EtOAc is ethyl acetate; EtOH is ethanol; Ex. Is example(s); h is hour(s); HATU is 1-[bis(dimethylamino)methylene]-1H-1,2,3-triazolo[4,5-b]pyridinium 3-oxid hexafluorophosphate; IPA is 2-propanol; [Ir(cod)Ome]$_2$ is (1,5-cyclooctadiene)(methoxy)iridium(I) dimer; Int. is intermediate(s); MeCN is acetonitrile; MTBE is methyl tert-butyl ether; NMP is 1-methyl-2-pyrrolidinone; $Pd_2(dba)_3$ is tris(dibenzylideneacetone)dipalladium(0); Pd(dppf)$Cl_2$ is [1,1'-bis(diphenylphosphino)ferrocene]dichloropalladium(II); Pd(dtbpf)$Cl_2$ is [1,1'-bis(di-tert-butylphosphino)ferrocene]dichloropalladium(II); Pd(Oac)$_2$ is palladium(II) acetate; $Pd(PPh_3)_4$ is tetrakis(triphenylphosphine)palladium(0); $PhCF_3$ is α,α,α-trifluorotoluene; PhMe is toluene; PyBOP is (benzotriazol-1-yloxy)tripyrrolidinophosphonium hexafluorophosphate; RockPhos Pd G3 is [(2-di-tert-butylphosphino-3-methoxy-6-methyl-2',4',6'-triisopropyl-1,1'-biphenyl)-2-(2-aminobiphenyl)]palladium(II) methanesulfonate; rpm is revolutions per minute; rt is room temperature; SFC is supercritical fluid chromatography; T3P is 2,4,6-tripropyl-1,3,5,2,4,6-trioxatriphosphorinane-2,4,6-trioxide; TBDPS is tert-butyldiphenylsilyl; t-BuXPhos is 2-di-tert-butylphosphino-2',4',6'-triisopropylbiphenyl; TFA is trifluoroacetic acid; THF is tetrahydrofuran; Xphos Pd G2 is chloro(2-dicyclohexylphosphino-2',4',6'-triisopropyl-1,1'-biphenyl)[2-(2'-amino-1,1'-biphenyl)]palladium(II).

It is understood that a chiral center in a compound may exist in the "S" or "R" stereo-configuration, or as a mixture of both. Within a molecule, each bond drawn as a straight line from a chiral center encompasses each of the (R) and (S) stereoisomers as well as mixtures thereof unless otherwise noted. For compounds in the Examples that contain a chiral center, isomer mixtures may have been separated, providing one or both of an isomer 1 (the faster eluting isomer) and an isomer 2 (the slower eluting isomer), based on their observed elution order resulting from the separation as performed in the Example. Elution time and/or order of separated isomers may differ if performed under conditions different than those employed herein. Absolute stereochemistry (R or S) of the chiral center in each of isomer "1" and/or isomer "2" separated stereoisomers in the intermediates and Examples was not determined, and "1" and "2" only refer to elution order resulting from the purification conditions as performed.

General Procedures

The following reaction schemes and Examples illustrate methods which may be employed for the synthesis of the compounds of Formula (I) described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural Formula I.

The compounds of the present disclosure can be prepared according to the procedures of the following Examples, using appropriate materials. The compounds illustrated in the examples are not, however, to be construed as forming the only genus that is considered as the invention. The Examples further illustrate details for the preparation of the compounds of the present disclosure. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature.

Reactions sensitive to moisture or air were performed under nitrogen or argon using anhydrous solvents and reagents. The progress of reactions was determined by either liquid chromatography-mass spectrometry (LC-MS) or analytical thin layer chromatography (TLC) usually performed with Merck KGaA glass-backed TLC plates, silica gel 60 $F_{254}$. All temperatures are degrees Celsius unless otherwise noted. Mass spectra (MS) were measured either by electrospray ionization mass spectroscopy (ESI) or by atmospheric pressure chemical ionization mass spectroscopy (APCI).

In general, compounds of Formula (I) can be prepared by amide coupling of appropriately functionalized carboxylic acids of Formula (II) and amines of Formula (III). Acids of Formula (II) and amines of Formula (III) are commercially available or may be synthesized from appropriate intermediates. Other synthetic methods to prepare compounds of Formula (I) are presented for the exemplification of compounds. Further, compounds of Formula (I) can be prepared by reaction procedures generally known in the art.

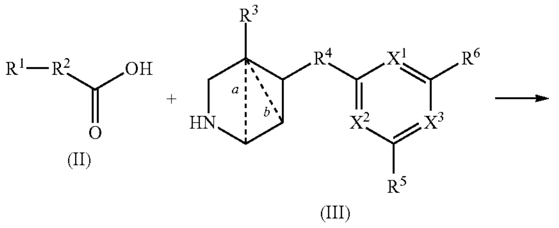

-continued

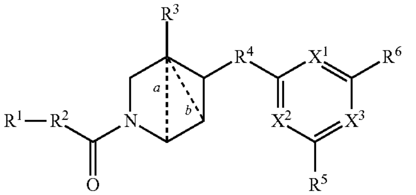

(I)

In some sub-embodiments, compounds of Formula (I) can be prepared by the following reaction procedure:

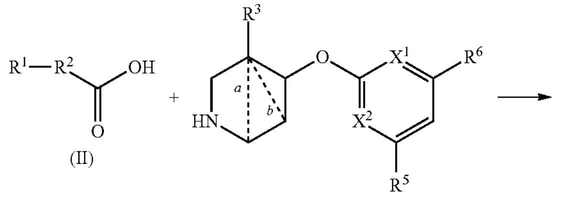

(II)

(III)

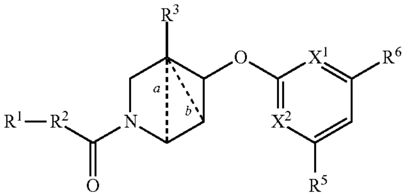

(I)

Analytical LC-MS was commonly performed on a Waters SQD single quadrupole mass spectrometer with electrospray ionization in positive ion detection mode (mass range set at 150-900 daltons, data collected in centroid mode and scan time set to 0.2 seconds) and a Waters Acquity UPLC system (binary solvent manager, sample manager, and TUV). The column used was a Waters Acquity BEH C18 1×50 mm, 1.7 μm, heated to 50° C. The mobile phases used were modified with either acidic or basic additives. The acidic mobile phase consisted of water (with 0.1% TFA modifier) for Solvent A and 100% MeCN for Solvent B. A two-minute run was established at a flow rate of 0.3 mL/min with initial conditions of 95% Solvent A and ramping up to 99% Solvent B at 1.60 minutes and holding at 99% Solvent B for 0.40 minutes. The injection volume was 0.5 μL using partial loop needle overfill injection mode. The TUV monitored wavelength 215 or 254 nm with a sampling rate of 20 points/second, normal filter constant and absorbance data mode. The basic mobile phase consisted of water (with 0.05% $NH_4OH$ modifier) for solvent A and 100% MeCN for solvent B. A two-minute run was established at a flow rate of 0.3 mL/min with Initial conditions of 99% Solvent A and ramping up to 99% Solvent B at 1.90 minutes and holding at 99% Solvent B for 0.10 minutes. A five-minute run was established at a flow rate of 0.3 mL/min with initial conditions of 95% Solvent A and ramping up to 99% Solvent B at 4.90 minutes and holding at 99% Solvent B for 0.10 minutes. For both methods, the injection volume was 5.0 μL using Partial Loop Needle Overfill Injection mode. The TUV monitored wavelength 215 nm with a sampling rate of 20 points/second, normal filter constant and absorbance data mode. Alternatively, a commonly used system consisted of a Waters ZQ™ platform with electrospray ionization in positive ion detection mode with an Agilent 1100 series HPLC with autosampler. The column was commonly a Waters Xterra MS C18, 3.0×50 mm, 5 μm or a Waters Acquity UPLC® BEH C18 1.0×50 mm, 1.7 m. The flow rate was 1 mL/min, and the injection volume was 10 μL. UV detection was in the range 210-400 nm. The mobile phase consisted of solvent A (water with 0.05% TFA modifier) and solvent B (MeCN with 0.05% TFA modifier) with a gradient of 100% solvent A for 0.7 min changing to 100% solvent B over 3.75 min, maintained for 1.1 min, then reverting to 100% solvent A over 0.2 min.

Preparative reverse-phase chromatography was generally carried out on a Teledyne ISCO ACCQPrep HP125 or HP150 apparatus equipped with UV and ELSD detectors. The UV detector typically monitored wavelengths of 215 and 254 nm. The column was commonly one of the following: Waters XBridge Prep C18 OBD 5 μm 30×150 mm, Waters XBridge Prep C18 OBD 5 μm 30×250 mm, Waters XBridge Prep C18 OBD 5 μm 50×250 mm, Waters SunFire Prep C18 OBD 5 μm 30×150 mm, Waters SunFire Prep C18 OBD 10 m 30×150 mm, Waters SunFire Prep C18 OBD 5 μm 50×250 mm, Waters SunFire Prep C18 OBD 10 μm 50×250 mm, or Phenomenex Luna Prep C18 5 μm 50×250 mm. The mobile phases consisted of mixtures of MeCN (with 0.1% TFA modifier) and water (with 0.1% TFA modifier). Alternatively, a commonly used system was a Waters Chromatography Workstation configured with an LCMS system consisting of: Waters ZQ™ single quad MS system with Electrospray Ionization, Waters 2525 Gradient Pump, Waters 2767 Injector/Collector, Waters 996 PDA Detector. MS conditions were: 150-750 amu, positive electrospray, collection triggered by MS. Columns used were commonly a Waters SunFire C18 5 μm 30×150 mm, a Boston Green ODS 5 μm 150×30 mm, or a YMC-Actus Triart C18 5 μm 150×30 mm column. The mobile phases consisted of mixtures of MeCN (10-100%) in water (with 0.1% TFA modifier). Flow rates were maintained at 50 mL/min, and the UV detection range was 210-400 nm. An additional preparative HPLC system used was a Gilson Workstation consisting of: Gilson GX-281 Injector/Collector, Gilson UV/VIS-155 Detector, Gilson 333 and 334 Pumps, and either a Phenomenex Gemini-NX C18 5 μm 50×250 mm column, a Waters XBridge Prep C18 OBD 5 m 30×250 mm, or a Welch Xtimate C18 5 μm 150×25 mm. The mobile phases consisted of mixtures of acetonitrile (0-75%) in water containing 5 mM $(NH_4)HCO_3$. Flow rates were maintained at 50 mL/min for the Waters XBridge column, 90 mL/min for the Phenomenex Gemini column, and 25 L/min for the Welch Xtimate column. The UV detection range was 210-400 nm. Mobile phase gradients were optimized for the individual compounds.

Silica gel chromatography was usually performed using an ISCO CombiFlash Rf apparatus, a Biotage® Flash Chromatography apparatus (Dyax Corp.), or an ISCO CombiFlash® Companion XL apparatus on silica gel (60 Å pore size) in pre-packed RediSep Rf, RediSep Rf Gold, or SepaFlash columns. Mobile phases generally consisted of mixtures of hexanes, petroleum ether, or DCM with EtOAc, 3:1 EtOAc:EtOH, or MeOH. Mobile phase gradients were optimized for the individual compounds.

Chiral chromatography was commonly performed by supercritical fluid chromatography with a column chosen from one of the following: ChiralPak AD, ChiralPak AD-3, ChiralPak AD-H, ChiralPak AS, ChiralPak AS-3, ChiralPak AS-H, ChiralPak IB-N, ChiralPak OD-H, ChiralPak OJ-3, ChiralPak OJ-H, Phenomenex-Cellulose-2, or (S,S)Whelk-O1. Mobile phases consisted of mixtures of $CO_2$ or hexane with MeOH, EtOH, or IPA using 0.05-0.1% DEA or $NH_4OH$ modifier. Mobile phase gradients were optimized for the individual compounds. Pressure was typically maintained at 100 bar, and flow rates ranged from 50-200 mL/min. UV monitoring was generally carried out at 220 or 205 nM.

$^1$H NMR data were typically acquired using a Bruker NEO 500 MHz NMR spectrometer equipped with a room temperature 5 mm BBF iProbe, a Bruker Avance NEO 400 MHz NMR spectrometer equipped with a Bruker PI HR-BBO400S1-BBF/H/D-5.0-Z SP probe, or a Bruker Avance ITT 500 MHz NMR spectrometer equipped with a Bruker 5 mm PABBO probe. Chemical shift values are reported in delta (δ) units, parts per million (ppm). Chemical shifts for $^1$H NMR spectra are given relative to signals for residual non-deuterated solvent ($CDCl_3$ referenced at δ 7.26 ppm; DMSO-$d_6$ referenced at δ 2.50 ppm and $CD_3OD$ referenced at δ 3.31 ppm). Multiplets are reported by the following abbreviations: s=singlet, d=doublet, t=triplet, q=quartet, dd=doublet of doublets, m=multiplet or overlap of non-equivalent resonances. Coupling constants (J) are reported in Hertz (Hz). When compounds appear as mixtures of rotamers by NMR, spectral data corresponding to the major species observed in solution are reported.

Scheme:

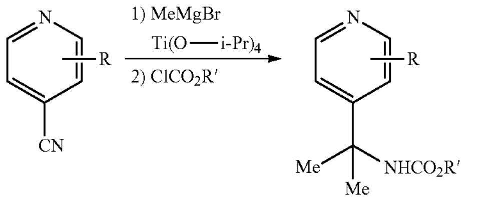

Intermediate A-1

Benzyl (2-(2,6-dichloropyridin-4-yl)propan-2-yl)carbamate

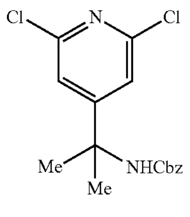 [SMILES: CC(C)(NC(=O)OCc1ccccc1)c1cc(Cl)nc(Cl)c1]

Step 1: 2-(2,6-dichloropyridin-4-yl)propan-2-amine

A solution of methylmagnesium bromide (3.0 M in $Et_2O$, 1.7 L, 5.2 mol) was added dropwise over 1 h to a 0° C. mixture of 2,6-dichloroisonicotinonitrile (0.30 kg, 1.7 mol) in PhMe (1.5 L). The mixture was warmed up to 25° C. and stirred for 1 h. The mixture was cooled to 0° C. and titanium(IV) isopropoxide (490 g, 1.7 mol) was added dropwise over 0.5 h. The mixture was heated to 100° C. and stirred for 1 h. The mixture was cooled to 5-10° C., and treated with a solution of $Na_2CO_3$ (saturated aq., 5 L) at 5-10° C. The mixture was filtered, and the filter cake was washed with EtOAc (800 mL×3). The filtrate was separated, and the organic phase was concentrated to afford the title compound.

Step 2: benzyl (2-(2,6-dichloropyridin-4-yl)propan-2-yl)carbamate

Benzyl chloroformate (250 g, 1.5 mol) was added dropwise over 0.5 h to a 0° C. mixture of 2-(2,6-dichloropyridin-4-yl)propan-2-amine (270 g, 1.3 mol), DIPEA (190 g, 1.5 mol), and DCM (2.7 L). The mixture was warmed up to 25° C. and stirred for 12 h. The mixture was washed with hydrochloric acid (1N, 800 mL×3), dried with anhydrous sodium sulfate, filtered, and concentrated. The material was triturated (MTBE/EtOAc=10:1, 800 mL) at 25° C. for 12 h. The mixture was filtered and concentrated under reduced pressure to afford the title compound.

Utilizing the procedures described in the preparation of Intermediate A-1, the following compounds were prepared substituting the appropriate reagents for 2,6-dichloroisonicotinonitrile

| Int. | Structure | Name |
|---|---|---|
| A-2 | 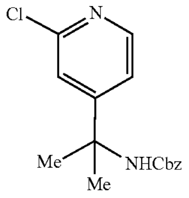 [SMILES: CC(C)(NC(=O)OCc1ccccc1)c1ccnc(Cl)c1] | benzyl (2-(2-chloropyridin-4-yl)propan-2-yl)carbamate |

Scheme:

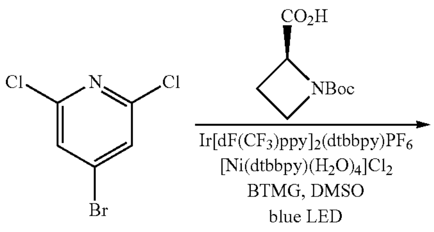

-continued

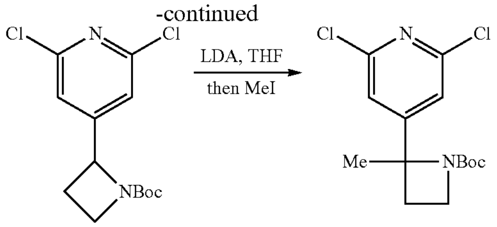

Intermediate A-3 tert-butyl rac-2-(2,6-dichloropyridin-4-yl)-2-methyl-azetidine-1-carboxylate

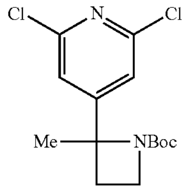 [SMILES: CC(C)(C)OC(=O)N1CCC1(C)c1cc(Cl)nc(Cl)c1]

Step 1: tert-butyl rac-2-(2,6-dichloropyridin-4-yl) azetidine-1-carboxylate

4-Bromo-2,6-dichloropyridine (0.50 g, 2.2 mmol), (S)-1-(tert-butoxycarbonyl)azetidine-2-carboxylic acid (0.49 mg, 2.4 mmol), [4,4'-bis(1,1-dimethylethyl)-2,2'-bipyridine-N1, N1']bis[3,5-difluoro-2-[5-(trifluoromethyl)-2-pyridinyl-N] phenyl-C]iridium(III) hexafluorophosphate (25 mg, 0.022 mmol), and [4,4'-bis(1,1-dimethylethyl)-2,2'-bipyridine] nickel(II) dichloride tetrahydrate (11 mg, 0.023 mmol) were combined in a screw cap vial. To this was added DMSO (22 mL) and 2-tert-butyl-1,1,3,3-tetramethylguanidine (0.90 mL, 4.4 mmol). $N_2$ was bubbled through the mixture for 5 min. The vial was capped then irradiated in a PennOC Photoreactor® (wavelength: 450 nm; LED intensity: 100%; fan speed: 5000 rpm; stir: 1200 rpm). After 4 h the mixture was diluted with $H_2O$ then extracted with EtOAc (4×). The combined organic layers were washed with $H_2O$ and brine, dried with anhydrous magnesium sulfate, filtered, and concentrated. The residue was subjected to silica gel chromatography (0-25% (25% EtOH/EtOAc)/heptane) to afford the title compound.

Step 2: tert-butyl rac-2-(2,6-dichloropyridin-4-yl)-2-methylazetidine-1-carboxylate A solution of tert-butyl rac-2-(2,6-dichloropyridin-4-yl) azetidine-1-carboxylate (0.24 g, 0.79 mmol) in THF (4.0 mL) was cooled to −78° C. To this was added lithium diisopropylamide (2.0 M in THF/heptane/ethylbenzene, 0.56 mL, 1.1 mmol) slowly. After 30 min, iodomethane (0.10 mL, 1.6 mmol) was added. After 10 minutes the cooling bath was removed and the mixture warmed to rt. After stirring an additional 3 h, the mixture was treated with MeOH then concentrated. The residue was dissolved in DMSO (3 mL) and subjected to reverse phase HPLC (5-95% MeCN/water with 0.1% TFA modifier). Fractions containing product were combined and concentrated to afford the title compound.

Scheme:

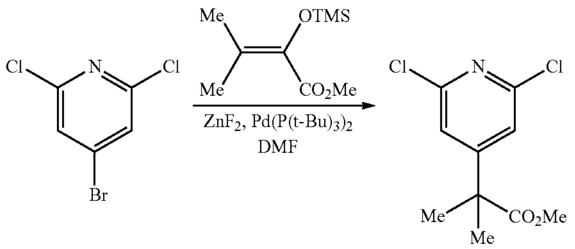

Intermediate A-4 methyl 2-(2,6-dichloropyridin-4-yl)-2-methylpropanoate

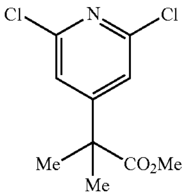 [SMILES: COC(=O)C(C)(C)c1cc(Cl)nc(Cl)c1]

4-Bromo-2,6-dichloropyridine (0.50 g, 2.2 mmol) and $ZnF_2$ (0.11 g, 1.1 mmol) were combined in a screw cap vial. DMF (9.0 mL) was added and $N_2$ was bubbled through the mixture for 1 min. Bis(tri-t-butylphosphine)palladium(0) (57 mg, 0.11 mmol) and ((1-methoxy-2-methylprop-1-en-1-yl)oxy)trimethylsilane (0.68 mL, 3.3 mmol) were added. $N_2$ was bubbled through the mixture for 1 min. The vial was capped then heated to 85° C. for 18 h. The mixture was cooled to rt, diluted with $H_2O$, and extracted with EtOAc (3×). The combined organic layers were washed with $H_2O$ and brine, dried over anhydrous magnesium sulfate, filtered, and concentrated. The residue was subjected to silica gel chromatography (0-25% EtOAc/hexanes) to afford the title compound.

Scheme:

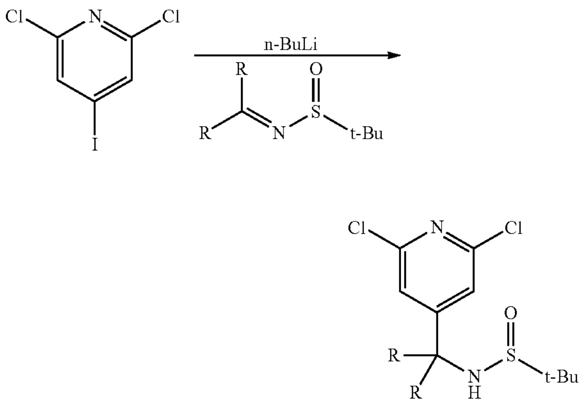

Intermediate A-5

N-(1-(2,6-dichloropyridin-4-yl)cyclobutyl)-2-methylpropane-2-sulfinamide

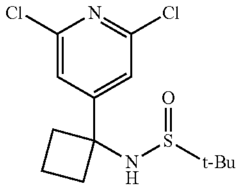 [SMILES: CC(C)(C)S(=O)NC1(c2cc(Cl)nc(Cl)c2)CCC1]

To a −78° C. solution of 2,6-dichloro-4-iodopyridine (1.0 g, 3.7 mmol) in THF (12 mL) was added n-butyllithium (2.5 M in hexane, 2.9 mL, 7.3 mmol) and the mixture was stirred for 30 min. A solution of N-cyclobutylidene-2-methylpropane-2-sulfinamide (0.63 g, 3.7 mmol) in THF (8.0 mL) was added slowly. The mixture was warmed to rt and stirred for 1 h. Water (10 mL) was added and the mixture was extracted with EtOAc (20 mL×3). The combined organic extracts were dried over anhydrous sodium sulfate, filtered, and concentrated. The residue was subjected to silica gel chromatography (0-60% EtOAc/petroleum ether) to afford the title compound.

Utilizing the procedures described in the preparation of Intermediate A-5, the following compound was prepared substituting the appropriate reagent for N-cyclobutylidene-2-methylpropane-2-sulfinamide.

| Int. | Structure | Name |
|---|---|---|
| A-6 | 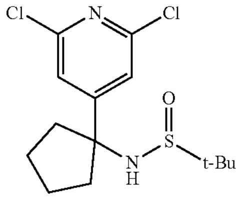 [SMILES: CC(C)(C)S(=O)NC1(c2cc(Cl)nc(Cl)c2)CCCC1] | N-(1-(2,6-dichloropyridin-4-yl)cyclopentyl)-2-methylpropane-2-sulfinamide |

Scheme:

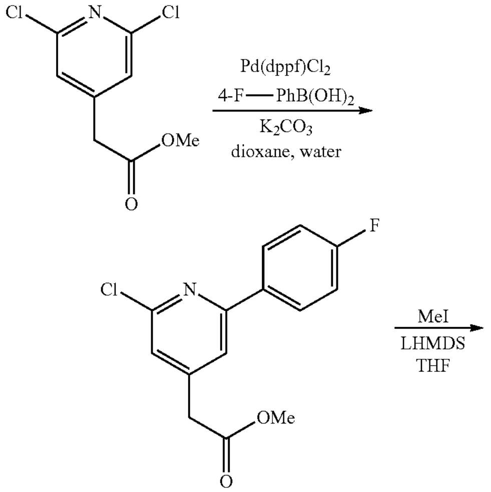

-continued

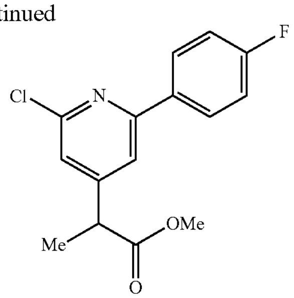

Intermediate B methyl 2-(2-chloro-6-(4-fluorophenyl)pyridin-4-yl) propanoate

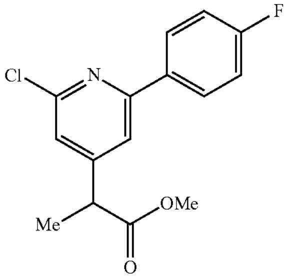 [SMILES: COC(=O)C(C)c1cc(Cl)nc(-c2ccc(F)cc2)c1]

Step 1: methyl 2-(2-chloro-6-(4-fluorophenyl)pyridin-4-yl)acetate

Under an atmosphere of nitrogen, a mixture of methyl 2-(2,6-dichloropyridin-4-yl)acetate (0.030 kg, 0.14 mol), (4-fluorophenyl)boronic acid (19 g, 0.14 mol), Pd(dppf)$Cl_2$ (5.0 g, 6.8 mmol), potassium carbonate (38 g, 0.27 mol), 1,4-dioxane (0.40 L), and water (0.040 L) was stirred at 100° C. for 2 h. The mixture was cooled to rt, filtered, and concentrated under reduced pressure. The residue was subjected to silica gel chromatography (0-8% EtOAc/petroleum ether) to afford the title compound.

Step 2: methyl 2-(2-chloro-6-(4-fluorophenyl)pyridin-4-yl)propanoate

Under an atmosphere of nitrogen, to a −78° C. solution of methyl 2-(2-chloro-6-(4-fluorophenyl)pyridin-4-yl)acetate (14 g, 0.050 mol) in THF (0.15 L) was added a solution of lithium bis(trimethylsilyl)amide (1.0 M in THF, 0.060 L, 0.060 mol). The mixture was stirred for 30 min and iodomethane (6.3 mL, 0.10 mol) was added dropwise. The mixture was warmed to rt and stirred for 2 h. Water (100 mL) was added and the mixture was extracted with EtOAc (100 mL×3). The combined organic extracts were washed with brine (100 mL), dried over anhydrous sodium sulfate, and concentrated under reduced pressure. The residue was subjected to silica gel chromatography (0-5% EtOAc/petroleum ether) to afford the title compound.

Utilizing the procedures described in the preparation of Intermediate A-1, the following compounds were prepared substituting the appropriate reagents for 2,6-dichloroisonicotinonitrile and benzyl chloroformate.

| Int. | Structure | Name |
|---|---|---|
| C-01 | 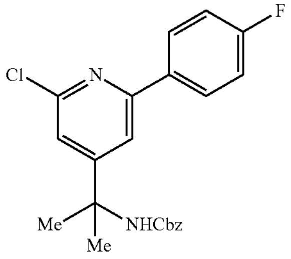 [SMILES: CC(C)(NC(=O)OCc1ccccc1)c1cc(Cl)nc(-c2ccc(F)cc2)c1] | benzyl (2-(2-chloro-6-(4-fluorophenyl)pyridin-4-yl)propan-2-yl)carbamate |
| C-02 | 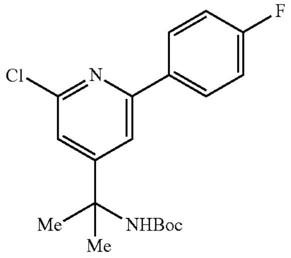 [SMILES: CC(C)(C)OC(=O)NC(C)(C)c1cc(Cl)nc(-c2ccc(F)cc2)c1] | tert-butyl (2-(2-chloro-6-(4-fluorophenyl)pyridin-4-yl)propan-2-yl)carbamate |

Scheme:

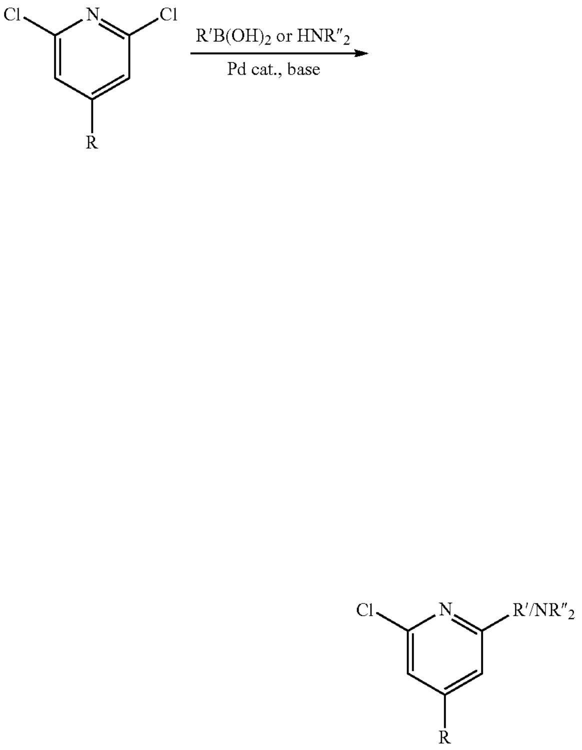

Intermediate C-03

Benzyl (2-(2-chloro-6-(4-(trifluoromethyl)phenyl) pyridin-4-yl)propan-2-yl)carbamate

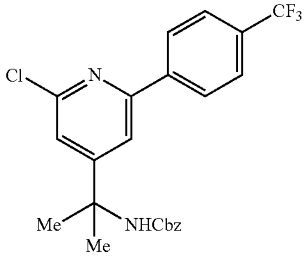 [SMILES: CC(C)(NC(=O)OCc1ccccc1)c1cc(Cl)nc(-c2ccc(C(F)(F)F)cc2)c1]

To a mixture of benzyl (2-(2,6-dichloropyridin-4-yl)propan-2-yl)carbamate (Int. A-1, 2.0 g, 5.9 mmol) and (4-(trifluoromethyl)phenyl)boronic acid (1.0 g, 5.3 mmol) in $H_2O$ (4.0 mL) and 1,4-dioxane (0.020 L) was added $K_2CO_3$ (1.6 g, 12 mmol). The resulting mixture was degassed (evacuated and backfilled with nitrogen×3) then Pd(dppf)$Cl_2$ (0.43 g, 0.59 mmol) was added. The mixture was heated at 100° C. for 2 h. The mixture was cooled to rt, filtered, concentrated under reduced pressure. The residue was subjected to silica gel chromatography (0-10% EtOAc/petroleum ether) to afford the title compound.

Utilizing the procedures described in the preparation of Intermediate C-03, the following compounds were prepared substituting the appropriate reagents for benzyl (2-(2,6-dichloropyridin-4-yl)propan-2-yl)carbamate and (4-(trifluoromethyl)phenyl)boronic acid.

| Int. | Structure | Name | Comments |
| --- | --- | --- | --- |
| C-04 | 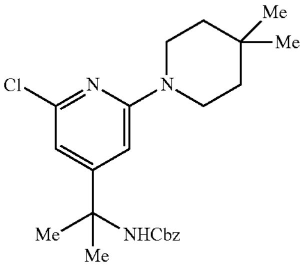 [SMILES: CC1(C)CCN(c2cc(C(C)(C)NC(=O)OCc3ccccc3)cc(Cl)n2)CC1] | benzyl (2-(2-chloro-6-(4,4-dimethylpiperidin-1-yl)pyridin-4-yl)propan-2-yl)carbamate | Int. A-1 (5.9 mmol), 4,4-dimethylpiperidine (5.3 mmol), $Pd_2(dba)_3$ (0.15 mmol), BINAP (0.23 mmol), $Cs_2CO_3$ (8.8 mmol), PhMe (0.040 L), 100° C., 18 h |
| C-05 | 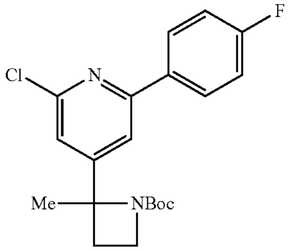 [SMILES: CC(C)(C)OC(=O)N1CCC1(C)c1cc(Cl)nc(-c2ccc(F)cc2)c1] | tert-butyl rac-2-(2-chloro-6-(4-fluorophenyl)pyridin-4-yl)-2-methylazetidine-1-carboxylate | Int. A-3 (0.40 mmol), (4-fluorophenyl)boronic acid (0.48 mmol), $Pd(dppf)Cl_2$•DCM (0.020 mmol), $K_2CO_3$ (2M aq., 0.60 mmol), 1,4-dioxane (3.0 mL), 80° C., 18 h |
| C-06 | 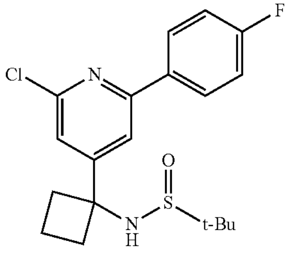 [SMILES: CC(C)(C)S(=O)NC1(c2cc(Cl)nc(-c3ccc(F)cc3)c2)CCC1] | N-(1-(2-chloro-6-(4-fluorophenyl)pyridin-4-yl)cyclobutyl)-2-methylpropane-2-sulfinamide | Int. A-5 (0.56 mmol), (4-fluorophenyl)boronic acid (0.56 mmol), $Pd(OAc)_2$ (0.028 mmol), PPh3 (0.056 mmol), $K_2CO_3$ (1.7 mmol), MeCN (5.0 mL), MeOH (2.5 mL), 50° C., 2 h |
| C-07 | 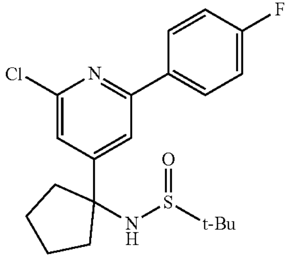 [SMILES: CC(C)(C)S(=O)NC1(c2cc(Cl)nc(-c3ccc(F)cc3)c2)CCCC1] | N-(1-(2-chloro-6-(4-fluorophenyl)pyridin-4-yl)cyclopentyl)-2-methylpropane-2-sulfinamide | Int. A-6 (2.7 mmol), (4-fluorophenyl)boronic acid (2.4 mmol), $Pd(dppf)Cl_2$ (0.27 mmol), $K_2CO_3$ (8.1 mmol), 1,4-dioxane (6.0 mL), water (6.0 mL), 90° C., 1.5 h |
| C-08 | 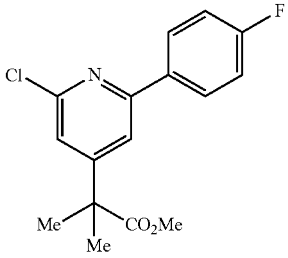 [SMILES: COC(=O)C(C)(C)c1cc(Cl)nc(-c2ccc(F)cc2)c1] | methyl 2-(2-chloro-6-(4-fluorophenyl)pyridin-4-yl)-2-methylpropanoate | Int. A-4 (0.40 mmol), (4-fluorophenyl)boronic acid (0.48 mmol), $Pd(dppf)Cl_2$•DCM (0.021 mmol), $K_2CO_3$ (2M aq., 0.60 mmol), 1,4-dioxane (3.0 mL), 80° C., 18 h |

Scheme:

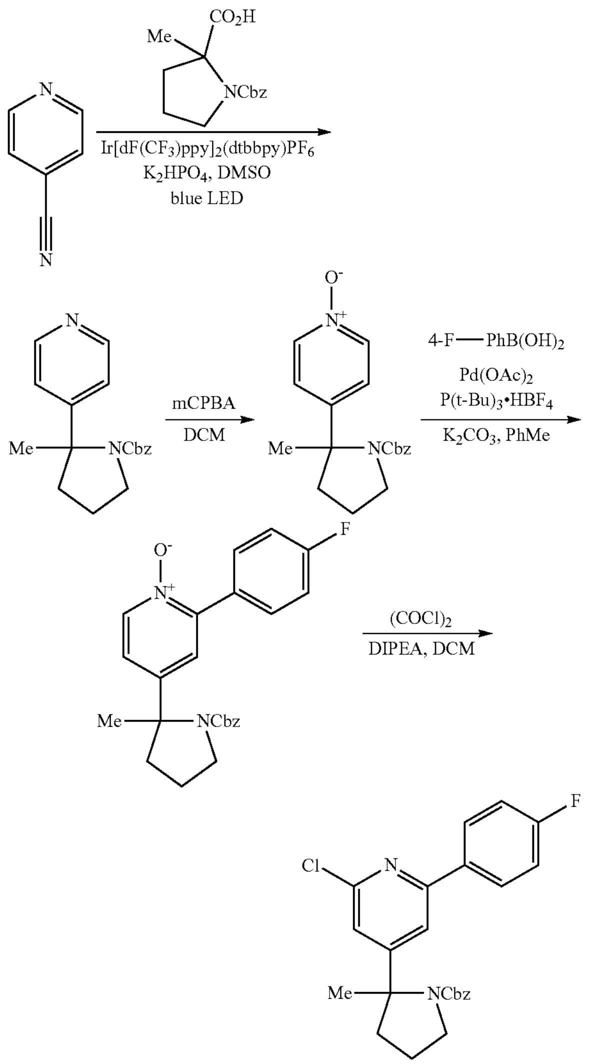

Intermediate C-09

Benzyl rac-2-(2-chloro-6-(4-fluorophenyl)pyridin-4-yl)-2-methylpyrrolidine-1-carboxylate

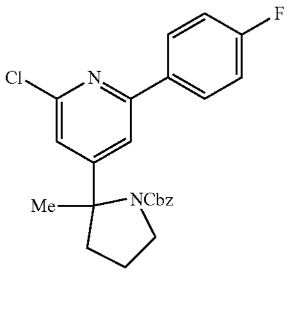 [SMILES: CC1(c2cc(Cl)nc(-c3ccc(F)cc3)c2)CCCN1C(=O)OCc1ccccc1]

Step 1: benzyl rac-2-methyl-2-(pyridin-4-yl)pyrrolidine-1-carboxylate

Isonicotinonitrile (0.30 g, 2.9 mmol), 1-((benzyloxy)carbonyl)-2-methylpyrrolidine-2-carboxylic acid (1.5 g, 5.8 mmol), [4,4'-bis(1,1-dimethylethyl)-2,2'-bipyridine-N1,N1'] bis[3,5-difluoro-2-[5-(trifluoromethyl)-2-pyridinyl-N]phenyl-C]iridium(III) hexafluorophosphate (65 mg, 0.060 mmol) and $K_2HPO_4$ (1.5 g, 8.7 mmol) were combined in a screw cap vial. To this was added DMSO (28 mL). $N_2$ was bubbled through the mixture for 10 min. The vial was capped and then irradiated in a PennOC Photoreactor® (wavelength: 450 nm; LED intensity: 100%; fan speed: 5000 rpm; stir: 1200 rpm). After 24 h, the mixture was diluted with a solution of $NaHCO_3$ (saturated aq.) and extracted with EtOAc (3×). The combined organic extracts were washed with $H_2O$ and brine, dried over anhydrous sodium sulfate, filtered, and concentrated. The residue was subjected to silica gel chromatography (0-50% (25% EtOH:EtOAc)/heptane) to afford the title compound.

Step 2: rac-4-(1-((benzyloxy)carbonyl)-2-methylpyrrolidin-2-yl)pyridine 1-oxide

To a rt solution of benzyl rac-2-methyl-2-(pyridin-4-yl) pyrrolidine-1-carboxylate (0.51 g, 1.7 mmol) in DCM (0.010 L) was added 3-chloroperoxybenzoic acid (0.64 g, 2.6 mmol). After 3 h the mixture was concentrated. The residue was subjected to silica gel chromatography (0-100% (25% EtOH:EtOAc)/heptane) to afford the title compound.

Step 3: rac-4-(1-((benzyloxy)carbonyl)-2-methylpyrrolidin-2-yl)-2-(4-fluorophenyl)pyridine 1-oxide 1-Bromo-4-fluorobenzene (0.13 mL, 1.2 mmol), rac-4-(1-((benzyloxy)carbonyl)-2-methylpyrrolidin-2-yl)pyridine 1-oxide (0.44 g, 1.4 mmol), and $K_2CO_3$ (0.33 g, 2.4 mmol) were combined in a screw cap vial. To this was added toluene (4.0 mL). $N_2$ was bubbled through the mixture for 1 min. $Pd(OAc)_2$ (27 mg, 0.12 mmol) and tri-tert-butylphosphonium tetrafluoroborate (42 mg, 0.15 mmol) were added. The vial was capped then heated to 120° C. overnight. The resulting mixture was cooled to rt, diluted with EtOAc, filtered through a pad of Celite® (eluted with EtOAc), and concentrated. The residue was subjected to silica gel chromatography (0-100% (25% EtOH:EtOAc)/heptane) to afford the title compound.

Step 4: benzyl rac-2-(2-chloro-6-(4-fluorophenyl) pyridin-4-yl)-2-methylpyrrolidine-1-carboxylate A solution of rac-4-(1-((benzyloxy)carbonyl)-2-methylpyrrolidin-2-yl)-2-(4-fluorophenyl)pyridine 1-oxide (0.19 g, 0.47 mmol) in DCM (2.5 mL) was cooled to 0° C. To this was added triethylamine (0.27 mL, 1.9 mmol), then oxalyl chloride (0.085 mL, 0.97 mmol) slowly. After 30 min, the mixture warmed to rt and stirred for 3.5 h. The mixture was diluted with a solution of $NaHCO_3$ (saturated aq.) and then extracted with DCM (3×). The combined organic extracts were dried over anhydrous magnesium sulfate, filtered, and concentrated. The residue was subjected to silica gel chromatography (0-50% (25% EtOH:EtOAc)/heptane) to afford the title compound.

Scheme:

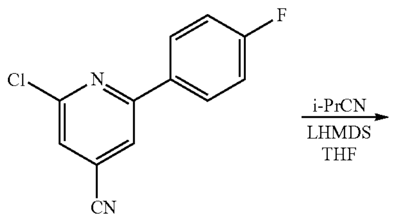

-continued

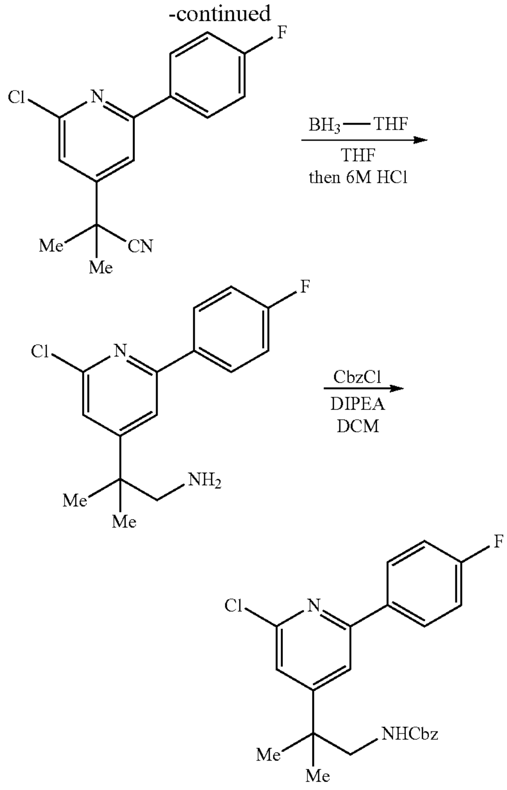

Intermediate C-10

Benzyl (2-(2-chloro-6-(4-fluorophenyl)pyridin-4-yl)-2-methylpropyl)carbamate

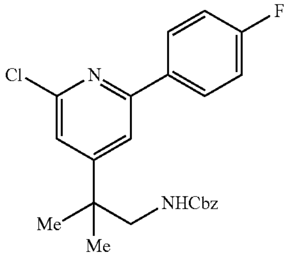 [SMILES: CC(C)(CNC(=O)OCc1ccccc1)c1cc(Cl)nc(-c2ccc(F)cc2)c1]

Step 1: 2-(2-chloro-6-(4-fluorophenyl)pyridin-4-yl)-2-methylpropanenitrile

A solution of 2-chloro-6-(4-fluorophenyl)isonicotinonitrile (0.83 g, 3.6 mmol) and isobutyronitrile (0.42 mL, 4.7 mmol) in THF (18 mL) was cooled to −78° C. To this was added a solution of lithium bis(trimethylsilyl)amide (1.5M in THF, 3.0 mL, 4.5 mmol) slowly. After the addition was complete, the cooling bath was removed and the mixture warmed to rt. After 2 h, the mixture was diluted with a solution of $NH_4Cl$ (saturated aq.) and extracted with EtOAc (3×). The combined organic layers were dried over anhydrous magnesium sulfate, filtered, and concentrated. The mixture was subjected to silica gel chromatography (0-25% (25% EtOH:EtOAc)/heptane) to afford the title compound.

Step 2: 2-(2-chloro-6-(4-fluorophenyl)pyridin-4-yl)-2-methylpropan-1-amine hydrochloride To a solution of 2-(2-chloro-6-(4-fluorophenyl)pyridin-4-yl)-2-methylpropanenitrile (0.10 g, 0.36 mmol) in THF (2.0 mL) was added $BH_3$-THF (1.0M in THF, 1.0 mL, 1.0 mmol) slowly at rt. After stirring for 18 h, hydrochloric acid (6N, 1.0 mL) was slowly added, followed by MeOH (2.0 mL), and the mixture was stirred at rt for 5 h. The mixture was concentrated to afford the title compound as a HCl salt.

Step 3: benzyl (2-(2-chloro-6-(4-fluorophenyl)pyridin-4-yl)-2-methylpropyl)carbamate 2-(2-Chloro-6-(4-fluorophenyl)pyridin-4-yl)-2-methylpropan-1-amine hydrochloride (0.12 g, 0.36 mmol) was dissolved in DCM (3.0 mL) and treated with DIPEA (0.35 mL, 2.0 mmol) was added. The mixture was cooled to 0° C. and benzyl chloroformate (0.080 mL, 0.56 mmol) was added. The mixture was warmed to rt while stirring overnight. The mixture was concentrated and the residue was subjected to silica gel chromatography (0-25% (25% EtOH:EtOAc)/heptane) to afford the title compound.

Scheme:

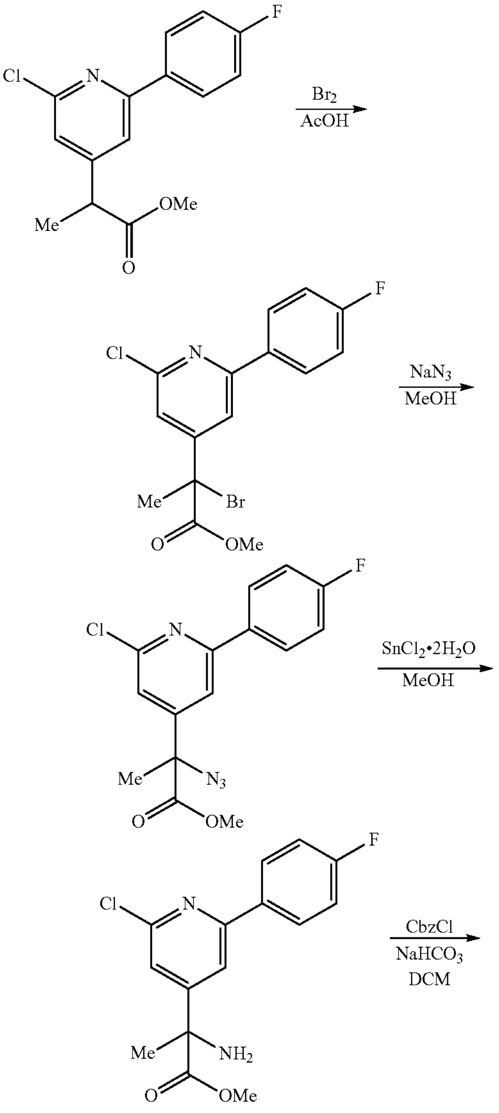

-continued

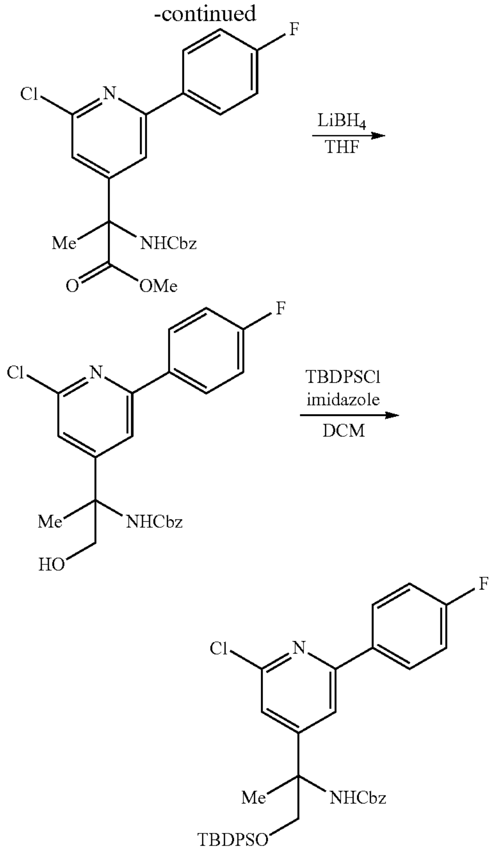

Intermediate C-11

Benzyl rac-(1-((tert-butyldiphenylsilyl)oxy)-2-(2-chloro-6-(4-fluorophenyl)pyridin-4-yl)propan-2-yl) carbamate

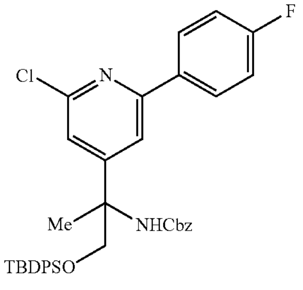

Step 1: methyl rac-2-bromo-2-(2-chloro-6-(4-fluorophenyl)pyridin-4-yl)propanoate To a solution of methyl 2-(2-chloro-6-(4-fluorophenyl) pyridin-4-yl)propanoate (Int. B, 2.0 g, 6.8 mmol) in acetic acid (0.020 L) was added bromine (0.39 mL, 7.5 mmol). The mixture was placed into a preheated oil bath at 100° C. and stirred for 8 h. The mixture was cooled to rt and concentrated under reduced pressure. EtOAc (40 mL) was added, and the mixture was washed with $Na_2S_2O_3$ (saturated aq., 20 mL), $NaHCO_3$ (saturated aq., 20 mL) and brine (20 mL×3). The organic solution was dried over anhydrous sodium sulfate, filtered, and concentrated under reduced pressure. The residue was subjected to silica gel chromatography (0-20% EtOAc/petroleum ether) to afford the title compound.

Step 2: methyl rac-2-azido-2-(2-chloro-6-(4-fluorophenyl)pyridin-4-yl)propanoate To a solution of methyl 2-bromo-2-(2-chloro-6-(4-fluorophenyl)pyridin-4-yl)propanoate (1.6 g, 4.3 mmol) in MeOH (0.020 L) was added sodium azide (1.3 g, 0.020 mol). The mixture was placed into a preheated oil bath at 60° C. and stirred for 5 h. The mixture was cooled to rt, water (20 mL) was added, and the mixture was treated with $NaHCO_3$ (aq. saturated) until pH=9. The mixture was extracted with EtOAc (30 mL×3) and the combined organic extracts were washed with brine (20 mL×3), dried over anhydrous sodium sulfate, filtered, and concentrated under reduced pressure to afford the title compound.

Step 3: methyl rac-2-amino-2-(2-chloro-6-(4-fluorophenyl)pyridin-4-yl)propanoate To a solution of methyl rac-2-azido-2-(2-chloro-6-(4-fluorophenyl)pyridin-4-yl)propanoate (1.4 g, 4.2 mmol) in MeOH (0.020 L) was added tin(II) chloride dihydrate (2.8 g, 13 mmol). The mixture was stirred at rt for 2 h. Water (10 mL) was added and the mixture was extracted with EtOAc (20 mL×3). The combined organic extracts were dried over anhydrous sodium sulfate, filtered, and concentrated under reduced pressure to afford the title compound.

Step 4: methyl rac-2-(((benzyloxy)carbonyl)amino)-2-(2-chloro-6-(4-fluorophenyl)pyridin-4-yl)propanoate To a solution of methyl rac-2-amino-2-(2-chloro-6-(4-fluorophenyl)pyridin-4-yl)propanoate (1.2 g, 3.1 mmol) in DCM (12 mL) was added $NaHCO_3$ (1.0 g, 12 mmol) and benzyl chloroformate (2.2 mL, 16 mmol). The mixture was stirred at rt for 1 h. Water (10 mL) was added and the mixture was extracted with EtOAc (30 mL×3). The combined organic extracts were dried over anhydrous sodium sulfate, filtered, and concentrated under reduced pressure. The residue was subjected to silica gel chromatography (25% EtOAc/petroleum ether) to afford the title compound.

Step 5: benzyl rac-(2-(2-chloro-6-(4-fluorophenyl) pyridin-4-yl)-1-hydroxypropan-2-yl)carbamate To a rt mixture of methyl rac-2-(((benzyloxy)carbonyl) amino)-2-(2-chloro-6-(4-fluorophenyl)pyridin-4-yl)propanoate (1.2 g, 2.7 mmol) in THF (15 mL) was added lithium borohydride (0.35 g, 16 mmol). The mixture was stirred at rt for 1 h. A solution of $NH_4Cl$ (saturated aq., 30 mL) was added and the mixture was extracted with EtOAc (20 mL×3). The combined organic extracts were dried over anhydrous sodium sulfate, filtered, and concentrated under reduced pressure. The residue was subjected to silica gel chromatography (30-50% EtOAc/petroleum ether) to afford the title compound.

Step 6: benzyl rac-(1-((tert-butyldiphenylsilyl)oxy)-2-(2-chloro-6-(4-fluorophenyl)pyridin-4-yl)propan-2-yl)carbamate To a solution of benzyl rac-(2-(2-chloro-6-(4-fluorophenyl)pyridin-4-yl)-1-hydroxypropan-2-yl)carbamate (0.50 g, 1.2 mmol) in DCM (0.010 L) was added imidazole (0.16 g, 2.4 mmol) and tert-butyl(chloro)diphenylsilane (0.66 g, 2.4 mmol). The mixture was stirred at rt for 12 h. Water (20 mL) was added and the mixture was extracted with DCM (30 mL×3). The combined organic extracts were dried over anhydrous sodium sulfate, filtered, and concentrated under reduced pressure. The residue was subjected to silica gel chromatography (0-20% EtOAc/petroleum ether) to afford the title compound.

Scheme:

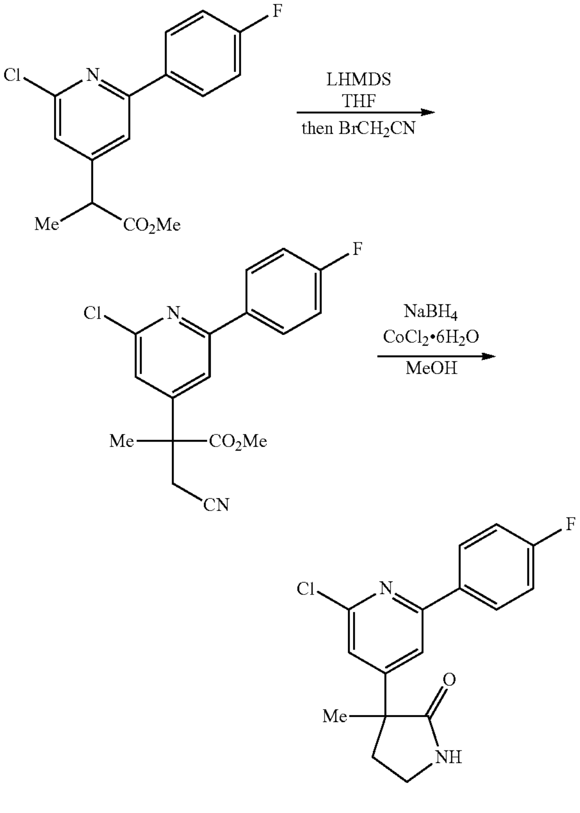

Intermediate C-12

Rac-3-(2-chloro-6-(4-fluorophenyl)pyridin-4-yl)-3-methylpyrrolidin-2-one

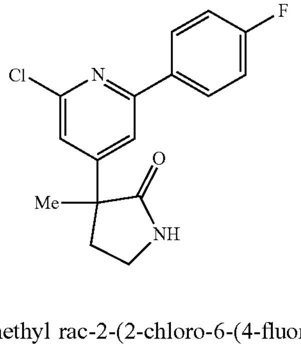

Step 1: methyl rac-2-(2-chloro-6-(4-fluorophenyl)pyridin-4-yl)-3-cyano-2-methylpropanoate To a −78° C. solution of methyl 2-(2-chloro-6-(4-fluorophenyl)pyridin-4-yl)propanoate (Int. B, 1.9 g, 6.5 mmol) in THF (0.030 L) was slowly added lithium bis(trimethylsilyl)amide (1.0M in THF, 8.4 mL, 8.4 mmol). After 1 h, 2-bromoacetonitrile (1.0 g, 8.4 mmol) was added, the cooling bath was removed, and the mixture warmed to rt. After 2 h, the mixture was treated with $H_2O$ (20 mL), then extracted with EtOAc (3×). The combined organic extracts were washed with brine, dried over anhydrous sodium sulfate, filtered, and concentrated. The residue was subjected to silica gel chromatography (0-20% EtOAc/petroleum ether) to afford the title compound.

Step 2: rac-3-(2-chloro-6-(4-fluorophenyl)pyridin-4-yl)-3-methylpyrrolidin-2-one Methyl rac-2-(2-chloro-6-(4-fluorophenyl)pyridin-4-yl)-3-cyano-2-methylpropanoate (2.0 g, 6.0 mmol) and cobalt (II) chloride hexahydrate (1.4 g, 6.0 mmol) were dissolved in MeOH (0.030 L). After stirring 5 min at 0° C., sodium borohydride (1.4 g, 36 mmol) was added portion-wise over 5 min, the cooling bath was removed, and the mixture warmed to rt. After 16 h, the mixture was treated with $NH_4Cl$ (saturated aq., 20 mL) then extracted with EtOAc (3×). The combined organic extracts were washed with brine, dried over anhydrous sodium sulfate, filtered, and concentrated. The residue was subjected to silica gel chromatography (0-35% EtOAc/petroleum ether) to afford the title compound.

Scheme:

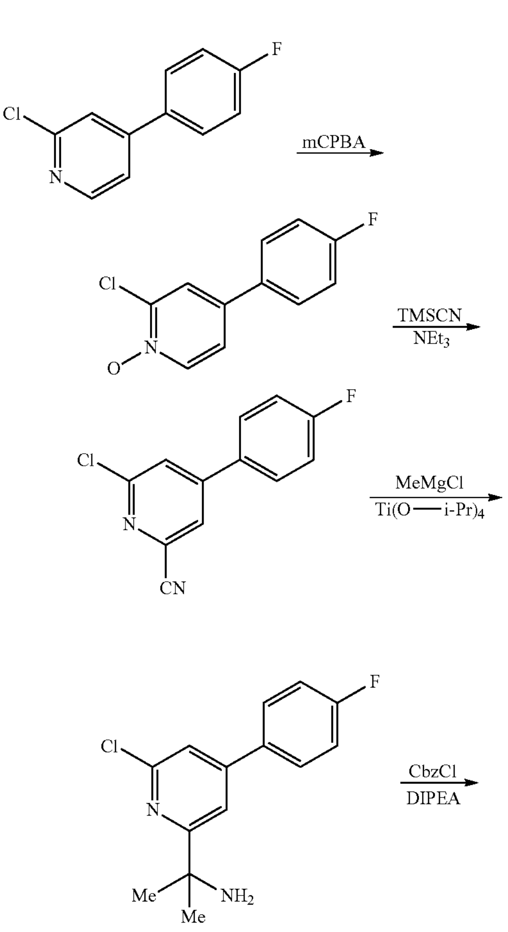

-continued

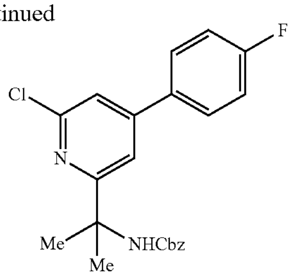

Intermediate C-13

Benzyl (2-(6-chloro-4-(4-fluorophenyl)pyridin-2-yl) propan-2-yl)carbamate

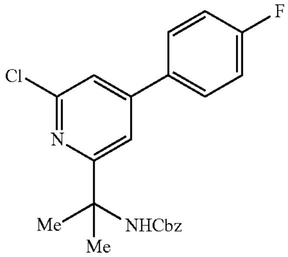 [SMILES: CC(C)(NC(=O)OCc1ccccc1)c1cc(-c2ccc(F)cc2)cc(Cl)n1]

Step 1: 2-chloro-4-(4-fluorophenyl)pyridine 1-oxide

To a solution of 2-chloro-4-(4-fluorophenyl)pyridine (5.8 g, 28 mmol) in DCM (0.10 mL) was added 3-chloroperoxybenzoic acid (15 g, 84 mmol) at rt. The mixture was then heated under an atmosphere of nitrogen at 50° C. for 12 h. The mixture was cooled to rt, $NaHCO_3$ (saturated aq., 100 mL) and $Na_2SO_3$ (saturated aq., 100 mL) were added, and the mixture was extracted with EtOAc (50 mL×4). The combined organic extracts were washed with brine (100 mL), dried over anhydrous sodium sulfate, filtered, and concentrated under reduced pressure. The residue was subjected to silica gel chromatography (0-70% EtOAc/petroleum ether) to afford the title compound.

Step 2: 6-chloro-4-(4-fluorophenyl)picolinonitrile

A solution of 2-chloro-4-(4-fluorophenyl)pyridine 1-oxide (4.3 g, 19 mmol), trimethylsilyl cyanide (11 g, 0.12 mol) and triethylamine (5.4 mL, 39 mmol) was heated under an atmosphere of nitrogen at 100° C. for 12 h. The mixture was cooled to rt, concentrated under reduced pressure, and the residue was subjected to silica gel chromatography (0-40% EtOAc/petroleum ether) to afford the title compound.

Step 3: 2-(6-chloro-4-(4-fluorophenyl)pyridin-2-yl) propan-2-amine

To a solution of 6-chloro-4-(4-fluorophenyl)picolinonitrile (2.7 g, 12 mmol) in THF (0.080 L) was slowly added methylmagnesium bromide (3.0 M in $Et_2O$, 19 mL, 58 mmol) at 0° C. The mixture was warmed to 25° C. and stirred for 30 min. Titanium isopropoxide (3.4 mL, 12 mmol) was added and the mixture was then heated at 80° C. for 12 h. The mixture was cooled to rt, treated with $NH_4Cl$ (saturated aq., 50 mL), and extracted with EtOAc (50 mL×3). The combined organic extracts were washed with brine (50 mL), dried over anhydrous sodium sulfate, filtered, and concentrated to afford the title compound.

Step 4: benzyl (2-(6-chloro-4-(4-fluorophenyl)pyridin-2-yl)propan-2-yl)carbamate To a mixture of 2-(6-chloro-4-(4-fluorophenyl)pyridin-2-yl)propan-2-amine (2.0 g, 7.6 mmol) and DIPEA (4.0 mL, 23 mmol) in DCM (0.040 L) was added benzyl chloroformate (2.2 mL, 15 mmol) at 0° C. The resulting mixture was warmed to rt and stirred for 12 h. The mixture was concentrated under reduced pressure and the residue was subjected to silica gel chromatography (0-20% EtOAc/petroleum ether) to afford the title compound.

Scheme:

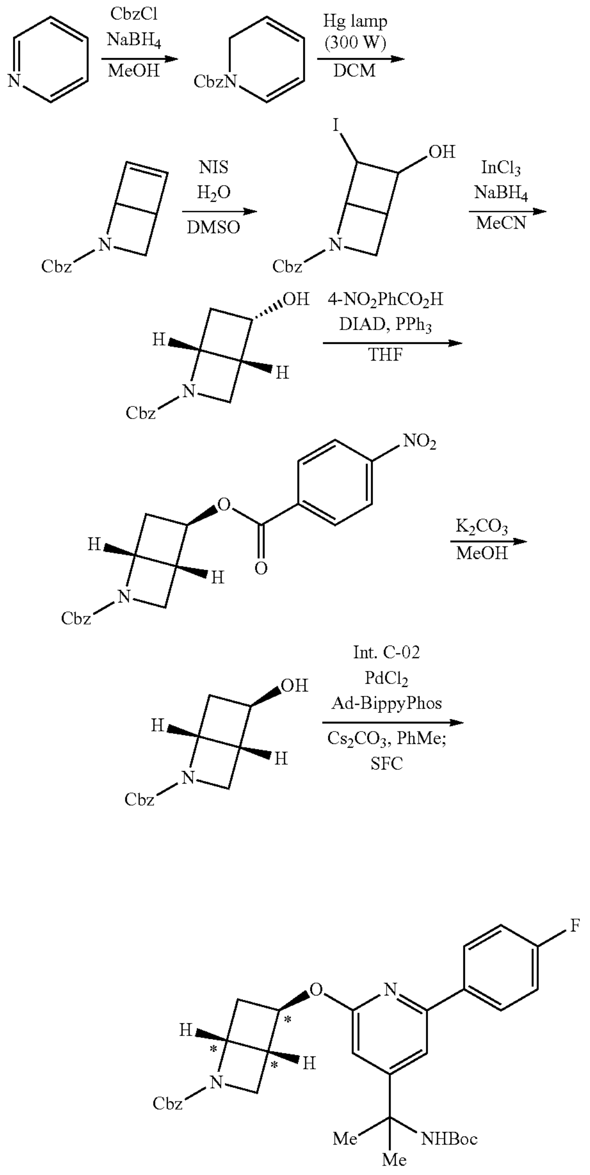

Intermediate D-ent-1

Benzyl rel-(1R,4R,5R)-5-((4-(2-((tert-butoxycarbonyl)amino)propan-2-yl)-6-(4-fluorophenyl)pyridin-2-yl)oxy)-2-azabicyclo[2.2.0]hexane-2-carboxylate (enantiomer 1) and Intermediate D-ent-2

Benzyl rel-(1R,4R,5R)-5-((4-(2-((tert-butoxycarbonyl)amino)propan-2-yl)-6-(4-fluorophenyl)pyridin-2-yl)oxy)-2-azabicyclo[2.2.0]hexane-2-carboxylate (enantiomer 2)

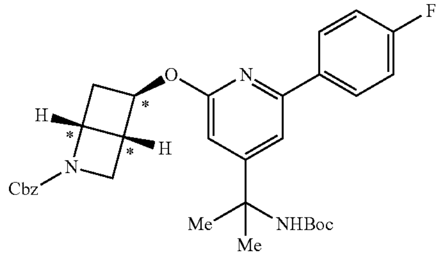 [SMILES: CC(C)(C)OC(=O)NC(C)(C)c1cc(O[C@@H]2C[C@@H]3[C@H]2CN3C(=O)OCc2ccccc2)nc(-c2ccc(F)cc2)c1]

Step 1: benzyl pyridine-1(2H)-carboxylate

To a −78° C. solution of anhydrous pyridine (12 g, 0.15 mol) in anhydrous MeOH (0.10 L) under argon was added sodium borohydride (5.7 g, 0.15 mol). Benzyl chloroformate (21 mL, 0.15 mol) was added dropwise and the mixture was stirred for 3 h. MTBE (100 mL) and water (100 mL) were added, and mixture was warmed to rt. The mixture was extracted with MTBE (100 mL×2) and the combined organic extracts were washed with water (100 mL×2) and brine (100 mL), dried over anhydrous magnesium sulfate, filtered, and concentrated under reduced pressure to afford the title compound.

Step 2: benzyl 2-azabicyclo[2.2.0]hex-5-ene-2-carboxylate

Under an atmosphere of nitrogen, a solution of benzyl pyridine-1(2H)-carboxylate (6.0 g, 25 mmol) in DCM (0.75 L) was irradiated (300 W, Photo-reactor, Hg lamp) for 6 h. The mixture was concentrated under reduced pressure and subjected to silica gel chromatography (0-17% EtOAc/petroleum ether) to afford the title compound.

Step 3: benzyl 5-hydroxy-6-iodo-2-azabicyclo[2.2.0]hexane-2-carboxylate

To a −5° C. solution of benzyl 2-azabicyclo[2.2.0]hex-5-ene-2-carboxylate (4.8 g, 22 mmol) in DMSO (72 mL) and water (72 mL) was added N-iodosuccinimide (15 g, 67 mmol) portion wise. The mixture was warmed to rt and stirred for 12 h. Water (100 mL) was added, and the mixture was extracted with EtOAc (50 mL×3). The combined organic extracts were washed with water (100 mL) and brine (100 mL), dried over anhydrous sodium sulfate, filtered, and concentrated under reduced pressure. The residue was subjected to silica gel chromatography (0-25% EtOAc/petroleum ether) to afford the title compound.

Step 4: benzyl rac-(1R,4R,5S)-5-hydroxy-2-azabicyclo[2.2.0]hexane-2-carboxylate

A mixture of freshly dried indium(III) chloride (4.4 g, 0.020 mol) and sodium borohydride (1.5 g, 0.040 mol) in MeCN (41 mL) was stirred at −78° C. for 10 min. The mixture was warmed to rt and benzyl 5-hydroxy-6-iodo-2-azabicyclo[2.2.0]hexane-2-carboxylate (5.5 g, 15 mmol) in MeCN (82 mL) was added dropwise. The mixture was stirred at rt for 2 h. The mixture was poured into water (60 mL) and extracted with EtOAc (40 mL×3). The combined organic extracts were washed with brine (50 mL), dried over anhydrous sodium sulfate, filtered, and concentrated under reduced pressure. The residue was subjected to silica gel chromatography (0-50% EtOAc/petroleum ether) to afford the title compound.

Step 5: benzyl rac-(1R,4R,5R)-5-((4-nitrobenzoyl)oxy)-2-azabicyclo[2.2.0]hexane-2-carboxylate To a 0° C. solution of benzyl rac-(1R,4R,5S)-5-hydroxy-2-azabicyclo[2.2.0]hexane-2-carboxylate (2.6 g, 11 mmol) and 4-nitrobenzoic acid (2.8 g, 17 mmol) in THF (0.080 L) was added triphenylphosphine (4.4 g, 17 mmol). Diisopropyl azodicarboxylate (4.6 g, 0.020 mol) was added and the mixture was stirred at rt for 12 h. The mixture was concentrated under reduced pressure and the residue was subjected to silica gel chromatography (0-17% EtOAc/petroleum ether) to afford the title compound.

Step 6: benzyl rac-(1R,4R,5R)-5-hydroxy-2-azabicyclo[2.2.0]hexane-2-carboxylate

To a solution of benzyl rac-(1R,4R,5R)-5-((4-nitrobenzoyl)oxy)-2-azabicyclo[2.2.0]hexane-2-carboxylate (5.5 g, 11 mmol) in MeOH (0.10 L) was added $K_2CO_3$ (6.0 g, 43 mmol). The mixture was stirred at rt for 2 hours. Water (100 mL) was added, and the mixture was extracted with EtOAc (50 mL×3). The combined organic extracts were washed with brine (20 mL×3), dried over anhydrous sodium sulfate, filtered, and concentrated under reduced pressure. The residue was subjected to silica gel chromatography (0-30% EtOAc/petroleum ether) to afford the title compound.

Step 7: benzyl rel-(1R,4R,5R)-5-((4-(2-((tert-butoxycarbonyl)amino)propan-2-yl)-6-(4-fluorophenyl)pyridin-2-yl)oxy)-2-azabicyclo[2.2.0]hexane-2-carboxylate (enantiomers 1 and 2)

Under an atmosphere of nitrogen, a mixture of tert-butyl (2-(2-chloro-6-(4-fluorophenyl)pyridin-4-yl)propan-2-yl) carbamate (Int. C-02, 5.2 g, 14 mmol), benzyl rac-(1R,4R,5R)-5-hydroxy-2-azabicyclo[2.2.0]hexane-2-carboxylate (2.2 g, 9.4 mmol), $(Ad\text{-}BippyPhos)_2PdCl_2$ (0.99 g, 0.66 mmol), $Cs_2CO_3$ (9.2 g, 28 mmol), and PhMe (0.18 L) were stirred at 90° C. for 24 h. The mixture was cooled to rt, filtered through a thin pad of silica gel (eluting with EtOAc), and concentrated under reduced pressure. The residue was subjected to silica gel chromatography (0-15% EtOAc/petroleum ether). The resulting mixture of two stereoisomers was subjected to chiral SFC (ChiralPak AD-3, 5-40% IPA (with 0.05% DEA modifier)/$CO_2$) to afford benzyl rel-(1R,4R,5R)-5-((4-(2-((tert-butoxycarbonyl)amino)propan-2-yl)-6-(4-fluorophenyl)pyridin-2-yl)oxy)-2-azabicyclo[2.2.0]hexane-2-carboxylate (enantiomer 1, faster eluting, Int. D-ent-1) and benzyl rel-(1R,4R,5R)-5-((4-(2-((tert-butoxycarbonyl)amino)propan-2-yl)-6-(4-fluorophenyl)pyridin-2-yl)oxy)-2-azabicyclo[2.2.0]hexane-2-carboxylate (enantiomer 2, slower eluting, Int. D-ent-2).

Scheme:

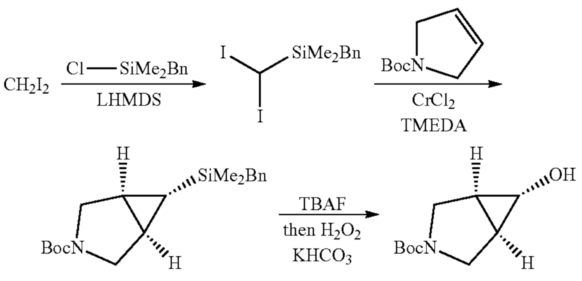

Intermediate E tert-butyl (1R,5S,6s)-6-hydroxy-3-azabicyclo[3.1.0]hexane-3-carboxylate

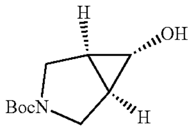 [SMILES: CC(C)(C)OC(=O)N1C[C@@H]2[C@@H](O)[C@@H]2C1]

Step 1: benzyl(diiodomethyl)dimethylsilane

Ten reactions were carried out in parallel. Lithium bis(trimethylsilyl)amide solution (1.0 M, 1.5 L, 1.5 mol) in isopropyl ether (3.0 L) was charged into a 10 L vessel. Diiodomethane (130 mL, 1.6 mol) was added to the mixture at −65° C. The mixture was stirred at −65° C. for 0.25 h. Benzylchlorodimethylsilane (0.20 kg, 1.1 mol, 0.20 L) was added and mixture was stirred at −65° C. for 3 h, then stirred at 25° C. for 12. The reactions were combined and treated with water (10 L). The mixture was extracted with MTBE (5 L×2). The organic layers were combined, washed with brine, and dried over anhydrous sodium sulfate. The mixture was filtered and concentrated under reduced pressure. The residue was subjected to silica gel chromatography (2-100% EtOAc/petroleum ether) to afford the title compound.

Step 2: tert-butyl (1R,5S,6s)-6-(benzyldimethylsilyl)-3-azabicyclo[3.1.0]hexane-3-carboxylate Fourteen reactions were carried out in parallel. Chromium (II) chloride (150 g, 1.2 mol) was charged to a 5 L vessel. THF (2.5 L) and N,N,N,N-tetramethylethylenediamine (360 mL, 2.4 mol) were added to the mixture at 25° C. over 0.5 h. Benzyl(diiodomethyl)dimethylsilane (240 g, 560 mmol) was added and the mixture was stirred at 25° C. for 0.5 h. tert-Butyl 2,5-dihydro-1H-pyrrole-1-carboxylate (0.050 kg, 0.30 mol) was added to the mixture at 25° C. The mixture was stirred at 50° C. for 18 h. The reactions were combined, and the mixture was treated with water (15 L) and extracted with MTBE (7 L×3). The combined organic extracts were washed with brine, dried over anhydrous sodium sulfate, filtered, and concentrated. The residue was subjected to silica gel chromatography (1-100% EtOAc/petroleum ether) to afford the title compound.

Step 3: tert-butyl (1R,5S,6s)-6-hydroxy-3-azabicyclo[3.1.0]hexane-3-carboxylate

Fourteen reactions were carried out in parallel. tert-Butyl (1R,5S,6s)-6-(benzyldimethylsilyl)-3-azabicyclo[3.1.0]hexane-3-carboxylate (0.070 kg, 210 mmol) in THF (2.1 L) was charged to a 10 L vessel. Tetrabutylammonium fluoride solution (1.0M in THF, 630 mL) was added and mixture was stirred for 0.5 h at 25° C. MeOH (2.1 L) and potassium bicarbonate (0.20 kg, 2.1 mol) was added into the reaction vessel at 0° C., followed by hydrogen peroxide (30 wt % in water, 0.10 L, 1.1 mol). The mixture was stirred at 0° C. for 0.5 h and at 25° C. for 16 h. The reactions were combined, and the mixture was treated with $Na_2SO_3$ (saturated aq., 25 L) and extracted with EtOAc (7 L×2). The combined organic extracts were washed with brine, dried over anhydrous sodium sulfate, filtered, and concentrated. The residue was subjected to silica gel chromatography (0-100% EtOAc/hexane) and then re-crystallized from n-heptane: MTBE=20:1 (9 L) to afford the title compound.

Intermediate F tert-butyl 6-hydroxy-1-methyl-3-azabicyclo[3.1.0]hexane-3-carboxylate

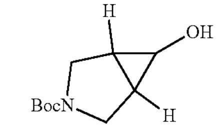 [SMILES: CC(C)(C)OC(=O)N1CC2C(O)C2C1]

Step 1: tert-butyl 6,6-dibromo-1-methyl-3-azabicyclo[3.1.0]hexane-3-carboxylate

A mixture of tert-butyl 3-methyl-2,5-dihydro-1H-pyrrole-1-carboxylate (15 g, 82 mmol), bromoform (62 g, 0.25 mol) and N-benzyl-N,N,N-triethylammonium chloride (0.75 g, 3.3 mmol) in DCM (0.40 L) and EtOH (8.0 mL) was cooled to 0° C. under an atmosphere of nitrogen. A solution of sodium hydroxide (50 wt % aq., 66 g, 0.82 mol) was added at 0° C. The mixture was warmed to 45° C. and stirred for 12 h. Water (150 mL) was added, and the mixture was extracted with DCM (80 mL×3). The combined organic solution was washed with brine (50 mL), dried over anhydrous sodium sulfate, filtered, and concentrated under reduced pressure. The residue was subjected to silica gel chromatography (0-5% EtOAc/petroleum ether) to afford the title compound.

Step 2: tert-butyl 6-hydroxy-1-methyl-3-azabicyclo[3.1.0]hexane-3-carboxylate

A solution of tert-butyl 6,6-dibromo-1-methyl-3-azabicyclo[3.1.0]hexane-3-carboxylate (2.0 g, 5.6 mmol) in THF (0.040 L) was cooled to −78° C. A solution of n-butyllithium (2.5 M in hexane, 2.7 mL, 6.8 mmol) was added dropwise and the mixture was stirred for 15 min. A solution of catecholborane (1.0 M in THF, 11 mL, 11 mmol) was added and the mixture was warmed to 50° C. and stirred for 12 h. The mixture was cooled to 0° C. and hydrogen peroxide (30% (w/w) aq., 2.9 mL, 28 mmol) and sodium hydroxide (2.5 M aq., 9.0 mL, 23 mmol) were added. This mixture was warmed rt and stirred for 12 h. $Na_2SO_3$ (saturated aq., 5 mL)

and water (20 mL) were added, and the mixture was extracted with EtOAc (30 mL×3). The combined organic solution was dried over anhydrous sodium sulfate, filtered, and concentrated under reduced pressure. The residue was subjected to silica gel chromatography (0-60% EtOAc/petroleum ether) to afford the title compound.

Scheme:

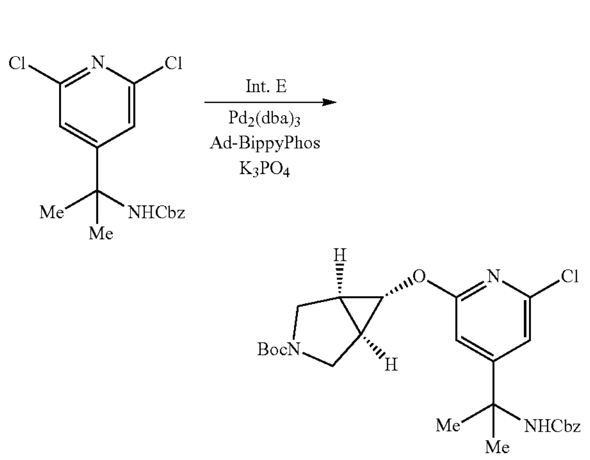

Intermediate G tert-butyl (1R,5S,6s)-6-((4-(2-(((benzyloxy)carbonyl)amino)propan-2-yl)-6-chloropyridin-2-yl)oxy)-3-azabicyclo[3.1.0]hexane-3-carboxylate

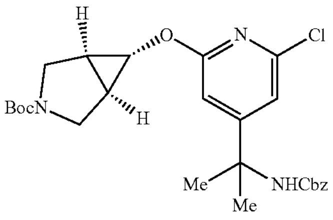 [SMILES: CC(C)(C)OC(=O)N1C[C@@H]2[C@H](C1)[C@H]2Oc1cc(C(C)(C)NC(=O)OCc2ccccc2)cc(Cl)n1]

A mixture of benzyl (2-(2,6-dichloropyridin-4-yl)propan-2-yl)carbamate (Int. A-1, 66 g, 65 mmol), tert-butyl (1R,5S,6s)-6-hydroxy-3-azabicyclo[3.1.0]hexane-3-carboxylate (Int. E, 0.030 kg, 0.050 mol), potassium phosphate tribasic (96 g, 150 mmol), Ad-BippyPhos (3.0 g, 1.5 mmol), and 1-4-dioxane (1.2 L) was purged and degassed with $N_2$ (5×) at 15° C. $Pd_2(dba)_3$ (1.7 g, 0.63 mmol) was added and the mixture was purged and degassed with $N_2$ (5×). The mixture was stirred at 70° C. for 16 h. The mixture was cooled to 15° C., washed with $NaHCO_3$ (saturated aq., 1.0 L), and filtered. The filter cake was washed with EtOAc (1.5 L) and the organic phase was separated. The aqueous phase was extracted with EtOAc (500 mL×4), and the combined organic mixture was dried with anhydrous sodium sulfate, filtered, and concentrated. The residue was subjected to silica gel chromatography (1-17% EtOAc/petroleum ether). The mixture was subjected to reverse phase HPLC (40-70% MeCN/water) to afford the title compound.

Intermediate G-01

Benzyl (2-(2-(((1R,5S,6s)-3-azabicyclo[3.1.0]hexan-6-yl)oxy)-6-chloropyridin-4-yl)propan-2-yl)carbamate

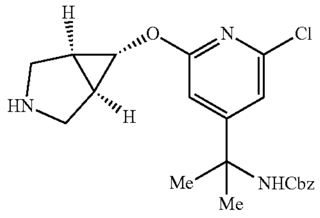 [SMILES: CC(C)(NC(=O)OCc1ccccc1)c1cc(Cl)nc(O[C@H]2[C@@H]3CNC[C@@H]32)c1]

To a solution of tert-butyl (1R,5S,6s)-6-((4-(2-(((benzyloxy)carbonyl)amino)propan-2-yl)-6-chloropyridin-2-yl)oxy)-3-azabicyclo[3.1.0]hexane-3-carboxylate (Int. G, 3.0 g, 6.0 mmol) in DCM (16 mL) under $N_2$ was added TFA (4.0 mL). The mixture was stirred at 25° C. for 2 h. The mixture was filtered and concentrated under reduced pressure to afford the title compound.

Scheme:

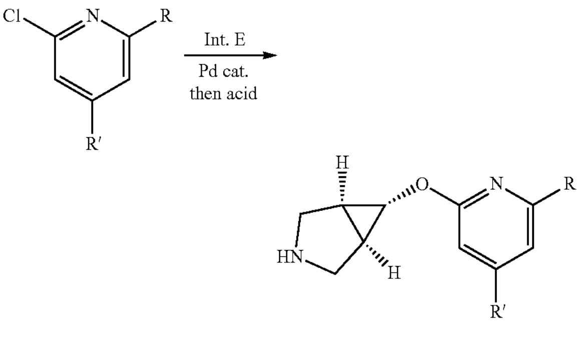

Intermediate H-01

2-(2-(((1R,5S,6s)-3-azabicyclo[3.1.0]hexan-6-yl)oxy)-6-(4-fluorophenyl)pyridin-4-yl)propan-2-amine

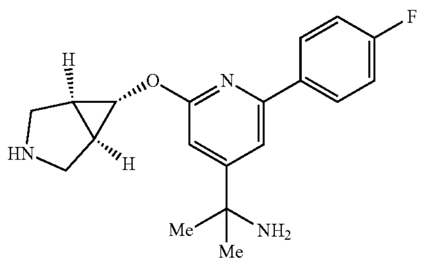 [SMILES: CC(C)(N)c1cc(O[C@H]2[C@@H]3CNC[C@@H]32)nc(-c2ccc(F)cc2)c1]

Step 1: tert-butyl (1R,5S,6s)-6-((4-(2-((tert-butoxycarbonyl)amino)propan-2-yl)-6-(4-fluorophenyl)pyridin-2-yl)oxy)-3-azabicyclo[3.1.0]hexane-3-carboxylate Under an atmosphere of nitrogen, a mixture of tert-butyl (2-(2-chloro-6-(4-fluorophenyl)pyridin-4-yl)propan-2-yl)

carbamate (Int. C-02, 1.0 g, 2.7 mmol), tert-butyl (1R,5S,6s)-6-hydroxy-3-azabicyclo[3.1.0]hexane-3-carboxylate (Int. E, 0.60 g, 3.0 mmol), $Cs_2CO_3$ (2.7 g, 8.2 mmol), Ad-BippyPhos (0.18 g, 0.27 mmol), $Pd_2(dba)_3$ (0.13 g, 0.14 mmol), and 1,4-dioxane (14 mL) was stirred at 85° C. for 2 h. The mixture was cooled to rt, filtered, and concentrated under reduced pressure. The residue was subjected to silica gel chromatography (0-50% EtOAc/hexanes) to afford the title compound.

Step 2: 2-(2-(((1R,5S,6s)-3-azabicyclo[3.1.0]hexan-6-yl)oxy)-6-(4-fluorophenyl)pyridin-4-yl)propan-2-amine To a 0° C. solution of tert-butyl (1R,5S,6s)-6-((4-(2-((tert-butoxycarbonyl)amino)propan-2-yl)-6-(4-fluorophenyl)pyridin-2-yl)oxy)-3-azabicyclo[3.1.0]hexane-3-carboxylate (1.3 g, 2.4 mmol) in DCM (0.020 L) was added a solution of HCl (4.0 M in 1,4-dioxane, 6.1 mL, 24 mmol). The mixture was warmed to rt and stirred for 1 h. The mixture was concentrated under reduced pressure, suspended in $Et_2O$, cooled to 0° C., and filtered. The filter cake was dried under reduced pressure to afford the title compound as a HCl salt.

Intermediate H-02

Benzyl (2-(2-(((1R,5S,6s)-3-azabicyclo[3.1.0]hexan-6-yl)oxy)-6-(4-fluorophenyl)pyridin-4-yl)propan-2-yl)carbamate

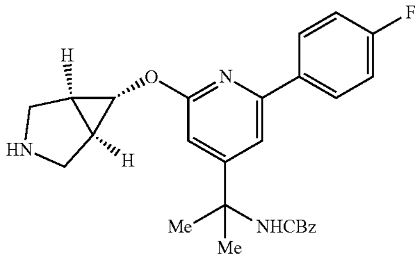

Step 1: tert-butyl (1R,5S,6s)-6-((4-(2-(((benzyloxy)carbonyl)amino)propan-2-yl)-6-(4-fluorophenyl)pyridin-2-yl)oxy)-3-azabicyclo[3.1.0]hexane-3-carboxylate Under an atmosphere of nitrogen, a mixture of benzyl (2-(2-chloro-6-(4-fluorophenyl)pyridin-4-yl)propan-2-yl) carbamate (Int. C-01, 1.0 g, 2.5 mmol), tert-butyl (1R,5S,6s)-6-hydroxy-3-azabicyclo[3.1.0]hexane-3-carboxylate (Int. E, 0.50 g, 2.5 mmol), $K_3PO_4$ (1.6 g, 7.5 mmol), Ad-BippyPhos (0.17 g, 0.25 mmol), $Pd(OAc)_2$ (28 mg, 0.13 mmol), CPME (0.010 L), and $PhCF_3$ (0.010 L) was stirred at 90° C. for 16 h. The mixture was cooled to rt, filtered through a thin pad of silica gel (eluted with EtOAc), and concentrated under reduced pressure. The residue was subjected to silica gel chromatography (0-45% EtOAc/petroleum ether) to afford the title compound.

Step 2: benzyl (2-(2-(((1R,5S,6s)-3-azabicyclo[3.1.0]hexan-6-yl)oxy)-6-(4-fluorophenyl)pyridin-4-yl)propan-2-yl)carbamate To a mixture of tert-butyl (1R,5S,6s)-6-((4-(2-(((benzyloxy)carbonyl)amino)propan-2-yl)-6-(4-fluorophenyl)pyridin-2-yl)oxy)-3-azabicyclo[3.1.0]hexane-3-carboxylate (1.4 g, 2.5 mmol) in DCM (0.010 L) was added TFA (2.0 mL). The mixture was stirred at rt for 1 h and concentrated under reduced pressure. The residue was subjected to silica gel chromatography (0-10% MeOH/DCM) to afford the title compound.

Utilizing the procedures described in the synthesis of Intermediate H-02, the following compound was prepared substituting the appropriate reagents for benzyl (2-(2-chloro-6-(4-fluorophenyl)pyridin-4-yl)propan-2-yl)carbamate.

| Int | Structure | Name | Comments |
|---|---|---|---|
| H-03 | 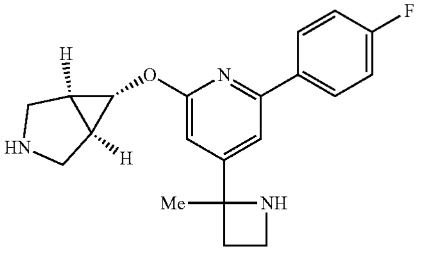 [SMILES: CC1(c2cc(O[C@H]3[C@@H]4CNC[C@@H]43)nc(-c3ccc(F)cc3)c2)CCN1] | rac-(1R,5S,6s)-6-((6-(4-fluorophenyl)-4-(2-methylazetidin-2-yl)pyridin-2-yl)oxy)-3-azabicyclo[3.1.0]hexane | Step 1: Int. C-05 (0.11 mmol), Int. E (0.15 mmol), $Pd_2(dba)_3$ (6.6 μmol), Ad-BippyPhos (12 μmol), $Cs_2CO_3$ (0.34 mmol), PhMe (1.0 mL), 85° C., overnight; Step 2: HCl (4.0N in dioxane), rt, 4 h; Form: HCl salt |
| H-04 | 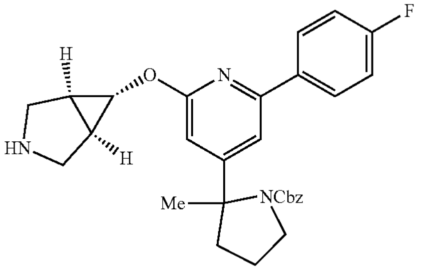 [SMILES: CC1(c2cc(O[C@H]3[C@@H]4CNC[C@@H]43)nc(-c3ccc(F)cc3)c2)CCCN1C(=O)OCc1ccccc1] | benzyl rac-2-(2-(((1R,5S,6s)-3-azabicyclo[3.1.0]hexan-6-yl)oxy)-6-(4-fluorophenyl)pyridin-4-yl)-2-methylpyrrolidine-1-carboxylate | Step 1: Int. C-09 (0.13 mmol), Int. E (0.15 mmol), $Pd_2(dba)_3$ (6.6 μmol), Ad-BippyPhos (14 μmol), $Cs_2CO_3$ (0.38 mmol), 1,4-dioxane (1.0 mL), 85° C., 3 h; Step 2: HCl (4.0N in dioxane), rt, 2 h; Form: HCl salt |

-continued

| Int | Structure | Name | Comments |
|---|---|---|---|
| H-05 | 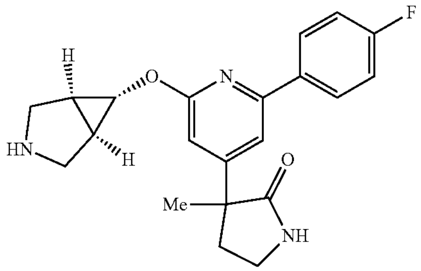 [SMILES: CC1(c2cc(O[C@H]3[C@@H]4CNC[C@@H]43)nc(-c3ccc(F)cc3)c2)CCNC1=O] | rac-3-(2-(((1R,5S,6s)-3 azabicyclo[3.1.0] hexan-6-yl)oxy)-6-(4-fluorophenyl)pyridin-4-yl)-3-methylpyrrolidin-2-one | Step 1: Int. C-12 (0.82 mmol), Int. E (0.82 mmol), $Pd_2(dba)_3$ (0.041 mmol), Ad-BippyPhos (0.082 mmol), $Cs_2CO_3$ (2.5 mmol), PhMe (0.010 L), 90° C., 16 h; Step 2: TFA; Form: TFA salt |
| H-06 | 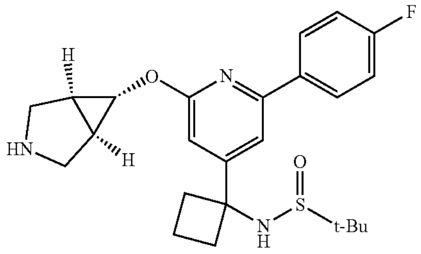 [SMILES: CC(C)(C)S(=O)NC1(c2cc(O[C@H]3[C@@H]4CNC[C@@H]43)nc(-c3ccc(F)cc3)c2)CCC1] | N-(1-(2-(((1R,5S,6s)-3-azabicyclo[3.1.0] hexan-6-yl)oxy)-6-(4-fluorophenyl)pyridin-4-yl)cyclobutyl)-2-methylpropane-2-sulfinamide | Step 1: Int. C-06 (1.1 mmol), Int. E (1.7 mmol), $Pd(OAc)_2$ (0.055 mmol), Ad-BippyPhos (0.11 mmol), $K_3PO_4$ (3.3 mmol), $PhCF_3$ (8.0 mL), CPME (8.0 mL), 90° C., 16 h; Step 2: TFA (1.0 mL), DCM (4.0 mL), 30° C., 1 h; Form: TFA salt |
| H-07 | 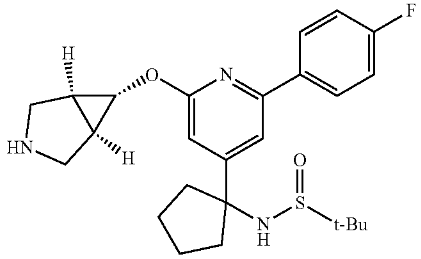 [SMILES: CC(C)(C)S(=O)NC1(c2cc(O[C@H]3[C@@H]4CNC[C@@H]43)nc(-c3ccc(F)cc3)c2)CCCC1] | N-(1-(2-(((1R,5S,6s)-3-azabicyclo[3.1.0] hexan-6-yl)oxy)-6-(4-fluorophenyl)pyridin-4-yl)cyclopentyl)-2-methylpropane-2-sulfinamide | Step 1: Int. C-07 (1.0 mmol), Int. E (1.5 mmol), $Pd(OAc)_2$ (0.051 mmol), Ad-BippyPhos (0.10 mmol), $K_3PO_4$ (3.0 mmol), $PhCF_3$ (2.0 mL), CPME (2.0 mL), 90° C., 16 h; Step 2: TFA (0.50 mL), DCM (2.0 mL), 30° C., 1 h; Form: TFA salt |
| H-08 | 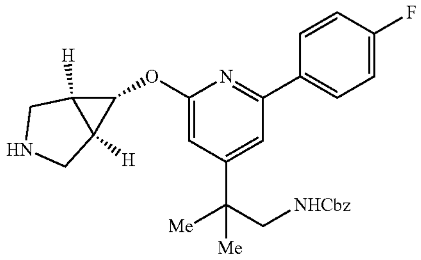 [SMILES: CC(C)(CNC(=O)OCc1ccccc1)c1cc(O[C@H]2[C@@H]3CNC[C@@H]32)nc(-c2ccc(F)cc2)c1] | benzyl (2-(2-(((1R,5S,6s)-3-azabicyclo[3.1.0] hexan-6-yl)oxy)-6-(4-fluorophenyl)pyridin-4-yl)-2-methylpropyl) carbamate | Step 1: Int. C-08 (0.34 mmol), Int. E (0.44 mmol), $Pd_2(dba)_3$ (0.020 mmol), Ad-BippyPhos (0.040 mmol), $Cs_2CO_3$ (1.0 mmol), PhMe (3.0 mL), 85° C. overnight; Step 2: HCl (4.0N in 1,4-dioxane, 8.0 mmol), rt, 2 h; Form: HCl salt |
| H-09 | 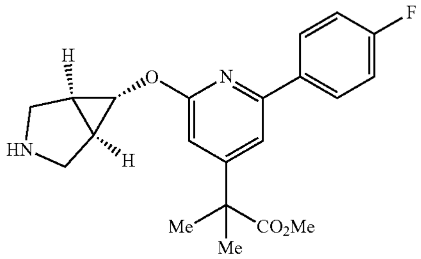 [SMILES: COC(=O)C(C)(C)c1cc(O[C@H]2[C@@H]3CNC[C@@H]32)nc(-c2ccc(F)cc2)c1] | methyl 2-(2-(((1R,5S,6s)-3-azabicyclo[3.1.0] hexan-6-yl)oxy)-6-(4-fluorophenyl)pyridin-4-yl)-2-methylpropanoate | Step 1: Int. C-09 (0.13 mmol), Int. E (0.16 mmol), $Pd_2(dba)_3$ (6.6 μmol), Ad-BippyPhos (14 μmol), $Cs_2CO_3$ (0.38 mmol), PhMe (1.0 mL), 85° C. overnight; Step 2: HCl (4.0N in 1,4-dioxane, 4.0 mmol), rt, 2.5 h; Form: HCl salt |
| H-10 | 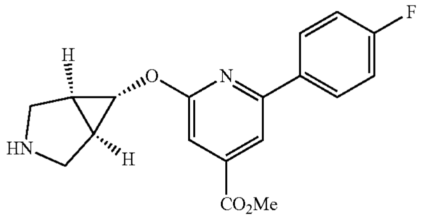 [SMILES: COC(=O)c1cc(O[C@H]2[C@@H]3CNC[C@@H]32)nc(-c2ccc(F)cc2)c1] | methyl 2-(((1R,5S,6s)-3-azabicyclo[3.1.0] hexan-6-yl)oxy)-6-(4-fluorophenyl) isonicotinate | Step 1: methyl 2-chloro-6-(4-fluorophenyl)isonicotinate (0.75 mmol), Int. E (0.90 mmol), $Pd_2(dba)_3$ (0.040 mmol), Ad-BippyPhos (0.075 mmol), 1,4-dioxane (4.0 mL), 85° C., 1 h; Step 2: HCl (4.0M in 1,4-dioxane, 0.10 mL), DCM (2.0 mL), rt, 1 h |

-continued

| Int | Structure | Name | Comments |
| --- | --- | --- | --- |
| H-11 | 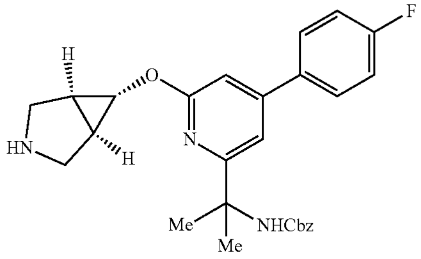 [SMILES: CC(C)(NC(=O)OCc1ccccc1)c1cc(-c2ccc(F)cc2)cc(O[C@H]2[C@@H]3CNC[C@@H]32)n1] | benzyl (2-(6-(((1R,5S,6s)-3-azabicyclo[3.1.0]hexan-6-yl)oxy)-4-(4-fluorophenyl)pyridin-2-yl)propan-2-yl)carbamate | — |

Scheme:

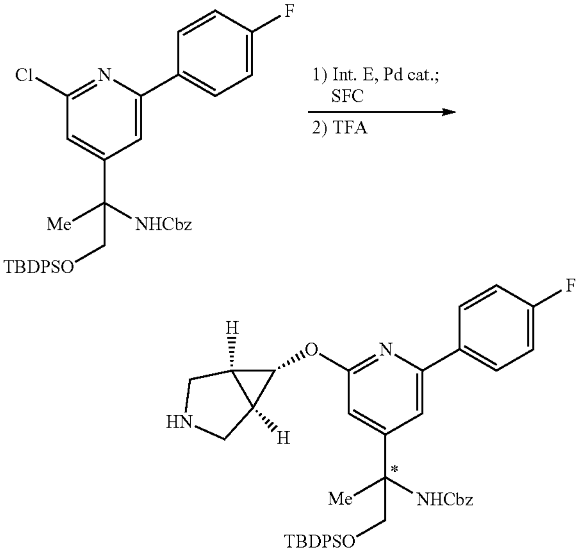

Intermediate H-12-ent-1

Benzyl ent-(2-(2-(((1R,5S,6s)-3-azabicyclo[3.1.0]hexan-6-yl)oxy)-6-(4-fluorophenyl)pyridin-4-yl)-1-((tert-butyldiphenylsilyl)oxy)propan-2-yl)carbamate (enantiomer 1) and Intermediate H-12-ent-2

Benzyl ent-(2-(2-(((1R,5S,6s)-3-azabicyclo[3.1.0]hexan-6-yl)oxy)-6-(4-fluorophenyl)pyridin-4-yl)-1-((tert-butyldiphenylsilyl)oxy)propan-2-yl)carbamate (enantiomer 2)

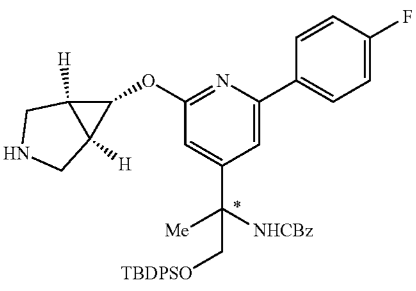

Step 1: tert-butyl ent-(1R,5S,6s)-6-((6-(4-fluorophenyl)-4-(5,9,9-trimethyl-3-oxo-1,8,8-triphenyl-2,7-dioxa-4-aza-8-siladecan-5-yl)pyridin-2-yl)oxy)-3-azabicyclo[3.1.0]hexane-3-carboxylate (enantiomers 1 and 2)

Under an atmosphere of argon, a mixture of benzyl rac-(1-((tert-butyldiphenylsilyl)oxy)-2-(2-chloro-6-(4-fluorophenyl)pyridin-4-yl)propan-2-yl)carbamate (Int. C-11, 0.80 g, 1.2 mmol) and tert-butyl (1R,5S,6s)-6-hydroxy-3-azabicyclo[3.1.0]hexane-3-carboxylate (Int. E, 0.27 g, 1.3 mmol), Ad-BippyPhos (81 mg, 0.12 mmol), $Pd_2(dba)_3$ (56 mg, 0.061 mmol), $Cs_2CO_3$ (1.2 g, 3.7 mmol), and PhMe (15 mL) was stirred at 90° C. for 12 h. The mixture was cooled to rt, filtered through a thin pad of silica gel (eluted w/EtOAc), and concentrated under reduced pressure. The residue was subjected to silica gel chromatography (0-25% EtOAc/petroleum ether). The mixture of two enantiomers was subjected to chiral SFC ((S,S)Whelk-01, 40% MeOH (with 0.05% DEA modifier)/$CO_2$) to afford the title compounds, tert-butyl ent-(1R,5S,6s)-6-((6-(4-fluorophenyl)-4-(5,9,9-trimethyl-3-oxo-1,8,8-triphenyl-2,7-dioxa-4-aza-8-siladecan-5-yl)pyridin-2-yl)oxy)-3-azabicyclo[3.1.0]hexane-3-carboxylate (enantiomer 1, faster eluting) and tert-butyl ent-(1R,5S,6s)-6-((6-(4-fluorophenyl)-4-(5,9,9-trimethyl-3-oxo-1,8,8-triphenyl-2,7-dioxa-4-aza-8-siladecan-5-yl)pyridin-2-yl)oxy)-3-azabicyclo[3.1.0]hexane-3-carboxylate (enantiomer 2, slower eluting).

Step 2-1: benzyl ent-(2-(2-(((1R,5S,6s)-3-azabicyclo[3.1.0]hexan-6-yl)oxy)-6-(4-fluorophenyl)pyridin-4-yl)-1-((tert-butyldiphenylsilyl)oxy)propan-2-yl)carbamate (enantiomer 1)

To a solution of tert-butyl ent-(1R,5S,6s)-6-((6-(4-fluorophenyl)-4-(5,9,9-trimethyl-3-oxo-1,8,8-triphenyl-2,7-dioxa-4-aza-8-siladecan-5-yl)pyridin-2-yl)oxy)-3-azabicyclo[3.1.0]hexane-3-carboxylate (enantiomer 1, faster eluting, 0.31 g, 0.38 mmol) in DCM (5.0 mL) was added TFA (2.0 mL). The mixture was stirred at rt for 1 h. The mixture was concentrated under reduced pressure to afford the title compound (Int. H-12-ent-1).

Step 2-2: benzyl ent-(2-(2-(((1R,5S,6s)-3-azabicyclo[3.1.0]hexan-6-yl)oxy)-6-(4-fluorophenyl)pyridin-4-yl)-1-((tert-butyldiphenylsilyl)oxy)propan-2-yl)carbamate (enantiomer 2)

To a solution of tert-butyl ent-(1R,5S,6s)-6-((6-(4-fluorophenyl)-4-(5,9,9-trimethyl-3-oxo-1,8,8-triphenyl-2,7-dioxa-4-aza-8-siladecan-5-yl)pyridin-2-yl)oxy)-3-azabicyclo

[3.1.0]hexane-3-carboxylate (enantiomer 2, slower eluting, 0.31 g, 0.38 mmol) in DCM (5.0 mL) was added TFA (2.0 mL). The mixture was stirred at rt for 1 h. The mixture was concentrated under reduced pressure to afford the title compound (Int. H-12-ent-2).

Scheme:

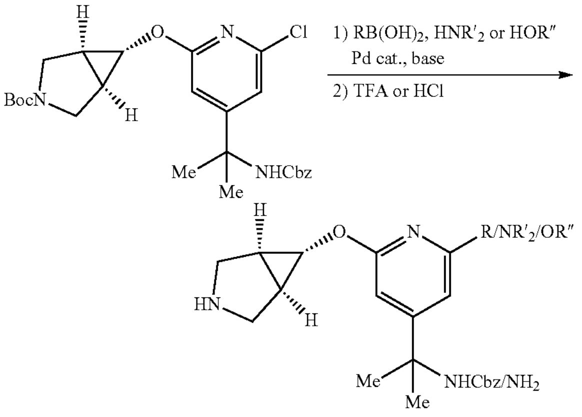

Intermediate H-13

Benzyl (2-(2-(((1R,5S,6s)-3-azabicyclo[3.1.0]hexan-6-yl)oxy)-6-(2,4-difluorophenyl)pyridin-4-yl)propan-2-yl)carbamate

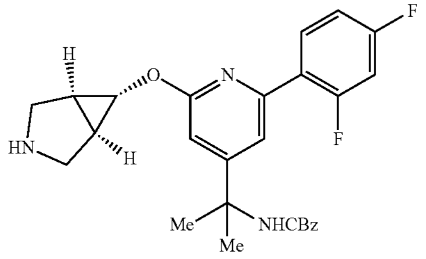

Step 1: tert-butyl (1R,5S,6s)-6-((4-(2-(((benzyloxy)carbonyl)amino)propan-2-yl)-6-(2,4-difluorophenyl)pyridin-2-yl)oxy)-3-azabicyclo[3.1.0]hexane-3-carboxylate Under an atmosphere of nitrogen, a mixture of tert-butyl (1R,5S,6s)-6-((4-(2-(((benzyloxy)carbonyl)amino)propan-2-yl)-6-chloropyridin-2-yl)oxy)-3-azabicyclo[3.1.0]hexane-3-carboxylate (Int. G, 0.50 g, 0.10 mmol), 2,4-difluorophenylboronic acid (0.19 g, 1.2 mmol), XPhos Pd G2 (78 mg, 0.10 mmol), $K_3PO_4$ (1.0 M aq., 3.0 mL, 3.0 mmol), and 1,4-dioxane (5.0 mL) was stirred at 100° C. for 2 h. The mixture was cooled to rt, filtered, and concentrated under reduced pressure. The residue was subjected to silica gel chromatography (0-20% (3:1 EtOAc/EtOH)/hexanes) to afford the title compound.

Step 2: benzyl (2-(2-(((1R,5S,6s)-3-azabicyclo[3.1.0]hexan-6-yl)oxy)-6-(2,4-difluorophenyl)pyridin-4-yl)propan-2-yl)carbamate To a solution of tert-butyl (1R,5S,6s)-6-((4-(2-(((benzyloxy)carbonyl)amino)propan-2-yl)-6-(2,4-difluorophenyl)pyridin-2-yl)oxy)-3-azabicyclo[3.1.0]hexane-3-carboxylate (0.50 g, 0.86 mmol) in DCM (0.050 L) was added a solution of HCl (4.0 M in 1,4-dioxane, 1.0 mL, 4.3 mmol). The reaction mixture was stirred at rt for 1 hour. The reaction was concentrated under reduced pressure to afford the title compound as a HCl salt.

Scheme:

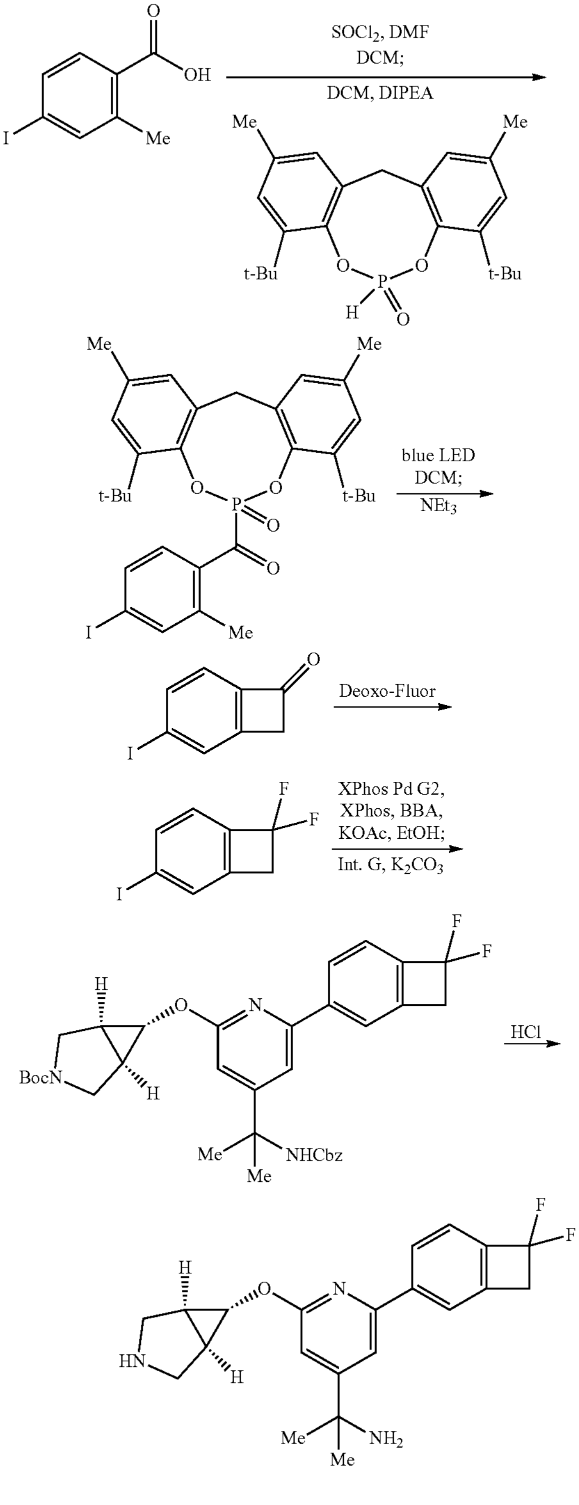

Intermediate H-14

2-(2-(((1R,5S,6s)-3-azabicyclo[3.1.0]hexan-6-yl)oxy)-6-(7,7-difluorobicyclo[4.2.0]octa-1(6),2,4-trien-3-yl)pyridin-4-yl)propan-2-amine

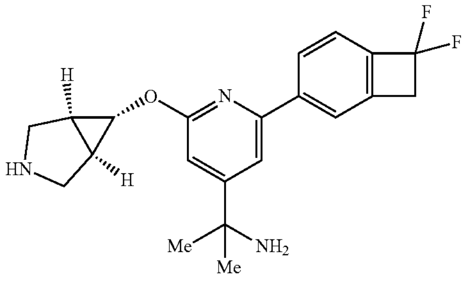 [SMILES: CC(C)(N)c1cc(O[C@H]2[C@@H]3CNC[C@@H]32)nc(-c2ccc3c(c2)CC3(F)F)c1]

Step 1: (4,8-di-tert-butyl-2,10-dimethyl-6-oxido-12H-dibenzo[d,g][1,3,2]dioxaphosphocin-6-yl)(4-iodo-2-methylphenyl)methanone To a solution of 4-iodo-2-methylbenzoic acid (4.1 g, 16 mmol) in DCM (31 mL) was added a solution of oxalyl chloride (2.0 M in DCM, 2.7 mL, 31 mmol), followed by DMF (2 drops). The mixture was heated at reflux for 1 h. The mixture was concentrated under reduced pressure. DCM (31 mL) and DIPEA (14 mL, 78 mmol) were added then a solution of 4,8-di-tert-butyl-2,10-dimethyl-12H-dibenzo[d,g][1,3,2]dioxaphosphocine 6-oxide (6.0 g, 16 mmol) in DCM (31 mL) was added dropwise over 1 h. The mixture was stirred at rt for 6 h. DCM (50 mL) was added, and the mixture was washed with hydrochloric acid (1N, 50 mL) and a solution of $NaHCO_3$ (saturated aq., 50 mL). The organic fraction was dried over anhydrous magnesium sulfate, filtered, and concentrated under reduced pressure. The residue was subjected to silica gel chromatography (0-30% EtOAc/hexanes) to afford the title compound.

Step 2: 3-iodobicyclo[4.2.0]octa-1(6),2,4-trien-7-one

A solution of (4,8-di-tert-butyl-2,10-dimethyl-6-oxido-12H-dibenzo[d,g][1,3,2]dioxaphosphocin-6-yl)(4-iodo-2-methylphenyl)methanone (4.7 g, 7.4 mmol) in PhMe (15 mL) was irradiated in a PennOC Photoreactor® (wavelength: 420 nm; LED intensity: 100%; fan speed: 5000 rpm; stir: 1200 rpm) for 12 h. Triethylamine (1.0 mL, 7.4 mmol) was added, and the mixture was heated to 45° C. for 4 h. The mixture was subjected to silica gel chromatography (0-15% EtOAc/hexanes) to afford the title compound.

Step 3: 7,7-difluoro-3-iodobicyclo[4.2.0]octa-1(6),2,4-triene

A mixture of bis(2-methoxyethyl)aminosulfur trifluoride (0.93 mL, 5.0 mmol) and 3-iodobicyclo[4.2.0]octa-1(6),2,4-trien-7-one (250 mg, 1.0 mmol) was stirred at 50° C. for 16 h. A 0° C. solution of $NaHCO_3$ (saturated aq., 30 mL) was added dropwise and the mixture was extracted with DCM (30 mL×3). The combined organic solution was dried over anhydrous magnesium sulfate, filtered, and concentrated under reduced pressure. The residue was subjected to silica gel chromatography (hexanes) to afford the title compound.

Step 4: tert-Butyl (1R,5S,6s)-6-((4-(2-(((benzyloxy)carbonyl)amino)propan-2-yl)-6-(7,7-difluorobicyclo[4.2.0]octa-1(6),2,4-trien-3-yl)pyridin-2-yl)oxy)-3-azabicyclo[3.1.0]hexane-3-carboxylate Under an atmosphere of nitrogen, a mixture of 7,7-difluoro-3-iodobicyclo[4.2.0]octa-1(6),2,4-triene (0.20 g, 0.74 mmol), XPhos Pd G2 (58 mg, 0.074 mmol), XPhos (0.070 g, 0.15 mmol), tetrahydroxydiboron (0.20 g, 2.2 mmol), potassium acetate (0.22 g, 2.2 mmol), and ethanol (7.4 mL) was stirred at 80° C. for 2 h. A solution of $K_2CO_3$ (1.8M aq., 1.2 mL, 2.2 mmol) and tert-butyl (1R,5S,6s)-6-((4-(2-(((benzyloxy)carbonyl)amino)propan-2-yl)-6-chloropyridin-2-yl)oxy)-3-azabicyclo[3.1.0]hexane-3-carboxylate (Int. G, 0.37 g, 0.74 mmol) were added and the mixture was stirred at 80° C. for 2 h. The mixture was cooled to rt, a solution of $KH_2PO_4$ (saturated aq., 20 mL) was added, and the mixture was extracted with EtOAc (20 mL×3). The combined organic solution was dried over anhydrous magnesium sulfate, filtered, and concentrated under reduced pressure. The residue was subjected to silica gel chromatography (0-100% EtOAc/hexanes) to afford the title compound.

Step 5: 2-(2-(((1R,5S,6s)-3-Azabicyclo[3.1.0]hexan-6-yl)oxy)-6-(7,7-difluorobicyclo[4.2.0]octa-1(6),2,4-trien-3-yl)pyridin-4-yl)propan-2-amine A mixture of tert-butyl (1R,5S,6s)-6-((4-(2-(((benzyloxy)carbonyl)amino)propan-2-yl)-6-(7,7-difluorobicyclo[4.2.0]octa-1(6),2,4-trien-3-yl)pyridin-2-yl)oxy)-3-azabicyclo[3.1.0]hexane-3-carboxylate (0.41 g, 0.68 mmol) and hydrochloric acid (37%, 6.7 mL) was stirred at 80° C. for 10 min. The mixture was cooled to rt, diluted with water (10 mL), and loaded onto a Flash SCX-2 cartridge (preconditioned with MeOH). The cartridge was washed with MeOH (2 CV) and eluted with a methanolic solution of $NH_3$ (2N, 2 CV). The eluent was concentrated under reduced pressure. The residue was dissolved in DCM (0.010 L), then HCl (4.0 M in 1,4-dioxane, 1.7 mL, 6.8 mmol) was added. The mixture was stirred at rt for 15 min and concentrated under reduced pressure to afford the title compound as a HCl salt.

Intermediate H-15

2-(2-(((1R,5S,6s)-3-azabicyclo[3.1.0]hexan-6-yl)oxy)-6-(bicyclo[1.1.1]pentan-1-ylmethoxy)pyridin-4-yl)propan-2-amine

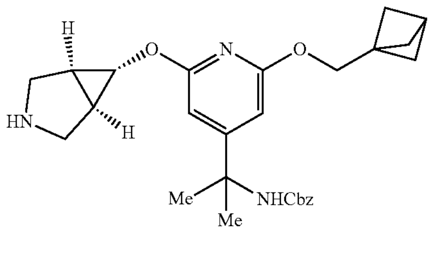 [SMILES: CC(C)(NC(=O)OCc1ccccc1)c1cc(OCC23CC(C2)C3)nc(O[C@H]2[C@@H]3CNC[C@@H]32)c1]

Step 1: tert-butyl (1R,5S,6s)-6-((4-(2-(((benzyloxy)carbonyl)amino)propan-2-yl)-6-(bicyclo[1.1.1]pentan-1-ylmethoxy)pyridin-2-yl)oxy)-3-azabicyclo[3.1.0]hexane-3-carboxylate Tert-butyl (1R,5S,6s)-6-((4-(2-(((benzyloxy)carbonyl)amino)propan-2-yl)-6-chloropyridin-2-yl)oxy)-3-azabicyclo[3.1.0]hexane-3-carboxylate (Int. G, 0.050 g, 0.10 mmol), bicyclo[1.1.1]pentan-1-ylmethanol (15 mg, 0.15 mmol), and $Cs_2CO_3$ (97 mg, 0.30 mmol) were combined in a screw cap vial. PhMe (0.50 mL) was added, and nitrogen was bubbled through the mixture for 1 min. RockPhos Pd G3 (9.0 mg, 11 μmol) was added, and the vial was capped then heated to 90° C. overnight. The mixture was cooled to rt, EtOAc was added, and the mixture was filtered through a 0.45 μm syringe filter (eluted with EtOAc). The filtrate was concentrated under reduced pressure to afford a mixture of the title compound and tert-butyl (1R,5S,6s)-6-((4-(2-aminopropan-2-yl)-6-(bicyclo[1.1.1]pentan-1-ylmethoxy)pyridin-2-yl)oxy)-3-azabicyclo[3.1.0]hexane-3-carboxylate.

Step 2: 2-(2-(((1R,5S,6s)-3-azabicyclo[3.1.0]hexan-6-yl)oxy)-6-(bicyclo[1.1.1]pentan-1-ylmethoxy)pyridin-4-yl)propan-2-amine The mixture from step 1 was taken up in hydrochloric acid (37%, 0.50 mL) then placed in a pre-heated block at 80° C. After 10 min the mixture was cooled to rt. The mixture was diluted with DMSO (0.50 mL) then subjected to reverse phase HPLC (5-50% MeCN/water with 0.1% TFA modifier). Fractions containing product were pooled then concentrated. The residue was taken up in MeCN then transferred to a screw cap vial. Two volumes of hydrochloric acid (1N aq.) was added. The mixture was frozen (dry ice/acetone) then lyophilized to afford the title compound as a HCl salt.

Intermediate H-16

Benzyl (2-(2-(((1R,5S,6s)-3-azabicyclo[3.1.0]hexan-6-yl)oxy)-6-(4-cyclopropyl-1H-pyrazol-1-yl)pyridin-4-yl)propan-2-yl)carbamate

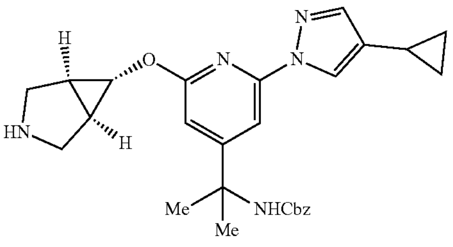 [SMILES: CC(C)(NC(=O)OCc1ccccc1)c1cc(O[C@H]2[C@@H]3CNC[C@@H]32)nc(-n2cc(C3CC3)cn2)c1]

Step 1: tert-butyl (1R,5S,6s)-6-((4-(2-(((benzyloxy)carbonyl)amino)propan-2-yl)-6-(4-cyclopropyl-1H-pyrazol-1-yl)pyridin-2-yl)oxy)-3-azabicyclo[3.1.0]hexane-3-carboxylate Under an atmosphere of nitrogen, a mixture of tert-butyl (1R,5S,6s)-6-((4-(2-(((benzyloxy)carbonyl)amino)propan-2-yl)-6-chloropyridin-2-yl)oxy)-3-azabicyclo[3.1.0]hexane-3-carboxylate (Int. G, 0.19 g, 0.38 mmol), 4-cyclopropyl-1H-pyrazole (83 mg, 0.77 mmol), $Pd_2(dba)_3$ (18 mg, 0.019 mmol), t-BuXPhos (16 mg, 0.038 mmol), $K_3PO_4$ (0.25 g, 1.2 mmol), and tert-butanol (6.0 mL) was stirred at 80° C. for 16 h. The mixture was cooled to rt, filtered, and concentrated under reduced pressure. The residue was subjected to silica gel chromatography (0-50% EtOAc/petroleum ether) to afford the title compound.

Step 2: benzyl (2-(2-(((1R,5S,6s)-3-azabicyclo[3.1.0]hexan-6-yl)oxy)-6-(4-cyclopropyl-1H-pyrazol-1-yl)pyridin-4-yl)propan-2-yl)carbamate To a solution of tert-butyl (1R,5S,6s)-6-((4-(2-(((benzyloxy)carbonyl)amino)propan-2-yl)-6-(4-cyclopropyl-1H-pyrazol-1-yl)pyridin-2-yl)oxy)-3-azabicyclo[3.1.0]hexane-3-carboxylate (0.19 g, 0.29 mmol) in DCM (5.0 mL) was added TFA (1.0 mL). The mixture was stirred at rt for 1 h and concentrated under reduced pressure to afford the title compound.

Scheme:

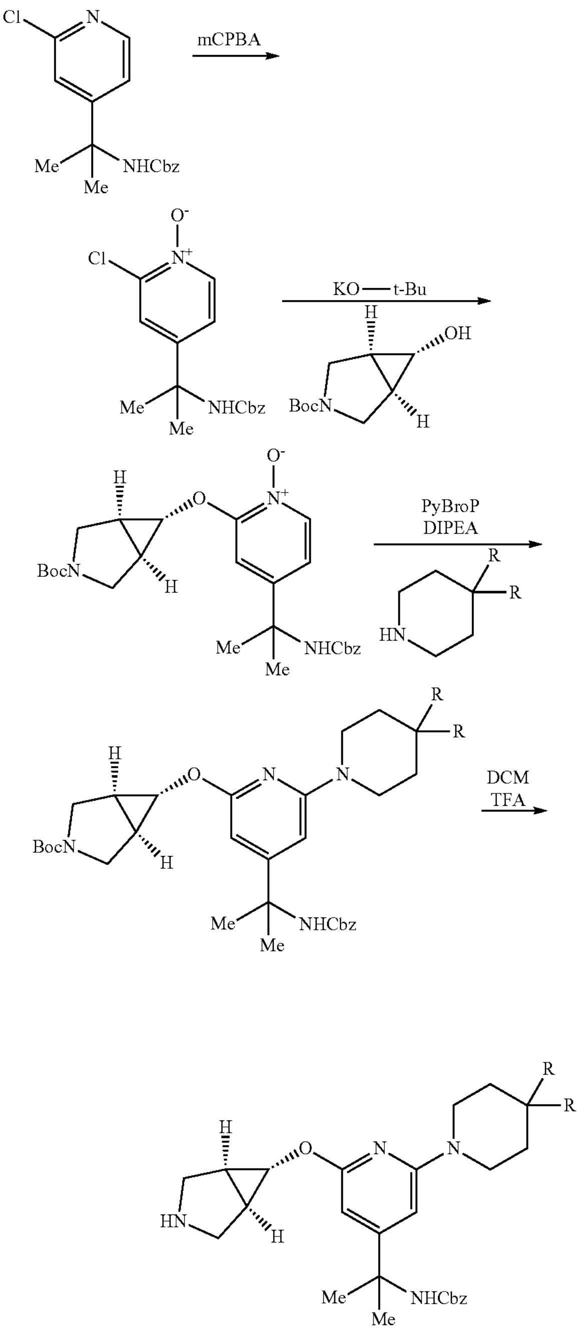

Intermediate H-17

Benzyl (2-(2-(((1R,5S,6s)-3-azabicyclo[3.1.0]hexan-6-yl)oxy)-6-(4,4-dimethylpiperidin-1-yl)pyridin-4-yl)propan-2-yl)carbamate

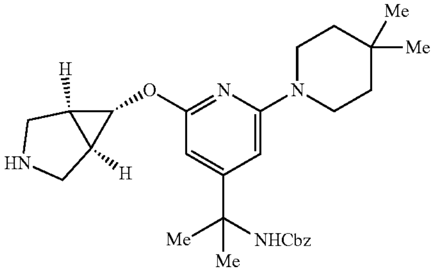 [SMILES: CC1(C)CCN(c2cc(C(C)(C)NC(=O)OCc3ccccc3)cc(O[C@H]3[C@@H]4CNC[C@@H]43)n2)CC1]

Step 1: benzyl (2-(2-chloropyridin-4-yl)propan-2-yl) carbamate 1-oxide

To a solution of benzyl (2-(2-chloropyridin-4-yl)propan-2-yl)carbamate (Int. A-2, 4.4 g, 14 mmol) in DCM (72 mL) was added 3-chloroperoxybenzoic acid (77 wt % with water, 4.8 g, 22 mmol). The mixture was stirred at rt for 16 h. The reaction was diluted with DCM (75 mL) and washed with $Na_2SO_3$ (saturated aq., 100 mL), $NaHCO_3$ (saturated aq., 100 mL), and brine (100 mL). The organic solution was dried over anhydrous magnesium sulfate, filtered, and concentrated under reduced pressure. The residue was subjected to silica gel chromatography (0-20% (25% EtOH/EtOAc)/DCM) to afford the title compound.

Step 2: tert-butyl (1R,5S,6s)-6-((4-(2-(((benzyloxy) carbonyl)amino)propan-2-yl)pyridin-2-yl)oxy)-3-azabicyclo[3.1.0]hexane-3-carboxylate N-oxide To a solution of benzyl (2-(2-chloropyridin-4-yl)propan-2-yl)carbamate 1-oxide (2.0 g, 6.3 mmol) and tert-butyl (1R,5S,6s)-6-hydroxy-3-azabicyclo[3.1.0]hexane-3-carboxylate (Int E, 1.3 g, 6.3 mmol) in THF (63 mL) was added potassium tert-butoxide (1.0M in THF, 6.9 mL, 6.9 mmol). The mixture was heated to 60° C. for 3 d. The mixture was cooled to rt and diluted with water (100 mL) and EtOAc (200 mL). The organic solution was washed with brine (150 mL), dried over anhydrous magnesium sulfate, filtered, and concentrated under reduced pressure. The residue was subjected to silica gel chromatography (0-25% (25% EtOH/EtOAc)/DCM) to afford the title compound.

Step 3: tert-butyl (1R,5S,6s)-6-((4-(2-(((benzyloxy) carbonyl)amino)propan-2-yl)-6-(4,4-dimethylpiperidin-1-yl)pyridin-2-yl)oxy)-3-azabicyclo[3.1.0] hexane-3-carboxylate To a mixture of tert-butyl (1R,5S,6s)-6-((4-(2-(((benzyloxy)carbonyl)amino)propan-2-yl)pyridin-2-yl)oxy)-3-azabicyclo[3.1.0]hexane-3-carboxylate N-oxide (0.55 g, 1.1 mmol) and 4,4-dimethylpiperidine-HCl (0.21 g, 1.4 mmol) in DCM (4.6 mL) was added DIPEA (0.99 mL, 5.7 mmol) and bromotripyrrolidinophosphonium hexafluorophosphate (0.69 g, 1.5 mmol). The mixture was stirred at rt for 16 h. The mixture was diluted with EtOAc (40 mL) and washed with $NaHCO_3$ (saturated. aq., 40 mL), water (40 mL), and brine (40 mL). The organic solution was dried over anhydrous magnesium sulfate, filtered, and concentrated under reduced pressure. The residue was subjected to silica gel chromatography (0-15% (25% EtOH/EtOAc)/hexanes) to afford the title compound.

Step 4: benzyl (2-(2-(((1R,5S,6s)-3-azabicyclo [3.1.0]hexan-6-yl)oxy)-6-(4,4-dimethylpiperidin-1-yl)pyridin-4-yl)propan-2-yl)carbamate To a solution of tert-butyl (1R,5S,6s)-6-((4-(2-(((benzyloxy)carbonyl)amino)propan-2-yl)-6-(4,4-dimethylpiperidin-1-yl)pyridin-2-yl)oxy)-3-azabicyclo[3.1.0]hexane-3-carboxylate (0.36 g, 0.62 mmol) in DCM (4.7 mL) was added TFA (1.6 mL). The mixture was stirred at rt for 16 h. The mixture was poured into sodium hydroxide (1N aq., 50 mL) and the pH was adjusted to >12 with sodium hydroxide (6 N aq.). The mixture was extracted with DCM (50 mL×3) and the combined organic extracts were dried over anhydrous magnesium sulfate, filtered, and concentrated under reduced pressure to afford the title compound.

Utilizing the procedures described in the synthesis of Intermediate H-17, the following compound was prepared substituting the appropriate reagents for 4,4-dimethylpiperidine-HCl.

| Int. | Structure | Name |
|---|---|---|
| H-18 | 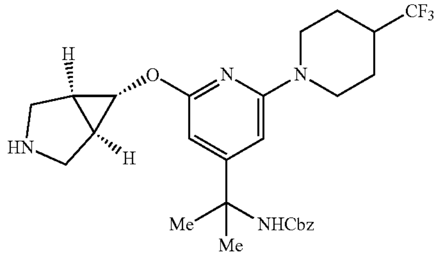 [SMILES: CC(C)(NC(=O)OCc1ccccc1)c1cc(O[C@H]2[C@@H]3CNC[C@@H]32)nc(N2CCC(C(F)(F)F)CC2)c1] | benzyl (2-(2-(((1R,5S,6s)-3-azabicyclo[3.1.0]hexan-6-yl)oxy)-6-(4-(trifluoromethyl)piperidin-1-yl)pyridin-4-yl)propan-2-yl)carbamate |

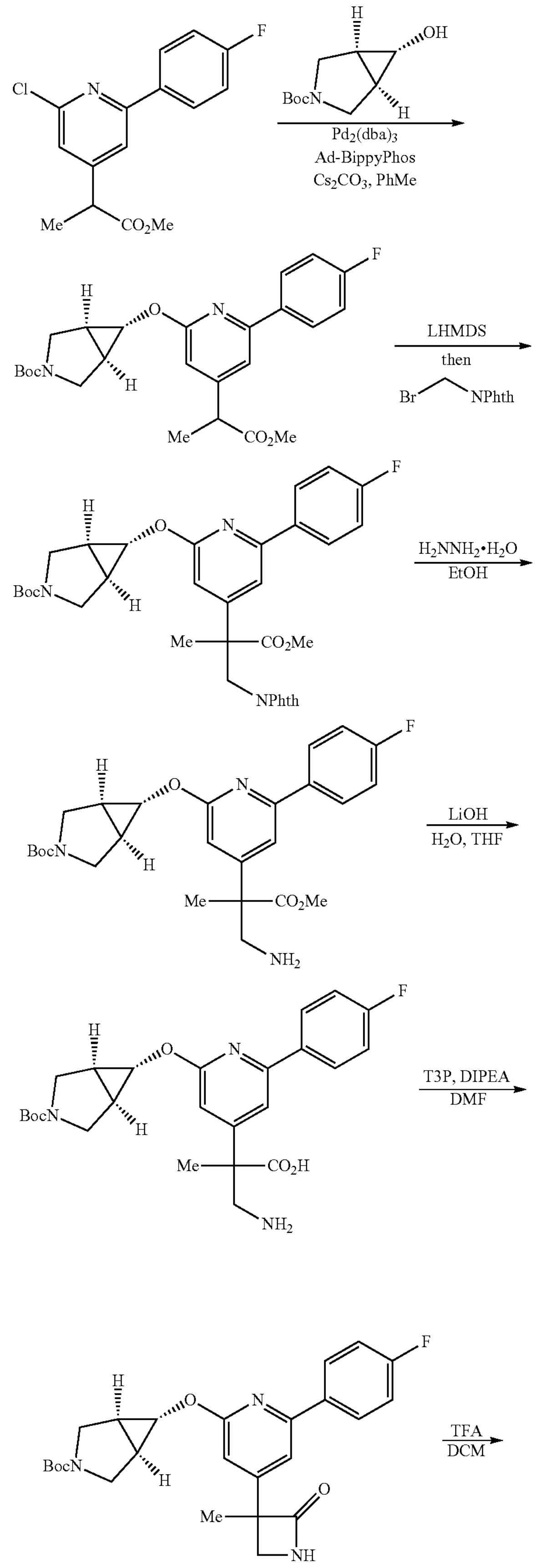

-continued

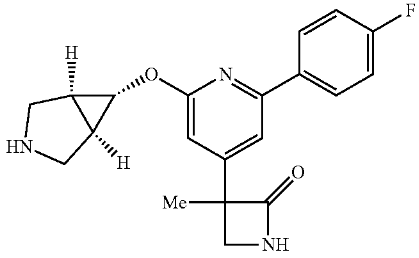 [SMILES: CC1(c2cc(O[C@H]3[C@@H]4CNC[C@@H]43)nc(-c3ccc(F)cc3)c2)CNC1=O]

Intermediate H-19

3-(2-(((1R,5S,6s)-3-azabicyclo[3.1.0]hexan-6-yl) oxy)-6-(4-fluorophenyl)pyridin-4-yl)-3-methylazetidin-2-one

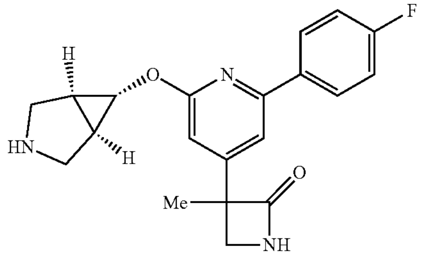 [SMILES: CC1(c2cc(O[C@H]3[C@@H]4CNC[C@@H]43)nc(-c3ccc(F)cc3)c2)CNC1=O]

Step 1: tert-butyl (1R,5S,6s)-6-((6-(4-fluorophenyl)-4-(1-methoxy-1-oxopropan-2-yl)pyridin-2-yl)oxy)-3-azabicyclo[3.1.0]hexane-3-carboxylate In glove box, a mixture of methyl 2-(2-chloro-6-(4-fluorophenyl)pyridin-4-yl)propanoate (Int. B, 1.0 g, 3.5 mmol), tert-butyl (1R,5S,6s)-6-hydroxy-3-azabicyclo[3.1.0] hexane-3-carboxylate (Int. E, 0.70 g, 3.5 mmol), $Pd_2(dba)_3$ (0.16 g, 0.18 mmol), Ad-BippyPhos (0.23 g, 0.35 mmol) and $Cs_2CO_3$ (3.4 g, 11 mmol) in PhMe (0.040 L) was heated to 90° C. After 16 h, the mixture was cooled to rt, filtered, and concentrated. The residue was subjected to silica gel chromatography (0-20% EtOAc/petroleum ether) to afford the title compound.

Step 2: tert-butyl rac-(1R,5S,6s)-6-((4-(3-(1,3-dioxoisoindolin-2-yl)-1-methoxy-2-methyl-1-oxopropan-2-yl)-6-(4-fluorophenyl)pyridin-2-yl)oxy)-3-azabicyclo[3.1.0]hexane-3-carboxylate To a −78° C. solution of tert-butyl (1R,5S,6s)-6-((6-(4-fluorophenyl)-4-(1-methoxy-1-oxopropan-2-yl)pyridin-2-yl)oxy)-3-azabicyclo[3.1.0]hexane-3-carboxylate (1.0 g, 2.2 mmol) in THF (15 mL) was slowly added lithium bis(trimethylsilyl)amide (1.0 M in THF, 2.9 mL, 2.9 mmol). After 1 h, a solution of 2-(bromomethyl)isoindoline-1,3-dione (0.79 g, 3.3 mmol) in THF (5.0 mL) was added. After 2 h, the mixture was warmed to 0° C. and a solution of $NH_4Cl$ (saturated aq.) was added. The resulting mixture was warmed to rt and extracted with EtOAc (3×). The combined organic extracts were washed with brine, dried over anhydrous sodium sulfate, filtered, and concentrated. The residue was subjected to silica gel chromatography (0-30% EtOAc/petroleum ether) to afford the title compound.

Step 3: tert-butyl rac-(1R,5S,6s)-6-((4-(3-amino-1-methoxy-2-methyl-1-oxopropan-2-yl)-6-(4-fluorophenyl)pyridin-2-yl)oxy)-3-azabicyclo[3.1.0]hexane-3-carboxylate To a rt mixture of tert-butyl rac-(1R,5S,6s)-6-((4-(3-(1,3-dioxoisoindolin-2-yl)-1-methoxy-2-methyl-1-oxopropan-2-yl)-6-(4-fluorophenyl)pyridin-2-yl)oxy)-3-azabicyclo[3.1.0]hexane-3-carboxylate (0.60 g, 0.98 mmol) in EtOH (15 mL) was added hydrazine hydrate (0.49 g, 9.8 mmol). After 12 h, the mixture was filtered and concentrated. The residue was subjected to silica gel chromatography (EtOAc) to afford the title compound.

Step 4: rac-3-amino-2-(2-(((1R,5S,6s)-3-(tert-butoxycarbonyl)-3-azabicyclo[3.1.0]hexan-6-yl)oxy)-6-(4-fluorophenyl)pyridin-4-yl)-2-methylpropanoic acid To a rt mixture of tert-butyl rac-(1R,5S,6s)-6-((4-(3-amino-1-methoxy-2-methyl-1-oxopropan-2-yl)-6-(4-fluorophenyl)pyridin-2-yl)oxy)-3-azabicyclo[3.1.0]hexane-3-carboxylate (0.30 g, 0.61 mmol) in THF (5.0 mL) and $H_2O$ (5.0 mL) was added LiOH (73 mg, 3.0 mmol). After 12 h, the mixture was concentrated to remove volatile organic solvents then washed with DCM (2×). The aqueous solution was acidified (pH=6) with hydrochloric acid (1N) and concentrated under reduced pressure. DCM (10 mL) and MeOH (10 mL) were added, and the mixture was stirred at rt for 1 h. The mixture was filtered and concentrated under reduced pressure to afford the title compound.

Step 5: tert-butyl rac-(1R,5S,6s)-6-((6-(4-fluorophenyl)-4-(3-methyl-2-oxoazetidin-3-yl)pyridin-2-yl)oxy)-3-azabicyclo[3.1.0]hexane-3-carboxylate To a rt solution of rac-3-amino-2-(2-(((1R,5S,6s)-3-(tert-butoxycarbonyl)-3-azabicyclo[3.1.0]hexan-6-yl)oxy)-6-(4-fluorophenyl)pyridin-4-yl)-2-methylpropanoic acid (240 mg, 0.41 mmol) in DMF (8.0 mL) was added DIPEA (0.20 mL, 1.2 mmol) and T3P (50 wt % in EtOAc, 390 mg, 0.61 mmol). After 1 h, the mixture was diluted with $H_2O$ (10 mL) then extracted with EtOAc (3×). The combined organic extracts were washed with brine, dried over anhydrous sodium sulfate, filtered, and concentrated. The residue was purified by prep-TLC (67% EtOAc/petroleum ether) to afford the title compound.

Step 6: rac-3-(2-(((1R,5S,6s)-3-azabicyclo[3.1.0]hexan-6-yl)oxy)-6-(4-fluorophenyl)pyridin-4-yl)-3-methylazetidin-2-one To a rt solution of tert-butyl rac-(1R,5S,6s)-6-((6-(4-fluorophenyl)-4-(3-methyl-2-oxoazetidin-3-yl)pyridin-2-yl)oxy)-3-azabicyclo[3.1.0]hexane-3-carboxylate (110 mg, 0.24 mmol) in DCM (3.0 mL) was added TFA (1.0 mL). After 30 min, the mixture was concentrated to afford the title compound as a TFA salt.

Scheme:

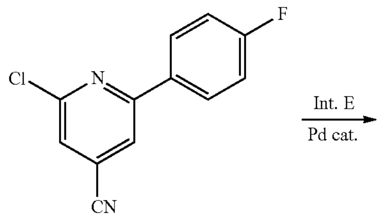

-continued

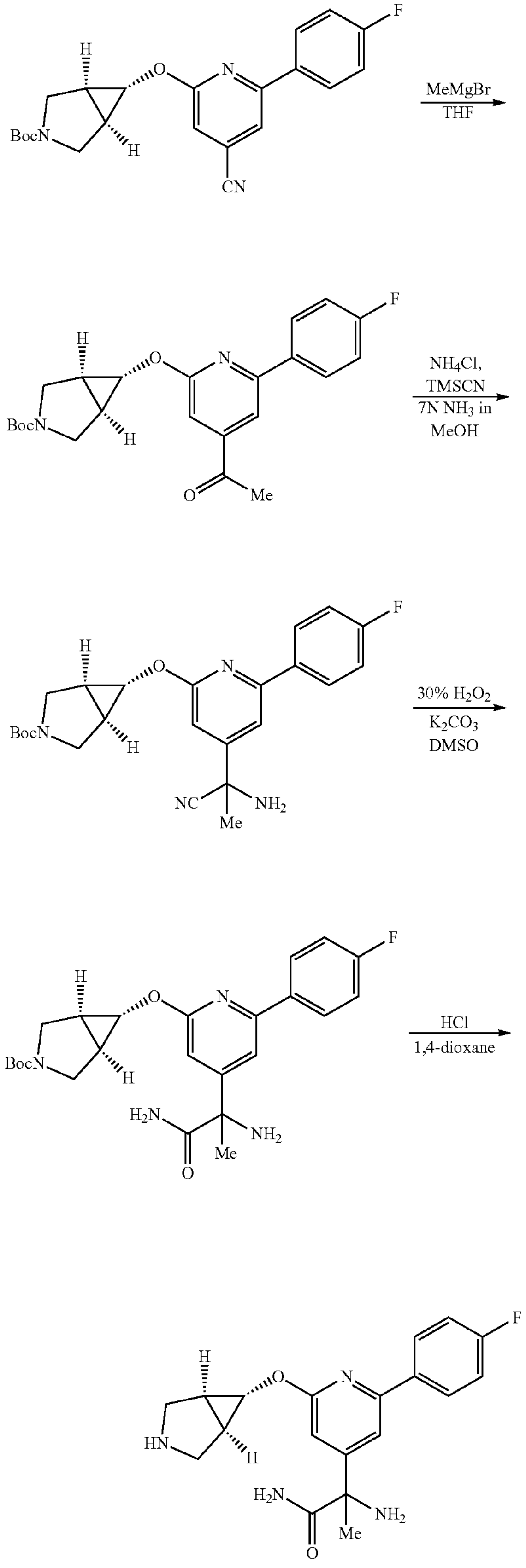

Intermediate H-20

Rac-2-(2-(((1R,5S,6s)-3-azabicyclo[3.1.0]hexan-6-yl)oxy)-6-(4-fluorophenyl)pyridin-4-yl)-2-aminopropanamide

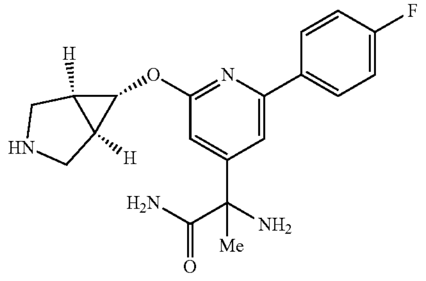 [SMILES: CC(N)(C(N)=O)c1cc(O[C@H]2[C@@H]3CNC[C@@H]32)nc(-c2ccc(F)cc2)c1]

Step 1: tert-butyl (1R,5S,6s)-6-((4-cyano-6-(4-fluorophenyl)pyridin-2-yl)oxy)-3-azabicyclo[3.1.0]hexane-3-carboxylate Under an atmosphere of nitrogen, a mixture of tert-butyl (1R,5S,6s)-6-hydroxy-3-azabicyclo[3.1.0]hexane-3-carboxylate (Int. E, 420 mg, 2.1 mmol), 2-chloro-6-(4-fluorophenyl)isonicotinonitrile (470 mg, 2.0 mmol), $Pd_2(dba)_3$ (92 mg, 0.10 mmol), Ad-BippyPhos (130 mg, 0.20 mmol), $Cs_2CO_3$ (2.0 g, 6.0 mmol), and 1,4-dioxane (0.010 L) were stirred at 85° C. for 18 h. The mixture was cooled to rt, diluted with EtOAc (50 mL), and washed with $NaHCO_3$ (saturated aq., 50 mL). The organic solution was dried over anhydrous magnesium sulfate, filtered, and concentrated under reduced pressure. The residue was subjected to silica gel chromatography (DCM) to afford the title compound.

Step 2: tert-butyl (1R,5S,6s)-6-((4-acetyl-6-(4-fluorophenyl)pyridin-2-yl)oxy)-3-azabicyclo[3.1.0]hexane-3-carboxylate To a rt solution of tert-butyl (1R,5S,6s)-6-((4-cyano-6-(4-fluorophenyl)pyridin-2-yl)oxy)-3-azabicyclo[3.1.0]hexane-3-carboxylate (0.30 g, 0.76 mmol) in THF (6.0 mL) was slowly added MeMgBr (3.0 M in $Et_2O$, 2.6 mL, 7.7 mmol). After 3 h, the mixture was quenched with $NH_4Cl$ (saturated aq.), diluted with $H_2O$, and extracted with EtOAc (3×). The organic solution was dried over anhydrous magnesium sulfate, filtered, and concentrated under reduced pressure. The residue was subjected to silica gel chromatography (0-25% (25% EtOAc/EtOH)/heptane) to afford the title compound.

Step 3: tert-butyl rac-(1R,5S,6s)-6-((4-(1-amino-1-cyanoethyl)-6-(4-fluorophenyl)pyridin-2-yl)oxy)-3-azabicyclo[3.1.0]hexane-3-carboxylate To a mixture of tert-butyl (1R,5S,6s)-6-((4-acetyl-6-(4-fluorophenyl)pyridin-2-yl)oxy)-3-azabicyclo[3.1.0]hexane-3-carboxylate (75 mg, 0.18 mmol) and a methanolic solution of ammonia (7.0M, 1.0 mL) was added $NH_4Cl$ (0.030 g, 0.56 mmol) then trimethylsilyl cyanide (0.075 mL, 0.56 mmol). The mixture was stirred at rt overnight then concentrated. The residue was taken up in EtOAc, filtered, and concentrated. The residue was subjected to silica gel chromatography (0-25% (25% EtOAc/EtOH)/heptane) to afford the title compound.

Step 4: tert-butyl rac-(1R,5S,6s)-6-((4-(1,2-diamino-1-oxopropan-2-yl)-6-(4-fluorophenyl)pyridin-2-yl)oxy)-3-azabicyclo[3.1.0]hexane-3-carboxylate To a rt solution of tert-butyl rac-(1R,5S,6s)-6-((4-(1-amino-1-cyanoethyl)-6-(4-fluorophenyl)pyridin-2-yl)oxy)-3-azabicyclo[3.1.0]hexane-3-carboxylate (0.060 g, 0.14 mmol) in DMSO (1.0 mL) was added $K_2CO_3$ (76 mg, 0.55 mmol) then $H_2O_2$ (30 wt % in water, 0.14 mL, 1.4 mmol). The mixture was stirred overnight, diluted with $H_2O$, and extracted with EtOAc (3×). The organic solution was dried over anhydrous sodium sulfate, filtered, and concentrated under reduced pressure to afford the title compound.

Step 5: rac-2-(2-(((1R,5S,6s)-3-azabicyclo[3.1.0]hexan-6-yl)oxy)-6-(4-fluorophenyl)pyridin-4-yl)-2-aminopropanamide A mixture of tert-butyl rac-(1R,5S,6s)-6-((4-(1,2-diamino-1-oxopropan-2-yl)-6-(4-fluorophenyl)pyridin-2-yl)oxy)-3-azabicyclo[3.1.0]hexane-3-carboxylate (65 mg, 0.14 mmol) and HCl (4.0N in 1,4-dioxane, 1.0 mL) was stirred at rt for 30 min. The mixture was concentrated to afford the title compound as a HCl salt.

Scheme:

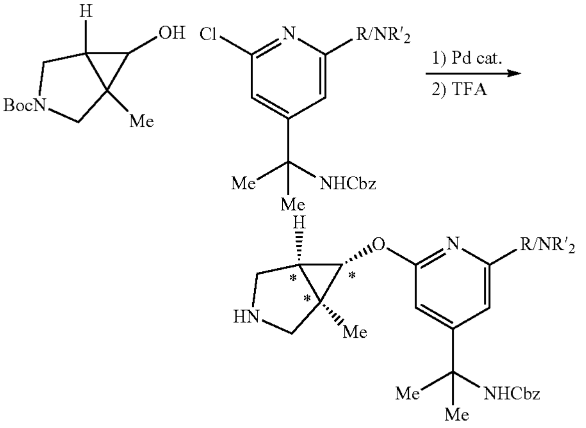

Intermediates I-1-ent-1 and I-1-ent-2

Benzyl rel-(2-(2-(4-fluorophenyl)-6-(((1R,5S,6S)-1-methyl-3-azabicyclo[3.1.0]hexan-6-yl)oxy)pyridin-4-yl)propan-2-yl)carbamate (enantiomers 1 and 2)

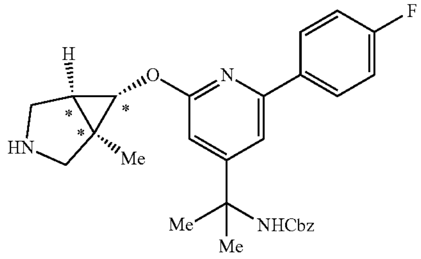 [SMILES: CC(C)(NC(=O)OCc1ccccc1)c1cc(O[C@H]2[C@@H]3CNC[C@@]32C)nc(-c2ccc(F)cc2)c1]

Step 1: tert-butyl rel-(1R,5S,6S)-6-((4-(2-(((benzyloxy)carbonyl)amino)propan-2-yl)-6-(4-fluorophenyl)pyridin-2-yl)oxy)-1-methyl-3-azabicyclo[3.1.0]hexane-3-carboxylate (enantiomers 1 and 2)

Under an atmosphere of nitrogen, a mixture of tert-butyl 6-hydroxy-1-methyl-3-azabicyclo[3.1.0]hexane-3-carboxylate (Int. F, 1.3 g, 4.3 mmol), benzyl (2-(2-chloro-6-(4-fluorophenyl)pyridin-4-yl)propan-2-yl)carbamate (Int. C-01, 1.7 g, 1.3 mmol), $Pd(OAc)_2$ (48 mg, 0.21 mmol), Ad-BippyPhos (0.28 g, 0.43 mmol), $K_3PO_4$ (2.7 g, 13 mmol), $PhCF_3$ (0.010 L), and CPME (0.010 L) were stirred at 95° C. for 12 h. The mixture was filtered and concentrated under reduced pressure. The residue was subjected to silica gel chromatography (0-15% EtOAc/petroleum ether) to afford the title compound. The material was subjected to chiral SFC (ChiralPak OJ-H, 5-40% EtOH (with 0.05% DEA modifier)/$CO_2$) to afford tert-butyl rel-(1R,5S,6S)-6-((4-(2-(((benzyloxy)carbonyl)amino)propan-2-yl)-6-(4-fluorophenyl)pyridin-2-yl)oxy)-1-methyl-3-azabicyclo[3.1.0]hexane-3-carboxylate (enantiomer 1, faster eluting) and tert-butyl rel-(1R,5S,6S)-6-((4-(2-(((benzyloxy)carbonyl)amino)propan-2-yl)-6-(4-fluorophenyl)pyridin-2-yl)oxy)-1-methyl-3-azabicyclo[3.1.0]hexane-3-carboxylate (enantiomer 2, slower eluting).

Step 2-1: benzyl rel-(2-(2-(4-fluorophenyl)-6-(((1R,5S,6S)-1-methyl-3-azabicyclo[3.1.0]hexan-6-yl)oxy)pyridin-4-yl)propan-2-yl)carbamate (enantiomer 1, Int. I-1-ent-1)

To a mixture of tert-butyl rel-(1R,5S,6S)-6-((4-(2-(((benzyloxy)carbonyl)amino)propan-2-yl)-6-(4-fluorophenyl)pyridin-2-yl)oxy)-1-methyl-3-azabicyclo[3.1.0]hexane-3-carboxylate (enantiomer 1, 0.31 mg, 0.53 mmol) in DCM (5.0 mL) was added TFA (1.0 mL). The resulting mixture was stirred at rt for 1 h. The mixture was concentrated under reduced pressure to afford the title compound.

Step 2-2: benzyl rel-(2-(2-(4-fluorophenyl)-6-(((1R,5S,6S)-1-methyl-3-azabicyclo[3.1.0]hexan-6-yl)oxy)pyridin-4-yl)propan-2-yl)carbamate (enantiomer 2, Int. I-1-ent-2)

To a mixture of tert-butyl rel-(1R,5S,6S)-6-((4-(2-(((benzyloxy)carbonyl)amino)propan-2-yl)-6-(4-fluorophenyl)pyridin-2-yl)oxy)-1-methyl-3-azabicyclo[3.1.0]hexane-3-carboxylate (enantiomer 2, 0.30 mg, 0.52 mmol) in DCM (5.0 mL) was added TFA (1.0 mL). The resulting mixture was stirred at rt for 1 h. The mixture was concentrated under reduced pressure to afford the title compound.

Utilizing the procedures described in the synthesis of Intermediate I-1, the following compound was prepared substituting the appropriate reagents for benzyl (2-(2-chloro-6-(4-fluorophenyl)pyridin-4-yl)propan-2-yl)carbamate.

| Int. | Structure | Name | Comments |
|---|---|---|---|
| I-2 | 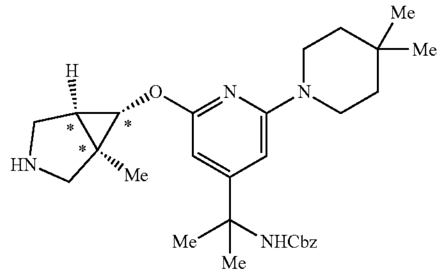 [SMILES: CC1(C)CCN(c2cc(C(C)(C)NC(=O)OCc3ccccc3)cc(O[C@H]3[C@@H]4CNC[C@@]43C)n2)CC1] | benzyl rac-(2-(2-(4,4-dimethylpiperidin-1-yl)-6-(((1R,5S,6S)-1-methyl-3-azabicyclo[3.1.0]hexan-6-yl)oxy)pyridin-4-yl)propan-2-yl)carbamate | Step 1: Int. C-04 (1.9 mmol), Int. F (1.9 mmol), Ad-BippyPhos (0.19 mmol), $Pd_2(dba)_3$ (0.096 mmol), $Cs_2CO_3$ (5.8 mmol), PhMe (0.020 mL), 90° C., 16 h |

Intermediate J

Benzyl (2-(2-(((1R,5S,6s)-3-(2-chloro-4-(difluoromethyl)thiazole-5-carbonyl)-3-azabicyclo[3.1.0]hexan-6-yl)oxy)-6-(4-fluorophenyl)pyridin-4-yl)propan-2-yl)carbamate

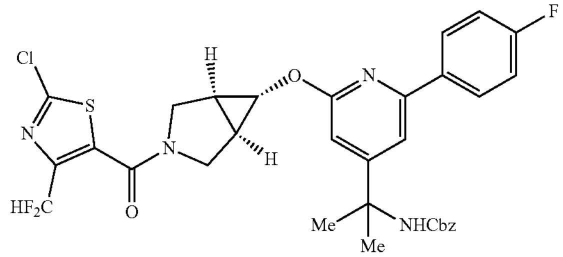

A mixture of 2-chloro-4-(difluoromethyl)thiazole-5-carboxylic acid (0.12 g, 0.54 mmol), benzyl (2-(2-(((1R,5S,6s)-3-azabicyclo[3.1.0]hexan-6-yl)oxy)-6-(4-fluorophenyl)pyridin-4-yl)propan-2-yl)carbamate (Int. H-02, 0.25 g, 0.54 mmol), HATU (0.21 g, 0.54 mmol), DIPEA (0.28 mL, 1.6 mmol), and DCM (2.7 mL) was stirred for 1 h at rt. The mixture was subjected to silica gel chromatography (0-40% (25% EtOH/EtOAc)/hexanes) to afford the title compound.

Scheme:

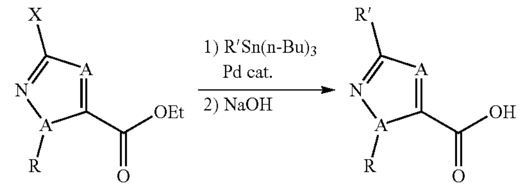

Intermediate K-01

4-methyl-2-(oxazol-2-yl)thiazole-5-carboxylic acid

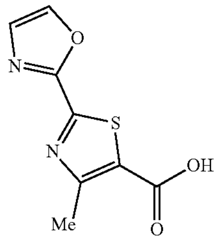 [SMILES: Cc1nc(-c2ncco2)sc1C(=O)O]

Step 1: ethyl 4-methyl-2-(oxazol-2-yl)thiazole-5-carboxylate

Under an atmosphere of nitrogen, a mixture of ethyl 2-bromo-4-methylthiazole-5-carboxylate (0.15 g, 0.60 mmol), 2-(tributylstannyl)oxazole (0.21 g, 0.60 mmol), $Pd(PPh_3)_4$ (69 mg, 0.060 mmol) and 1,4-dioxane (3.0 mL) was stirred at 100° C. for 16 h. The mixture was cooled to rt, filtered, and concentrated under reduced pressure. The residue was subjected to silica gel chromatography (0-60% (3:1 EtOAc/EtOH)/hexanes) to afford the title compound.

Step 2: 4-methyl-2-(oxazol-2-yl)thiazole-5-carboxylic acid

To a solution of ethyl 4-methyl-2-(oxazol-2-yl)thiazole-5-carboxylate (94 mg, 0.40 mmol) in EtOH (1.0 mL) and THF (1.0 mL) was added sodium hydroxide (1.0 N aq., 0.60 mL, 0.60 mmol). The reaction mixture was stirred at rt for 1 h and concentrated under reduced pressure. The crude residue was dissolved in MeOH (1.0 mL), hydrochloric acid (1N, 0.20 mL) was added, and the mixture was concentrated under reduced pressure to afford the title compound.

Utilizing the procedures described in the synthesis of Intermediate K-01, the following compound was prepared substituting the appropriate reagents for 2-(tributylstannyl)oxazole and ethyl 2-bromo-4-methylthiazole-5-carboxylate.

| Int. | Structure | Name |
|---|---|---|
| K-02 | 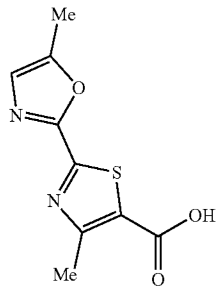 [SMILES: Cc1cnc(-c2nc(C)c(C(=O)O)s2)o1] | 4-methyl-2-(5-methyloxazol-2-yl)thiazole-5-carboxylic acid |
| K-03 | 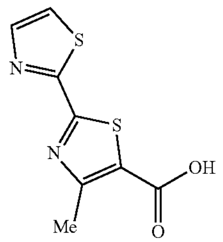 [SMILES: Cc1nc(-c2nccs2)sc1C(=O)O] | 4-methyl-[2,2'-bithiazole]-5-carboxylic acid |
| K-04 | 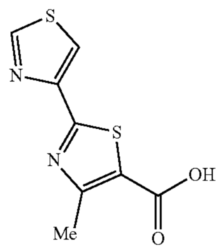 [SMILES: Cc1nc(-c2cscn2)sc1C(=O)O] | 4-methyl-[2,4'-bithiazole]-5-carboxylic acid |

-continued

| Int. | Structure | Name |
|---|---|---|
| K-05 | 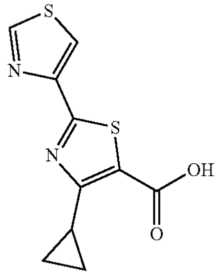 [SMILES: O=C(O)c1sc(-c2cscn2)nc1C1CC1] | 4-cyclopropyl-[2,4'-bithiazole]-5-carboxylic acid |
| K-06 | 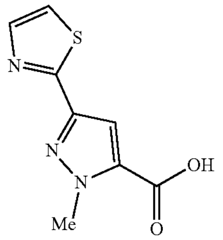 [SMILES: Cn1nc(-c2nccs2)cc1C(=O)O] | 1-methyl-3-(thiazol-2-yl)-1H-pyrazole-5-carboxylic acid |
| K-07 | 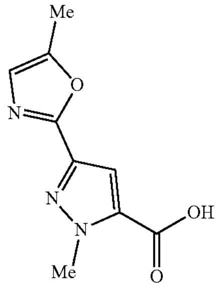 [SMILES: Cc1cnc(-c2cc(C(=O)O)n(C)n2)o1] | 1-methyl-3-(5-methyloxazol-2-yl)-1H-pyrazole-5-carboxylic acid |
| K-08 | 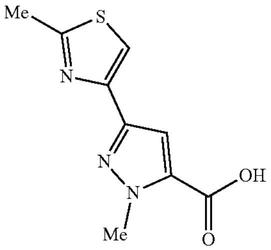 [SMILES: Cc1nc(-c2cc(C(=O)O)n(C)n2)cs1] | 1-methyl-3-(2-methylthiazol-4-yl)-1H-pyrazole-5-carboxylic acid |

Intermediate K-09

1-methyl-3-(thiazol-4-yl)-1H-1,2,4-triazole-5-carboxylic acid

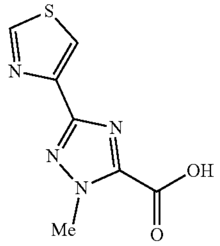 [SMILES: Cn1nc(-c2cscn2)nc1C(=O)O]

Step 1: ethyl 1-methyl-3-(thiazol-4-yl)-1H-1,2,4-triazole-5-carboxylate

To a solution of ethyl 3-bromo-1-methyl-1H-1,2,4-triazole-5-carboxylate (0.090 g, 0.39 mmol) in 1,4-dioxane (8.0 mL) was added 4-(tributylstannyl)thiazole (0.29 g, 0.77 mmol) and $Pd(PPh_3)_4$ (44 mg, 0.040 mmol) under $N_2$ then the mixture was heated at 110° C. for 12 h. The mixture was cooled to rt then a solution of potassium fluoride (saturated aq., 5 mL) was added. After 30 minutes the mixture was extracted with EtOAc (3×). The combined organic extracts were washed with brine, dried over anhydrous sodium sulfate, filtered, and concentrated. The residue was purified by prep-TLC (50% EtOAc/petroleum ether) to afford the title compound.

Step 2: 1-methyl-3-(thiazol-4-yl)-1H-1,2,4-triazole-5-carboxylic acid

To a mixture of ethyl 1-methyl-3-(thiazol-4-yl)-1H-1,2,4-triazole-5-carboxylate (0.080 g, 0.34 mmol) in THF (5.0 mL) and $H_2O$ (3.0 mL) was added LiOH (16 mg, 0.67 mmol). The mixture was stirred at rt for 2 h. The mixture was concentrated to remove volatile organic solvents then washed with DCM (2×). The aqueous solution was acidified (pH=6) with hydrochloric acid (1 N) and concentrated under reduced pressure. MeOH (5 mL) and DCM (5 mL) were added, and the mixture was stirred at rt for 1 h. The mixture was filtered and concentrated under reduced pressure to afford the title compound.

Scheme:

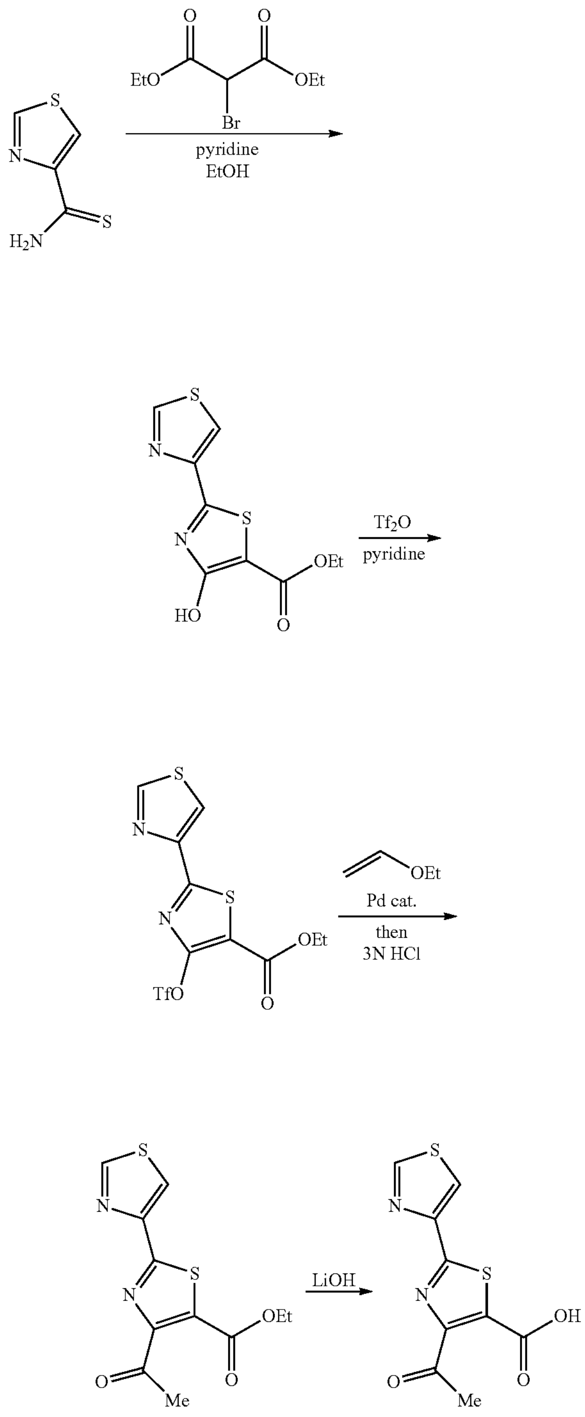

Intermediate K-10

4-acetyl-[2,4'-bithiazole]-5-carboxylic acid

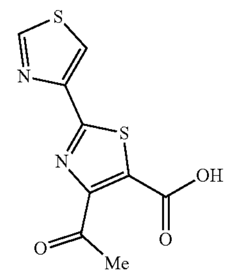 [SMILES: CC(=O)c1nc(-c2cscn2)sc1C(=O)O]

Step 1: ethyl 4-hydroxy-[2,4'-bithiazole]-5-carboxylate

A solution of thiazole-4-carbothioamide (0.70 g, 4.9 mmol), diethyl 2-bromomalonate (1.3 g, 5.3 mmol) and pyridine (1.6 mL, 19 mmol) in EtOH (0.020 L) was stirred at 80° C. under an atmosphere of nitrogen for 12 h. The mixture was cooled to rt and filtered. The filter cake was dried under reduced pressure to afford the title compound.

Step 2: ethyl 4-(((trifluoromethyl)sulfonyl)oxy)-[2,4'-bithiazole]-5-carboxylate Trifluoromethanesulfonic anhydride (0.20 mL, 1.2 mmol) was added dropwise to a solution of ethyl 4-hydroxy-[2,4'-bithiazole]-5-carboxylate (0.20 mL, 2.3 mmol) in DCM (7.0 mL) at 0° C. under an atmosphere of nitrogen. Then the mixture was warmed to rt and stirred for 12 h. The mixture was concentrated under reduced pressure and the residue was subjected to prep-TLC (25% EtOAc/petroleum ether) to afford the title compound.

Step 3: ethyl 4-acetyl-[2,4'-bithiazole]-5-carboxylate

Under an atmosphere of nitrogen, a mixture of ethyl 4-(((trifluoromethyl)sulfonyl)oxy)-[2,4'-bithiazole]-5-carboxylate (0.49 g, 1.2 mmol), PhMe (0.010 L), triethylamine (0.50 mL, 3.8 mmol), 1,3-bis(diphenylphosphino)propane (77 mg, 0.19 mmol), ethoxyethene (1.1 g, 15 mmol), and $Pd(OAc)_2$ (42 mg, 0.19 mmol) was stirred at 110° C. for 12 h. The mixture was concentrated under reduced pressure. EtOAc (30 mL) was added, and the solution was washed with brine (10 mL×2), dried over anhydrous sodium sulfate, filtered, and concentrated under reduced pressure. THF (8.0 mL) and hydrochloric acid (3.0N, 2.0 mL, 6.0 mmol) were added and the mixture stirred at rt for 1 h. Water (10 mL) was added to the mixture and extracted with EtOAc (15 mL×3). The combined organic solution was washed with brine (15 mL), dried over anhydrous sodium sulfate, filtered, and concentrated under reduced pressure. The residue was subjected to silica gel chromatography (0-30% EtOAc/petroleum ether) to afford the title compound.

Step 4: 4-acetyl-[2,4'-bithiazole]-5-carboxylic acid

To a mixture of ethyl 4-acetyl-[2,4'-bithiazole]-5-carboxylate (0.050 g, 0.18 mmol) in EtOH (2.0 mL) and water (2.0 mL) was added LiOH (11 mg, 0.44 mmol). The mixture was stirred at rt for 1 h. The mixture was concentrated, and the aqueous layer was washed with DCM (10 mL×2). The aqueous phase was acidified (pH=4) with hydrochloric acid (1 N) and extracted with EtOAc (10 mL×3). The combined organic solution was dried over anhydrous sodium sulfate, filtered, and concentrated under reduced pressure to afford the title compound.

Scheme:

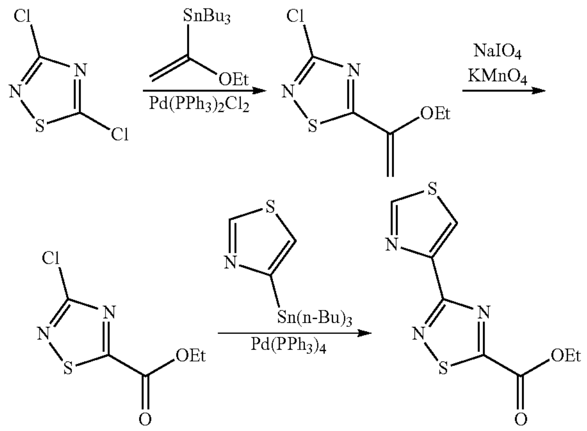

Intermediate K-11

Ethyl 3-(thiazol-4-yl)-1,2,4-thiadiazole-5-carboxylate

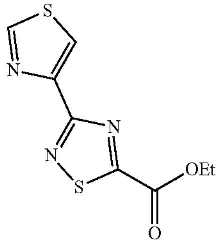 [SMILES: CCOC(=O)c1nc(-c2cscn2)ns1]

Step 1: 3-chloro-5-(1-ethoxyvinyl)-1,2,4-thiadiazole

Under an atmosphere of nitrogen, a mixture of 3,5-dichloro-1,2,4-thiadiazole (6.3 g, 41 mmol), tributyl(1-ethoxyvinyl)stannane (14 mL, 41 mmol), bis(triphenylphosphine)palladium(II) dichloride (2.9 g, 4.1 mmol), and DMF (0.060 L) was stirred at 60° C. for 12 h. The mixture was cooled to rt and a solution of potassium fluoride (saturated aq., 10 mL) was added. The mixture was stirred for 30 min and extracted with EtOAc (30 mL×3). The combined organic mixture was washed with brine (20 mL), dried over anhydrous sodium sulfate, filtered, and concentrated under reduced pressure. The residue was subjected to silica gel chromatography (0-5% EtOAc/petroleum ether) to afford the title compound.

Step 2: ethyl 3-chloro-1,2,4-thiadiazole-5-carboxylate

To a mixture of 3-chloro-5-(1-ethoxyvinyl)-1,2,4-thiadiazole (2.0 g, 11 mmol), 1,4-dioxane (15 mL), and $H_2O$ (5.0 mL) was added $NaIO_4$ (4.5 g, 21 mmol) and $KMnO_4$ (0.33 g, 2.1 mmol). The mixture was stirred at rt for 1 h. A solution of $NaHCO_3$ (saturated aq., 0.010 L) was added and the mixture was stirred at rt for 30 min. The mixture was extracted with EtOAc (20 mL×3). The combined organic solution was washed with brine (20 mL), dried over anhydrous sodium sulfate, filtered, and concentrated under reduced pressure. The residue was subjected to silica gel chromatography (0-5% EtOAc/petroleum ether) to afford the title compound.

Step 3: ethyl 3-(thiazol-4-yl)-1,2,4-thiadiazole-5-carboxylate

To a solution of ethyl 3-chloro-1,2,4-thiadiazole-5-carboxylate (0.18 g, 0.93 mmol) in 1,4-dioxane (0.010 L) was added 4-(tributylstannyl)thiazole (0.42 g, 1.1 mmol) and $Pd(PPh_3)_4$ (0.11 g, 0.093 mmol) under $N_2$. The mixture was heated at 100° C. for 15 h. The mixture was cooled to rt and a solution of potassium fluoride (saturated aq., 10 mL) was added. The mixture was stirred at rt for 30 min and extracted with EtOAc (3×). The combined organic extracts were washed with brine, dried over anhydrous sodium sulfate, filtered, and concentrated. The residue was subjected to silica gel chromatography (0-30% EtOAc/petroleum ether) to afford the title compound.

Scheme:

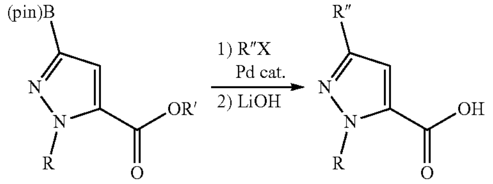

Intermediate L-1

1-methyl-3-(thiazol-4-yl)-1H-pyrazole-5-carboxylic acid

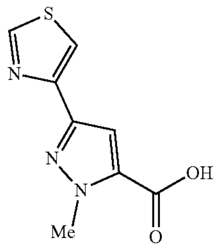 [SMILES: Cn1nc(-c2cscn2)cc1C(=O)O]

Step 1: methyl 1-methyl-3-(thiazol-4-yl)-1H-pyrazole-5-carboxylate

To a mixture of methyl 1-methyl-3-(4,4,5,5-tetramethyl-1,3,2-dioxaborolan-2-yl)-1H-pyrazole-5-carboxylate (2.0 g, 7.5 mmol), 4-bromothiazole (1.2 g, 7.5 mmol) and $Na_2CO_3$ (2.4 g, 23 mmol) in DME (0.040 L) and water (4.0 mL) was added [1,1'-bis(di-tert-butylphosphino)ferrocene]dichloropalladium(II) (0.25 g, 0.38 mmol) at 25° C. The mixture was stirred at 90° C. for 12 h. The reaction mixture was diluted with water (15 mL) and extracted with EtOAc (30 mL×3). The combined organic solution was washed with brine (20 mL×2), dried over anhydrous $Na_2SO_4$, filtered, and concentrated under reduced pressure. The residue was subjected to silica gel chromatography (20-35% EtOAc/petroleum ether) to afford the title compound.

Step 2: 1-methyl-3-(thiazol-4-yl)-1H-pyrazole-5-carboxylic acid

To a mixture of methyl 1-methyl-3-(thiazol-4-yl)-1H-pyrazole-5-carboxylate (1.2 g, 5.4 mmol) in THF (0.010 L) and water (0.010 L) was added LiOH (0.64 g, 27 mmol). The mixture was stirred at rt for 0.5 h. The mixture was concentrated under reduced pressure and washed with DCM (10 mL×2). The aqueous solution was acidified (pH=4) with a solution of HCl (1N aq.) and concentrated under reduced pressure. MeOH (10 mL) and DCM (10 mL) was added, and the mixture was stirred at 25° C. for 1 h. The mixture was filtered, and filtrate was concentrated under reduced pressure to afford the title compound.

Scheme:

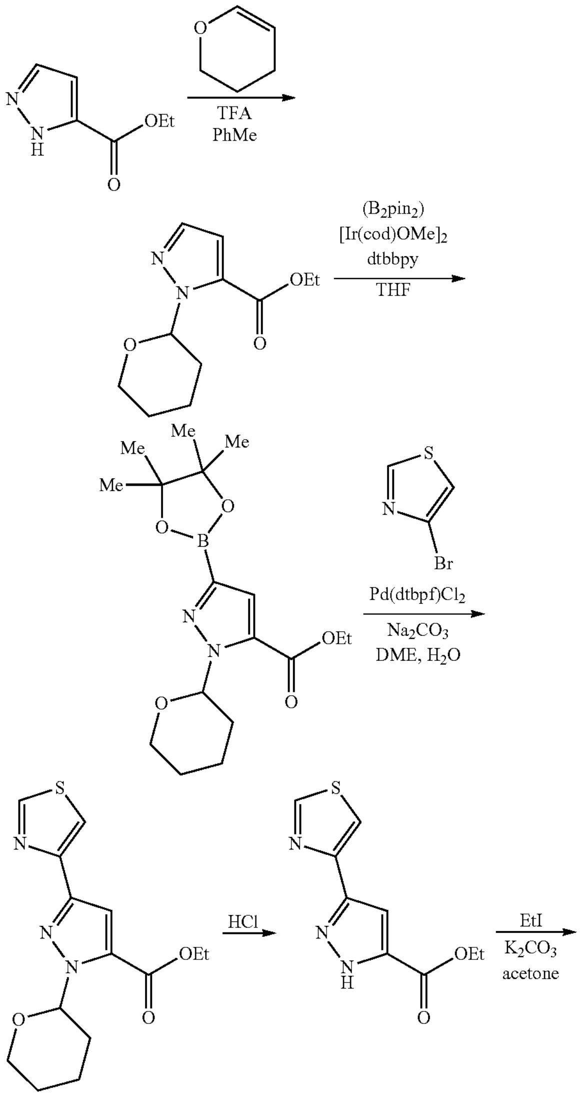

-continued

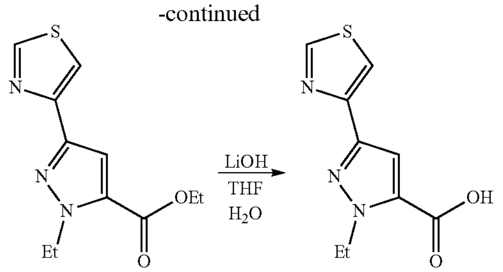

Intermediate L-2

1-ethyl-3-(thiazol-4-yl)-1H-pyrazole-5-carboxylic acid

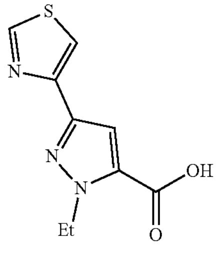 [SMILES: CCn1nc(-c2cscn2)cc1C(=O)O]

Step 1: ethyl 1-(tetrahydro-2H-pyran-2-yl)-1H-pyrazole-5-carboxylate

To a solution of ethyl 1H-pyrazole-5-carboxylate (5.0 g, 36 mmol) in PhMe (0.030 L) were added 3,4-dihydro-2H-pyran (3.2 g, 38 mmol) and TFA (0.027 mL, 0.36 mmol). The mixture was stirred at 80° C. for 2 h. The mixture was concentrated under reduced pressure. Water (30 mL) was added, and the mixture was extracted with EtOAc (30 mL×3). The combined organic solution was dried over anhydrous sodium sulfate, filtered, and concentrated under reduced pressure. The residue was subjected to silica gel chromatography (0-60% EtOAc/petroleum ether) to afford the title compound.

Step 2: ethyl 1-(tetrahydro-2H-pyran-2-yl)-3-(4,4,5,5-tetramethyl-1,3,2-dioxaborolan-2-yl)-1H-pyrazole-5-carboxylate Under an atmosphere of nitrogen, a mixture of ethyl 1-(tetrahydro-2H-pyran-2-yl)-1H-pyrazole-5-carboxylate (4.8 g, 21 mmol), 4,4,4',4',5,5,5',5'-octamethyl-2,2'-bi(1,3,2-dioxaborolane) (5.4 g, 21 mmol), 4,4'-di-tert-butyl-2,2'-bipyridine (0.57 g, 2.1 mmol), $[Ir(cod)OMe]_2$ (0.71 g, 1.1 mmol), and THF (0.080 L) were stirred at 80° C. for 12 h. Water (20 mL) was added and the mixture was extracted with EtOAc (30 mL×3). The combined organic solution was washed with brine (20 mL×3), dried over anhydrous sodium sulfate, filtered, concentrated under reduced pressure. The residue was subjected to reverse-phase chromatography (35% MeCN/water) to afford the title compound.

Step 3: ethyl 1-(tetrahydro-2H-pyran-2-yl)-3-(thiazol-4-yl)-1H-pyrazole-5-carboxylate A mixture of ethyl 1-(tetrahydro-2H-pyran-2-yl)-3-(4,4,5,5-tetramethyl-1,3,2-dioxaborolan-2-yl)-1H-pyrazole-5- carboxylate (1.0 g, 2.9 mmol), 4-bromothiazole (0.70 g, 4.3 mmol), [1,1'-bis(di-tert-butylphosphino)ferrocene]dichloropalladium(II) (0.19 g, 0.29 mmol), $Na_2CO_3$ (0.91 g, 8.6 mmol), DME (0.040 L) and water (4.0 mL) was stirred at 100° C. for 12 h. Water (30 mL) was added, and the mixture was extracted with EtOAc (30 mL×3). The combined organic solution was washed with brine (30 mL×3), dried over anhydrous sodium sulfate, filtered, and concentrated under reduced pressure. The residue was subjected to silica gel chromatography (0-50% EtOAc/petroleum ether) to afford the title compound.

Step 4: ethyl 3-(thiazol-4-yl)-1H-pyrazole-5-carboxylate

A solution of ethyl 1-(tetrahydro-2H-pyran-2-yl)-3-(thiazol-4-yl)-1H-pyrazole-5-carboxylate (0.85 g, 2.8 mmol) in hydrochloric acid (37%, 2.0 mL) was stirred at 80° C. for 10 min. The mixture was concentrated under reduced pressure to afford the title compound.

Step 5: ethyl 1-ethyl-3-(thiazol-4-yl)-1H-pyrazole-5-carboxylate

Under an atmosphere of nitrogen, a mixture of ethyl 3-(thiazol-4-yl)-1H-pyrazole-5-carboxylate (0.52 g, 2.3 mmol), $K_2CO_3$ (0.97 g, 7.0 mmol), iodoethane (0.90 mL, 12 mmol), and acetone (0.030 L) was heated at 70° C. for 19 h. The mixture was cooled to rt, filtered, and concentrated under reduced pressure. EtOAc (50 mL) was added, and the mixture was washed with water (50 mL), hydrochloric acid (1 N, 50 mL), and brine (50 mL). The mixture was concentrated under reduced pressure and subjected to silica gel chromatography (0-50% EtOAc/petroleum ether) to afford the title compound.

Step 6: 1-ethyl-3-(thiazol-4-yl)-1H-pyrazole-5-carboxylic acid

To a mixture of ethyl 1-ethyl-3-(thiazol-4-yl)-1H-pyrazole-5-carboxylate (0.030 g, 0.12 mmol) in THF (2.0 mL) and water (2.0 mL) was added LiOH (8.6 mg, 0.36 mmol). The mixture was stirred at rt for 2 h. The mixture was concentrated under reduced pressure and washed with DCM (10 mL×2). The aqueous solution was acidified (pH=4) with hydrochloric acid (1N) and the mixture was concentrated under reduced pressure. MeOH/DCM (1:5, 20 mL) was added and the mixture was stirred at rt for 1 h. The mixture was filtered and concentrated under reduced pressure to afford the title compound.

Scheme:

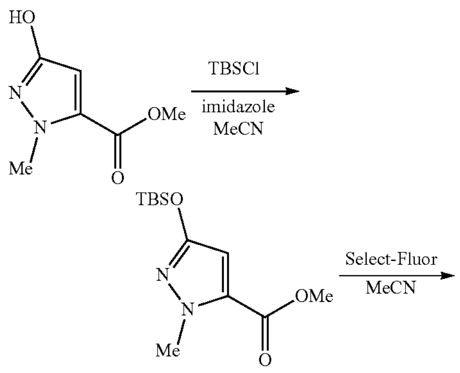

-continued

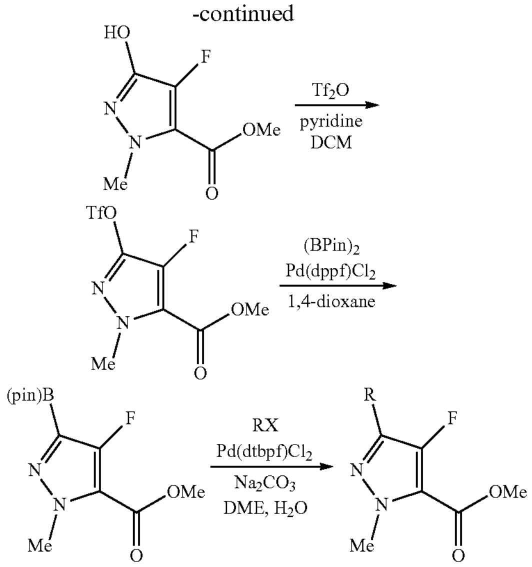

Intermediate M-1 methyl 4-fluoro-1-methyl-3-(oxazol-2-yl)-1H-pyrazole-5-carboxylate

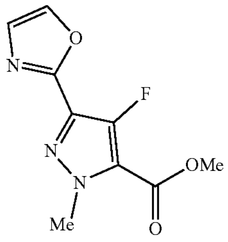 [SMILES: COC(=O)c1c(F)c(-c2ncco2)nn1C]

Step 1: methyl 3-((tert-butyldimethylsilyl)oxy)-1-methyl-1H-pyrazole-5-carboxylate To a rt solution of methyl 3-hydroxy-1-methyl-1H-pyrazole-5-carboxylate (5.0 g, 32 mmol) in MeCN (0.050 L) was added imidazole (3.5 g, 51 mmol) and tert-butyldimethylsilyl chloride (7.2 g, 48 mmol). After 1 h, the mixture was diluted with $H_2O$ and extracted with EtOAc (3×). The combined organic extracts were washed with brine, dried over anhydrous sodium sulfate, filtered, and concentrated to afford the title compound.

Step 2: methyl 4-fluoro-3-hydroxy-1-methyl-1H-pyrazole-5-carboxylate

To a solution of methyl 3-((tert-butyldimethylsilyl)oxy)-1-methyl-1H-pyrazole-5-carboxylate (7.5 g, 28 mmol) in MeCN (0.10 L) was added 1-chloromethyl-4-fluoro-1,4-diazoniabicyclo[2.2.2]octane bis(tetrafluoroborate) (15 g, 42 mmol). The mixture was heated at 90° C. for 30 min. The mixture was cooled to rt, diluted with $H_2O$, and extracted with EtOAc (3×). The combined organic extracts were washed with brine, dried over anhydrous sodium sulfate, filtered, and concentrated. The residue was subjected to reverse phase liquid chromatography (74% MeCN/water) to afford the title compound.

Step 3: methyl 4-fluoro-1-methyl-3-(((trifluoromethyl)sulfonyl)oxy)-1H-pyrazole-5-carboxylate To a 0° C. solution of methyl 4-fluoro-3-hydroxy-1-methyl-1H-pyrazole-5-carboxylate (1.1 g, 6.3 mmol) in DCM (12 mL) was added pyridine (0.50 mL, 6.3 mmol) then trifluoromethanesulfonic anhydride (1.2 mL, 7.0 mmol) dropwise. The mixture was slowly warmed to rt and stirred for 2 h. The mixture was diluted with $H_2O$ then extracted with DCM (3×). The combined organic extracts were washed with brine, dried over anhydrous sodium sulfate, filtered, and concentrated to afford the title compound.

Step 4: methyl 4-fluoro-1-methyl-3-(4,4,5,5-tetramethyl-1,3,2-dioxaborolan-2-yl)-1H-pyrazole-5-carboxylate In glovebox, to a solution of methyl 4-fluoro-1-methyl-3-(((trifluoromethyl)sulfonyl)oxy)-1H-pyrazole-5-carboxylate (1.5 g, 4.9 mmol), bis(pinacolato)diboron (1.9 g, 7.4 mmol), and potassium acetate (1.4 g, 15 mmol) in 1,4-dioxane (15 mL) was added $Pd(dppf)Cl_2$ (0.18 g, 0.25 mmol). The mixture was stirred at 90° C. for 12 h. The mixture was cooled to rt, diluted with PhMe and $H_2O$, and filtered through a pad of celite. The filtrate layers were separated, and the aqueous layer extracted with PhMe (3×). The combined organic extracts were washed with brine, dried over anhydrous sodium sulfate, filtered, and concentrated. The residue was slurried in pentane, filtered, and the filtrate was concentrated to afford the title compound.

Step 5: methyl 4-fluoro-1-methyl-3-(oxazol-2-yl)-1H-pyrazole-5-carboxylate

Under an atmosphere of nitrogen, a mixture of methyl 4-fluoro-1-methyl-3-(4,4,5,5-tetramethyl-1,3,2-dioxaborolan-2-yl)-1H-pyrazole-5-carboxylate (1.5 g, 2.6 mmol), 2-bromooxazole (0.39 g, 2.6 mmol), $Na_2CO_3$ (0.84 g, 7.9 mmol), $Pd(dtbpf)Cl_2$ (0.086 g, 0.13 mmol), DME (0.020 L), and $H_2O$ (2.0 mL) was heated to 90° C. for 2 h. The mixture was cooled to rt, diluted with $H_2O$, and extracted with EtOAc (3×). The combined organic extracts were washed with brine, dried over anhydrous sodium sulfate, filtered, and concentrated. The residue was purified by prep-TLC (25% EtOAc/petroleum ether) to afford the title compound. Utilizing the procedures described in the synthesis of Intermediate M-1, the following compound was prepared substituting the appropriate reagents for 2-bromooxazole in Step 5.

| Int. # | Structure | Name |
| --- | --- | --- |
| M-2 | 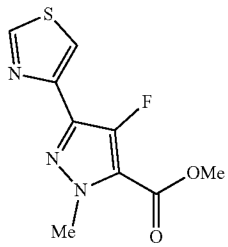 [SMILES: COC(=O)c1c(F)c(-c2cscn2)nn1C] | methyl 4-fluoro-1-methyl-3-(thiazol-4-yl)-1H-pyrazole-5-carboxylate |

Scheme:

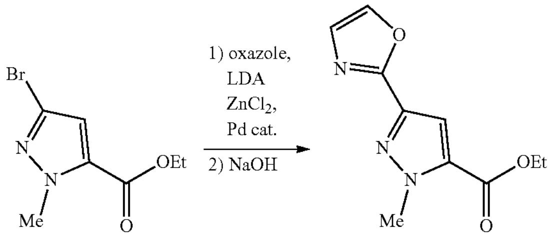 [SMILES: CCOC(=O)c1cc(Br)nn1C ; CCOC(=O)c1cc(-c2ncco2)nn1C]

Intermediate N 1-methyl-3-(oxazol-2-yl)-1H-pyrazole-5-carboxylic acid

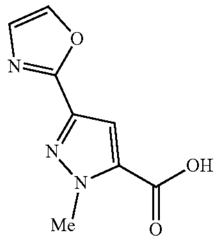 [SMILES: Cn1nc(-c2ncco2)cc1C(=O)O]

Step 1: ethyl 1-methyl-3-(oxazol-2-yl)-1H-pyrazole-5-carboxylate

To a −15° C. solution of oxazole (0.42 mL, 6.4 mmol) in THF (21 mL) was added a solution of lithium bis(trimethylsilyl)amide (1.0 M in THF, 8.6 mL, 8.6 mmol) dropwise over 15 min. The mixture was stirred at −15° C. for 30 min. A solution of zinc chloride (0.50M in THF, 28 mL, 14 mmol) was injected and the mixture was stirred at −15° C. for 15 min. The solution was warmed to rt, stirred for 30 min, and added to a mixture of ethyl 3-bromo-1-methyl-1H-pyrazole-5-carboxylate (1.0 g, 4.3 mmol) and $Pd(dppf)Cl_2$ (0.16 g, 0.22 mmol). The mixture was stirred at 75° C. for 12 h. The mixture was cooled to rt, $NH_4Cl$ (saturated aq., 50 mL) and EtOAc (75 mL) were added, and the mixture was washed with water (75 mL) and brine (75 mL). The organic solution was dried over anhydrous magnesium sulfate, filtered, and concentrated under reduced pressure. The residue was subjected to silica gel chromatography (0-15% (25% EtOH/EtOAc)/hexanes) to afford the title compound.

Step 2: 1-methyl-3-(oxazol-2-yl)-1H-pyrazole-5-carboxylic acid

To a solution of ethyl 1-methyl-3-(oxazol-2-yl)-1H-pyrazole-5-carboxylate (0.85 g, 3.8 mmol) in EtOH (9.6 mL) and THF (9.6 mL) was added a solution of sodium hydroxide (1.0N aq., 5.8 mL, 5.8 mmol). The mixture was stirred at rt for 4 h and concentrated under reduced pressure. The mixture was dissolved in a solution of sodium hydroxide (0.05 M aq., 75 mL) and washed with DCM (50 mL×3). The aqueous solution was acidified (pH=1) with hydrochloric acid (1N). The mixture was stirred at rt for 12 h, filtered, and the filter cake was washed with water (10 mL×3). The filter cake was subjected to reverse phase HPLC (0-90% MeCN/water with 0.1% TFA modifier) to afford the title compound.

Scheme:

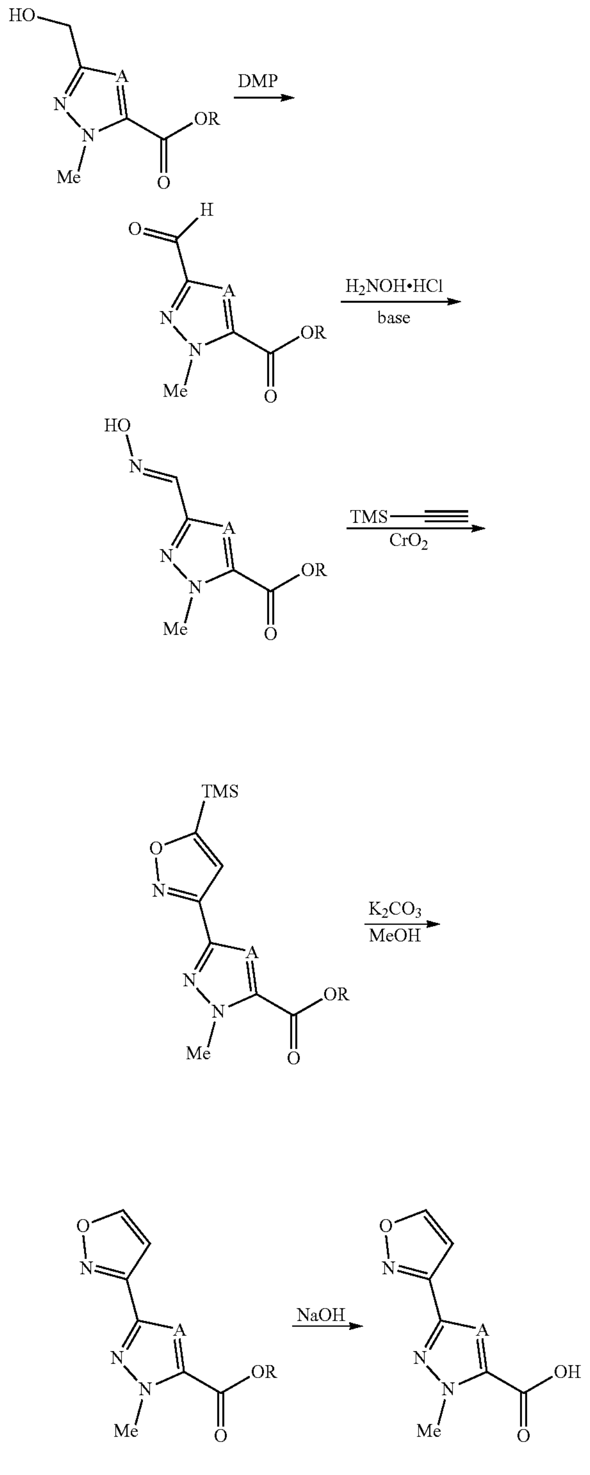

Intermediate 0-1

2-(isoxazol-3-yl)-4-methylthiazole-5-carboxylic acid

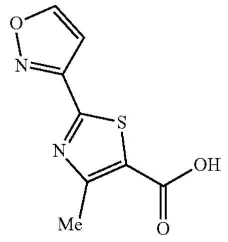 [SMILES: Cc1nc(-c2ccon2)sc1C(=O)O]

Step 1: methyl 2-formyl-4-methylthiazole-5-carboxylate

To a solution of methyl 2-(hydroxymethyl)-4-methylthiazole-5-carboxylate (0.50 g, 2.7 mmol) in DCM (13 mL) was added 1,1,1-tris(acetyloxy)-1,1-dihydro-1,2-benziodoxol-3-(1H)-one (1.4 g, 3.2 mmol). The mixture was stirred at ambient temperature for 1 h. DCM (10 mL), $Na_2S_2O_3$ (saturated aq., 5 mL), $NaHCO_3$ (saturated aq., 5 mL) were added, and the mixture was stirred for 10 min. The layers were separated, and the aqueous layer was back-extracted with DCM (10 mL). The combined organic solution was dried over anhydrous sodium sulfate, filtered, and concentrated under reduced pressure to afford the title compound.

Step 2: methyl 2-((hydroxyimino)methyl)-4-methylthiazole-5-carboxylate

To a mixture of methyl 2-formyl-4-methylthiazole-5-carboxylate (0.50 g, 2.7 mmol) and hydroxylamine hydrochloride (0.19 g. 2.7 mmol) in EtOH (13 mL) was added pyridine (0.22 mL, 2.7 mmol). The reaction mixture was stirred at ambient temperature for 30 min and concentrated under reduced pressure to afford the title compound.

Step 3: methyl 4-methyl-2-(5-(trimethylsilyl)isoxazol-3-yl)thiazole-5-carboxylate A mixture of methyl 2-((hydroxyimino)methyl)-4-methylthiazole-5-carboxylate (0.15 g, 0.75 mmol), $CrO_2$ (0.63 g, 7.5 mmol), trimethylsilylacetylene (0.32 mL, 2.3 mmol), and MeCN (7.5 mL) was stirred at 80° C. overnight. The reaction mixture was filtered through celite and concentrated under reduced pressure. The residue was subjected to silica gel chromatography (0-20% EtOAc/hexanes) to afford the title compound.

Step 4: methyl 2-(isoxazol-3-yl)-4-methylthiazole-5-carboxylate

A suspension of methyl 4-methyl-2-(5-(trimethylsilyl)isoxazol-3-yl)thiazole-5-carboxylate (0.080 g, 0.27 mmol) and potassium carbonate (37 mg, 0.27 mmol) in MeOH (1.5 mL) was stirred at ambient temperature for 1 h and concentrated under reduced pressure. EtOAc (5 mL) was added, and the mixture was washed with $NaHCO_3$ (saturated aq., 5 mL) and brine (5 mL). The organic solution was dried over anhydrous sodium sulfate, filtered, and concentrated under reduced pressure to afford the title compound.

Step 5: 2-(isoxazol-3-yl)-4-methylthiazole-5-carboxylic acid

To a solution of methyl 2-(isoxazol-3-yl)-4-methylthiazole-5-carboxylate (58 mg, 0.26 mmol) in MeOH (1.0 mL) was added a solution of sodium hydroxide (1.0N aq., 0.26 mL, 0.52 mmol). The reaction mixture was stirred at for 80° C. for 1 h and concentrated under reduced pressure. The crude residue was dissolved in EtOAc (3.0 mL), washed with hydrochloric acid (1N), dried over anhydrous sodium sulfate, filtered and concentrated to afford the title compound.

Utilizing the procedures described in the synthesis of Intermediate 0-1, the following compound was prepared substituting the appropriate reagents for methyl 2-formyl-4-methylthiazole-5-carboxylate.

| Int. | Structure | Name | Comments |
|---|---|---|---|
| O-2 | 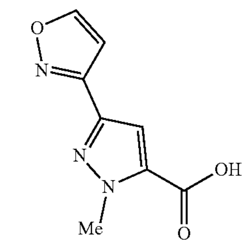 [SMILES: Cn1nc(-c2ccon2)cc1C(=O)O] | 3-(isoxazol-3-yl)-1-methyl-1H-pyrazole-5-carboxylic acid | Step 2: ethyl 3-formyl-1-methyl-1H-pyrazole-5-carboxylate (2.7 mmol), $NH_2$—OH•HCl (3.3 mmol), NaOH (3.3 mmol), EtOH/$H_2O$ (3:1), 65° C., 1 h |

Scheme:

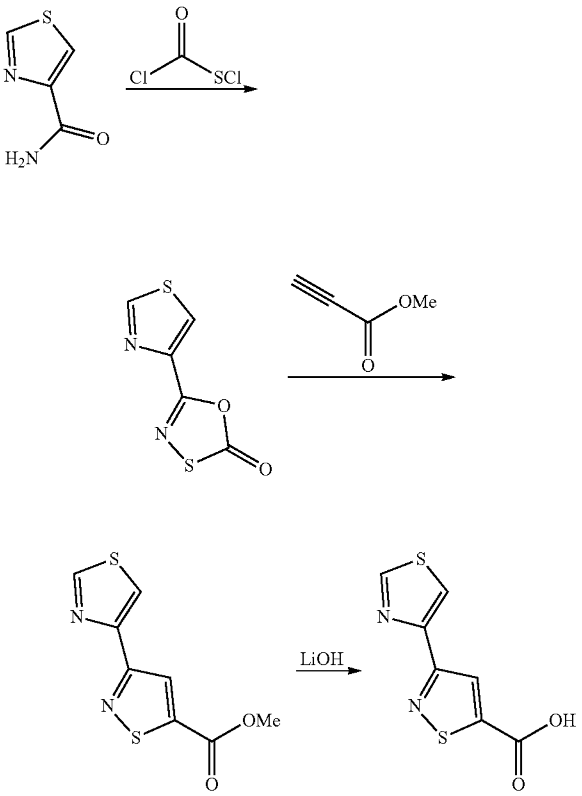

Intermediate P 3-(thiazol-4-yl)isothiazole-5-carboxylic acid

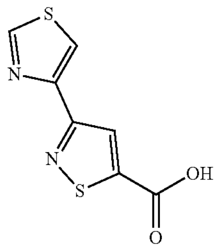 [SMILES: O=C(O)c1cc(-c2cscn2)ns1]

Step 1: 5-(thiazol-4-yl)-1,3,4-oxathiazol-2-one

To a mixture of thiazole-4-carboxamide (0.50 g, 3.9 mmol) in THF (8.0 mL) was added carbonochloridic hypochlorous thioanhydride (0.60 mL, 7.0 mmol) under an atmosphere of nitrogen at 0° C. The resulting mixture was stirred at 25° C. for 12 h. The organic layer was concentrated under reduced pressure to afford the title compound.

Step 2: methyl 3-(thiazol-4-yl)isothiazole-5-carboxylate

To a mixture of 5-(thiazol-4-yl)-1,3,4-oxathiazol-2-one (0.30 g, 1.6 mmol) in xylene (5.0 mL) was added methyl propiolate (2.0 mL, 32 mmol) under an atmosphere of nitrogen at 25° C. The resulting mixture was stirred at 145° C. for 3 d. The mixture was concentrated under reduced pressure. The residue was subjected to prep-TLC (25% EtOAc/petroleum ether) to afford the title compound.

Step 3: 3-(thiazol-4-yl)isothiazole-5-carboxylic acid

To a mixture of methyl 3-(thiazol-4-yl)isothiazole-5-carboxylate (130 mg, 0.55 mmol) in MeOH (3.0 mL) and water (3.0 mL) was added LiOH (27 mg, 1.1 mmol). The mixture was stirred at 25° C. for 2 h. The mixture was concentrated under reduced pressure and the aqueous layer was washed with DCM (5 mL×2). The aqueous solution was acidified (pH=4) with hydrochloric acid (1 N). The aqueous phase was extracted with EtOAc (10 mL×3). The combined organic solution was washed with brine (10 mL), dried over anhydrous $Na_2SO_4$, filtered and concentrated under reduced pressure to afford the title compound.

Intermediate Q 3-(5-fluorothiazol-4-yl)-1-methyl-1H-pyrazole-5-carboxylic acid

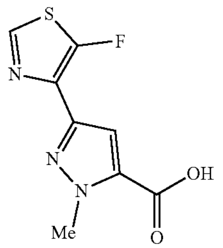 [SMILES: Cn1nc(-c2ncsc2F)cc1C(=O)O]

Step 1: methyl 3-(5-fluorothiazol-4-yl)-1-methyl-1H-pyrazole-5-carboxylate

To a solution of methyl 1-methyl-3-(thiazol-4-yl)-1H-pyrazole-5-carboxylate (prepared as in L-1 Step 1, 0.60 g, 2.2 mmol) in MeCN (25 mL) was added (1-chloromethyl-4-fluoro-1,4-diazoniabicyclo[2.2.2]octane bis(tetrafluoroborate) (1.1 g, 3.2 mmol), and the mixture was stirred at 80° C. for 12 hours. A solution of $NaHCO_3$ (saturated aq., 10 mL) was added and the mixture was extracted with DCM (20 mL×3). The combined organic solution was washed with brine (30 mL), dried over anhydrous sodium sulfate, filtered, and concentrated under reduced pressure. The mixture was subjected to reverse phase HPLC (29-49% MeCN/water with 0.1% TFA modifier) and lyophilized to afford the title compound.

Step 2: 3-(5-fluorothiazol-4-yl)-1-methyl-1H-pyrazole-5-carboxylic acid

To a mixture of methyl 3-(5-fluorothiazol-4-yl)-1-methyl-1H-pyrazole-5-carboxylate (0.14 g, 0.58 mmol) in THF (3.0 mL) and water (3.0 mL) was added LiOH (28 mg, 1.2 mmol). The mixture was stirred at 25° C. for 0.5 h. The mixture was concentrated under reduced pressure and extracted with DCM (10 mL×2). The aqueous solution was acidified (pH=4) with hydrochloric acid (1N) and concentrated under reduced pressure. DCM (10 mL) and MeOH (10 mL) were added, and the mixture was stirred at rt for 1 h. The mixture was filtered, and filtrate was concentrated under reduced pressure to afford the title compound.

Scheme:

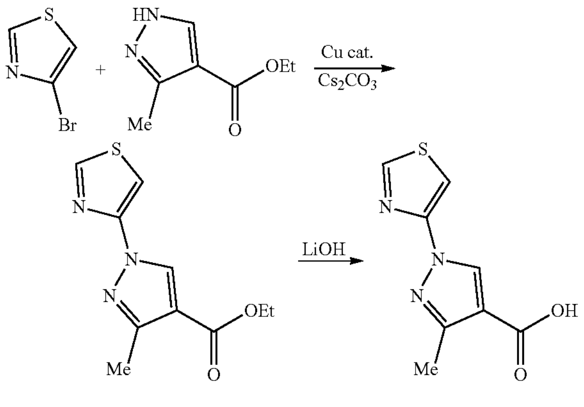

Intermediate R 3-methyl-1-(thiazol-4-yl)-1H-pyrazole-4-carboxylic acid

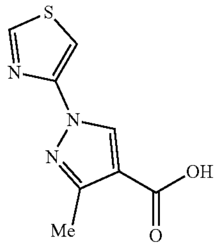 [SMILES: Cc1nn(-c2cscn2)cc1C(=O)O]

Step 1: ethyl 3-methyl-1-(thiazol-4-yl)-1H-pyrazole-4-carboxylate

A mixture of ethyl 3-methyl-1H-pyrazole-4-carboxylate (0.50 g, 3.2 mmol), trans-1,2-diaminocyclohexane (74 mg, 0.65 mmol), 4-bromothiazole (1.1 g, 6.5 mmol), $Cs_2CO_3$ (2.1 g, 6.5 mmol), CuI (62 mg, 0.32 mmol), and DMA (15 mL) was stirred at 100° C. for 12 h. The mixture was cooled to rt, poured into water (20 mL) and extracted with MTBE (20 mL×3). The combined organic solution was washed with brine (20 mL), dried over anhydrous sodium sulfate, filtered, and concentrated under reduced pressure. The residue was subjected to silica gel chromatography (0-80% EtOAc/petroleum ether) to afford the title compound.

Step 2: 3-methyl-1-(thiazol-4-yl)-1H-pyrazole-4-carboxylic acid

To a mixture of ethyl 3-methyl-1-(thiazol-4-yl)-1H-pyrazole-4-carboxylate (0.080 g, 0.34 mmol) in THF (3.0 mL) and water (3.0 mL) was added LiOH (81 mg, 3.4 mmol). The mixture was stirred at rt for 2 h, concentrated under reduced pressure, and washed with DCM (10 mL×2). The aqueous mixture was acidified (pH=4) with hydrochloric acid (1 N) and concentrated under reduced pressure. The material was stirred in MeOH/DCM (20 mL of a 1:10 mixture) at rt for 1 h. The mixture was filtered and concentrated under reduced pressure to afford the title compound.

Scheme:

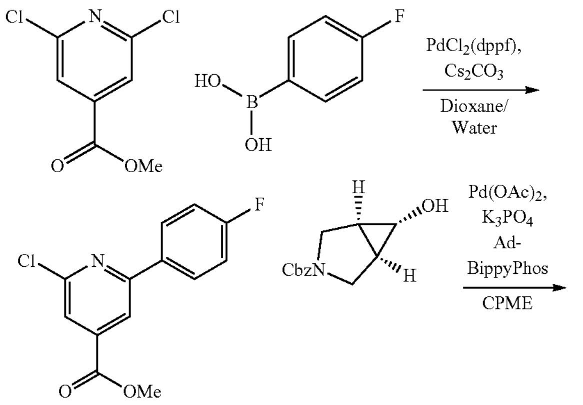

-continued

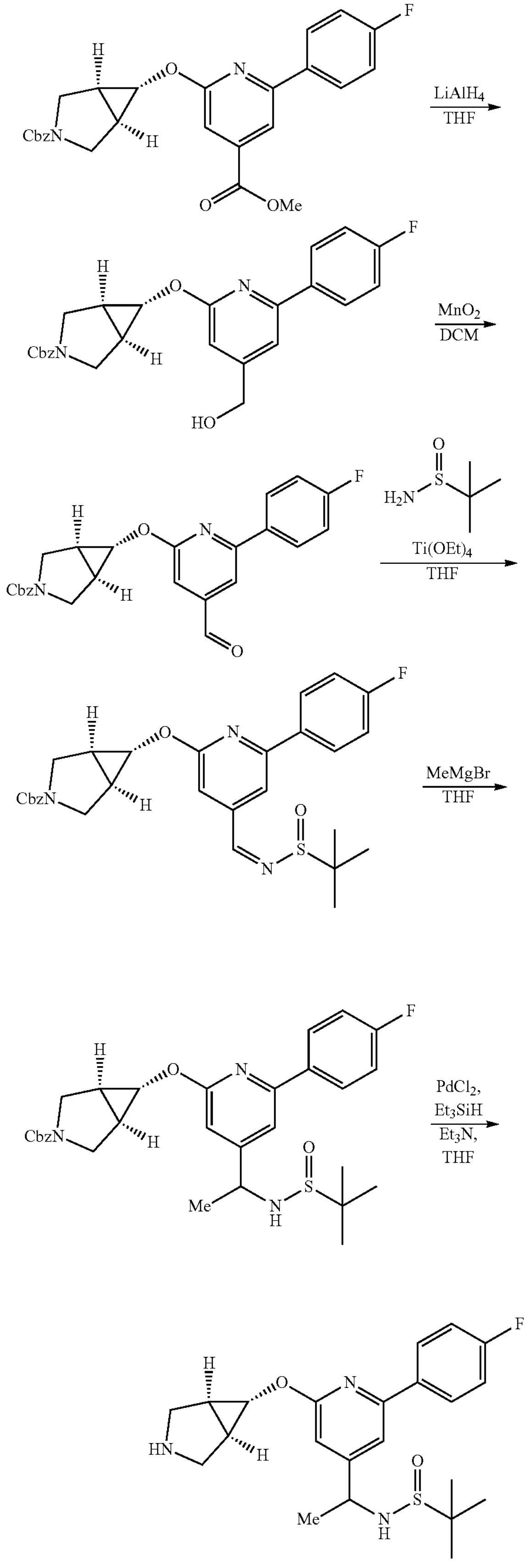

Intermediate S

N-(1-(2-(((1R,5S,6s)-3-azabicyclo[3.1.0]hexan-6-yl)oxy)-6-(4-fluorophenyl)pyridin-4-yl)ethyl)-2-methylpropane-2-sulfinamide

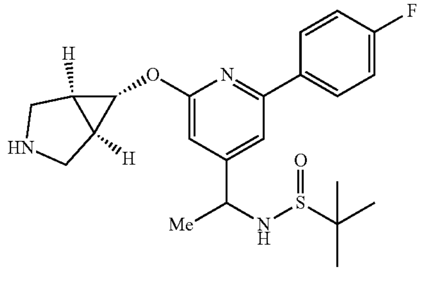 [SMILES: CC(NS(=O)C(C)(C)C)c1cc(O[C@H]2[C@@H]3CNC[C@@H]32)nc(-c2ccc(F)cc2)c1]

Step 1: methyl 2-chloro-6-(4-fluorophenyl)isonicotinate

To a mixture of methyl 2,6-dichloroisonicotinate (0.010 kg, 49 mmol), (4-fluorophenyl)boronic acid (6.6 g, 47 mmol) and $Cs_2CO_3$ (24 g, 73 mmol) in 1,4-dioxane (0.50 L) and water (26 mL) was added $PdCl_2$(dppf) (2.7 g, 3.6 mmol) at 25° C. The mixture was stirred at 25° C. for 12 h. The mixture was filtered and the filtrate was extracted with EtOAc (100 mL×3). The combined organic extracts were washed with brine (50 mL×2), dried over anhydrous sodium sulfate, filtered and concentrated under reduced pressure. The residue was subjected to silica gel chromatography (0-10% EtOAc/petroleum ether) to afford the title compound.

Step 2: benzyl (1R,5S,6s)-6-((6-(4-fluorophenyl)-4-(methoxycarbonyl)pyridin-2-yl)oxy)-3-azabicyclo[3.1.0]hexane-3-carboxylate In glove box, $Pd(OAc)_2$ (85 mg, 0.38 mmol) was added to a solution of benzyl (1R,5S,6s)-6-hydroxy-3-azabicyclo[3.1.0]hexane-3-carboxylate (1.8 g, 7.5 mmol), methyl 2-chloro-6-(4-fluorophenyl)isonicotinate (2.0 g, 7.5 mmol), $K_3PO_4$ (4.8 g, 23 mmol), 5-(di((3S,5S,7S)-adamantan-1-yl)phosphanyl)-1',3',5'-triphenyl-1'H-1,4'-bipyrazole (0.50 g, 0.75 mmol) in CPME (0.020 L) and $CF_3Ph$ (0.020 L). The mixture was heated to 90° C. After 16 h, the mixture was cooled, filtered through silica gel (eluting with EtOAc) and concentrated under reduced pressure. The residue was subjected to silica gel chromatography (0-25% EtOAc/petroleum ether) to afford the title compound.

Step 3: benzyl (1R,5S,6s)-6-((6-(4-fluorophenyl)-4-(hydroxymethyl)pyridin-2-yl)oxy)-3-azabicyclo[3.1.0]hexane-3-carboxylate To a mixture of benzyl (1R,5S,6s)-6-((6-(4-fluorophenyl)-4-(methoxycarbonyl)pyridin-2-yl)oxy)-3-azabicyclo[3.1.0]hexane-3-carboxylate (1.5 g, 3.2 mmol) in THF (15 mL) was added $LiAlH_4$ (1.0 M in THF) (8.1 mL, 8.1 mmol) at −78° C. After 30 min, the reaction was quenched with water (0.20 mL), 15% NaOH (0.60 mL aqueous solution) and additional water (0.20 mL). The reaction was warmed to 0° C. and stirred for 10 min. Anhydrous magnesium sulfate was added and the mixture was filtered and concentrated under reduced pressure to afford the title compound.

Step 4: benzyl (1R,5S,6s)-6-((6-(4-fluorophenyl)-4-formylpyridin-2-yl)oxy)-3-azabicyclo[3.1.0]hexane-3-carboxylate To a mixture of benzyl (1R,5S,6s)-6-((6-(4-fluorophenyl)-4-(hydroxymethyl)pyridin-2-yl)oxy)-3-azabicyclo[3.1.0]hexane-3-carboxylate (0.90 g, 2.1 mmol) in DCM (0.020 L) was added manganese (IV) oxide (1.8 g, 21 mmol) at 25° C. The resulting mixture was stirred at 40° C. for 18 h. The mixture was filtered and concentrated under reduced pressure to afford the title compound.

Step 5: benzyl (1R,5S,6s)-6-((4-((Z)-((tert-butylsulfinyl)imino)methyl)-6-(4-fluorophenyl)pyridin-2-yl)oxy)-3-azabicyclo[3.1.0]hexane-3-carboxylate To a mixture of benzyl (1R,5S,6s)-6-((6-(4-fluorophenyl)-4-formylpyridin-2-yl)oxy)-3-azabicyclo[3.1.0]hexane-3-carboxylate (0.85 g, 2.0 mmol) and 2-methylpropane-2-sulfinamide (0.29 g, 2.4 mmol) in THF (0.020 L) was added tetraethoxytitanium (0.90 g, 3.9 mmol) at 25° C. After 18 h, the reaction mixture was quenched with brine (25 mL). The mixture was filtered and extracted with EtOAc (50 mL×3). The combined organic extracts were dried over anhydrous sodium sulfate, filtered and concentrated under reduced pressure. The residue was purified by silica gel chromatography (0-30% EtOAc/petroleum ether) to afford the title compound.

Step 6: benzyl (1R,5S,6s)-6-((4-(1-((tert-butylsulfinyl)amino)ethyl)-6-(4-fluorophenyl)pyridin-2-yl)oxy)-3-azabicyclo[3.1.0]hexane-3-carboxylate To a mixture of benzyl (1R,5S,6s)-6-((4-((Z)-((tert-butylsulfinyl)imino)methyl)-6-(4-fluorophenyl)pyridin-2-yl)oxy)-3-azabicyclo[3.1.0]hexane-3-carboxylate (0.45 g, 0.84 mmol) in THF (0.010 L) was added methylmagnesium bromide (1.0 M in $Et_2O$) (0.42 mL, 1.3 mmol) at 0° C. The resulting mixture was stirred at 25° C. After 1 h, the reaction mixture was quenched with $NH_4Cl$ (saturated aq., 20 mL) and extracted with EtOAc (25 mL×3). The combined organic extracts were washed with brine (25 mL), dried over anhydrous sodium sulfate, filtered and concentrated under reduced pressure to afford the title compound.

Step 7: N-(1-(2-(((1R,5S,6s)-3-azabicyclo[3.1.0]hexan-6-yl)oxy)-6-(4-fluorophenyl)pyridin-4-yl)ethyl)-2-methylpropane-2-sulfinamide To a solution of benzyl (1R,5S,6s)-6-((4-(1-((tert-butylsulfinyl)amino)ethyl)-6-(4-fluorophenyl)pyridin-2-yl)oxy)-3-azabicyclo[3.1.0]hexane-3-carboxylate (0.43 g, 0.78 mmol) in THF (5.0 mL) was added triethylamine (0.40 mL, 3.1 mmol), triethylsilane (0.45 g, 3.9 mmol) and palladium (II) chloride (28 mg, 0.16 mmol). The mixture was stirred at 25° C. for 1 h. The mixture was filtered and concentrated under reduced pressure to afford the title compound.

Scheme:

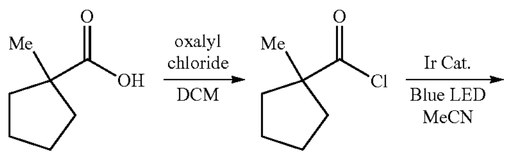

-continued

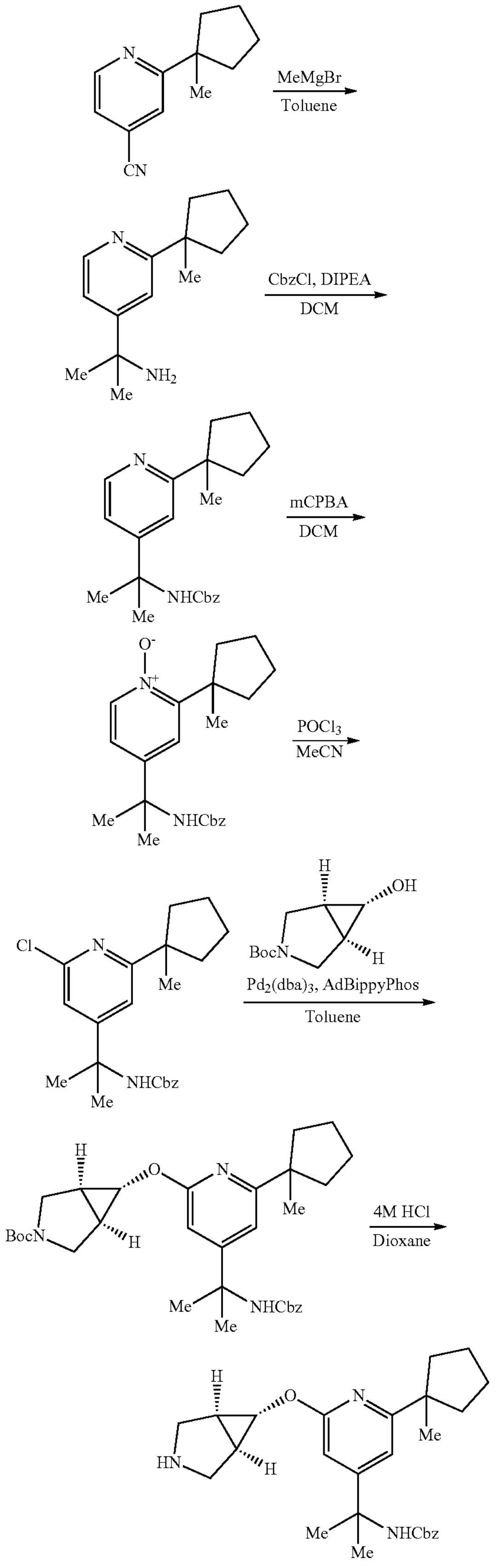

Intermediate T

Benzyl (2-(2-(((1R,5S,6s)-3-azabicyclo[3.1.0]hexan-6-yl)oxy)-6-(1-methylcyclopentyl)pyridin-4-yl)propan-2-yl)carbamate

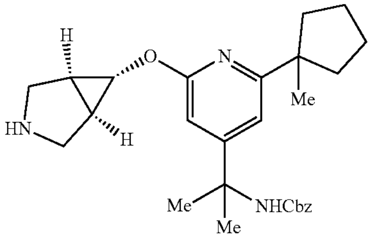 [SMILES: CC1(c2cc(C(C)(C)NC(=O)OCc3ccccc3)cc(O[C@H]3[C@@H]4CNC[C@@H]43)n2)CCCC1]

Step 1: 1-methylcyclopentane-1-carbonyl chloride

To a solution of 1-methylcyclopentane-1-carboxylic acid (1.3 g, 9.8 mmol) in DCM (0.050 L) was added oxalyl chloride (1.1 mL, 13 mmol) followed by two drops of DMF (gas evolution). After 3 h, gas evolution had ceased and the reaction was concentrated under reduced pressure to afford the title compound.

Step 2: 2-(1-methylcyclopentyl)isonicotinonitrile

To a solution of 4-cyanopyridine 1-oxide (0.98 g, 8.1 mmol) and $[Ir[(ppy)_2(dtbbpy)]PF_6$ (74 mg, 0.081 mmol) in MeCN (2.0 mL) was added a solution of 1-methylcyclopentane-1-carbonyl chloride (1.4 g, 9.8 mmol) in MeCN (2.0 mL). The reaction was placed under $N_2$ and irradiated with a Photobox (50% blue LED, fan: 6800 rpm, stir rate: 1200 rpm) at 25° C. After 18 h, the mixture was poured into $NaHCO_3$ (saturated aq.). The resulting mixture was extracted with DCM (3×). The combined organic extracts were dried with anhydrous magnesium sulfate, filtered, and concentrated under reduced pressure. The residue was subjected to silica gel chromatography (0-25% EtOAc/heptane) to afford the title compound Step 3: 2-(2-(1-methylcyclopentyl)pyridin-4-yl)propan-2-amine To a 0° C. solution of 2-(1-methylcyclopentyl)isonicotinonitrile (0.34 g, 1.8 mmol) in toluene (0.010 L) was slowly added MeMgBr (3.0M, 1.9 mL, 5.7 mmol). After 30 min, titanium(IV) isopropoxide (0.55 mL, 1.9 mmol) was added slowly. After 30 min, the reaction was warmed to 25° C. After 18 h, the mixture was quenched with NaOH (2M aq., 1 mL). After 30 min, the mixture was filtered and concentrated under reduced pressure to afford the title compound.

Step 4: benzyl (2-(2-(1-methylcyclopentyl)pyridin-4-yl)propan-2-yl)carbamate

A solution of 2-(2-(1-methylcyclopentyl)pyridin-4-yl)propan-2-amine (0.40 g, 1.8 mmol) in DCM (0.010 L) was cooled to 0° C. To this was added DIPEA (0.48 mL, 2.8 mmol) then CbzCl (0.79 mL, 2.4 mmol). After 30 min the reaction was warmed to 25° C. After 1 h, the reaction was concentrated under reduced pressure. The residue was subjected to silica gel chromatography (0-25% EtOAc/heptane) to afford the title compound Step 5: 4-(2-(((benzyloxy)carbonyl)amino)propan-2-yl)-2-(1-methylcyclopentyl)pyridine 1-oxide To a solution of benzyl (2-(2-(1-methylcyclopentyl)pyridin-4-yl)propan-2-yl)carbamate (0.41 g, 1.1 mmol) in DCM (6.0 mL) was added m-CPBA (0.34 g, 1.5 mmol). After 5 h, the mixture was diluted with $NaHCO_3$ (saturated aq.) and extracted with DCM (3×). The combined organic extracts were dried with anhydrous magnesium sulfate, filtered, and concentrated under reduced pressure. The residue was subjected to silica gel chromatography (0-100% 3:1 EtOAc:EtOH/heptane) to afford the title compound Step 6: benzyl (2-(2-chloro-6-(1-methylcyclopentyl)pyridin-4-yl)propan-2-yl)carbamate To a solution of 4-(2-(((benzyloxy)carbonyl)amino)propan-2-yl)-2-(1-methylcyclopentyl)pyridine 1-oxide (0.33 g, 0.90 mmol) in MeCN (5.0 mL) was added $POCl_3$ (0.30 mL, 3.2 mmol). The mixture was heated to 80° C. After 18 h, additional $POCl_3$ (1.0 mL, 11 mmol) was added and the reaction continued to heat at 80° C. After 18 h, the reaction was concentrated under reduced pressure. The reaction was quenched with $NaHCO_3$ (saturated aq.) and extracted with DCM. The organic mixture was concentrated under reduced pressure. The residue was subjected to silica gel chromatography (0-100% 3:1 EtOAc:EtOH/heptane) to afford the title compound Step 7: tert-butyl (1R,5S,6s)-6-((4-(2-(((benzyloxy)carbonyl)amino)propan-2-yl)-6-(1-methylcyclopentyl)pyridin-2-yl)oxy)-3-azabicyclo[3.1.0]hexane-3-carboxylate A mixture of benzyl (2-(2-chloro-6-(1-methylcyclopentyl)pyridin-4-yl)propan-2-yl)carbamate (68 mg, 0.18 mmol), tert-butyl (1R,5S,6s)-6-hydroxy-3-azabicyclo[3.1.0]hexane-3-carboxylate (Int. E, 44 mg, 0.22 mmol), $Cs_2CO_3$ (0.18 g, 0.53 mmol), $Pd_2(dba)_3$ (9.0 mg, 9.8 μmol), AdBippyPhos (13 mg, 0.020 mmol), and toluene (1.5 mL) was placed under $N_2$ and stirred at 85° C. After 4 h, the reaction was cooled, diluted with EtOAc, filtered and concentrated under reduced pressure. The residue was subjected to silica gel chromatography (0-100% EtOAc/heptane) to afford the title compound.

Step 8: benzyl (2-(2-(((1R,5S,6s)-3-azabicyclo[3.1.0]hexan-6-yl)oxy)-6-(1-methylcyclopentyl)pyridin-4-yl)propan-2-yl)carbamate A solution of tert-butyl (1R,5S,6s)-6-((4-(2-(((benzyloxy)carbonyl)amino)propan-2-yl)-6-(1-methylcyclopentyl)pyridin-2-yl)oxy)-3-azabicyclo[3.1.0]hexane-3-carboxylate (45 mg, 0.082 mmol) in HCl (4.0M in dioxane, 1.0 mL) stirred at 25° C. After 3 h, the reaction was concentrated under reduced pressure to afford the title compound.

Scheme:

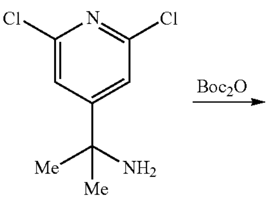

-continued

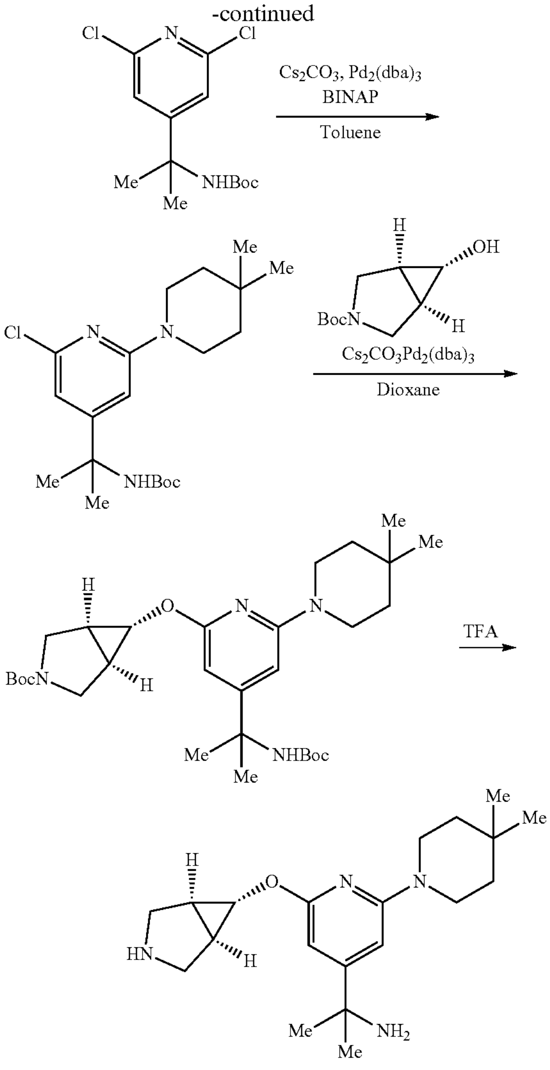

Intermediate U

Benzyl (2-(2-(((1R,5S,6s)-3-azabicyclo[3.1.0]hexan-6-yl)oxy)-6-(4,4-dimethylpiperidin-1-yl)pyridin-4-yl)propan-2-yl)carbamate

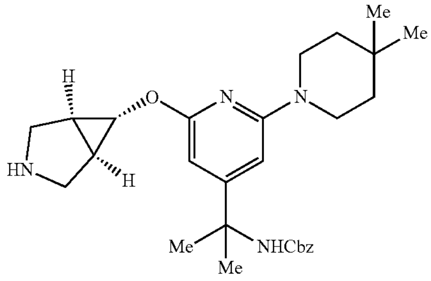 [SMILES: CC1(C)CCN(c2cc(C(C)(C)NC(=O)OCc3ccccc3)cc(O[C@H]3[C@@H]4CNC[C@@H]43)n2)CC1]

Step 1: tert-butyl (2-(2,6-dichloropyridin-4-yl)propan-2-yl)carbamate

To a solution of 2-(2,6-dichloropyridin-4-yl)propan-2-amine (2.0 g, 9.8 mmol) in toluene (0.020 L) was added di-tert-butyl dicarbonate (2.7 mL, 12 mmol) and triethylamine (4.1 mL, 29 mmol). The resulting mixture was stirred at 25° C. for 16 h. The reaction was quenched with water (50 mL) and extracted with EtOAc (50 mL×2). The combined organic extracts were washed with brine (50 mL), dried over anhydrous sodium sulfate, filtered and concentrated under reduced pressure. The residue was subjected to silica gel chromatography (0-10% EtOAc/petroleum ether) to afford the title compound.

Step 2: tert-butyl (2-(2-chloro-6-(4,4-dimethylpiperidin-1-yl)pyridin-4-yl)propan-2-yl)carbamate A mixture of tert-butyl (2-(2,6-dichloropyridin-4-yl)propan-2-yl)carbamate (4.4 g, 14 mmol), 4,4-dimethylpiperidine (1.9 g, 13 mmol), $Pd_2(dba)_3$ (0.30 g, 0.33 mmol), BINAP (0.41 g, 0.65 mmol), $Cs_2CO_3$ (11 g, 33 mmol), and toluene (0.10 L) was stirred at 100° C. for 16 h. The mixture was cooled to room temperature, diluted with EtOAc (200 mL), and washed with brine (200 mL). The organic extracts were dried over anhydrous magnesium sulfate, filtered, and concentrated under reduced pressure. The residue was subjected to silica gel chromatography (0-10% 3:1 EtOAc:EtOH/hexanes) to afford the title compound.

Step 3: tert-butyl (1R,5S,6s)-6-((4-(2-((tert-butoxycarbonyl)-12-azanyl)propan-2-yl)-6-(4,4-dimethylpiperidin-1-yl)pyridin-2-yl)oxy)-3-azabicyclo[3.1.0]hexane-3-carboxylate A mixture of tert-butyl (1R,5S,6s)-6-hydroxy-3-azabicyclo[3.1.0]hexane-3-carboxylate (0.94 g, 4.7 mmol), tert-butyl (2-(2-chloro-6-(4,4-dimethylpiperidin-1-yl)pyridin-4-yl)propan-2-yl)carbamate (1.5 g, 3.9 mmol), $Pd_2(dba)_3$ (0.072 g, 0.079 mmol), 5-(di((3S,5S,7S)-adamantan-1-yl)phosphanyl)-1',3',5'-triphenyl-1'H-1,4'-bipyrazole (0.10 g, 0.16 mmol), $Cs_2CO_3$ (3.8 g, 12 mmol), and 1,4-dioxane (0.020 L) was stirred at 85° C. for 14 h. The mixture was cooled to room temperature, diluted with EtOAc (60 mL), and washed with water (60 mL) and brine (60 mL). The organic mixture was dried over anhydrous magnesium sulfate, filtered, and concentrated under reduced pressure. The residue was subjected to silica gel chromatography (0-20% EtOAc/hexanes) to afford the title compound.

Step 4: 2-(2-(((1R,5S,6s)-3-azabicyclo[3.1.0]hexan-6-yl)oxy)-6-(4,4-dimethylpiperidin-1-yl)pyridin-4-yl)propan-2-amine To a solution of tert-butyl (1R,5S,6s)-6-((4-(2-((tert-butoxycarbonyl)amino)propan-2-yl)-6-(4,4-dimethylpiperidin-1-yl)pyridin-2-yl)oxy)-3-azabicyclo[3.1.0]hexane-3-carboxylate (1.0 g, 1.9 mmol) in DCM (14 mL) was added TFA (4.7 mL). The reaction was stirred at 25° C. for 16 h. The mixture was poured into NaOH (1N aq., 50 mL), the pH was adjusted to pH>12, and extracted with DCM (50 mL×3). The combined organic extracts were dried over anhydrous magnesium sulfate, filtered, and concentrated under reduced pressure to afford the title compound.

Scheme:

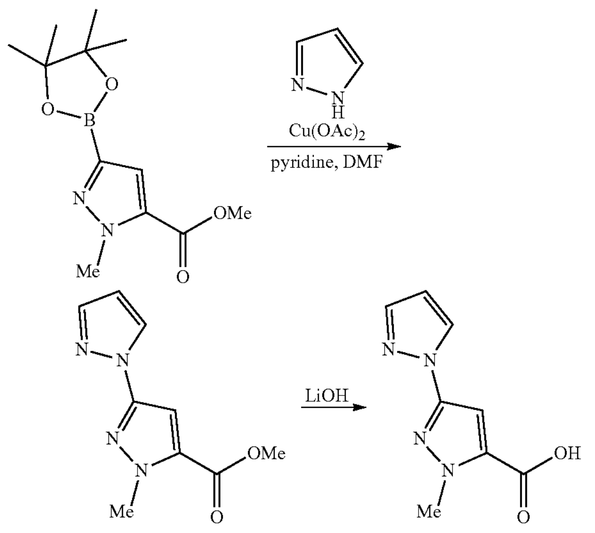

Intermediate V

1'-methyl-1'H-[1,3'-bipyrazole]-5'-carboxylic acid

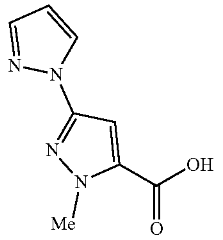 [SMILES: Cn1nc(-n2cccn2)cc1C(=O)O]

Step 1: methyl 1'-methyl-1'H-[1,3'-bipyrazole]-5'-carboxylate

To a solution of methyl 1-methyl-3-(4,4,5,5-tetramethyl-1,3,2-dioxaborolan-2-yl)-1H-pyrazole-5-carboxylate (1.0 g, 3.8 mmol) and 1H-pyrazole (0.34 g, 5.0 mmol) in DMF (0.030 L) was added pyridine (1.5 mL, 19 mmol) and copper(II) acetate monohydrate (0.75 g, 3.8 mmol). The reaction was placed under an atmosphere of $O_2$ and heated to 80° C. After 12 h, the reaction was cooled to room temperature, diluted with water (15 mL) and extracted with EtOAc (20 mL×3). The combined organic extracts were washed with brine (20 mL), dried over anhydrous sodium sulfate, filtered and concentrated under reduced pressure. The residue was subjected to silica gel chromatography (0-25% EtOAc/petroleum ether) to afford the title compound.

Step 2: 1'-methyl-1'H-[1,3'-bipyrazole]-5'-carboxylic acid

To a solution of methyl 1'-methyl-1'H-[1,3'-bipyrazole]-5'-carboxylate (0.12 g, 0.58 mmol) in MeOH (3.0 mL) and water (2.0 mL) was added LiOH (28 mg, 1.2 mmol). The reaction was stirred at 25° C. for 2 h. The mixture was concentrated under reduced pressure. Water (5 mL) was added and the pH was adjusted to ~3 with HCl (1M aqueous). The mixture was extracted with EtOAc (10 mL×3). The combined organic extracts were washed with brine (20 mL), dried over anhydrous sodium sulfate, filtered and concentrated under reduced pressure to afford the title compound.

Scheme:

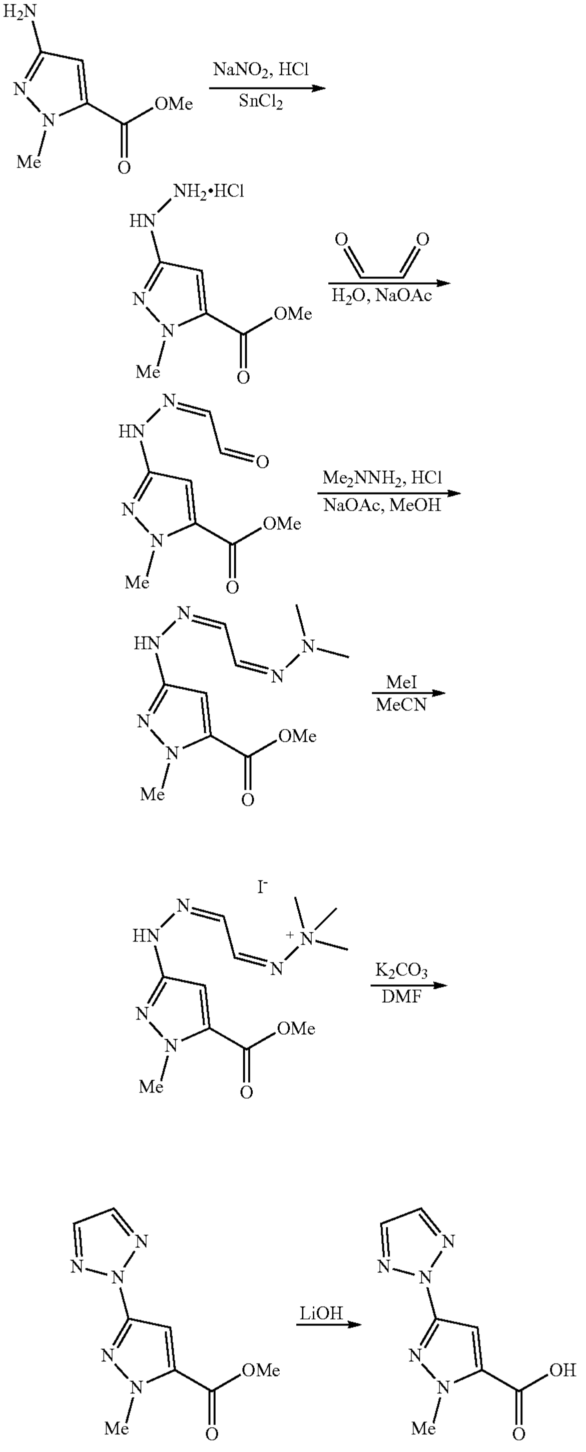

Intermediate W

1'-methyl-1'H-[1,3'-bipyrazole]-5'-carboxylic acid

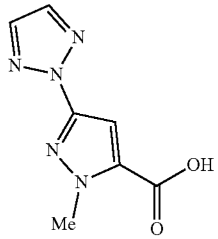 [SMILES: Cn1nc(-n2nccn2)cc1C(=O)O]

Step 1: methyl 3-hydrazinyl-1-methyl-1H-pyrazole-5-carboxylate hydrochloride

A solution of sodium nitrite (0.11 g, 1.6 mmol) in water (1.5 mL) was added to a 0° C. solution of methyl 3-amino-1-methyl-1H-pyrazole-5-carboxylate (0.17 g, 1.1 mmol) in hydrochloric acid (37%, 2.0 mL). After stirring for 30 min, a solution of $SnCl_2 \cdot 2H_2O$ (0.45 g, 2.1 mmol) in hydrochloric acid (37%, 3.3 mL) was added. The mixture was warmed to 25° C. and stirred for 2 h. The mixture was concentrated under reduced pressure and co-evaporated with EtOH (5 mL×2) to afford the title compound.

Step 2: methyl 1-methyl-3-(2-(2-oxoethylidene) hydrazinyl)-1H-pyrazole-5-carboxylate To a solution of methyl 3-hydrazineyl-1-methyl-1H-pyrazole-5-carboxylate (0.020 g, 0.12 mmol) in water (2.0 mL) was added a solution of oxalaldehyde (17 mg, 0.12 mmol) in water (0.50 mL) followed by a solution of sodium acetate (9.6 mg, 0.12 mmol) in water (0.50 mL). The mixture was stirred at 25° C. for 30 min. The mixture was lyophilized to afford the title compound.

Step 3: methyl 3-(2-(2-(2,2-dimethylhydrazono) ethylidene)hydrazinyl)-1-methyl-1H-pyrazole-5-carboxylate To a solution of methyl 1-methyl-3-(2-(2-oxoethylidene) hydrazineyl)-1H-pyrazole-5-carboxylate (0.080 g, 0.38 mmol) in MeOH (5.0 mL) and toluene (2.5 mL) was added sodium acetate (47 mg, 0.57 mmol) followed by 1,1-dimethylhydrazine hydrochloride (44 mg, 0.46 mmol). The mixture was stirred at 25° C. After 12 h, water (10 mL) was added and mixture was extracted with EtOAc (10 mL×3). The combined organic extracts were washed with brine (30 mL), dried over anhydrous sodium sulfate, filtered and concentrated under reduced pressure to afford the title compound.

Step 4: 2-(2-(2-(5-(methoxycarbonyl)-1-methyl-1H-pyrazol-3-yl)hydrazono)ethylidene)-1,1,1-trimethylhydrazin-1-ium iodide To a solution of methyl 3-(2-(2-(2,2-dimethylhydrazineylidene)ethylidene)hydrazineyl)-1-methyl-1H-pyrazole-5-carboxylate (0.090 g, 0.36 mmol) in MeCN (3.0 mL) was added iodomethane (0.11 mL, 1.8 mmol). The mixture was stirred at 25° C. for 12 h. The reaction was diluted with EtOAc (5 mL) and concentrated under reduced pressure to afford the title compound.

Step 5: methyl 1-methyl-3-(2H-1,2,3-triazol-2-yl)-1H-pyrazole-5-carboxylate

To a solution of 2-(2-(2-(5-(methoxycarbonyl)-1-methyl-1H-pyrazol-3-yl)hydrazineylidene)ethylidene)-1,1,1-trimethylhydrazin-1-ium iodide (0.13 g, 0.33 mmol) in DMF (3.0 mL) was added $K_2CO_3$ (91 mg, 0.66 mmol). The mixture was stirred at 50° C. for 2 h. The reaction was cooled to room temperature, diluted with water (5 mL), and extracted with EtOAc (10 mL×3). The combined organic extracts were washed with brine (10 mL), dried over anhydrous sodium sulfate, filtered and concentrated under reduced pressure. The residue was subjected to prep-TLC (25% EtOAc/petroleum ether) to afford the title compound.

Step 6: 1-methyl-3-(2H-1,2,3-triazol-2-yl)-1H-pyrazole-5-carboxylic acid

A mixture of methyl 1-methyl-3-(2H-1,2,3-triazol-2-yl)-1H-pyrazole-5-carboxylate (65 mg, 0.31 mmol), LiOH (15 mg, 0.63 mmol), MeOH (3.0 mL), and water (3.0 mL) was stirred at 25° C. After 2 h, the mixture was concentrated under reduced pressure. The mixture was diluted with water (5 mL) and extracted with DCM (3 mL×2). The aqueous layer was acidified with HCl (1M aqueous) to pH ~3 and extracted with EtOAc (10 mL×3). The combined organic extracts were dried over anhydrous sodium sulfate, filtered and concentrated under reduced pressure to afford the title compound.

EXAMPLES

Scheme:

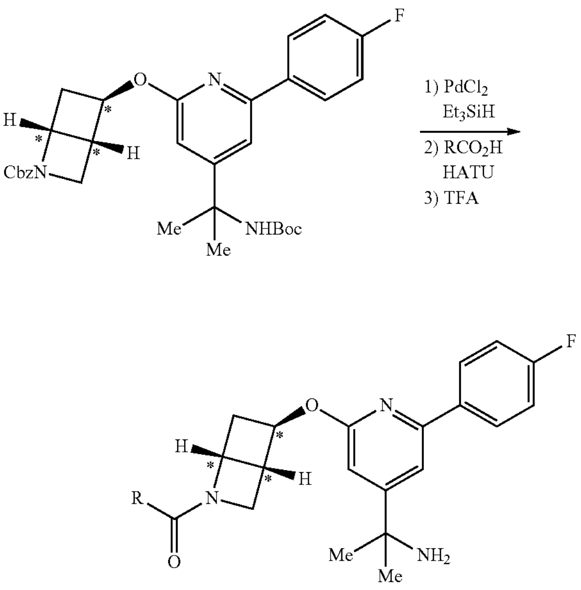

Example 1 rel-((1R,4R,5R)-5-((4-(2-aminopropan-2-yl)-6-(4-fluorophenyl)pyridin-2-yl)oxy)-2-azabicyclo[2.2.0]hexan-2-yl)(1-methyl-3-(thiazol-4-yl)-1H-pyrazol-5-yl)methanone (enantiomer 2)

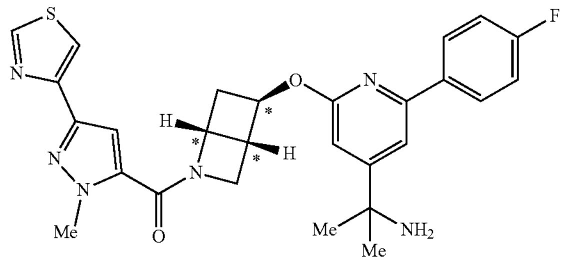 [SMILES: Cn1nc(-c2cscn2)cc1C(=O)N1C[C@@H]2[C@H]1C[C@H]2Oc1cc(C(C)(C)N)cc(-c2ccc(F)cc2)n1]

Step 1: tert-butyl rel-(2-(2-(((1R,4R,5R)-2-azabicyclo[2.2.0]hexan-5-yl)oxy)-6-(4-fluorophenyl)pyridin-4-yl)propan-2-yl)carbamate (enantiomer 2)

To a mixture of benzyl rel-(1R,4R,5R)-5-((4-(2-((tert-butoxycarbonyl)amino)propan-2-yl)-6-(4-fluorophenyl)pyridin-2-yl)oxy)-2-azabicyclo[2.2.0]hexane-2-carboxylate (Int. D-ent-2, 0.10 g, 0.18 mmol) and palladium(II) chloride (3.2 mg, 0.018 mmol) in DCM (1.8 mL) was added triethylamine (0.25 mL, 1.8 mmol) and triethylsilane (0.14 mL, 0.89 mmol). The mixture was stirred at rt for 1 h and filtered through a pad of celite (eluted with DCM, 5 mL×3) to afford the title compound.

Step 2: rel-((1R,4R,5R)-5-((4-(2-aminopropan-2-yl)-6-(4-fluorophenyl)pyridin-2-yl)oxy)-2-azabicyclo[2.2.0]hexan-2-yl)(1-methyl-3-(thiazol-4-yl)-1H-pyrazol-5-yl)methanone (enantiomer 2)

To a mixture of 1-methyl-3-(thiazol-4-yl)-1H-pyrazole-5-carboxylic acid (37 mg, 0.18 mmol), tert-butyl rel-(2-(2-(((1R,4R,5R)-2-azabicyclo[2.2.0]hexan-5-yl)oxy)-6-(4-fluorophenyl)pyridin-4-yl)propan-2-yl)carbamate (enantiomer 2, 76 mg, 0.18 mmol), DIPEA (0.093 mL, 0.53 mmol), and DCM (1.8 mL) was added HATU (68 mg, 0.18 mmol). The mixture was stirred at rt for 16 h and concentrated under reduced pressure. DCM (1.3 mL) and TFA (0.45 mL) were injected and the mixture was stirred at rt for 2 h. The mixture was poured into NaOH (1N aq., 30 mL) and extracted with DCM (25 mL×3). The combined organic solution was dried over anhydrous magnesium sulfate, filtered, and concentrated under reduced pressure. The mixture was subjected to reverse phase HPLC (10-100% MeCN/water with 0.1% TFA modifier). The appropriate fractions were passaged through a SCX-2 column, which was washed with MeOH (2 mL×3) and eluted with a methanolic solution of ammonia (2N, 2 mL×3) to afford the title compound. MS m/z $(M+H)^+$: calculated 519.2, observed 519.5. $^1H$ NMR (500 MHz, DMSO-$d^6$) rotameric mixture: δ 9.20-9.15 (m, 1H), 8.16-8.09 (m, 2H), 8.01-7.96 (m, 1H), 7.76-7.69 (m, 1H), 7.36-7.26 (m, 2H), 7.13 and 6.81 (s, 1H), 6.94-6.89 (m, 1H), 5.62-5.52 (m, 1H), 5.11-5.04 and 4.88-4.80 (m, 1H), 4.88-4.80 and 4.49-4.42 (m, 1H), 4.73-4.67 and 4.34-4.28 (m, 1H), 4.12 (s, 3H), 3.18-3.09 (m, 1H), 3.06-2.97 (m, 1H), 2.80-2.70 and 2.68-2.58 (m, 1H), 2.35 (br s, 2H), 1.39 (s, 6H) ppm.

Utilizing the procedures described in EXAMPLE 1, the following compound was prepared substituting the appropriate reagents for 1-methyl-3-(thiazol-4-yl)-1H-pyrazole-5-carboxylic acid. The compound was isolated as a TFA salt.

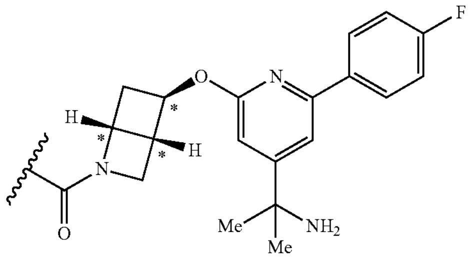 [SMILES: *C(=O)N1C[C@@H]2[C@H]1C[C@H]2Oc1cc(C(C)(C)N)cc(-c2ccc(F)cc2)n1]

| Ex. # | Structure | Name | Calc'd $[M + H]^+$ | Observed $[M + H]^+$ |
|---|---|---|---|---|
| 2 | 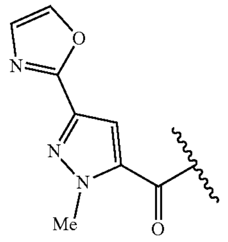 [SMILES: *C(=O)c1cc(-c2ncco2)nn1C] | rel-((1R,4R,5R)-5-((4-(2-aminopropan-2-yl)-6-(4-fluorophenyl)pyridin-2-yl)oxy)-2-azabicyclo[2.2.0]hexan-2-yl)(1-methyl-3-(oxazol-2-yl)-1H-pyrazol-5-yl)methanone (enantiomer 2) | 503.2 | 503.5 |

Scheme:

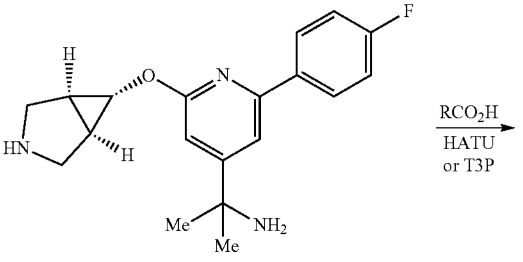

-continued

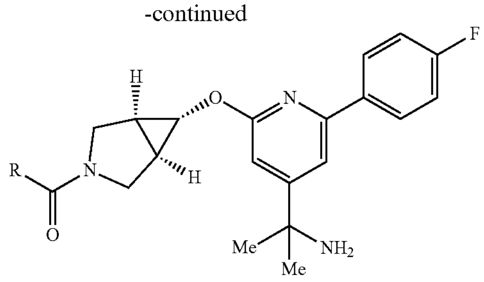

Example 3

((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(oxazol-2-yl)thiazol-5-yl)methanone

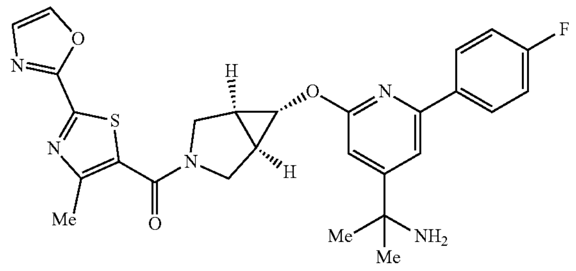 [SMILES: Cc1nc(-c2ncco2)sc1C(=O)N1C[C@@H]2[C@H](C1)[C@H]2Oc1cc(C(C)(C)N)cc(-c2ccc(F)cc2)n1]

A mixture of 2-(2-(((1R,5S,6s)-3-azabicyclo[3.1.0]hexan-6-yl)oxy)-6-(4-fluorophenyl)pyridin-4-yl)propan-2-amine·HCl (Int. H-01, 0.050 g, 0.13 mmol), 4-methyl-2-(oxazol-2-yl)thiazole-5-carboxylic acid (Int. K-01, 19 mg, 0.090 mmol), DMF (0.70 mL), DIPEA (65 μL, 0.38 mmol), and HATU (33 mg, 0.090 mmol) was stirred at rt for 16 h. The mixture was subjected to reverse phase HPLC (10-100% MeCN/water with 0.1% TFA modifier). The appropriate fractions were combined, treated with $NaHCO_3$ (saturated aq., 5 mL), and extracted with DCM (3×5 mL). The combined organic extracts were washed with brine (5 mL), dried with anhydrous sodium sulfate, filtered, and concentrated under reduced pressure to afford the title compound. MS m/z: $(M+H)^+$: calculated 520.2; found 520.1. $^1H$ NMR (500 MHz, $CDCl_3$) δ 8.04-7.97 (m, 2H), 7.82 (s, 1H), 7.51 (s, 1H), 7.34 (s, 1H), 7.20-7.13 (m, 2H), 6.78 (s, 1H), 4.24 (br s, 1H), 4.05 (s, 1H), 3.85 (br s, 1H), 3.79-3.72 (m, 2H), 2.61 (s, 3H), 2.14-1.92 (m, 2H), 1.66-1.53 (br s, 2H), 1.50 (s, 6H) ppm.

Utilizing the procedures described in EXAMPLE 3, the following compounds were prepared substituting the appropriate reagents for 4-methyl-2-(oxazol-2-yl)thiazole-5-carboxylic acid. Following HPLC purification, examples were concentrated to afford TFA salts or extracted under basic conditions to afford free bases.

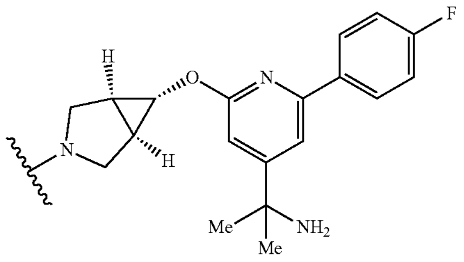 [SMILES: *N1C[C@@H]2[C@H](C1)[C@H]2Oc1cc(C(C)(C)N)cc(-c2ccc(F)cc2)n1]

| Ex # | Structure | Name | Calc'd $[M + H]^+$ | Observed $[M + H]^+$ | Comments |
|---|---|---|---|---|---|
| 4 | 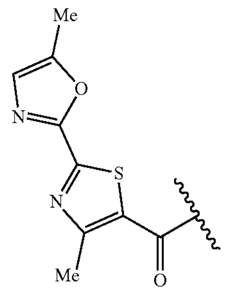 [SMILES: *C(=O)c1sc(-c2ncc(C)o2)nc1C] | ((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(5-methyloxazol-2-yl)thiazol-5-yl)methanone | 534.2 | 534.2 | Free base |
| 5 | 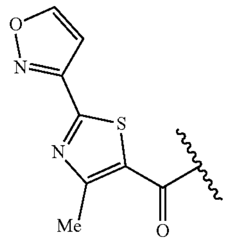 [SMILES: *C(=O)c1sc(-c2ccon2)nc1C] | ((1R,5S,6s)-6-((4-(2-aminopropan-2-yl)-6-(4-fluorophenyl)pyridin-2-yl)oxy)-3-azabicyclo[3.1.0]hexan-3-yl)(2-(isoxazol-3-yl)-4-methylthiazol-5-yl)methanone | 520.2 | 520.2 | TFA salt |

-continued

| Ex # | Structure | Name | Calc'd [M + H]+ | Observed [M + H]+ | Comments |
|---|---|---|---|---|---|
| 6 | 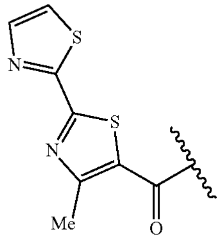 [SMILES: *C(=O)c1sc(-c2nccs2)nc1C] | ((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-[2,2'-bithiazol]-5-yl)methanone | 536.2 | 536.1 | TFA salt |
| 7 | 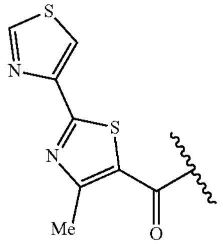 [SMILES: *C(=O)c1sc(-c2cscn2)nc1C] | ((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-[2,4'-bithiazol]-5-yl)methanone | 536.2 | 536.1 | Free base |
| 8 | 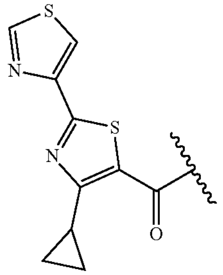 [SMILES: *C(=O)c1sc(-c2cscn2)nc1C1CC1] | ((1R,5S,6s)-6-((4-(2-aminopropan-2-yl)-6-(4-fluorophenyl)pyridin-2-yl)oxy)-3-azabicyclo[3.1.0]hexan-3-yl)(4-cyclopropyl-[2,4'-bithiazol]-5-yl)methanone | 562.2 | 562.3 | TFA salt |
| 9 | 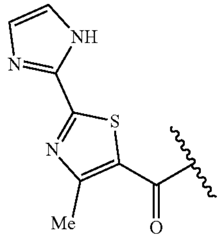 [SMILES: *C(=O)c1sc(-c2ncc[nH]2)nc1C] | (2-(1H-imidazol-2-yl)-4-methylthiazol-5-yl)((1R,5S,6s)-6-((4-(2-aminopropan-2-yl)-6-(4-fluorophenyl)pyridin-2-yl)oxy)-3-azabicyclo[3.1.0]hexan-3-yl)methanone | 519.2 | 519.1 | TFA salt |
| 10 | 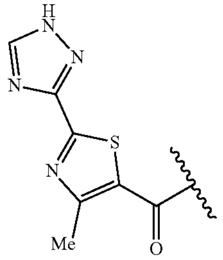 [SMILES: *C(=O)c1sc(-c2nc[nH]n2)nc1C] | ((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(1H-1,2,4-triazol-5-yl)thiazol-5-yl)methanone | 520.2 | 520.1 | TFA salt |
| 11 | 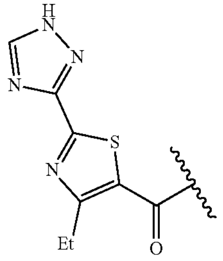 [SMILES: *C(=O)c1sc(-c2nc[nH]n2)nc1CC] | ((1R,5S,6s)-6-((4-(2-aminopropan-2-yl)-6-(4-fluorophenyl)pyridin-2-yl)oxy)-3-azabicyclo[3.1.0]hexan-3-yl)(4-ethyl-2-(1H-1,2,4-triazol-3-yl)thiazol-5-yl)methanone | 534.2 | 534.1 | TFA salt |

-continued

| Ex # | Structure | Name | Calc'd [M + H]$^+$ | Observed [M + H]$^+$ | Comments |
|---|---|---|---|---|---|
| 12 | 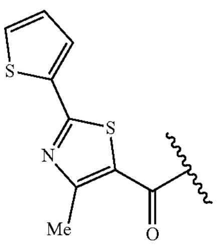 [SMILES: *C(=O)c1sc(-c2cccs2)nc1C] | ((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(thiophen-2-yl)thiazol-5-yl)methanone | 535.2 | 535.1 | TFA salt |
| 13 | 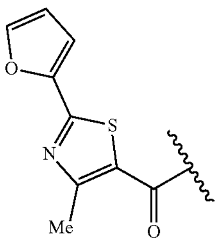 | ((1R,5S,6s)-6-((4-(2-aminopropan-2-yl)-6-(4-fluorophenyl)pyridin-2-yl)oxy)-3-azabicyclo[3.1.0]hexan-3-yl)(2-(furan-2-yl)-4-methylthiazol-5-yl)methanone | 519.2 | 519.1 | TFA salt |

Example 14

((1R,5S,6s)-6-((4-(2-aminopropan-2-yl)-6-(4-fluorophenyl)pyridin-2-yl)oxy)-3-azabicyclo[3.1.0]hexan-3-yl)(4-difluoromethyl)-[2,4'-bithiazol]-5 yl)methanone

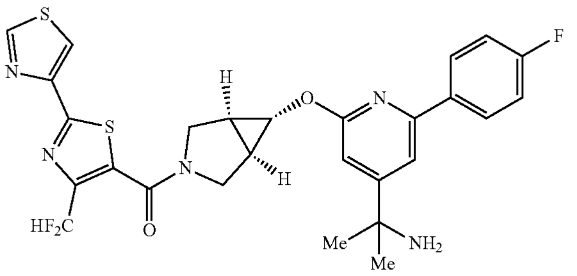

A mixture of benzyl (2-(2-(((1R,5S,6s)-3-(2-chloro-4-(difluoromethyl)thiazole-5-carbonyl)-3-azabicyclo[3.1.0]hexan-6-yl)oxy)-6-(4-fluorophenyl)pyridin-4-yl)propan-2-yl)carbamate (Int. J, 15 mg, 0.023 mmol), 4-(tributylstannyl)thiazole (17 mg, 0.046 mmol), $Pd(PPh_3)_4$ (2.6 mg, 2.3 μmol) and 1,4-dioxane (0.50 mL) was stirred at 100° C. for 2 h. The mixture was cooled to rt, filtered, and concentrated under reduced pressure. Hydrochloric acid (37%, 0.25 mL) was added, the mixture was stirred at 80° C. for 10 min and concentrated. The residue was dissolved in DMSO (1 mL), subjected to mass directed reverse phase HPLC (MeCN/water with 0.1% TFA modifier), and the appropriate fractions were concentrated to afford the title compound as a TFA salt. MS m/z $(M+H)^+$: calculated 572.2; found 572.3. $^1H$ NMR (500 MHz, DMSO-$d^6$) δ 9.33-9.30 (m, 1H), 8.58-8.50 (m, 1H), 8.24-8.17 (m, 2H), 7.75 (s, 1H), 7.38-7.31 (m, 2H), 7.23 (t, J=53.4 Hz, 1H), 6.87 (s, 1H), 4.15 (s, 1H), 4.05 (d, J=12.2 Hz, 1H), 3.82-3.63 (m, 2H), 3.45-3.40 (m, 1H), 2.18-2.10 (m, 1H), 2.02-1.95 (m, 1H), 1.65 (s, 6H) ppm.

Utilizing the procedures described in EXAMPLE 14, the following compound was prepared substituting the appropriate reagents for 4-(tributylstannyl)thiazole.

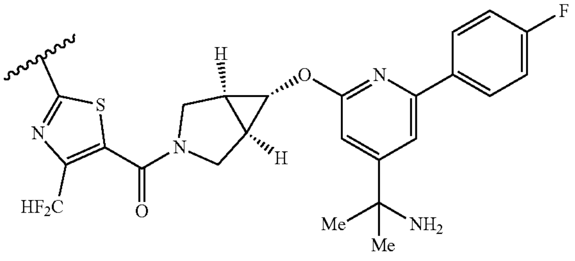

| Ex # | Structure | Name | Calc'd [M + H]$^+$ | Observed [M + H]$^+$ |
|---|---|---|---|---|
| 15 | 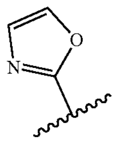 [SMILES: *c1ncco1] | ((1R,5S,6s)-6-((4-(2-aminopropan-2-yl)-6-(4-fluorophenyl)pyridin-2-yl)oxy)-3-azabicyclo[3.1.0]hexan-3-yl)(4-(difluoromethyl)-2-(oxazol-2-yl)thiazol-5-yl)methanone | 556.2 | 556.3 |

Scheme:

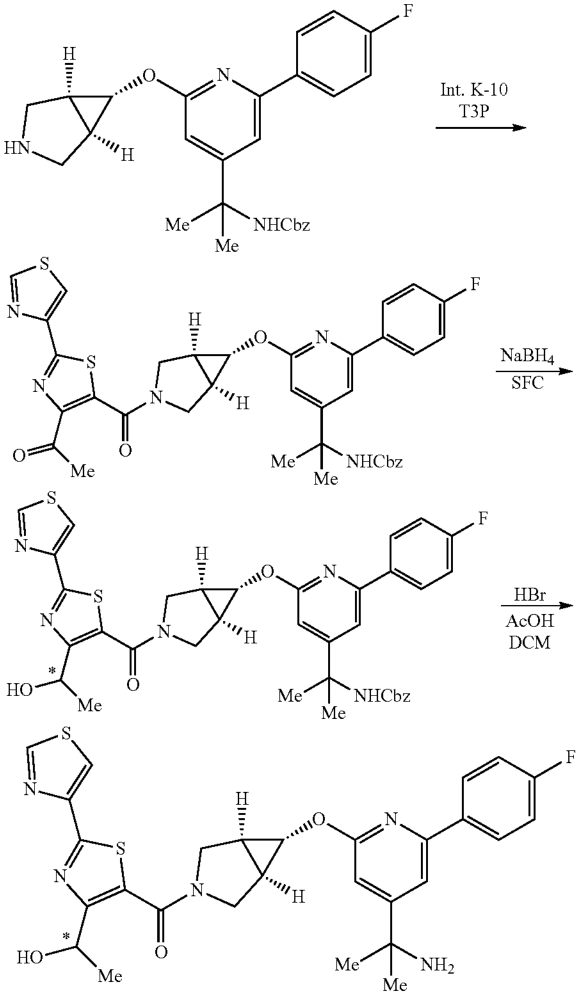

Examples 16A

Ent-((1R,5S,6S)-6-((4-(2-aminopropan-2-yl)-6-(4-fluorophenyl)pyridin-2-yl)oxy)-3-azabicyclo[3.1.0]hexan-3-yl)(4-(1-hydroxyethyl)-[2,4'-bithiazol]-5-yl)methanone (enantiomer 1) and Example 16B ent-((1R,5S,6S)-6-((4-(2-aminopropan-2-yl)-6-(4-fluorophenyl)pyridin-2-yl)oxy)-3-azabicyclo[3.1.0]hexan-3-yl)(4-(1-hydroxyethyl)-[2,4'-bithiazol]-5-yl)methanone (enantiomer 2)

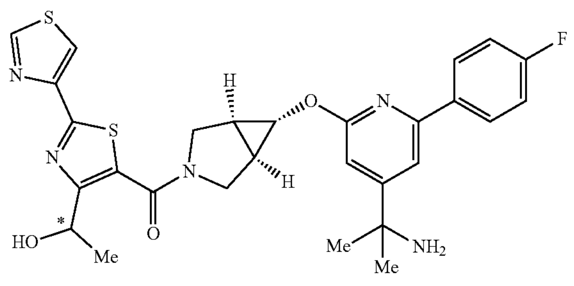 [SMILES: CC(O)c1nc(-c2cscn2)sc1C(=O)N1C[C@@H]2[C@H](C1)[C@H]2Oc1cc(C(C)(C)N)cc(-c2ccc(F)cc2)n1]

Step 1: benzyl (2-(2-(((1R,5S,6s)-3-(4-acetyl-[2,4'-bithiazole]-5-carbonyl)-3-azabicyclo[3.1.0]hexan-6-yl)oxy)-6-(4-fluorophenyl)pyridin-4-yl)propan-2-yl)carbamate A mixture of 4-acetyl-[2,4'-bithiazole]-5-carboxylic acid (Int. K-10, 0.040 g, 0.16 mmol), DIPEA (0.10 mL, 0.47 mmol), benzyl (2-(2-(((1R,5S,6s)-3-azabicyclo[3.1.0]hexan-6-yl)oxy)-6-(4-fluorophenyl)pyridin-4-yl)propan-2-yl)carbamate (Int. H-02, 0.080 g, 0.17 mmol) and T3P (0.20 g, 0.32 mmol, 50 wt % in EtOAc) in DMF (5.0 mL) was stirred at rt for 30 min. The mixture was diluted with water (5 mL) and extracted with EtOAc (10 mL×3). The combined organic extracts were washed with brine (10 mL) and concentrated under reduced pressure. The residue was subjected to prep-TLC (50% EtOAc/petroleum ether) to afford the title compound.

Step 2: benzyl ent-(2-(2-(4-fluorophenyl)-6-(((1R,5S,6R)-3-(4-(1-hydroxyethyl)-[2,4'-bithiazole]-5-carbonyl)-3-azabicyclo[3.1.0]hexan-6-yl)oxy)pyridin-4-yl)propan-2-yl)carbamate (enantiomers 1 and 2)

To a solution of benzyl (2-(2-(((1R,5S,6s)-3-(4-acetyl-[2,4'-bithiazole]-5-carbonyl)-3-azabicyclo[3.1.0]hexan-6-yl)oxy)-6-(4-fluorophenyl)pyridin-4-yl)propan-2-yl)carbamate (0.090 g, 0.13 mmol) in MeOH (3.0 mL) was added sodium borohydride (9.8 mg, 0.26 mmol) under an atmosphere of nitrogen at 0° C. The reaction mixture was stirred at 0° C. for 40 min. The mixture was diluted with water (5 mL) and extracted with EtOAc (5 mL×3). The combined organic solution was dried over anhydrous sodium sulfate, filtered, and concentrated under reduced pressure. The residue was subjected to prep-TLC (50% EtOAc/petroleum ether) to afford the title compound as a racemic mixture. The mixture of two stereoisomers was subjected to chiral SFC (ChiralPak AS-3, 40% EtOH (with 0.05% DEA modifier)/$CO_2$) to afford the title compounds, enantiomer 1 (faster eluting) and enantiomer 2 (slower eluting).

Step 3-1: ent-((1R,5S,6R)-6-((4-(2-aminopropan-2-yl)-6-(4-fluorophenyl)pyridin-2-yl)oxy)-3-azabicyclo[3.1.0]hexan-3-yl)(4-(1-hydroxyethyl)-[2,4'-bithiazol]-5-yl)methanone (enantiomer 1)

To a solution of benzyl ent-(2-(2-(4-fluorophenyl)-6-(((1R,5S,6R)-3-(4-(1-hydroxyethyl)-[2,4'-bithiazole]-5-carbonyl)-3-azabicyclo[3.1.0]hexan-6-yl)oxy)pyridin-4-yl)propan-2-yl)carbamate (enantiomer 1, 35 mg, 0.050 mmol) in DCM (3.0 mL) was added HBr (33% in AcOH, 49 mg, 0.20 mmol). The mixture was stirred at 25° C. for 40 min. The pH of the mixture was adjusted to pH=9 with $NH_4OH$. The mixture was concentrated under reduced pressure and subjected to reverse phase HPLC (25-55% MeCN/water with 0.1% TFA modifier) to afford the title compound as a TFA salt. MS m/z $(M+Na)^+$: calculated 588.2, observed 588.1. $^1H$ NMR (400 MHz, $CD_3OD$) δ 9.10 (d, J=1.6 Hz, 1H), 8.33 (s, 1H), 8.21-8.11 (m, 2H), 7.61 (s, 1H), 7.22 (t, J=8.8 Hz, 2H), 6.80 (s, 1H), 5.11-5.02 (m, 1H), 4.25-4.06 (m, 2H), 3.96-3.66 (m, 3H), 2.19-2.09 (m, 1H), 2.02-1.87 (m, 1H), 1.75 (s, 6H), 1.59 (d, J=6.0 Hz, 3H) ppm.

Step 3-2: ent-((1R,5S,6S)-6-((4-(2-aminopropan-2-yl)-6-(4-fluorophenyl)pyridin-2-yl)oxy)-3-azabicyclo[3.1.0]hexan-3-yl)(4-(1-hydroxyethyl)-[2,4'-bithiazol]-5-yl)methanone (enantiomer 2)

To a solution of benzyl ent-(2-(2-(4-fluorophenyl)-6-(((1R,5S,6R)-3-(4-(1-hydroxyethyl)-[2,4'-bithiazole]-5-carbonyl)-3-azabicyclo[3.1.0]hexan-6-yl)oxy)pyridin-4-yl) propan-2-yl)carbamate (enantiomer 2, 38 mg, 0.054 mmol) in DCM (3.0 mL) was added HBr (33% in AcOH, 53 mg, 0.22 mmol). The mixture was stirred at 25° C. for 40 min. The pH of the mixture was adjusted to pH=9 with $NH_4OH$. The mixture was concentrated under reduced pressure and subjected to reverse phase HPLC (25-55% MeCN/water with 0.1% TFA modifier) to afford the title compound as a TFA salt. MS m/z $(M+H)^+$: calculated 566.2, observed 566.3. $^1H$ NMR (500 MHz, $CD_3OD$) δ 9.10 (d, J=1.8 Hz, 1H), 8.33 (d, J=1.8 Hz, 1H), 8.20-8.13 (m, 2H), 7.61 (d, J=1.2 Hz, 1H), 7.27-7.20 (m, 2H), 6.80 (d, J=1.2 Hz, 1H), 5.06 (q, J=6.0 Hz, 1H), 4.24-4.09 (m, 2H), 3.95-3.69 (m, 3H), 2.19-2.09 (m, 1H), 2.02-1.88 (m, 1H), 1.76 (s, 6H), 1.59 (d, J=6.0 Hz, 3H) ppm.

Example 17

((1R,5S,6s)-6-((4-(2-aminopropan-2-yl)-6-(4-fluoro-phenyl)pyridin-2-yl)oxy)-3-azabicyclo[3.1.0]hexan-3-yl)(1-methyl-3-(oxazol-2-yl)-1H-pyrazol-5-yl) methanone

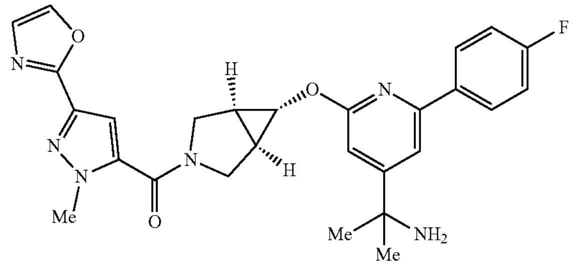 [SMILES: Cn1nc(-c2ncco2)cc1C(=O)N1C[C@@H]2[C@H](C1)[C@H]2Oc1cc(C(C)(C)N)cc(-c2ccc(F)cc2)n1]

HATU (0.35 g, 0.92 mmol) was added to a solution of 2-(2-(((1R,5S,6s)-3-azabicyclo[3.1.0]hexan-6-yl)oxy)-6-(4-fluorophenyl)pyridin-4-yl)propan-2-amine·HCl (Int. H-01, 0.40 g, 0.92 mmol), 1-methyl-3-(oxazol-2-yl)-1H-pyrazole-5-carboxylic acid (Int. N, 0.18 g, 0.92 mmol) and N-methylmorpholine (0.51 mL, 4.6 mmol) in DMSO (4.6 mL) and the mixture was stirred at rt for 1 h. A solution of $NaHCO_3$ (saturated aq., 30 mL) was added and the mixture was extracted with DCM (30 mL×3). The combined organic extracts were dried with anhydrous magnesium sulfate, filtered, and concentrated under reduced pressure. The mixture was subjected to reverse phase HPLC (5-95% MeCN/water with 0.1% TFA modifier). The appropriate fractions were concentrated under reduced pressure. A solution of $NaHCO_3$ (saturated aq., 30 mL) was added and the mixture was extracted with DCM (30 mL×3). The combined organic extracts were dried with anhydrous magnesium sulfate, filtered, and concentrated under reduced pressure to afford the title compound. MS m/z $(M+H)^+$: calculated 503.2, observed 503.3. $^1H$ NMR (500 MHz, $CD_3OD$) δ 8.11-8.06 (m, 2H), 7.99 (d, J=0.6 Hz, 1H), 7.62 (d, J=1.2 Hz, 1H), 7.32 (d, J=0.6 Hz, 1H), 7.19-7.14 (m, 3H), 6.85 (d, J=1.2 Hz, 1H), 4.24 (d, J=12.5 Hz, 1H), 4.07 (s, 3H), 4.03-3.96 (m, 3H), 3.75 (dd, J=12.5, 3.3 Hz, 1H), 2.11-2.05 (m, 2H), 1.50 (s, 6H) ppm.

Example 18

((1R,5S,6s)-6-((4-(2-aminopropan-2-yl)-6-(4-fluoro-phenyl)pyridin-2-yl)oxy)-3-azabicyclo[3.1.0]hexan-3-yl)(1-methyl-3-(thiazol-4-yl)-1H-pyrazol-5-yl) methanone

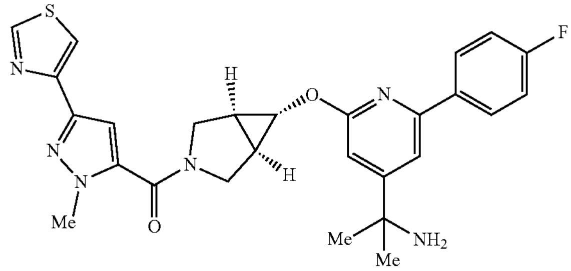 [SMILES: Cn1nc(-c2cscn2)cc1C(=O)N1C[C@@H]2[C@H](C1)[C@H]2Oc1cc(C(C)(C)N)cc(-c2ccc(F)cc2)n1]

1-Methyl-3-(thiazol-4-yl)-1H-pyrazole-5-carboxylic acid (Int. L-1, 0.31 g, 1.5 mmol) and HATU (0.84 mg, 2.2 mmol) were suspended in DMF (9.0 mL). 2-(2-(((1R,5S,6s)-3-azabicyclo[3.1.0]hexan-6-yl)oxy)-6-(4-fluorophenyl)pyridin-4-yl)propan-2-amine·HCl (Int. H-01, 0.80 g, 1.8 mmol) and triethylamine (0.77 mL, 5.5 mmol) were added. The mixture was stirred at rt for 30 min and then was subjected to reverse phase HPLC (15-95% MeCN/water with 0.1% TFA modifier). The appropriate fractions were poured into a solution of $NaHCO_3$ (saturated aq., 30 mL) and extracted with EtOAc (30 mL×3). The combined organic extracts were washed with $NaHCO_3$ (saturated aq., 30 mL) and brine (30 mL), dried with anhydrous magnesium sulfate, filtered, and concentrated under reduced pressure to afford the title compound. MS m/z $(M+H)^+$: calculated 519.2, observed 519.3. $^1H$ NMR (500 MHz, $CD_3OD$) δ 9.08 (s, 1H), 8.13-8.05 (m, 2H), 7.91 (s, 1H), 7.61 (s, 1H), 7.16 (t, J=7.8 Hz, 2H), 7.07 (s, 1H), 6.84 (s, 1H), 4.25 (d, J=12.6 Hz, 1H), 4.12-4.06 (m, 1H), 4.04 (s, 3H), 3.99 (m, 2H), 3.75 (d, J=11.1 Hz, 1H), 2.13-2.03 (m, 2H), 1.53 (s, 6H) ppm.

Example 19

((1R,5S,6s)-6-((4-(2-aminopropan-2-yl)-6-(4-fluoro-phenyl)pyridin-2-yl)oxy)-3-azabicyclo[3.1.0]hexan-3-yl)(1-ethyl-3-(thiazol-4-yl)-1H-pyrazol-5-yl) methanone

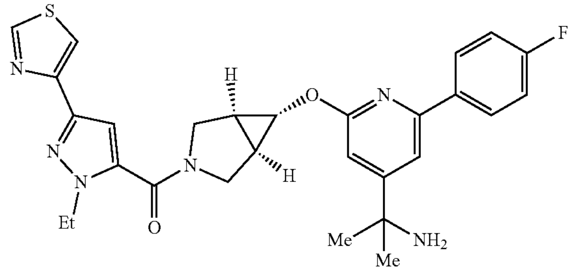 [SMILES: CCn1nc(-c2cscn2)cc1C(=O)N1C[C@@H]2[C@H](C1)[C@H]2Oc1cc(C(C)(C)N)cc(-c2ccc(F)cc2)n1]

Step 1: benzyl (2-(2-(((1R,5S,6s)-3-(1-ethyl-3-(thiazol-4-yl)-1H-pyrazole-5-carbonyl)-3-azabicyclo [3.1.0]hexan-6-yl)oxy)-6-(4-fluorophenyl)pyridin-4-yl)propan-2-yl)carbamate To a of solution of 1-ethyl-3-(thiazol-4-yl)-1H-pyrazole-5-carboxylic acid (Int. L-2, 0.040 g, 0.18 mmol) and benzyl (2-(2-(((1R,5S,6s)-3-azabicyclo[3.1.0]hexan-6-yl)oxy)-6-(4-fluorophenyl)pyridin-4-yl)propan-2-yl)carbamate (Int. H-02, 83 mg, 0.18 mmol) in DMF (3.0 mL) were added DIPEA (0.10 mL, 0.54 mmol) and T3P (50 wt. % in EtOAc, 0.34 g, 0.54 mmol). The mixture was stirred at rt for 30 min, water (5 mL) was added and the mixture was extracted with EtOAc (5 mL×3). The combined organic extracts were dried with anhydrous sodium sulfate, filtered, and concentrated under reduced pressure. The residue was subjected to prep-TLC (50% EtOAc/petroleum ether, $R_f$=0.3) to afford the title compound.

Step 2: ((1R,5S,6s)-6-((4-(2-aminopropan-2-yl)-6-(4-fluorophenyl)pyridin-2-yl)oxy)-3-azabicyclo[3.1.0]hexan-3-yl)(1-ethyl-3-(thiazol-4-yl)-1H-pyrazol-5-yl)methanone A mixture of benzyl (2-(2-(((1R,5S,6s)-3-(1-ethyl-3-(thiazol-4-yl)-1H-pyrazole-5-carbonyl)-3-azabicyclo[3.1.0]hexan-6-yl)oxy)-6-(4-fluorophenyl)pyridin-4-yl)propan-2-yl)carbamate (95 mg, 0.14 mmol) and hydrochloric acid (37%, 1.0 mL) was stirred at 80° C. for 10 min. The mixture was cooled to rt and subjected to reverse phase HPLC (23-53% MeCN/water with 0.1% TFA modifier) and lyophilized to afford the title compound as a TFA salt. MS m/z $(M+H)^+$: calculated 533.2, observed 533.2. $^1$H NMR (400 MHz, $CD_3OD$) δ 9.09 (s, 1H), 8.16-8.08 (m, 2H), 7.93 (d, J=1.2 Hz, 1H), 7.61 (s, 1H), 7.17 (t, J=8.8 Hz, 2H), 7.04 (s, 1H), 6.82 (s, 1H), 4.46-4.35 (m, 2H), 4.26 (d, J=12.2 Hz, 1H), 4.08-3.93 (m, 3H), 3.74 (dd, J=12.2, 4.4 Hz, 1H), 2.15-2.03 (m, 2H), 1.76 (s, 6H), 1.44 (t, J=7.2 Hz, 3H) ppm.

Example 20

((1R,5S,6s)-6-((4-(2-aminopropan-2-yl)-6-(4-fluorophenyl)pyridin-2-yl)oxy)-3-azabicyclo[3.1.0]hexan-3-yl)(3-(5-fluorothiazol-4-yl)-1-methyl-1H-pyrazol-5-yl)methanone

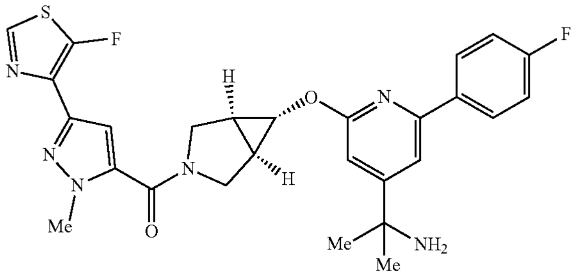 [SMILES: Cn1nc(-c2ncsc2F)cc1C(=O)N1C[C@@H]2[C@H](C1)[C@H]2Oc1cc(C(C)(C)N)cc(-c2ccc(F)cc2)n1]

Step 1: benzyl (2-(2-(4-fluorophenyl)-6-(((1R,5S,6s)-3-(3-(5-fluorothiazol-4-yl)-1-methyl-1H-pyrazole-5-carbonyl)-3-azabicyclo[3.1.0]hexan-6-yl)oxy)pyridin-4-yl)propan-2-yl)carbamate A mixture of 3-(5-fluorothiazol-4-yl)-1-methyl-1H-pyrazole-5-carboxylic acid (Int. Q, 35 mg, 0.15 mmol), HATU (88 mg, 0.23 mmol), DIPEA (0.20 mL, 0.77 mmol), and DMF (4.0 mL) was stirred at rt for 10 min. Benzyl (2-(2-(((1R,5S,6s)-3-azabicyclo[3.1.0]hexan-6-yl)oxy)-6-(4-fluorophenyl)pyridin-4-yl)propan-2-yl)carbamate·TFA (Int. H-02, 89 mg, 0.15 mmol) was added and the mixture was stirred at rt for 1 h. Water (10 mL) was added and the mixture was extracted with EtOAc (30 mL×3). The combined organic extracts were washed with brine (30 mL), dried with anhydrous sodium sulfate, filtered, and concentrated under reduced pressure. The residue was subjected to silica gel chromatography (0-100% EtOAc/petroleum ether) to afford the title compound.

Step 2: ((1R,5S,6s)-6-((4-(2-aminopropan-2-yl)-6-(4-fluorophenyl)pyridin-2-yl)oxy)-3-azabicyclo[3.1.0]hexan-3-yl)(3-(5-fluorothiazol-4-yl)-1-methyl-1H-pyrazol-5-yl)methanone A mixture of benzyl (2-(2-(4-fluorophenyl)-6-(((1R,5S,6s)-3-(3-(5-fluorothiazol-4-yl)-1-methyl-1H-pyrazole-5-carbonyl)-3-azabicyclo[3.1.0]hexan-6-yl)oxy)pyridin-4-yl)propan-2-yl)carbamate (83 mg, 0.12 mmol) and hydrochloric acid (37% aq., 1.0 mL) was stirred at 80° C. for 10 min. The mixture was adjusted to pH=7 with $NH_4OH$ and subjected to reverse phase HPLC (25-45% MeCN/water with 0.1% TFA modifier). The appropriate fractions were lyophilized to afford the title compound as a TFA salt. MS m/z $(M+H)^+$: calculated 537.2, observed 537.2. $^1$H NMR (400 MHz, $CD_3OD$) δ 8.62 (d, J=2.0 Hz, 1H), 8.13 (dd, J=8.5, 5.5 Hz, 2H), 7.60 (s, 1H), 7.21 (t, J=9.0 Hz, 2H), 6.98 (s, 1H), 6.81 (d, J=1.5 Hz, 1H), 4.25 (d, J=13.0 Hz, 1H), 4.05 (s, 1H), 4.04 (s, 3H), 4.03-3.95 (m, 2H), 3.76 (dd, J=12.5, 4.5 Hz, 1H), 2.14-2.03 (m, 2H), 1.76 (s, 6H) ppm.

Example 21

((1R,5S,6s)-6-((4-(2-aminopropan-2-yl)-6-(4-fluorophenyl)pyridin-2-yl)oxy)-3-azabicyclo[3.1.0]hexan-3-yl)(3-(isoxazol-3-yl)-1-methyl-1H-pyrazol-5-yl)methanone

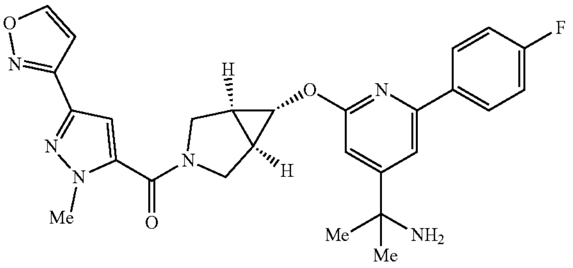 [SMILES: Cn1nc(-c2ccon2)cc1C(=O)N1C[C@@H]2[C@H](C1)[C@H]2Oc1cc(C(C)(C)N)cc(-c2ccc(F)cc2)n1]

To a mixture of 3-(isoxazol-3-yl)-1-methyl-1H-pyrazole-5-carboxylic acid (Int. O-2, 35 mg, 0.18 mmol) and HATU (0.10 g, 0.28 mmol) in DMF (1.0 mL) was added 2-(2-(((1R,5S,6s)-3-azabicyclo[3.1.0]hexan-6-yl)oxy)-6-(4-fluorophenyl)pyridin-4-yl)propan-2-amine·HCl (Int. H-01, 0.10 g, 0.23 mmol) and triethylamine (0.10 mL, 0.69 mmol). The mixture was stirred at rt for 30 min. The mixture was subjected to reverse phase HPLC (10-95% MeCN/water with 0.1% TFA modifier). The appropriate fractions were diluted with EtOAc (75 mL), washed with $NaHCO_3$ (saturated aq., 75 mL), dried with anhydrous magnesium sulfate, filtered, and concentrated under reduced pressure to afford the title compound. MS m/z $(M+H)^+$: calculated 503.2, observed 503.2. $^1$H NMR (500 MHz, $CD_3OD$) δ 8.73 (s, 1H), 8.12-8.05 (m, 2H), 7.61 (s, 1H), 7.16 (t, J=8.6 Hz, 2H), 7.10 (s, 1H), 6.88 (s, 1H), 6.85 (s, 1H), 4.25 (d, J=12.5 Hz, 1H), 4.05 (s, 3H), 4.02-3.94 (m, 3H), 3.78-3.72 (m, 1H), 2.11-2.04 (m, 2H), 1.51 (s, 6H) ppm.

Utilizing the procedure described in EXAMPLE 21, the following compounds were prepared substituting the appropriate reagents for 3-(isoxazol-3-yl)-1-methyl-1H-pyrazole-5-carboxylic acid. Compounds prepared as TFA salts were lyophilized following HPLC purification (MeCN/water with 0.1% TFA modifier).

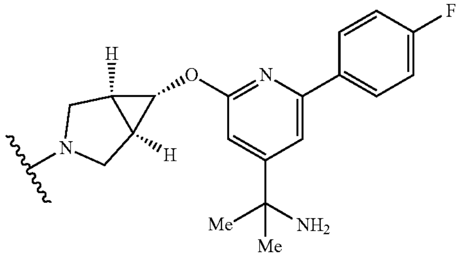 [SMILES: *N1C[C@@H]2[C@H](C1)[C@H]2Oc1cc(C(C)(C)N)cc(-c2ccc(F)cc2)n1]

Scheme:

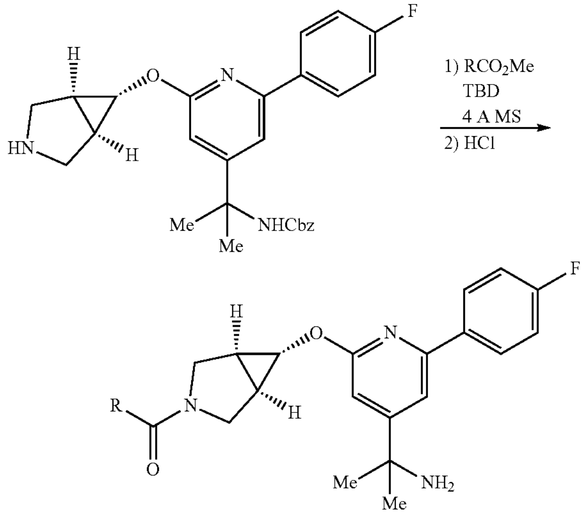

| Ex # | Structure | Name | Calc'd $[M + H]^+$ | Observed $[M + H]^+$ | Comments |
|---|---|---|---|---|---|
| 22 | 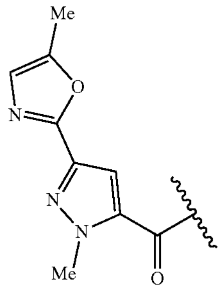 [SMILES: *C(=O)c1cc(-c2ncc(C)o2)nn1C] | ((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(5-methyloxazol-2-yl)-1H-pyrazol-5-yl)methanone | 517.2 | 517.1 | TFA salt |
| 23 | 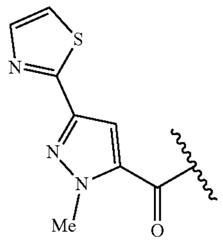 [SMILES: *C(=O)c1cc(-c2nccs2)nn1C] | ((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(thiazol-2-yl)-1H-pyrazol-5-yl)methanone | 519.2 | 519.1 | Free base |
| 24 | 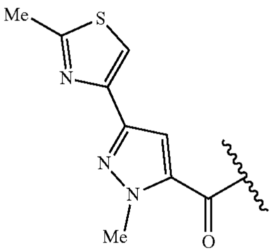 [SMILES: *C(=O)c1cc(-c2csc(C)n2)nn1C] | ((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(2-methylthiazol-4-yl)-1H-pyrazol-5-yl)methanone | 533.2 | 533.2 | Free base |

Example 25

((1R,5S,6s)-6-((4-(2-aminopropan-2-yl)-6-(4-fluorophenyl)pyridin-2-yl)oxy)-3-azabicyclo[3.1.0]hexan-3-yl)(4-fluoro-1-methyl-3-(thiazol-4-yl)-1H-pyrazol-5-yl)methanone

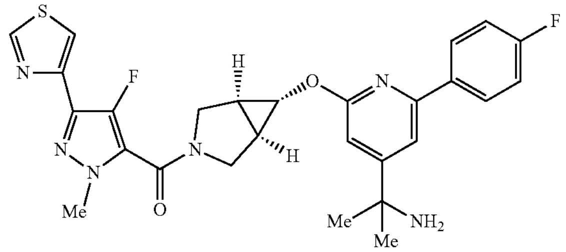 [SMILES: Cn1nc(-c2cscn2)c(F)c1C(=O)N1C[C@@H]2[C@H](C1)[C@H]2Oc1cc(C(C)(C)N)cc(-c2ccc(F)cc2)n1]

Step 1: benzyl (2-(2-(((1R,5S,6s)-3-(4-fluoro-1-methyl-3-(thiazol-4-yl)-1H-pyrazole-5-carbonyl)-3-azabicyclo[3.1.0]hexan-6-yl)oxy)-6-(4-fluorophenyl)pyridin-4-yl)propan-2-yl)carbamate To a rt solution of methyl 4-fluoro-1-methyl-3-(thiazol-4-yl)-1H-pyrazole-5-carboxylate (Int. M-2, 99 mg, 0.22 mmol) and 1,5,7-triazabicyclo[4.4.0]dec-5-ene (0.12 g, 0.83 mmol) in THF (2.0 mL) was added 4 Å molecular sieves (0.050 g). After 10 minutes benzyl (2-(2-(((1R,5S,6s)-3-azabicyclo[3.1.0]hexan-6-yl)oxy)-6-(4-fluorophenyl)pyridin-4-yl)propan-2-yl)carbamate (Int. H-02, 0.040 g, 0.17 mmol) was added. After 12 h, the mixture was concentrated and the residue was purified by prep-TLC (67% EtOAc/petroleum ether) to afford the title compound.

Step 2: ((1R,5S,6s)-6-((4-(2-aminopropan-2-yl)-6-(4-fluorophenyl)pyridin-2-yl)oxy)-3-azabicyclo[3.1.0]hexan-3-yl)(4-fluoro-1-methyl-3-(thiazol-4-yl)-1H-pyrazol-5-yl)methanone A solution of benzyl (2-(2-(((1R,5S,6s)-3-(4-fluoro-1-methyl-3-(thiazol-4-yl)-1H-pyrazole-5-carbonyl)-3-azabicyclo[3.1.0]hexan-6-yl)oxy)-6-(4-fluorophenyl)pyridin-4-yl)propan-2-yl)carbamate (0.040 g, 0.060 mmol) in hydrochloric acid (37% aq., 0.50 mL) was heated at 80° C. for 10 minutes. The mixture was cooled to rt, concentrated, and subjected to reverse phase HPLC (15-35% MeCN/water with 0.05% TFA modifier). The appropriate fractions were concentrated to afford the title compound. MS m/z $(M+H)^+$: calculated 537.2, observed 537.2. $^1$H-NMR (400 MHz, $CD_3OD$) δ 9.47 (d, J=2.0 Hz, 1H), 8.17 (dd, J=8.8, 5.6 Hz, 2H), 8.03 (d, J=2.0 Hz, 1H), 7.66 (d, J=1.2 Hz, 1H), 7.25 (t, J=8.8 Hz, 2H), 6.88 (d, J=1.2 Hz, 1H), 4.25 (d, J=12.4 Hz, 1H), 4.13-4.05 (m, 2H), 4.01-3.92 (m, 4H), 3.81-3.72 (m, 1H), 2.19-2.12 (m, 1H), 2.11-2.04 (m, 1H), 1.77 (s, 6H) ppm.

Utilizing the procedures described in EXAMPLE 25, the following compounds were prepared substituting the appropriate reagents for methyl 4-fluoro-1-methyl-3-(thiazol-4-yl)-1H-pyrazole-5-carboxylate.

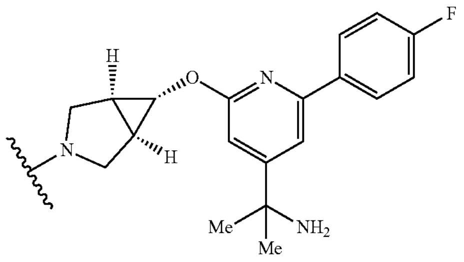 [SMILES: *N1C[C@@H]2[C@H](C1)[C@H]2Oc1cc(C(C)(C)N)cc(-c2ccc(F)cc2)n1]

| Ex # | Structure | Name | Calc'd $[M + H]^+$ | Observed $[M + H]^+$ |
|---|---|---|---|---|
| 26 | 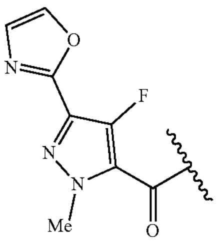 [SMILES: *C(=O)c1c(F)c(-c2ncco2)nn1C] | ((1R,5S,6s)-6-((4-(2-aminopropan-2-yl)-6-(4-fluorophenyl)pyridin-2-yl)oxy)-3-azabicyclo[3.1.0]hexan-3-yl)(4-fluoro-1-methyl-3-(oxazol-2-yl)-1H-pyrazol-5-yl)methanone | 521.2 | 521.1 |
| 27 | 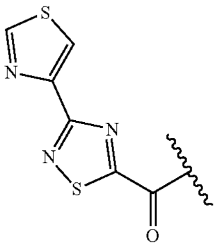 [SMILES: *C(=O)c1nc(-c2cscn2)ns1] | ((1R,5S,6s)-6-((4-(2-aminopropan-2-yl)-6-(4-fluorophenyl)pyridin-2-yl)oxy)-3-azabicyclo[3.1.0]hexan-3-yl)(3-(thiazol-4-yl)-1,2,4-thiadiazol-5-yl)methanone | 523.1 | 523.1 |

Utilizing the procedures described in EXAMPLE 19, the following compounds were prepared substituting the appropriate reagents for 1-ethyl-3-(thiazol-4-yl)-1H-pyrazole-5-carboxylic acid. Examples were purified by HPLC (MeCN/water (with 0.1% TFA or 0.05% HCl modifier) and concentrate under reduced pressure to afford the title compound as a TFA or HCl salt.

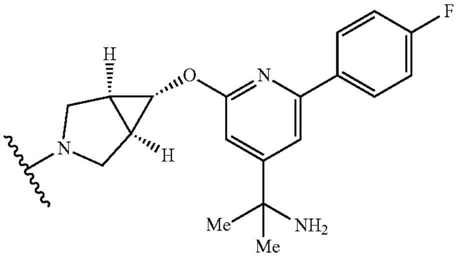 [SMILES: *N1C[C@@H]2[C@H](C1)[C@H]2Oc1cc(C(C)(C)N)cc(-c2ccc(F)cc2)n1]

Example 31

((1R,5S,6s)-6-((4-(2-aminopropan-2-yl)-6-(2,4-difluorophenyl)pyridin-2-yl)oxy)-3-azabicyclo[3.1.0]hexan-3-yl)(4-methyl-2-(oxazol-2-yl)thiazol-5-yl)

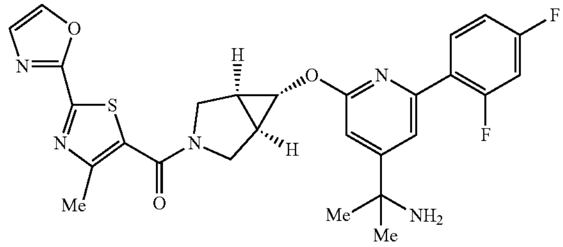

To a stirred solution of benzyl (2-(2-(((1R,5S,6s)-3-azabicyclo[3.1.0]hexan-6-yl)oxy)-6-(2,4-difluorophenyl)pyridin-

| Ex # | Structure | Name | Calc'd $[M + H]^+$ | Observed $[M + H]^+$ | Comments |
|---|---|---|---|---|---|
| 28 | 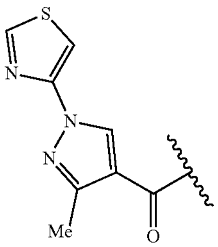 [SMILES: *C(=O)c1cn(-c2cscn2)nc1C] | ((1R,5S,6s)-6-((4-(2-aminopropan-2-yl)-6-(4-fluorophenyl)pyridin-2-yl)oxy)-3-azabicyclo[3.1.0]hexan-3-yl)(3-methyl-1-(thiazol-4-yl)-1H-pyrazol-4-yl)methanone | 519.2 | 519.2 | TFA salt |
| 29 | 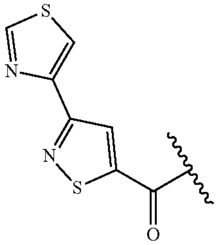 [SMILES: *C(=O)c1cc(-c2cscn2)ns1] | ((1R,5S,6s)-6-((4-(2-aminopropan-2-yl)-6-(4-fluorophenyl)pyridin-2-yl)oxy)-3-azabicyclo[3.1.0]hexan-3-yl)(3-(thiazol-4-yl)isothiazol-5-yl)methanone | 522.1 | 522.1 | HCl salt |
| 30 | 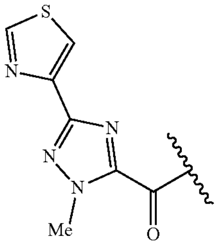 [SMILES: *C(=O)c1nc(-c2cscn2)nn1C] | ((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(thiazol-4-yl)-1H-1,2,4-triazol-5-yl)methanone | 520.2 | 520.2 | HCl salt |

4-yl)propan-2-yl)carbamate (Int. H-13, 15 mg, 0.029 mmol) and 4-methyl-2-(oxazol-2-yl)thiazole-5-carboxylic acid (Int. K-01 6.1 mg, 0.029 mmol) in DCM (0.50 mL) was added HATU (11 mg, 0.029 mmol) and then DIPEA (15 μL, 0.087 mmol). The mixture was stirred at rt for 1 h and then concentrated under reduced pressure. Hydrochloric acid (37% aq., 0.20 mL) was added, and the mixture was heated at 80° C. for 10 min, cooled to rt, and concentrated. The residue was dissolved in DMSO (1 mL) and subjected to mass directed reverse phase HPLC (MeCN/water with 0.1% TFA modifier) to afford the title compound as a TFA salt. MS m/z $(M+H)^+$: calculated 538.2; found 538.2. $^1H$ NMR (500 MHz, DMSO-$d^6$) 8.37-8.34 (m, 1H), 8.05-7.97 (m, 1H), 7.55 (s, 1H), 7.53-7.50 (m, 1H), 7.43-7.36 (m, 1H), 7.26-7.20 (m, 1H), 6.93 (s, 1H), 4.04 (s, 1H), 3.77-3.34 (m, 4H), 2.43 (s, 3H), 2.14-1.93 (m, 2H), 1.62 (s, 6H) ppm.

Utilizing the procedures described in EXAMPLE 31, the following compounds were prepared substituting the appropriate reagents for benzyl (2-(2-(((1R,5S,6s)-3-azabicyclo[3.1.0]hexan-6-yl)oxy)-6-(2,4-difluorophenyl)pyridin-4-yl)propan-2-yl)carbamate and 4-methyl-2-(oxazol-2-yl)thiazole-5-carboxylic acid. Following HPLC purification, examples were concentrated directly to afford TFA or HCl salts or extracted under basic conditions to afford free bases.

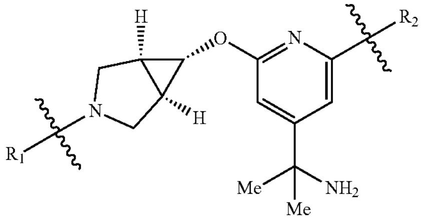

| Ex # | $R_1$ | $R_2$ | Name | Calc'd $[M + H]^+$ | Obs $[M + H]^+$ | Comments |
|---|---|---|---|---|---|---|
| 32 | 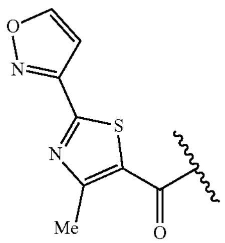 [SMILES: *C(=O)c1sc(-c2ccon2)nc1C] | 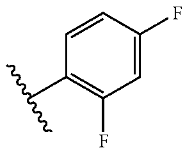 [SMILES: *c1ccc(F)cc1F] | ((1R,5S,6s)-6-((4-(2-aminopropan-2-yl)-6-(2,4-difluorophenyl)pyridin-2-yl)oxy)-3-azabicyclo[3.1.0]hexan-3-yl)(2-(isoxazol-3-yl)-4-methylthiazol-5-yl)methanone | 538.2 | 538.2 | TFA salt |
| 33 | 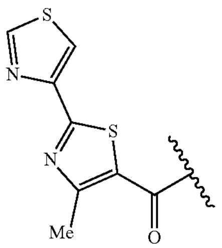 [SMILES: *C(=O)c1sc(-c2cscn2)nc1C] | 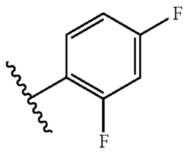 [SMILES: *c1ccc(F)cc1F] | ((1R,5S,6s)-6-((4-(2-aminopropan-2-yl)-6-(2,4-difluorophenyl)pyridin-2-yl)oxy)-3-azabicyclo[3.1.0]hexan-3-yl)(4-methyl-[2,4'-bithiazol]-5-yl)methanone | 554.1 | 554.1 | TFA salt |
| 34 | 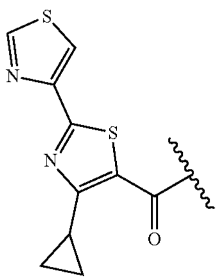 [SMILES: *C(=O)c1sc(-c2cscn2)nc1C1CC1] | 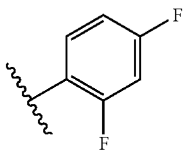 [SMILES: *c1ccc(F)cc1F] | ((1R,5S,6s)-6-((4-(2-aminopropan-2-yl)-6-(2,4-difluorophenyl)pyridin-2-yl)oxy)-3-azabicyclo[3.1.0]hexan-3-yl)(4-cyclopropyl-[2,4'-bithiazol]-5-yl)methanone | 580.2 | 580.3 | TFA salt |
| 35 | 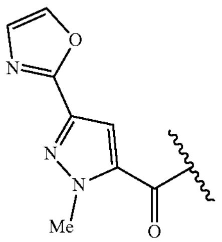 [SMILES: *C(=O)c1cc(-c2ncco2)nn1C] | 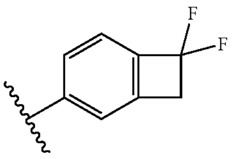 [SMILES: *c1ccc2c(c1)CC2(F)F] | ((1R,5S,6s)-6-((4-(2-aminopropan-2-yl)-6-(7,7-difluorobicyclo[4.2.0]octa-1(6),2,4-trien-3-yl)pyridin-2-yl)oxy)-3-azabicyclo[3.1.0]hexan-3-yl)(1-methyl-3-(oxazol-2-yl)-1H-pyrazol-5-yl)methanone | 547.2 | 547.2 | Free base |

-continued

| Ex # | $R_1$ | $R_2$ | Name | Calc'd $[M + H]^+$ | Obs $[M + H]^+$ | Comments |
|---|---|---|---|---|---|---|
| 36 | 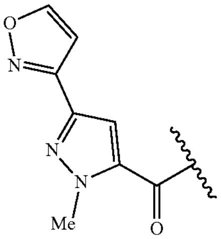 [SMILES: *C(=O)c1cc(-c2ccon2)nn1C] | 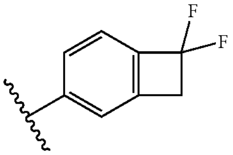 [SMILES: *c1ccc2c(c1)CC2(F)F] | ((1R,5S,6s)-6-((4-(2-aminopropan-2-yl)-6-(7,7-difluorobicyclo[4.2.0]octa-1(6),2,4-trien-3-yl)pyridin-2-yl)oxy)-3-azabicyclo[3.1.0]hexan-3-yl)(3-(isoxazol-3-yl)-1-methyl-1H-pyrazol-5-yl)methanone | 569.2 $(M + Na)^+$ | 569.2 | TFA salt |
| 37 | 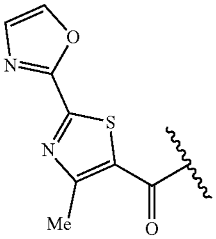 [SMILES: *C(=O)c1sc(-c2ncco2)nc1C] | 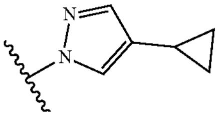 [SMILES: *n1cc(C2CC2)cn1] | ((1R,5S,6s)-6-((4-(2-aminopropan-2-yl)-6-(4-cyclopropyl-1H-pyrazol-1-yl)pyridin-2-yl)oxy)-3-azabicyclo[3.1.0]hexan-3-yl)(4-methyl-2-(oxazol-2-yl)thiazol-5-yl)methanone | 532.2 | 532.2 | HCl salt |
| 38 | 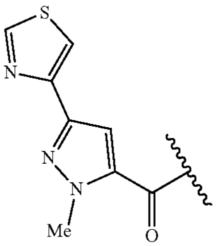 [SMILES: *C(=O)c1cc(-c2cscn2)nn1C] | 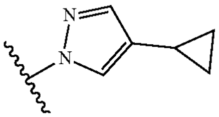 [SMILES: *n1cc(C2CC2)cn1] | ((1R,5S,6s)-6-((4-(2-aminopropan-2-yl)-6-(4-cyclopropyl-1H-pyrazol-1-yl)pyridin-2-yl)oxy)-3-azabicyclo[3.1.0]hexan-3-yl)(1-methyl-3-(thiazol-4-yl)-1H-pyrazol-5-yl)methanone | 531.2 | 531.4 | HCl salt |
| 39 | 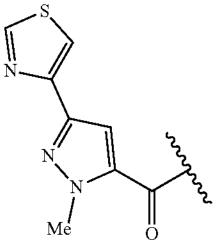 [SMILES: *C(=O)c1cc(-c2cscn2)nn1C] | 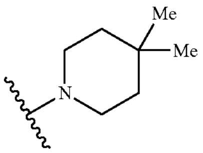 [SMILES: *N1CCC(C)(C)CC1] | ((1R,5S,6s)-6-((4-(2-aminopropan-2-yl)-6-(4,4-dimethylpiperidin-1-yl)pyridin-2-yl)oxy)-3-azabicyclo[3.1.0]hexan-3-yl)(1-methyl-3-(thiazol-4-yl)-1H-pyrazol-5-yl)methanone | 536.3 | 536.6 | Free base |
| 40 | 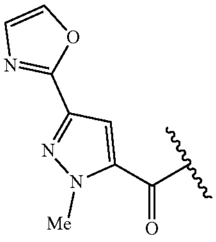 [SMILES: *C(=O)c1cc(-c2ncco2)nn1C] | 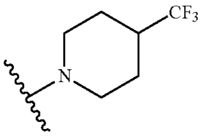 [SMILES: *N1CCC(C(F)(F)F)CC1] | ((1R,5S,6s)-6-((4-(2-aminopropan-2-yl)-6-(4-(trifluoromethyl)piperidin-1-yl)pyridin-2-yl)oxy)-3-azabicyclo[3.1.0]hexan-3-yl)(1-methyl-3-(oxazol-2-yl)-1H-pyrazol-5-yl)methanone | 560.3 | 560.4 | Free base |
| 41 | 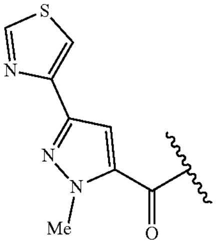 [SMILES: *C(=O)c1cc(-c2cscn2)nn1C] | 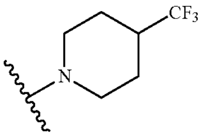 [SMILES: *N1CCC(C(F)(F)F)CC1] | ((1R,5S,6s)-6-((4-(2-aminopropan-2-yl)-6-(4-(trifluoromethyl)piperidin-1-yl)pyridin-2-yl)oxy)-3-azabicyclo[3.1.0]hexan-3-yl)(1-methyl-3-(thiazol-4-yl)-1H-pyrazol-5-yl)methanone | 576.2 | 576.3 | Free base |

-continued

| Ex # | $R_1$ | $R_2$ | Name | Calc'd [M + H]+ | Obs [M + H]+ | Comments |
|---|---|---|---|---|---|---|
| 42 | 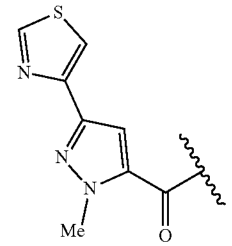 [SMILES: *C(=O)c1cc(-c2cscn2)nn1C] | 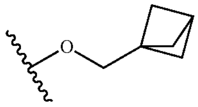 [SMILES: *OCC12CC(C1)C2] | ((1R,5S,6s)-6-((4-(2-aminopropan-2-yl)-6-(bicyclo[1.1.1]pentan-1-ylmethoxy)pyridin-2-yl)oxy)-3-azabicyclo[3.1.0]hexan-3-yl)(1-methyl-3-(thiazol-4-yl)-1H-pyrazol-5-yl)methanone | 521.2 | 521.2 | TFA salt |

Example 43A rel-((1R,5S,6S)-6-((4-(2-aminopropan-2-yl)-6-(4-fluorophenyl)pyridin-2-yl)oxy)-1-methyl-3-azabicyclo[3.1.0]hexan-3-yl)(1-methyl-3-(thiazol-4-yl)-1H-pyrazol-5-yl)methanone (enantiomer 1)

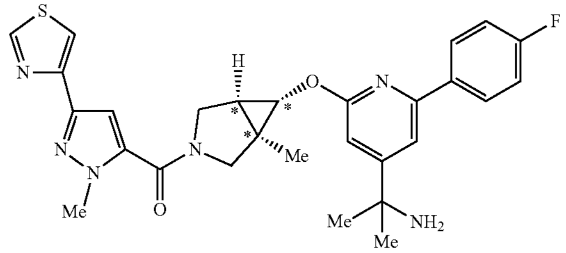 [SMILES: Cn1nc(-c2cscn2)cc1C(=O)N1C[C@H]2[C@H](Oc3cc(C(C)(C)N)cc(-c4ccc(F)cc4)n3)[C@@]2(C)C1]

Step 1: benzyl rel-(2-(2-(4-fluorophenyl)-6-(((1R,5S,6S)-1-methyl-3-(1-methyl-3-(thiazol-4-yl)-1H-pyrazole-5-carbonyl)-3-azabicyclo[3.1.0]hexan-6-yl)oxy)pyridin-4-yl)propan-2-yl)carbamate (enantiomer 1)

To a of solution of 1-methyl-3-(thiazol-4-yl)-1H-pyrazole-5-carboxylic acid (Int. L-1, 26 mg, 0.13 mmol) and benzyl rel-(2-(2-(4-fluorophenyl)-6-(((1R,5S,6S)-1-methyl-3-azabicyclo[3.1.0]hexan-6-yl)oxy)pyridin-4-yl)propan-2-yl)carbamate (Int. I-1-ent-1, 0.040 g, 0.084 mmol) in DMF (2.0 mL) were added DIPEA (0.10 mL, 0.25 mmol) and T3P (50 wt. % in EtOAc, 0.080 g, 0.13 mmol). The mixture was stirred at rt for 1 h, water (5 mL) was added, and the mixture was extracted with EtOAc (10 mL×3). The combined organic extracts were dried with anhydrous sodium sulfate, filtered, and concentrated under reduced pressure. The residue was subjected to prep-TLC (50% EtOAc/petroleum ether, $R_f$=0.35) to afford the title compound.

Step 2: rel-((1R,5S,6S)-6-((4-(2-aminopropan-2-yl)-6-(4-fluorophenyl)pyridin-2-yl)oxy)-1-methyl-3-azabicyclo[3.1.0]hexan-3-yl)(1-methyl-3-(thiazol-4-yl)-1H-pyrazol-5-yl)methanone (enantiomer 1)

A mixture of benzyl rel-(2-(2-(4-fluorophenyl)-6-(((1R,5S,6S)-1-methyl-3-(1-methyl-3-(thiazol-4-yl)-1H-pyrazole-5-carbonyl)-3-azabicyclo[3.1.0]hexan-6-yl)oxy)pyridin-4-yl)propan-2-yl)carbamate (enantiomer 1, 42 mg, 0.063 mmol) and hydrochloric acid (37%, 2.0 mL) was stirred at 80° C. for 10 min. The mixture was cooled to rt, filtered, concentrated under reduced pressure, and subjected to reverse phase HPLC (15-35% MeCN/water with 0.05% HCl modifier). The appropriate fractions were lyophilized to afford the title compound as a HCl salt. MS m/z $(M+H)^+$: calculated 533.2, observed 533.2. $^1H$ NMR ($CD_3OD$, 400 MHz) δ 9.64 (s, 1H), 8.30-8.04 (m, 3H), 7.66 (s, 1H), 7.20-7.15 (m, 3H), 6.92 (s, 1H), 4.29-4.25 (m, 1H), 4.07-3.98 (m, 5H), 3.95-3.52 (m, 2H), 1.78-1.72 (m, 7H), 1.35 (s, 3H) ppm.

Utilizing the procedures described in EXAMPLE 43A, the following compounds were prepared substituting the appropriate reagents for 1-methyl-3-(thiazol-4-yl)-1H-pyrazole-5-carboxylic acid and Int. J-1-ent-1. Examples were subjected to reverse phase HPLC (MeCN/water with either 0.1% TFA or 0.05% HCl modifiers) and lyophilized to afford TFA or HCl salts.

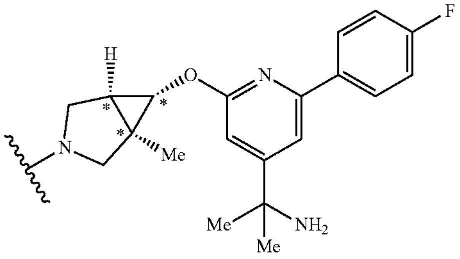 [SMILES: *N1C[C@H]2[C@H](Oc3cc(C(C)(C)N)cc(-c4ccc(F)cc4)n3)[C@@]2(C)C1]

| Ex # | Structure | Name | Calc'd [M + H]$^+$ | Observed [M + H]$^+$ | Comments |
|---|---|---|---|---|---|
| 43B | 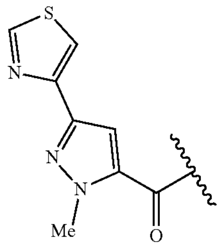 [SMILES: *C(=O)c1cc(-c2cscn2)nn1C] | rel-((1R,5S,6S)-6-((4-(2-aminopropan-2-yl)-6-(4-fluorophenyl)pyridin-2-yl)oxy)-1-methyl-3-azabicyclo[3.1.0]hexan-3-yl)(1-methyl-3-(thiazol-4-yl)-1H-pyrazol-5-yl)methanone (enantiomer 2) | 533.2 | 533.2 | Step 1: Int. I-1-ent-2 Form: HCl salt |
| 44A | 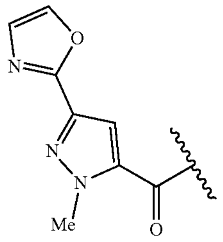 [SMILES: *C(=O)c1cc(-c2ncco2)nn1C] | rel-((1R,5S,6S)-6-((4-(2-aminopropan-2-yl)-6-(4-fluorophenyl)pyridin-2-yl)oxy)-1-methyl-3-azabicyclo[3.1.0]hexan-3-yl)(1-methyl-3-(oxazol-2-yl)-1H-pyrazol-5-yl)methanone (enantiomer 1) | 517.2 | 517.1 | Step 1: Int. I-1-ent-1 Form: TFA salt |
| 44B | 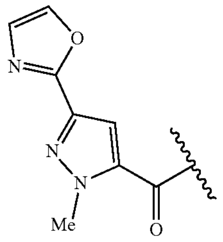 [SMILES: *C(=O)c1cc(-c2ncco2)nn1C] | rel-((1R,5S,6S)-6-((4-(2-aminopropan-2-yl)-6-(4-fluorophenyl)pyridin-2-yl)oxy)-1-methyl-3-azabicyclo[3.1.0]hexan-3-yl)(1-methyl-3-(oxazol-2-yl)-1H-pyrazol-5-yl)methanone (enantiomer 2) | 517.2 | 517.1 | Step 1: Int. I-1-ent-2 Form: TFA salt |
| 45A | 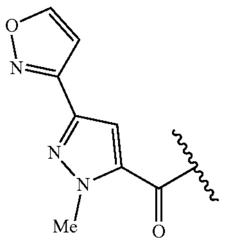 [SMILES: *C(=O)c1cc(-c2ccon2)nn1C] | rel-((1R,5S,6S)-6-((4-(2-aminopropan-2-yl)-6-(4-fluorophenyl)pyridin-2-yl)oxy)-1-methyl-3-azabicyclo[3.1.0]hexan-3-yl)(3-(isoxazol-3-yl)-1-methyl-1H-pyrazol-5-yl)methanone (enantiomer 1) | 517.2 | 517.1 | Step 1: Int. I-1-ent-1 Form: HCl salt |
| 45B | 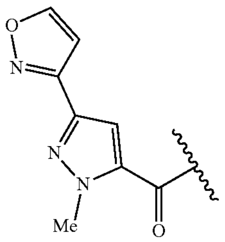 [SMILES: *C(=O)c1cc(-c2ccon2)nn1C] | rel-((1R,5S,6S)-6-((4-(2-aminopropan-2-yl)-6-(4-fluorophenyl)pyridin-2-yl)oxy)-1-methyl-3-azabicyclo[3.1.0]hexan-3-yl)(3-(isoxazol-3-yl)-1-methyl-1H-pyrazol-5-yl)methanone (enantiomer 2) | 517.2 | 517.1 | Step 1: Int. I-1-ent-2 Form: HCl salt |

Example 46A rel-((1R,5S,6S)-6-((4-(2-aminopropan-2-yl)-6-(4,4-dimethylpiperidin-1-yl)pyridin-2-yl)oxy)-1-methyl-3-azabicyclo[3.1.0]hexan-3-yl) (1-methyl-3-(thiazol-4-yl)-1H-pyrazol-5-yl)methanone (enantiomer 1)

and

Example 46B rel-((1R,5S,6S)-6-((4-(2-aminopropan-2-yl)-6-(4,4-dimethylpiperidin-1-yl)pyridin-2-yl)oxy)-1-methyl-3-azabicyclo[3.1.0]hexan-3-yl) (1-methyl-3-(thiazol-4-yl)-1H-pyrazol-5-yl)methanone (enantiomer 2)

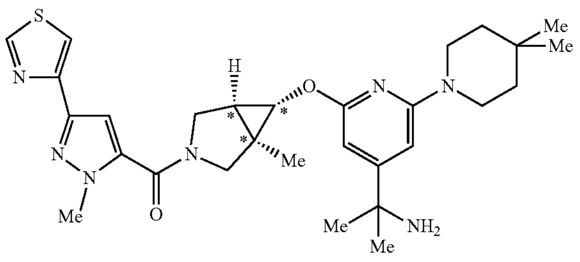 [SMILES: Cn1nc(-c2cscn2)cc1C(=O)N1C[C@H]2[C@H](Oc3cc(C(C)(C)N)cc(N4CCC(C)(C)CC4)n3)[C@@]2(C)C1]

Step 1: benzyl rel-(2-(2-(4,4-dimethylpiperidin-1-yl)-6-(((1R,5S,6S)-1-methyl-3-(1-methyl-3-(thiazol-4-yl)-1H-pyrazole-5-carbonyl)-3-azabicyclo[3.1.0]hexan-6-yl)oxy)pyridin-4-yl)propan-2-yl)carbamate (enantiomers 1 and 2)

A mixture of 1-methyl-3-(thiazol-4-yl)-1H-pyrazole-5-carboxylic acid (Int. L-1, 26 mg, 0.12 mmol), benzyl rac-(2-(2-(4,4-dimethylpiperidin-1-yl)-6-(((1R,5S,6S)-1-methyl-3-azabicyclo[3.1.0]hexan-6-yl)oxy)pyridin-4-yl)propan-2-yl)carbamate (Int. I-2, 0.060 g, 0.12 mmol), DMF (2.0 mL), DIPEA (0.10 mL, 0.37 mmol), and T3P (50 wt % in EtOAc, 120 mg, 0.18 mmol) was stirred at rt for 1 h. Water (5 mL) was added and the mixture was extracted with EtOAc (10 mL×3). The combined organic solution was dried over anhydrous sodium sulfate, filtered, and concentrated under reduced pressure. The residue was purified by prep-TLC (25% EtOAc/petroleum ether) to afford the title compound. The mixture of two stereoisomers was subjected to chiral SFC (ChiralPak AS, 35% IPA (with 0.1% $NH_4OH$ modifier)/$CO_2$) to afford benzyl rel-(2-(2-(4,4-dimethylpiperidin-1-yl)-6-(((1R,5S,6S)-1-methyl-3-(1-methyl-3-(thiazol-4-yl)-1H-pyrazole-5-carbonyl)-3-azabicyclo[3.1.0]hexan-6-yl)oxy)pyridin-4-yl)propan-2-yl)carbamate (enantiomer 1, faster eluting) and benzyl rel-(2-(2-(4,4-dimethylpiperidin-1-yl)-6-(((1R,5S,6S)-1-methyl-3-(1-methyl-3-(thiazol-4-yl)-1H-pyrazole-5-carbonyl)-3-azabicyclo[3.1.0]hexan-6-yl)oxy)pyridin-4-yl)propan-2-yl)carbamate (enantiomer 2, slower eluting).

Step 2-1: rel-((1R,5S,6S)-6-((4-(2-aminopropan-2-yl)-6-(4,4-dimethylpiperidin-1-yl)pyridin-2-yl)oxy)-1-methyl-3-azabicyclo[3.1.0]hexan-3-yl)(1-methyl-3-(thiazol-4-yl)-1H-pyrazol-5-yl)methanone (enantiomer 1)

A mixture of benzyl rel-(2-(2-(4,4-dimethylpiperidin-1-yl)-6-(((1R,5S,6S)-1-methyl-3-(1-methyl-3-(thiazol-4-yl)-1H-pyrazole-5-carbonyl)-3-azabicyclo[3.1.0]hexan-6-yl)oxy)pyridin-4-yl)propan-2-yl)carbamate (enantiomer 1, 23 mg, 0.034 mmol) and hydrochloric acid (37%, 2.0 mL) stirred at 80° C. for 10 min. The mixture was cooled to rt, diluted with MeOH (2 mL), and filtered. The mixture was subjected to reverse phase HPLC (25-45% MeCN/water with 0.05% HCl modifier) and lyophilized to afford EXAMPLE 46A as an HCl salt. MS m/z $(M+H)^+$: calculated 550.3, observed 550.2. $^1H$ NMR (500 MHz, $CD_3OD$) δ 9.19-9.04 (m, 1H), 7.97-7.89 (m, 1H), 7.03 (d, J=4.9 Hz, 1H), 6.42-6.32 (m, 1H), 6.10 (s, 1H), 4.29-4.20 (m, 1H), 4.04 (s, 3H), 4.00-3.90 (m, 1H), 3.85-3.67 (m, 2H), 3.65-3.47 (m, 5H), 1.73-1.60 (m, 7H), 1.40-1.21 (m, 7H), 0.96 (s, 3H), 0.91 (s, 3H) ppm.

Step 2-2: rel-((1R,5S,6S)-6-((4-(2-aminopropan-2-yl)-6-(4,4-dimethylpiperidin-1-yl)pyridin-2-yl)oxy)-1-methyl-3-azabicyclo[3.1.0]hexan-3-yl)(1-methyl-3-(thiazol-4-yl)-1H-pyrazol-5-yl)methanone (enantiomer 2)

A mixture of benzyl rel-(2-(2-(4,4-dimethylpiperidin-1-yl)-6-(((1R,5S,6S)-1-methyl-3-(1-methyl-3-(thiazol-4-yl)-1H-pyrazole-5-carbonyl)-3-azabicyclo[3.1.0]hexan-6-yl)oxy)pyridin-4-yl)propan-2-yl)carbamate (enantiomer 2, 22 mg, 0.032 mmol) and hydrochloric acid (37%, 3.0 mL) stirred at 80° C. for 10 min. The mixture was cooled to rt, diluted with MeOH (2 mL), and filtered. The mixture was subjected to reverse phase HPLC (25-45% MeCN/water with 0.05% HCl modifier) and lyophilized to afford EXAMPLE 46B as an HCl salt. MS m/z $(M+H)^+$: calculated 550.3, observed 550.2. $^1H$ NMR (500 MHz, $CD_3OD$) δ 9.14-9.04 (m, 1H), 7.97-7.88 (m, 1H), 7.03 (d, J=4.9 Hz, 1H), 6.41-6.28 (m, 1H), 6.10 (s, 1H), 4.29-4.20 (m, 1H), 4.04 (s, 3H), 4.01-3.94 (m, 1H), 3.84-3.68 (m, 2H), 3.66-3.46 (m, 5H), 1.74-1.58 (m, 7H), 1.40-1.22 (m, 7H), 0.96 (s, 3H), 0.91 (s, 3H) ppm.

Scheme:

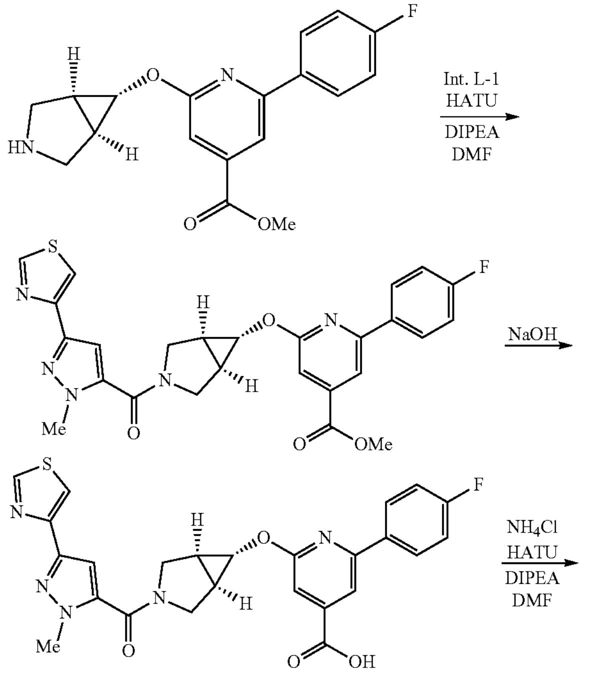

-continued

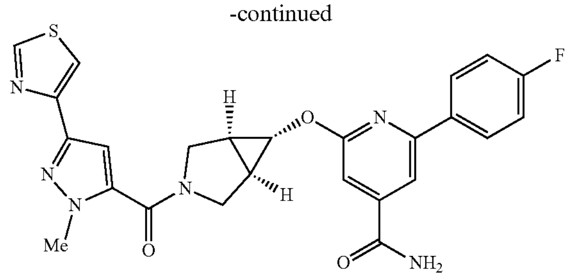

Example 47

2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)isonicotinamide

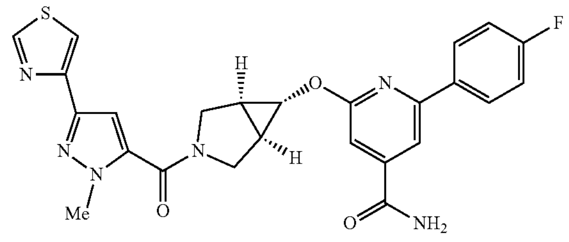 [SMILES: Cn1nc(-c2cscn2)cc1C(=O)N1C[C@@H]2[C@H](C1)[C@H]2Oc1cc(C(N)=O)cc(-c2ccc(F)cc2)n1]

Step 1: methyl 2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)isonicotinate To a stirred solution of methyl 2-(((1R,5S,6s)-3-azabicyclo[3.1.0]hexan-6-yl)oxy)-6-(4-fluorophenyl)isonicotinate (Int. H-10, 120 mg, 0.36 mmol) and 1-methyl-3-(thiazol-4-yl)-1H-pyrazole-5-carboxylic acid (Int. L-1, 75 mg, 0.36 mmol) in DCM (2.0 mL) was added HATU (210 mg, 0.54 mmol) followed by DIPEA (0.18 mL, 1.1 mmol). The mixture was stirred at rt for 1 h, poured into water (5 mL), and extracted with DCM (3×5 mL). The combined organic extracts were washed with $NaHCO_3$ (saturated aq., 5 mL) and brine (5 mL), dried with anhydrous sodium sulfate, filtered, and concentrated under reduced pressure. The residue was subjected to silica gel chromatography (0-70% (25% EtOH/EtOAc)/hexanes) to afford the title compound.

Step 2: 2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)isonicotinic acid To a solution of methyl 2-(4-fluorophenyl)-6-((3-(1-methyl-3-(thiazol-4-yl)-1H-pyrazole-5-carbonyl)-3-azabicyclo[3.1.0]hexan-6-yl)oxy)isonicotinate (96 mg, 0.19 mmol) in MeOH (1.0 mL) was added a solution of sodium hydroxide (1.0 M aq., 0.37 mL, 0.37 mmol). The mixture was heated at 80° C. for 1 h, cooled to rt, and concentrated under reduced pressure. The residue was dissolved in EtOAc (3.0 mL), washed with hydrochloric acid (1 N aq.), dried with anhydrous sodium sulfate, filtered, and concentrated to afford the title compound.

Step 3: 2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)isonicotinamide A mixture of 2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)isonicotinic acid (0.050 g, 0.10 mmol), ammonium chloride (16 mg, 0.30 mmol), DMF (0.50 mL), DIPEA (52 μL, 0.30 mmol), and HATU (56 mg, 0.10 mmol) was stirred at rt for 1 h. The mixture was subjected to reverse phase HPLC (10-100% MeCN/water with 0.1% TFA modifier). The appropriate fractions were treated with $NaHCO_3$ (saturated aq., 5 mL) and extracted with DCM (3×5 mL). The combined organic extracts were washed with brine (5 mL), dried with anhydrous sodium sulfate, filtered, and concentrated under reduced pressure to afford the title compound. MS m/z: $(M+H)^+$: calculated 505.2; found 505.2. $^1H$ NMR (500 MHz, DMSO-$d^6$) δ 9.18 (s, 1H), 8.28 (s, 1H), 8.21-8.14 (m, 2H), 7.98 (d, J=8.5 Hz, 2H), 7.77 (s, 1H), 7.34 (t, J=8.3 Hz, 2H), 7.20 (s, 1H), 7.05 (s, 1H), 4.13-4.07 (m, 1H), 4.07-4.04 (m, 1H), 3.97 (s, 3H), 3.96-3.90 (m, 2H), 3.70-3.64 (m, 1H), 2.14-2.05 (m, 2H) ppm.

Scheme:

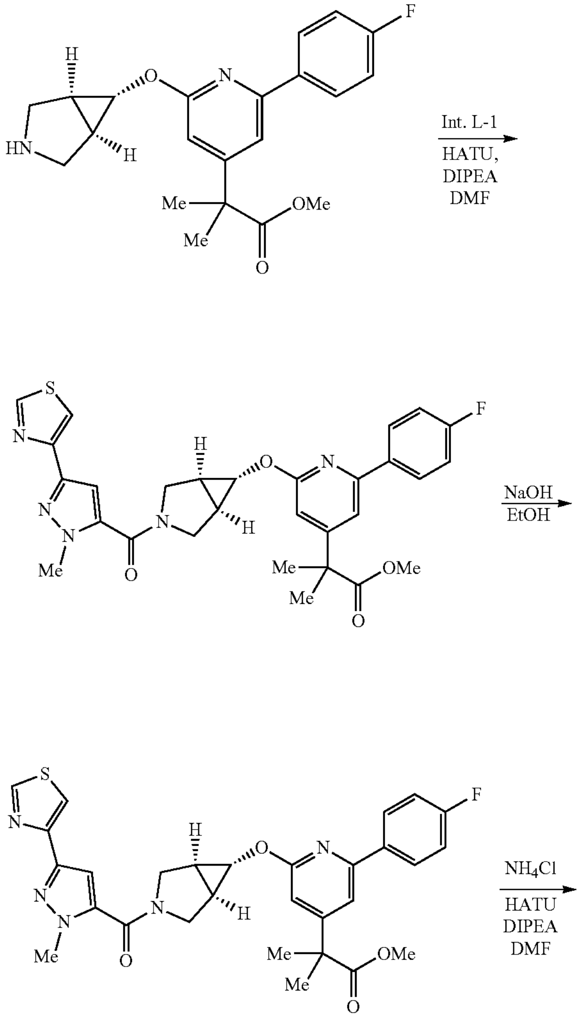

-continued

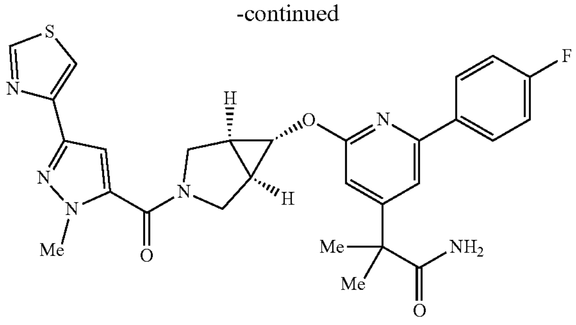

Example 48

2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-2-methylpropanamide

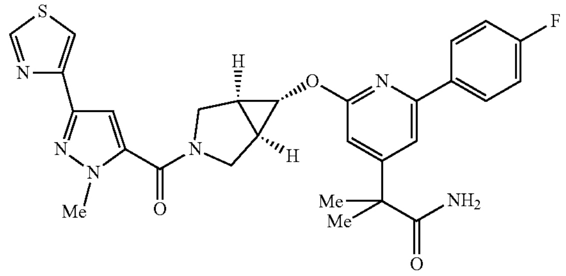 [SMILES: Cn1nc(-c2cscn2)cc1C(=O)N1C[C@@H]2[C@H](C1)[C@H]2Oc1cc(C(C)(C)C(N)=O)cc(-c2ccc(F)cc2)n1]

Step 1: methyl 2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-2-methylpropanoate To a rt mixture of methyl 2-(2-(((1R,5S,6s)-3-azabicyclo[3.1.0]hexan-6-yl)oxy)-6-(4-fluorophenyl)pyridin-4-yl)-2-methylpropanoate (Int. H-09, 0.040 g, 0.10 mmol), 1-methyl-3-(thiazol-4-yl)-1H-pyrazole-5-carboxylic acid (Int. L-1, 27 mg, 0.13 mmol), and DMF (1.0 mL) was added DIPEA (0.090 mL, 0.52 mmol) then HATU (49 mg, 0.13 mmol). The mixture was stirred for 18 h at rt and then subjected to reverse phase HPLC (5-95% MeCN/water with 0.1% TFA modifier). The appropriate fractions were concentrated to afford the title compound.

Step 2: 2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-2-methylpropanoic acid A mixture of methyl 2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-2-methylpropanoate (34 mg, 0.060 mmol), EtOH (0.50 mL), and NaOH (2.0 N aq., 0.15 mL, 0.30 mmol) was stirred at 90° C. for 4 h. The mixture was cooled to rt and concentrated. The residue was dissolved in a 2:1 mixture of $H_2O$:$CH_3CN$, to which hydrochloric acid (1 N aq., 0.31 mL) was added, and the resulting mixture was lyophilized to afford the title compound.

Step 3: 2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-2-methylpropanamide To a rt mixture of 2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-2-methylpropanoic acid (33 mg, 0.060 mmol), $NH_4Cl$ (16 mg, 0.31 mmol), DMF (1.0 mL), and DIPEA (0.060 mL, 0.34 mmol) was added HATU (35 mg, 0.090 mmol). After 4 h, the mixture was subjected to reverse phase HPLC (5-65% MeCN/water with 0.1% TFA modifier). The appropriate fractions were concentrated, neutralized, extracted, and concentrated to afford the title compound. MS m/z $(M+H)^+$: calculated 547.2, observed 547.1. $^1$H-NMR (500 MHz, DMSO-$d^6$) δ 9.18 (s, 1H), 8.11 (dd, J=8.4, 5.7 Hz, 2H), 7.97 (s, 1H), 7.49 (s, 1H), 7.31 (t, J=8.7 Hz, 2H), 7.11-6.98 (m, 3H), 6.70 (s, 1H), 4.06 (d, J=12.2 Hz, 1H), 4.01 (s, 1H), 3.91 (m, 3H), 3.95-3.88 (m, 2H), 3.70-3.64 (m, 1H), 2.10-2.01 (m, 2H), 1.48 (s, 6H) ppm.

Example 49A ent-2-amino-2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)propanamide (enantiomer 1) and Example 49B ent-2-amino-2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)propanamide (enantiomer 2)

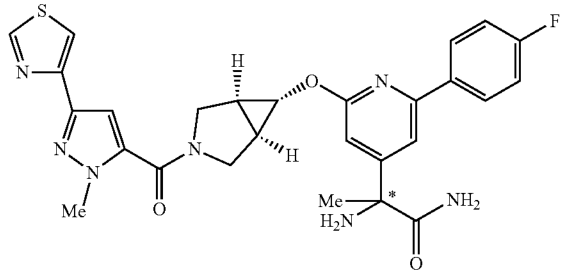 [SMILES: Cn1nc(-c2cscn2)cc1C(=O)N1C[C@@H]2[C@H](C1)[C@H]2Oc1cc(C(C)(N)C(N)=O)cc(-c2ccc(F)cc2)n1]

A mixture of 1-methyl-3-(thiazol-4-yl)-1H-pyrazole-5-carboxylic acid (Int. L-1, 0.030 g, 0.14 mmol), HATU (59 mg, 0.16 mmol), DMF (0.25 mL), and DIPEA (25 μL) was stirred at rt for 15 min. The mixture was transferred to a solution of rac-2-(2-(((1R,5S,6s)-3-azabicyclo[3.1.0]hexan-6-yl)oxy)-6-(4-fluorophenyl)pyridin-4-yl)-2-aminopropanamide·HCl (Int. H-20, 56 mg, 0.14 mmol) and DIPEA (0.10 mL) in DMF (0.75 mL) and stirred for 18 hr. The mixture was subjected to reverse phase HPLC (5-50% MeCN/water with 0.1% TFA modifier). The racemate was subjected to chiral SFC (AS-H, 40% EtOH (with 0.1% DEA modifier)/$CO_2$) to afford the title compounds. EXAMPLE 49A (faster eluting enantiomer): MS m/z $(M+H)^+$: calculated 548.2, observed 548.3. $^1$H-NMR (500 MHz, DMSO-$d^6$) δ 9.18 (d, J=1.9 Hz, 1H), 8.11 (dd, J=8.7, 5.6 Hz, 2H), 7.97 (d, J=1.9 Hz, 1H), 7.69 (s, 1H), 7.40 (s, 1H), 7.31 (t, J=8.8 Hz, 2H), 7.15 (s, 1H), 7.04 (s, 1H), 6.89 (s, 1H), 4.07

(d, J=12.4 Hz, 1H), 4.01-3.99 (m, 1H), 3.96 (s, 3H), 3.95-3.88 (m, 2H), 3.67 (dd, J=12.3, 4.3 Hz, 1H), 2.56 (br s, 2H), 2.10-2.00 (m, 2H), 1.54 (s, 3H) ppm. EXAMPLE 49B (slower eluting enantiomer): MS m/z $(M+H)^+$: calculated 548.2, observed 548.3. $^1$H-NMR (500 MHz, DMSO-d$^6$) δ 9.20-9.16 (m, 1H), 8.14-8.08 (m, 2H), 7.99-7.95 (m, 1H), 7.69 (s, 1H), 7.41 (s, 1H), 7.32 (t, J=8.5 Hz, 2H), 7.15 (s, 1H), 7.04 (s, 1H), 6.89 (s, 1H), 4.07 (d, J=12.4 Hz, 1H), 4.01-3.99 (m, 1H), 3.96 (s, 3H), 3.95-3.88 (m, 2H), 3.71-3.63 (m, 1H), 2.59 (br s, 2H), 2.11-2.00 (m, 2H), 1.55 (s, 3H) ppm.

Example 50A ent-3-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-3-methylazetidin-2-one (enantiomer 1) and Example 50B ent-3-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-3-methylazetidin-2-one (enantiomer 2)

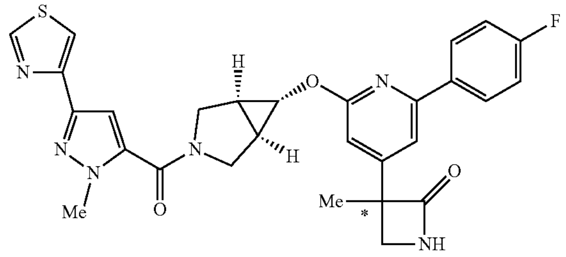 [SMILES: Cn1nc(-c2cscn2)cc1C(=O)N1C[C@@H]2[C@H](C1)[C@H]2Oc1cc(C2(C)CNC2=O)cc(-c2ccc(F)cc2)n1]

To a rt solution of 1-methyl-3-(thiazol-4-yl)-1H-pyrazole-5-carboxylic acid (Int. L-1, 38 mg, 0.18 mmol) in DMF (0.010 L) was added DIPEA (0.10 mL, 0.18 mmol), ent-3-(2-(((1R,5S,6s)-3-azabicyclo[3.1.0]hexan-6-yl)oxy)-6-(4-fluorophenyl)pyridin-4-yl)-3-methylazetidin-2-one (Int. H-19, 0.080 g, 0.18 mmol), and T3P (50 wt % in EtOAc, 120 mg, 0.18 mmol). After 1 h, the mixture was diluted with $H_2O$ (10 mL) and extracted with EtOAc (3×). The combined organic extracts were washed with brine, dried with anhydrous sodium sulfate, filtered, and concentrated. The residue was purified by prep-TLC (EtOAc). The racemate was subjected to chiral SFC (ChiralPak AS, 40% EtOH (with 0.1% $NH_4OH$ modifier)/$CO_2$) to afford the title compounds. EXAMPLE 50A (faster eluting enantiomer): MS m/z $(M+H)^+$: calculated 545.2, observed 545.1. $^1$H-NMR (500 MHz, $CD_3OD$) δ 9.11 (s, 1H), 8.19-8.06 (m, 2H), 7.94 (s, 1H), 7.54 (s, 1H), 7.19 (t, J=9.0 Hz, 2H), 7.10 (s, 1H), 6.84 (s, 1H), 4.27 (d, J=12.0 Hz, 1H), 4.09-4.00 (m, 6H), 3.82-3.73 (m, 1H), 3.61 (d, J=6.0 Hz, 1H), 3.50 (d, J=5.5 Hz, 1H), 2.17-2.07 (m, 2H), 1.71 (s, 3H) ppm. EXAMPLE 50B (slower eluting enantiomer): MS m/z $(M+H)^+$: calculated 545.2, observed 545.1. $^1$H-NMR (500 MHz, $CD_3OD$) δ 9.11 (s, 1H), 8.16-8.03 (m, 2H), 7.94 (s, 1H), 7.54 (s, 1H), 7.19 (t, J=9.0 Hz, 2H), 7.10 (s, 1H), 6.84 (s, 1H), 4.27 (d, J=12.0 Hz, 1H), 4.14-3.99 (m, 6H), 3.82-3.73 (m, 1H), 3.61 (d, J=6.0 Hz, 1H), 3.50 (d, J=5.5 Hz, 1H), 2.17-2.04 (m, 2H), 1.71 (s, 3H) ppm.

Example 51A ent-3-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-3-methylpyrrolidin-2-one (enantiomer 1) and Example 51B ent-3-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-3-methylpyrrolidin-2-one (enantiomer 2)

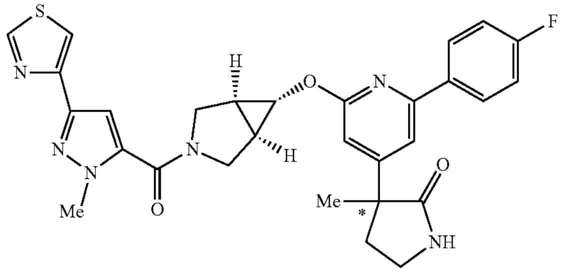 [SMILES: Cn1nc(-c2cscn2)cc1C(=O)N1C[C@@H]2[C@H](C1)[C@H]2Oc1cc(C2(C)CCNC2=O)cc(-c2ccc(F)cc2)n1]

To a rt solution of 1-methyl-3-(thiazol-4-yl)-1H-pyrazole-5-carboxylic acid (Int. L-1, 0.050 g, 0.24 mmol) in DMF (0.010 L) was added DIPEA (0.10 mL, 0.72 mmol) and rac-3-(2-(((1R,5S,6s)-3-azabicyclo[3.1.0]hexan-6-yl)oxy)-6-(4-fluorophenyl)pyridin-4-yl)-3-methylpyrrolidin-2-one (Int. H-05, 110 mg, 0.24 mmol) then T3P (50 wt % in EtOAc, 230 mg, 0.36 mmol). After 30 minutes, the mixture was diluted with $H_2O$ (15 mL) and extracted with EtOAc (3×). The combined organic extracts were washed with brine, dried with anhydrous sodium sulfate, filtered, and concentrated. The residue was purified by prep-TLC (EtOAc). The racemate was subjected to chiral SFC (ChiralPak OD-H, 50% EtOH (with 0.1% $NH_4OH$ modifier)/$CO_2$) to afford the title compounds. EXAMPLE 51A (faster eluting enantiomer): MS m/z $(M+H)^+$: calculated 559.2, observed 559.1. $^1$H-NMR (500 MHz, $CD_3OD$) δ 9.10 (s, 1H), 8.18-8.05 (m, 2H), 7.93 (s, 1H), 7.54 (s, 1H), 7.27-7.13 (m, 2H), 7.09 (s, 1H), 6.84 (s, 1H), 4.33-4.23 (m, 1H), 4.10-3.97 (m, 6H), 3.82-3.70 (m, 1H), 3.51-3.35 (m, 2H), 2.61-2.49 (m, 1H), 2.43-2.28 (m, 1H), 2.16-2.03 (m, 2H), 1.58 (s, 3H) ppm. EXAMPLE 51B (slower eluting enantiomer): MS m/z $(M+H)^+$: calculated 559.2, observed 559.1. $^1$H-NMR (500 MHz, $CD_3OD$) δ 8.98 (s, 1H), 8.01-7.93 (m, 2H), 7.81 (s, 1H), 7.42 (s, 1H), 7.06 (t, J=8.5 Hz, 2H), 6.97 (s, 1H), 6.71 (s, 1H), 4.18-4.11 (m, 1H), 3.97-3.87 (m, 6H), 3.70-3.61 (m, 1H), 3.36-3.23 (m, 2H), 2.48-2.39 (m, 1H), 2.28-2.18 (m, 1H), 2.03-1.92 (m, 2H), 1.46 (s, 3H) ppm.

Example 52

((1R,5S,6s)-6-((4-(1-aminocyclobutyl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone

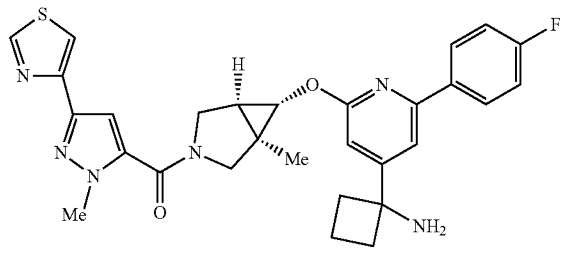 [SMILES: Cn1nc(-c2cscn2)cc1C(=O)N1C[C@H]2[C@H](Oc3cc(C4(N)CCC4)cc(-c4ccc(F)cc4)n3)[C@@]2(C)C1]

Step 1: N-(1-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)cyclobutyl)-2-methylpropane-2-sulfinamide To a rt solution of 1-methyl-3-(thiazol-4-yl)-1H-pyrazole-5-carboxylic acid (Int. L-1, 57 mg, 0.27 mmol) and HATU (0.10 g, 0.27 mmol) in DMF (0.010 L) were added DIPEA (0.10 mL, 0.81 mmol) and N-(1-(2-(((1R,5S,6s)-3-azabicyclo[3.1.0]hexan-6-yl)oxy)-6-(4-fluorophenyl)pyridin-4-yl)cyclobutyl)-2-methylpropane-2-sulfinamide (Int. H-06, 120 mg, 0.27 mmol). The mixture was stirred at rt for 12 h. Water (10 mL) was added and the mixture was extracted with EtOAc (20 mL×3). The combined organic extracts were dried with anhydrous sodium sulfate, filtered, and concentrated. The mixture was purified by prep-TLC (67% EtOAc/petroleum ether) to afford the title compound.

Step 2: ((1R,5S,6s)-6-((4-(1-aminocyclobutyl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone A mixture of N-(1-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)cyclobutyl)-2-methylpropane-2-sulfinamide (0.070 g, 0.11 mmol) in methanolic HCl (4.0 M, 5.0 mL) was stirred at rt for 1 h. The mixture was subjected to reverse phase HPLC (20-40% MeCN/water with 0.05% HCl) and concentrated to afford the title compound as a HCl salt. MS m/z $(M+H)^+$: calculated 531.2, observed 531.2. $^1$H-NMR (400 MHz, $CD_3OD$) δ 9.21 (s, 1H), 8.23-8.08 (m, 2H), 7.98 (s, 1H), 7.59 (s, 1H), 7.21 (t, J=8.8 Hz, 2H), 7.10 (s, 1H), 6.88 (d, J=0.8 Hz, 1H), 4.27 (d, J=12.4 Hz, 1H), 4.13-3.96 (m, 6H), 3.84-3.70 (m, 1H), 2.87-2.74 (m, 2H), 2.69-2.56 (m, 2H), 2.35-2.20 (m, 1H), 2.16-2.06 (m, 2H), 2.09-2.00 (m, 1H) ppm.

Utilizing the procedures described in EXAMPLE 52, the following compound was prepared substituting the appropriate reagents for Int. H-06.

| Ex # | Structure | Name | Calc'd $[M+H]^+$ | Observed $[M+H]^+$ |
|---|---|---|---|---|
| 53 | 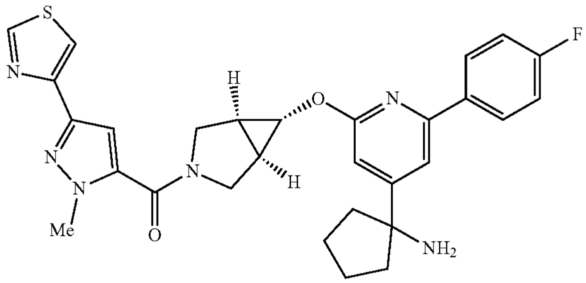 [SMILES: Cn1nc(-c2cscn2)cc1C(=O)N1C[C@@H]2[C@H](C1)[C@H]2Oc1cc(C2(N)CCCC2)cc(-c2ccc(F)cc2)n1] | ((1R,5S,6s)-6-((4-(1-aminocyclopentyl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone | 545.2 | 545.2 |

Example 54

((1R,5S,6s)-6-((4-(1-amino-2-methylpropan-2-yl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone

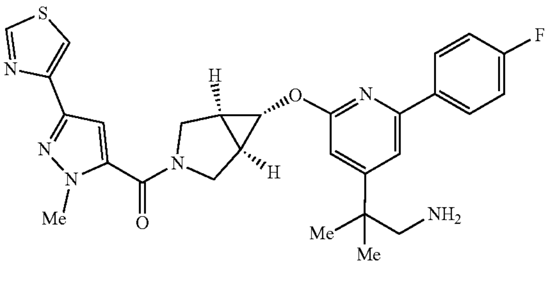 [SMILES: Cn1nc(-c2cscn2)cc1C(=O)N1C[C@@H]2[C@H](C1)[C@H]2Oc1cc(C(C)(C)CN)cc(-c2ccc(F)cc2)n1]

Step 1: benzyl (2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-2-methylpropyl)carbamate Benzyl (2-(2-(((1R,5S,6s)-3-azabicyclo[3.1.0]hexan-6-yl)oxy)-6-(4-fluorophenyl)pyridin-4-yl)-2-methylpropyl) carbamate hydrochloride (Int. H-08, 0.050 g, 0.10 mmol), 1-methyl-3-(thiazol-4-yl)-1H-pyrazole-5-carboxylic acid (Int. L-1, 25 mg, 0.12 mmol), and HATU (45 mg, 0.12 mmol) were combined in DMF (1.0 mL). DIPEA (0.085 mL, 0.49 mmol) was added and the mixture was stirred for 18 h. The mixture was subjected to reverse phase HPLC (5-95% MeCN/water with 0.1% TFA modifier) to afford the title compound.

Step 2: ((1R,5S,6s)-6-((4-(1-amino-2-methylpropan-2-yl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone A mixture of benzyl (2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-2-methylpropyl)carbamate (44 mg, 0.070 mmol) and hydrochloric acid (37% aq., 0.50 mL) was placed in a pre-heated block at 80° C. After 10 minutes, the mixture was removed, diluted with ice cold $H_2O$ (1.5 mL) and applied to a SCX ion exchange column. The column was washed with $H_2O$ and MeOH, eluted with 10% $NH_4OH$ in MeOH and the filtrate was concentrated to afford the title compound. MS m/z $(M+H)^+$: calculated 533.2, observed 533.3. $^1$H-NMR (500 MHz, DMSO-d$^6$) δ 9.18 (d, J=1.9 Hz, 1H), 8.17 (dd, J=8.6, 5.7 Hz, 2H), 7.97 (d, J=1.9 Hz, 1H), 7.56 (s, 1H), 7.29 (t, J=8.8 Hz, 2H), 7.04 (s, 1H), 6.71 (s, 1H), 4.09-4.04 (m, 1H), 4.02-4.00 (m, 1H), 3.96 (s, 3H), 3.95-3.88 (m, 2H), 3.67 (dd, J=12.3, 4.7 Hz, 1H), 2.78 (s, 2H), 2.11-2.00 (m, 2H), 1.27 (s, 6H) ppm.

Example 55A ent-((1R,5S,6s)-6-((6-(4-fluorophenyl)-4-(2-methylazetidin-2-yl)pyridin-2-yl)oxy)-3-azabicyclo[3.1.0]hexan-3-yl)(1-methyl-3-(thiazol-4-yl)-1H-pyrazol-5-yl)methanone (enantiomer 1) and Example 55B ent-((1R,5S,6s)-6-((6-(4-fluorophenyl)-4-(2-methylazetidin-2-yl)pyridin-2-yl)oxy)-3-azabicyclo[3.1.0]hexan-3-yl)(1-methyl-3-(thiazol-4-yl)-1H-pyrazol-5-yl)methanone (enantiomer 2)

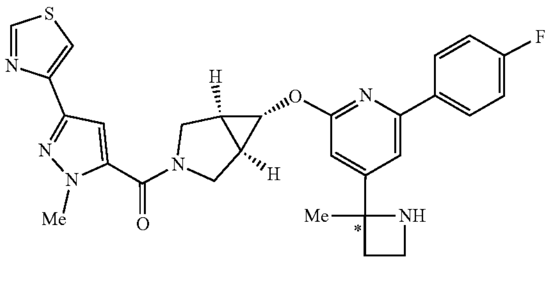 [SMILES: Cn1nc(-c2cscn2)cc1C(=O)N1C[C@@H]2[C@H](C1)[C@H]2Oc1cc(C2(C)CCN2)cc(-c2ccc(F)cc2)n1]

To a rt solution of rac-6-((6-(4-fluorophenyl)-4-(2-methylazetidin-2-yl)pyridin-2-yl)oxy)-3-azabicyclo[3.1.0]hexane-HCl (Int. H-03, 36 mg, 0.090 mmol) in DMF (1.0 mL) was added 1-methyl-3-(thiazol-4-yl)-1H-pyrazole-5-carboxylic acid (Int. L-1, 18 mg, 0.090 mmol), HATU (43 mg, 0.12 mmol), then DIPEA (0.080 mL, 0.46 mmol). The mixture stirred for 18 h and then subjected to reverse phase HPLC (5-65% MeCN/water with 0.1% TFA modifier). The racemate was subjected to chiral SFC (ChiralPak AD-H, 50% EtOH (with 0.1% DEA modifier)/$CO_2$) to afford the title compounds. EXAMPLE 55A (faster eluting enantiomer): MS m/z $(M+H)^+$: calculated 531.2, observed 531.3. $^1$H-NMR (500 MHz, DMSO-d$^6$) δ 9.18 (s, 1H), 8.13 (dd, J=8.4, 5.8 Hz, 2H), 7.97 (s, 1H), 7.53 (s, 1H), 7.31-7.27 (m, 2H), 7.04 (s, 1H), 6.79 (s, 1H), 4.07 (d, J=12.4 Hz, 1H), 4.00 (s, 1H), 3.96 (s, 3H), 3.95-3.88 (m, 2H), 3.70-3.58 (m, 2H), 3.18-3.13 (m, 1H), 2.40-2.32 (m, 2H), 2.10-2.00 (m, 2H), 1.60 (s, 3H) ppm. EXAMPLE 55B (slower eluting enantiomer): MS m/z $(M+H)^+$: calculated 531.2, observed 531.3. $^1$H-NMR (500 MHz, DMSO-d$^6$) δ 9.18 (s, 1H), 8.13 (dd, J=8.4, 5.8 Hz, 2H), 7.97 (s, 1H), 7.53 (s, 1H), 7.31-7.27 (m, 2H), 7.03 (s, 1H), 6.79 (s, 1H), 4.07 (d, J=12.3 Hz, 1H), 4.00 (s, 1H), 3.96 (s, 3H), 3.95-3.88 (m, 2H), 3.70-3.58 (m, 2H), 3.18-3.12 (m, 1H), 2.40-2.32 (m, 2H), 2.10-1.98 (m, 2H), 1.60 (s, 3H) ppm.

Example 56A ent-((1R,5S,6s)-6-((6-(4-fluorophenyl)-4-(2-methylpyrrolidin-2-yl)pyridin-2-yl)oxy)-3-azabicyclo[3.1.0]hexan-3-yl)(1-methyl-3-(thiazol-4-yl)-1H-pyrazol-5-yl)methanone (enantiomer 1) and Example 56B ent-((1R,5S,6s)-6-((6-(4-fluorophenyl)-4-(2-methylpyrrolidin-2-yl)pyridin-2-yl)oxy)-3-azabicyclo[3.1.0]hexan-3-yl)(1-methyl-3-(thiazol-4-yl)-1H-pyrazol-5-yl)methanone (enantiomer 2)

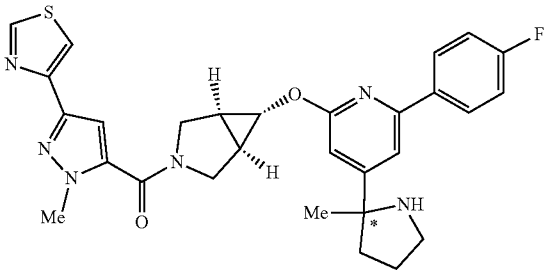 [SMILES: Cn1nc(-c2cscn2)cc1C(=O)N1C[C@@H]2[C@H](C1)[C@H]2Oc1cc(C2(C)CCCN2)cc(-c2ccc(F)cc2)n1]

Step 1: benzyl rac-2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-2-methylpyrrolidine-1-carboxylate A mixture of 1-methyl-3-(thiazol-4-yl)-1H-pyrazole-5-carboxylic acid (Int. L-1, 25 mg, 0.12 mmol), HATU (45 mg, 0.12 mmol), DMF (0.50 mL), and DIPEA (32 μL) was stirred at rt for 30 min. The mixture was added to a solution of benzyl rac-2-(2-((3-azabicyclo[3.1.0]hexan-6-yl)oxy)-6-(4-fluorophenyl)pyridin-4-yl)-2-methylpyrrolidine-1-carboxylate·HCl (Int. H-04, 47 mg, 0.090 mmol) in DMF (0.50 mL) and DIPEA (48 μL). The mixture stirred for 18 h at rt and then subjected to reverse phase HPLC (5-95% MeCN/water with 0.1% TFA modifier). The appropriate fractions were concentrated, and the residue was dissolved in $NaHCO_3$ (saturated aq.) and extracted with DCM (3×). The combined organic extracted were dried with anhydrous magnesium sulfate, filtered, and concentrated to afford the title compound.

Step 2: ent-((1R,5S,6s)-6-((6-(4-fluorophenyl)-4-(2-methylpyrrolidin-2-yl)pyridin-2-yl)oxy)-3-azabicyclo[3.1.0]hexan-3-yl)(1-methyl-3-(thiazol-4-yl)-1H-pyrazol-5-yl)methanone (enantiomers 1 and 2)

A mixture of benzyl rac-2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-2-methylpyrrolidine-1-carboxylate (0.040 g, 0.060 mmol) and hydrochloric acid (37% aq., 0.50 mL) was placed in a pre-heated block at 80° C. for 10 minutes. The mixture was removed, diluted with ice cold $H_2O$ (1.5 mL), and applied to a SCX ion exchange column. The column was washed with $H_2O$ and MeOH, eluted with 10% $NH_4OH$ in MeOH, and the filtrate was concentrated. The mixture was subjected to chiral SFC (ChiralPak OD-H, 30% EtOH (with 0.1% DEA modifier)/$CO_2$) to afford the title compounds. EXAMPLE 56A (faster eluting enantiomer): MS m/z $(M+H)^+$: calculated 545.2, observed 545.3. $^1$H-NMR (500 MHz, DMSO-$d^6$) δ 9.18 (d, J=1.9 Hz, 1H), 8.14 (dd, J=8.8, 5.6 Hz, 2H), 7.97 (d, J=1.8 Hz, 1H), 7.67 (s, 1H), 7.29 (t, J=8.7 Hz, 2H), 7.04 (s, 1H), 6.92 (d, J=3.9 Hz, 1H), 4.07 (d, J=12.4 Hz, 1H), 3.99 (s, 1H), 3.96 (s, 3H), 3.95-3.87 (m, 2H), 3.67 (dd, J=12.3, 4.3 Hz, 1H), 3.08-3.00 (m, 1H), 2.80-2.72 (m, 1H), 2.10-1.97 (m, 3H), 1.86-1.72 (m, 2H), 1.56-1.46 (1H), 1.39 (s, 3H) ppm. EXAMPLE 56B (slower eluting enantiomer): MS m/z $(M+H)^+$: calculated 545.2, observed 545.3. $^1$H-NMR (500 MHz, DMSO-$d^6$) δ 9.18 (d, J=1.9 Hz, 1H), 8.14 (dd, J=8.8, 5.6 Hz, 2H), 7.97 (d, J=1.9 Hz, 1H), 7.68 (s, 1H), 7.30 (t, J=8.8 Hz, 2H), 7.04 (s, 1H), 6.92 (d, J=3.5 Hz, 1H), 4.07 (d, J=12.2 Hz, 1H), 4.00 (s, 1H), 3.96 (s, 3H), 3.95-3.88 (m, 2H), 3.67 (dd, J=12.2, 4.4 Hz, 1H), 3.15-3.07 (m, 1H), 2.90-2.81 (m, 1H), 2.10-2.00 (m, 3H), 1.96-1.79 (m, 2H), 1.67-1.55 (m, 1H), 1.43 (s, 3H) ppm.

Example 57A ent-((1R,5S,6s)-6-((4-(2-amino-1-hydroxypropan-2-yl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone (enantiomer 1)

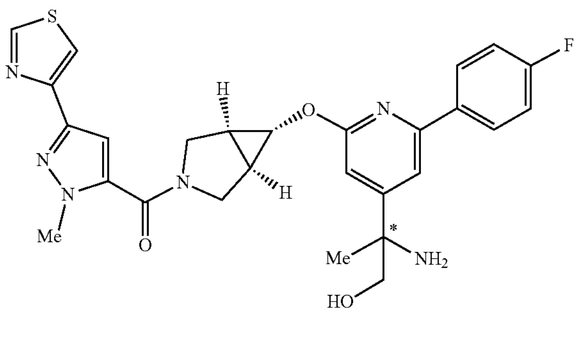 [SMILES: Cn1nc(-c2cscn2)cc1C(=O)N1C[C@@H]2[C@H](C1)[C@H]2Oc1cc(C(C)(N)CO)cc(-c2ccc(F)cc2)n1]

Step 1: benzyl ent-(1-((tert-butyldimethylsilyl)oxy)-2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)propan-2-yl) carbamate (enantiomer 1)

A mixture of 1-methyl-3-(thiazol-4-yl)-1H-pyrazole-5-carboxylic acid (Int. L-1, 15 mg, 0.070 mmol), benzyl ent-(2-(2-(((1R,5S,6s)-3-azabicyclo[3.1.0]hexan-6-yl)oxy)-6-(4-fluorophenyl)pyridin-4-yl)-1-((tert-butyldiphenylsilyl)oxy)propan-2-yl)carbamate (Int. H-12-ent-1, 0.050 g, 0.070 mmol), DMF (3.0 mL), DIPEA (0.10 mL, 0.070 mmol), and T3P (50 wt. % in EtOAc, 22 mg, 0.070 mmol) was stirred at rt for 1 h. Water (10 mL) was added and the mixture was extracted with EtOAc (15 mL×3). The combined organic extracts were washed with brine (20 mL×3), dried with anhydrous sodium sulfate, filtered, and concentrated under reduced pressure. The mixture was subjected to prep-TLC (50% EtOAc/petroleum ether) to afford the title compound.

Step 2: ent-((1R,5S,6s)-6-((4-(2-amino-1-hydroxypropan-2-yl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone (enantiomer 1)

A mixture of benzyl ent-(1-((tert-butyldimethylsilyl)oxy)-2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)propan-2-yl)carbamate (enantiomer 1, 0.050 g, 0.055 mmol) and hydrochloric acid (37% aq., 1.0 mL) was stirred at 80° C. for 10 min. The mixture was cooled to rt, concentrated under reduced pressure, subjected to reverse phase HPLC (19-39% MeCN/water containing 0.1% TFA) and lyophilized to afford the title compound as a TFA salt. MS m/z $(M+H)^+$: calculated 535.2, observed 535.1. $^1$H-NMR (400 MHz, $CD_3OD$) δ 9.09 (s, 1H), 8.16-8.10 (m, 2H), 7.92 (d, J=2.0 Hz, 1H), 7.58 (d, J=1.2 Hz, 1H), 7.20 (t, J=8.8 Hz, 2H), 7.08 (s, 1H), 6.80 (d, J=1.2 Hz, 1H), 4.26 (d, J=12.4 Hz, 1H), 4.09-3.99 (m, 6H), 3.91-3.86 (m, 1H), 3.82-3.73 (m, 2H), 2.12-2.06 (m, 2H), 1.70 (s, 3H) ppm.

Utilizing the procedures described in EXAMPLE 57A, the following compounds were prepared substituting the appropriate reagents for 1-methyl-3-(thiazol-4-yl)-1H-pyrazole-5-carboxylic acid and Int. H-12-ent-1.

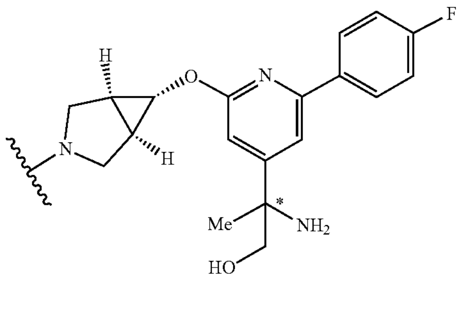 [SMILES: *N1C[C@@H]2[C@H](C1)[C@H]2Oc1cc(C(C)(N)CO)cc(-c2ccc(F)cc2)n1]

| Ex # | Structure | Name | Calc'd $[M + H]^+$ | Observed $[M + H]^+$ | Comments |
|---|---|---|---|---|---|
| 57B | 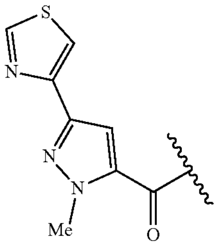 [SMILES: *C(=O)c1cc(-c2cscn2)nn1C] | ent-((1R,5S,6s)-6-((4-(2-amino-1-hydroxypropan-2-yl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone (enantiomer 2) | 535.2 | 535.1 | Step 1: Int. H-12-ent-2 |
| 58A | 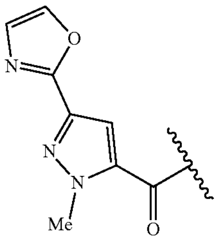 [SMILES: *C(=O)c1cc(-c2ncco2)nn1C] | ent-((1R,5S,6s)-6-((4-(2-amino-1-hydroxypropan-2-yl)-6-(4-fluorophenyl)pyridin-2-yl)oxy)-3-azabicyclo[3.1.0]hexan-3-yl)(1-methyl-3-(oxazol-2-yl)-1H-pyrazol-5-yl)methanone (enantiomer 1) | 519.2 | 519.4 | Step 1: Int. H-12-ent-1 |
| 58B | 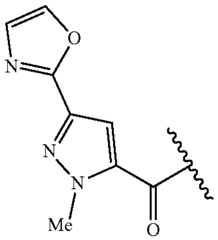 [SMILES: *C(=O)c1cc(-c2ncco2)nn1C] | ent-((1R,5S,6s)-6-((4-(2-amino-1-hydroxypropan-2-yl)-6-(4-fluorophenyl)pyridin-2-yl)oxy)-3-azabicyclo[3.1.0]hexan-3-yl)(1-methyl-3-(oxazol-2-yl)-1H-pyrazol-5-yl)methanone (enantiomer 2) | 519.2 | 519.1 | Step 1: Int. H-12-ent-2 |

Example 59

((1R,5S,6s)-6-((6-(2-aminopropan-2-yl)-4-(4-fluorophenyl)pyridin-2-yl)oxy)-3-azabicyclo[3.1.0]hexan-3-yl)(1-methyl-3-(thiazol-4-yl)-1H-pyrazol-5-yl)methanone

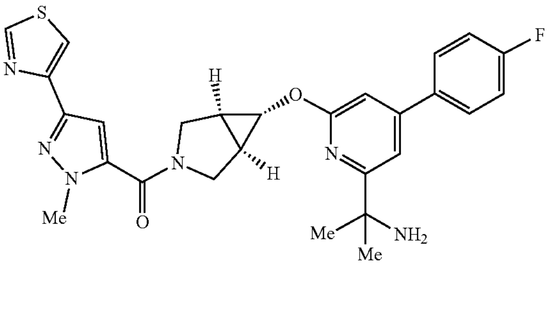 [SMILES: Cn1nc(-c2cscn2)cc1C(=O)N1C[C@@H]2[C@H](C1)[C@H]2Oc1cc(-c2ccc(F)cc2)cc(C(C)(C)N)n1]

Step 1: benzyl (2-(4-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-2-yl)propan-2-yl)carbamate A mixture of 1-methyl-3-(thiazol-4-yl)-1H-pyrazole-5-carboxylic acid (Int. L-1, 25 mg, 0.12 mmol), benzyl (2-(6-(((1R,5S,6s)-3-azabicyclo[3.1.0]hexan-6-yl)oxy)-4-(4-fluorophenyl)pyridin-2-yl)propan-2-yl)carbamate (Int. H-11, 55 mg, 0.12 mmol), DMF (2.0 mL), DIPEA (0.10 mL, 0.36 mmol), and T3P (50 wt. % in EtOAc, 0.11 g, 0.18 mmol) was stirred at rt for 1 h. Water (5 mL) was added and the mixture was extracted with EtOAc (10 mL×3). The combined organic extracts were dried with anhydrous sodium sulfate, filtered, and concentrated under reduced pressure. The mixture was subjected to prep-TLC (50% EtOAc/petroleum ether) to afford the title compound.

Step 2: ((1R,5S,6s)-6-((6-(2-aminopropan-2-yl)-4-(4-fluorophenyl)pyridin-2-yl)oxy)-3-azabicyclo[3.1.0]hexan-3-yl)(1-methyl-3-(thiazol-4-yl)-1H-pyrazol-5-yl)methanone A mixture of benzyl (2-(4-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-2-yl)propan-2-yl)carbamate (0.040 g, 0.061 mmol) and hydrochloric acid (37%, 1.0 mL) was stirred at 80° C. for 10 min. The mixture was subjected to reverse phase HPLC (15-35% MeCN/water containing 0.05% HCl) to afford the title compound as a HCl salt. MS m/z $(M+H)^+$: calculated 519.2, observed 519.1. $^1$H-NMR (400 MHz, $CD_3OD$) δ 9.09 (d, J=2.0 Hz, 1H), 7.91 (d, J=2.0 Hz, 1H), 7.79-7.75 (m, 2H), 7.44 (d, J=1.0 Hz, 1H), 7.24 (t, J=8.7 Hz, 2H), 7.09-7.04 (m, 2H), 4.22 (d, J=12.5 Hz, 1H), 4.14-4.09 (m, 1H), 4.06-3.98 (m, 5H), 3.77 (dd, J=12.6, 4.8 Hz, 1H), 2.16-2.06 (m, 2H), 1.77 (s, 6H) ppm.

Utilizing the procedures described in EXAMPLE 59, the following compound (EXAMPLE 60) was prepared substituting the appropriate reagents for 1-methyl-3-(thiazol-4-yl)-1H-pyrazole-5-carboxylic acid.

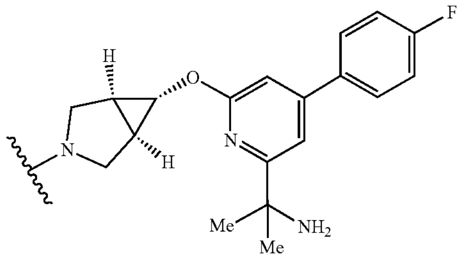 [SMILES: *N1C[C@@H]2[C@H](C1)[C@H]2Oc1cc(-c2ccc(F)cc2)cc(C(C)(C)N)n1]

(2.0 mL) was added DIPEA (0.10 mL, 0.57 mmol) and HATU (0.14 g, 0.36 mmol). The mixture was stirred at 25° C. for 15 min, then N-(1-(2-(((1R,5S,6s)-3-azabicyclo [3.1.0]hexan-6-yl)oxy)-6-(4-fluorophenyl)pyridin-4-yl) ethyl)-2-methylpropane-2-sulfinamide (Int. S, 0.10 g, 0.239 mmol) was added. The mixture was stirred at 25° C. for 1 h. Water (20 mL) was added and the mixture was extracted with EtOAc (25 mL×3). The combined organic extracts were washed with brine (15 mL), dried over anhydrous sodium sulfate, filtered and concentrated under reduced pressure. The residue was purified by prep-TLC (10% MeOH/DCM) to afford the title compound.

| Ex # | Structure | Name | Calc'd [M + H]$^+$ | Observed [M + H]$^+$ |
|---|---|---|---|---|
| 60 | 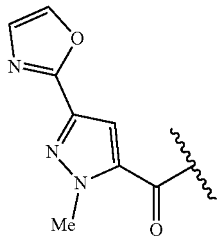 [SMILES: *C(=O)c1cc(-c2ncco2)nn1C] | ((1R,5S,6s)-6-((6-(2-aminopropan-2-yl)-4-(4-fluorophenyl)pyridin-2-yl)oxy)-3-azabicyclo[3.1.0]hexan-3-yl)(1-methyl-3-(oxazol-2-yl)-1H-pyrazol-5-yl)methanone | 503.2 | 503.2 |

Example 61A ent-((1R,5S,6s)-6-((4-(1-aminoethyl)-6-(4-fluorophenyl)pyridin-2-yl)oxy)-3-azabicyclo[3.1.0]hexan-3-yl)(1-methyl-3-(thiazol-4-yl)-1H-pyrazol-5-yl) methanone (enantiomer 1) and

Example 61B ent-((1R,5S,6s)-6-((4-(1-aminoethyl)-6-(4-fluorophenyl)pyridin-2-yl)oxy)-3-azabicyclo[3.1.0]hexan-3-yl)(1-methyl-3-(thiazol-4-yl)-1H-pyrazol-5-yl) methanone (enantiomer 2)

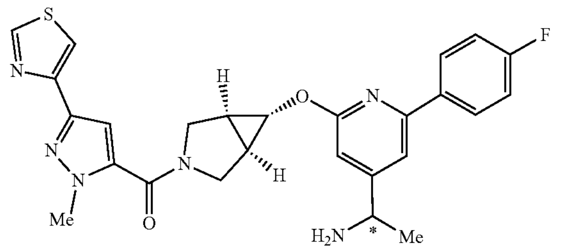 [SMILES: CC(N)c1cc(O[C@H]2[C@@H]3CN(C(=O)c4cc(-c5cscn5)nn4C)C[C@@H]32)nc(-c2ccc(F)cc2)c1]

Step 1: N-(1-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl) ethyl)-2-methylpropane-2-sulfinamide To a solution of 1-methyl-3-(thiazol-4-yl)-1H-pyrazole-5-carboxylic acid (Int. L-1, 0.050 g, 0.24 mmol) in DMF Step 2: ent-((1R,5S,6s)-6-((4-(1-aminoethyl)-6-(4-fluorophenyl)pyridin-2-yl)oxy)-3-azabicyclo[3.1.0] hexan-3-yl)(1-methyl-3-(thiazol-4-yl)-1H-pyrazol-5-yl)methanone (enantiomers 1 and 2)

A mixture of N-(1-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)ethyl)-2-methylpropane-2-sulfinamide (0.12 g, 0.20 mmol) and methanolic HCl (4.0 M, 3.0 mL) was stirred at 25° C. After 30 min, the mixture was concentrated under reduced pressure. The racemate was subjected to chiral SFC (DAICEL CHIRALCEL OD-H, 50% EtOH (with 0.1% $NH_3$—$H_2O$ modifier)/$CO_2$) to afford the title compounds. EXAMPLE 61A (faster eluting enantiomer): MS m/z $(M+H)^+$: calculated 505.6, observed 505.3. $^1$H-NMR (400 MHz, $CD_3OD$) δ 9.10 (d, J=2.0 Hz, 1H), 8.12 (dd, J=8.8, 5.6 Hz, 2H), 7.92 (d, J=2.0 Hz, 1H), 7.57 (s, 1H), 7.19 (t, J=8.8 Hz, 2H), 7.08 (s, 1H), 6.81 (s, 1H), 4.38-4.20 (m, 2H), 4.11-3.96 (m, 6H), 3.77-3.75 (m, 1H), 2.16-2.03 (m, 2H), 1.56 (d, J=6.8 Hz, 3H). EXAMPLE 61B (slower eluting enantiomer): MS m/z $(M+H)^+$: calculated 505.6, observed 505.3. $^1$H-NMR (400 MHz, $CD_3OD$) δ 9.10 (d, J=2.0 Hz, 1H), 8.14-8.06 (m, 2H), 7.92 (d, J=2.0 Hz, 1H), 7.54 (s, 1H), 7.18 (t, J=8.4 Hz, 2H), 7.08 (s, 1H), 6.79 (s, 1H), 4.28-4.26 (m, 1H), 4.14 (q, J=6.4 Hz, 1H), 4.10-3.97 (m, 6H), 3.76 (dd, J=12.4, 4.4 Hz, 1H), 2.15-2.04 (m, 2H), 1.45 (d, J=6.8 Hz, 3H).

Example 62A ent-((1R,5S,6s)-6-((4-(1-aminoethyl)-6-(4-fluorophenyl)pyridin-2-yl)oxy)-3-azabicyclo[3.1.0]hexan-3-yl)(3-(isoxazol-3-yl)-1-methyl-1H-pyrazol-5-yl) methanone (enantiomer 1) and Example 62B ent-((1R,5S,6s)-6-((4-(1-aminoethyl)-6-(4-fluorophenyl)pyridin-2-yl)oxy)-3-azabicyclo[3.1.0]hexan-3-yl)(3-(isoxazol-3-yl)-1-methyl-1H-pyrazol-5-yl) methanone (enantiomer 2)

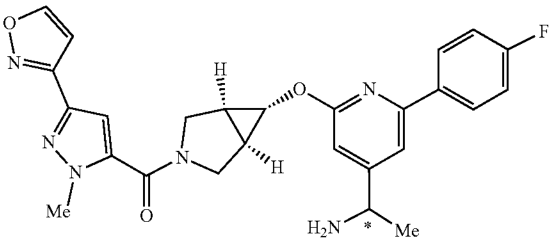 [SMILES: CC(N)c1cc(O[C@H]2[C@@H]3CN(C(=O)c4cc(-c5ccon5)nn4C)C[C@@H]32)nc(-c2ccc(F)cc2)c1]

Step 1: N-(1-(2-(4-fluorophenyl)-6-(((1R,5S,6s)-3-(3-(isoxazol-3-yl)-1-methyl-1H-pyrazole-5-carbonyl)-3-azabicyclo[3.1.0]hexan-6-yl)oxy)pyridin-4-yl)ethyl)-2-methylpropane-2-sulfinamide To a solution of 3-(isoxazol-3-yl)-1-methyl-1H-pyrazole-5-carboxylic acid (Int. 0-2, 0.050 g, 0.26 mmol) in DMF (0.010 L) was added DIPEA (0.20 mL, 0.78 mmol), PyBOP (0.16 g, 0.31 mmol) and N-(1-(2-(((1R,5S,6s)-3-azabicyclo[3.1.0]hexan-6-yl)oxy)-6-(4-fluorophenyl)pyridin-4-yl)ethyl)-2-methylpropane-2-sulfinamide (Int. S, 0.11 g, 0.26 mmol). The mixture was stirred at 25° C. for 30 min. Water (10 mL) was added and the mixture was extracted with EtOAc (15 mL×3). The combined organic extracts were washed with brine (15 mL), dried over anhydrous sodium sulfate, filtered and concentrated under reduced pressure. The residue was purified by prep-TLC (EtOAc) to afford the title compound.

Step 2: ent-((1R,5S,6s)-6-((4-(1-aminoethyl)-6-(4-fluorophenyl)pyridin-2-yl)oxy)-3-azabicyclo[3.1.0]hexan-3-yl)(3-(isoxazol-3-yl)-1-methyl-1H-pyrazol-5-yl)methanone (enantiomers 1 and 2)

A mixture of N-(1-(2-(4-fluorophenyl)-6-(((1R,5S,6s)-3-(3-(isoxazol-3-yl)-1-methyl-1H-pyrazole-5-carbonyl)-3-azabicyclo[3.1.0]hexan-6-yl)oxy)pyridin-4-yl)ethyl)-2-methylpropane-2-sulfinamide (15 mg, 0.025 mmol) and methanolic HCl (4.0 M, 2.0 mL) was stirred at 25° C. for 1 h. The mixture was subjected to reverse phase HPLC (MeCN/water with 0.1% TFA modifier). The racemate was subjected to chiral SFC (REGIS (R,R)WHELK-O1, 60% MeOH (with 0.1% $NH_3$—$H_2O$ modifier)/$CO_2$) to afford the title compounds. EXAMPLE 62A (faster eluting enantiomer): MS m/z $(M+H)^+$: calculated 489.2, observed 489.2. $^1$H-NMR (400 MHz, $CD_3OD$) δ 8.74 (d, J=1.6 Hz, 1H), 8.17-8.06 (m, 2H), 7.58 (s, 1H), 7.21 (t, J=8.8 Hz, 2H), 7.10 (s, 1H), 6.88 (d, J=1.6 Hz, 1H), 6.81 (s, 1H), 4.53 (q, J=6.8 Hz, 1H), 4.26 (d, J=12.4 Hz, 1H), 4.06 (s, 3H), 4.05-3.97 (m, 3H), 3.76 (d, J=12.8 Hz, 1H), 2.10 (s, 2H), 1.65 (d, J=6.8 Hz, 3H). EXAMPLE 62B (slower eluting enantiomer): MS m/z $(M+H)^+$: calculated 489.2, observed 489.2. $^1$H-NMR (400 MHz, $CD_3OD$) δ 8.74 (d, J=1.7 Hz, 1H), 8.19-8.04 (m, 2H), 7.57 (d, J=0.8 Hz, 1H), 7.25-7.17 (m, 2H), 7.11 (s, 1H), 6.89 (d, J=1.6 Hz, 1H), 6.81 (s, 1H), 4.53 (q, J=6.8 Hz, 1H), 4.26 (d, J=12.4 Hz, 1H), 4.06 (s, 3H), 4.05-3.97 (m, 3H), 3.76 (d, J=12.4 Hz, 1H), 2.10 (s, 2H), 1.65 (d, J=6.8 Hz, 3H).

Example 63

((1R,5S,6s)-6-((4-(2-aminopropan-2-yl)-6-(1-methylcyclopentyl)pyridin-2-yl)oxy)-3-azabicyclo[3.1.0]hexan-3-yl)(1-methyl-3-(thiazol-4-yl)-1H-pyrazol-5-yl)methanone

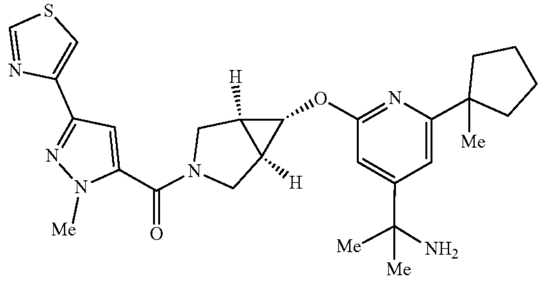 [SMILES: Cn1nc(-c2cscn2)cc1C(=O)N1C[C@@H]2[C@H](C1)[C@H]2Oc1cc(C(C)(C)N)cc(C2(C)CCCC2)n1]

Step 1: benzyl (2-(2-(((1R,5S,6s)-3-(1-methyl-3-(thiazol-4-yl)-1H-pyrazole-5-carbonyl)-3-azabicyclo[3.1.0]hexan-6-yl)oxy)-6-(1-methylcyclopentyl)pyridin-4-yl)propan-2-yl)carbamate To a solution of benzyl (2-(2-(((1R,5S,6s)-3-azabicyclo[3.1.0]hexan-6-yl)oxy)-6-(1-methylcyclopentyl)pyridin-4-yl)propan-2-yl)carbamate (Int. T, 37 mg, 0.082 mmol), 1-methyl-3-(thiazol-4-yl)-1H-pyrazole-5-carboxylic acid (Int. L-1, 22 mg, 0.11 mmol), and HATU (41 mg, 0.11 mmol) in DMF (0.75 mL) was added DIPEA (0.072 mL, 0.41 mmol). The mixture was stirred at 25° C. for 3 h. The mixture was filtered and concentrated under reduced pressure. The mixture was subjected to reverse phase HPLC (MeCN/water with 0.1% TFA modifier) to afford the title compound.

Step 2: ((1R,5S,6s)-6-((4-(2-aminopropan-2-yl)-6-(1-methylcyclopentyl)pyridin-2-yl)oxy)-3-azabicyclo[3.1.0]hexan-3-yl)(1-methyl-3-(thiazol-4-yl)-1H-pyrazol-5-yl)methanone A mixture of benzyl (2-(2-(((1R,5S,6s)-3-(1-methyl-3-(thiazol-4-yl)-1H-pyrazole-5-carbonyl)-3-azabicyclo[3.1.0]hexan-6-yl)oxy)-6-(1-methylcyclopentyl)pyridin-4-yl)propan-2-yl)carbamate (33 mg, 0.051 mmol) and hydrochloric acid (37%, 0.50 mL) was stirred at 80° C. After 10 min, the mixture was cooled to room temperature and diluted with water. The mixture was subjected to reverse phase HPLC (MeCN/water with 0.1% TFA modifier) to afford the title compound as a TFA salt. MS m/z $(M+H)^+$: calculated 507.3, observed 507.2. $^1$H-NMR (500 MHz, $CD_3OD$) δ 9.07 (s, 1H), 7.90 (s, 1H), 7.08 (d, J=1.4 Hz, 1H), 7.03 (s, 1H), 6.64 (d, J=1.4 Hz, 1H), 4.23 (d, J=12.5 Hz, 1H), 4.02 (s, 3H), 3.98

(s, 2H), 3.88 (s, 1H), 3.70 (dd, J=12.5, 4.3 Hz, 1H), 2.19-2.11 (m, 2H), 2.05-1.95 (m, 2H), 1.79-1.64 (m, 12H), 1.35 (s, 3H) ppm.

Example 64

((1R,5S,6s)-6-((4-(2-aminopropan-2-yl)-6-(4-(trifluoromethyl)piperidin-1-yl)pyridin-2-yl)oxy)-3-azabicyclo[3.1.0]hexan-3-yl)(3-(isoxazol-3-yl)-1-methyl-1H-pyrazol-5-yl)methanone

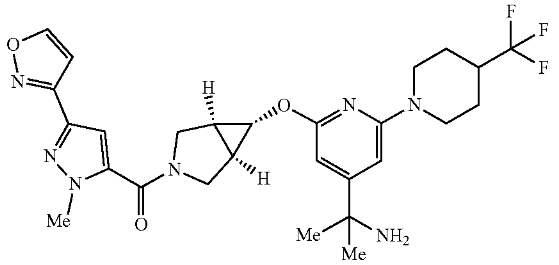 [SMILES: Cn1nc(-c2ccon2)cc1C(=O)N1C[C@@H]2[C@H](C1)[C@H]2Oc1cc(C(C)(C)N)cc(N2CCC(C(F)(F)F)CC2)n1]

Step 1: 2-(2-((3-azabicyclo[3.1.0]hexan-6-yl)oxy)-6-(4-(trifluoromethyl)piperidin-1-yl)pyridin-4-yl)propan-2-amine To a degassed solution of tert-butyl 6-((4-(2-(((benzyloxy)carbonyl)amino)propan-2-yl)-6-chloropyridin-2-yl)oxy)-3-azabicyclo[3.1.0]hexane-3-carboxylate (Int. G, 45 mg, 0.090 mmol), 4-(trifluoromethyl)piperidine hydrochloride (0.020 g, 0.11 mmol) and chloro-(2-dicyclohexylphosphino-2',6'-diisopropoxy-1,1'-biphenyl)[2-(2'-amino-1,1'-biphenyl)]palladium(II) (7.0 mg, 9.0 μmol) in THF (0.30 mL) was added sodium tert-butoxide (0.50M in THF, 0.13 mL, 0.27 mmol). The reaction heated to 60° C. for 18 h. The reaction was cooled to room temperature, diluted with EtOAc, filtered and concentrated under reduced pressure. The residue was dissolved in DCM (0.30 mL), HCl (4.0M in dioxane, 0.22 mL, 0.90 mmol) was injected, and the mixture was stirred at 25° C. After 1 h, the reaction was concentrated under reduced pressure. The residue was subjected to reverse phase HPLC (5-50% MeCN/water containing 0.1% TFA) to afford the title compound as a TFA salt.

Step 2: ((1R,5S,6s)-6-((4-(2-aminopropan-2-yl)-6-(4-(trifluoromethyl)piperidin-1-yl)pyridin-2-yl)oxy)-3-azabicyclo[3.1.0]hexan-3-yl)(3-(isoxazol-3-yl)-1-methyl-1H-pyrazol-5-yl)methanone A mixture of 2-(2-((3-azabicyclo[3.1.0]hexan-6-yl)oxy)-6-(4-(trifluoromethyl)piperidin-1-yl)pyridin-4-yl)propan-2-amine (4.0 mg, 0.010 mmol), HATU (2.0 mg, 5.0 μmol), 3-(isoxazol-3-yl)-1-methyl-1H-pyrazole-5-carboxylic acid (Int. 0-2, 1.0 mg, 5.0 μmol), DMF (1.0 mL), and DIPEA (0.090 mL, 0.031 mmol) was stirred at 25° C. After 30 min, the mixture was subjected to reverse phase HPLC (MeCN/water with 0.05% TFA modifier) to afford the title compound as a TFA salt. MS m/z $(M+H)^+$: calculated 560.3, observed 560.4. $^1$H-NMR (500 MHz, DMSO-$d^6$) δ 8.99 (d, J=1.6 Hz, 1H), 8.39 (s, 3H), 7.08 (s, 1H), 6.90 (d, J=1.6 Hz, 1H), 6.49 (s, 1H), 6.13 (s, 1H), 4.39 (d, J=12.6 Hz, 2H), 4.02 (d, J=12.5 Hz, 1H), 3.98-3.93 (m, 4H), 3.91 (dd, J=10.7, 4.2 Hz, 0.6H), 3.82-3.76 (m, 2H), 3.62 (dd, J=12.5, 4.3 Hz, 0.4H), 2.88 (t, J=12.5 Hz, 2H), 2.66-2.56 (m, 1H), 2.00-1.92 (m, 2H), 1.86-1.74 (m, 2H), 1.54 (s, 6H), 1.42-1.30 (m, 2H).

Example 65

((1R,5S,6s)-6-((4-(2-aminopropan-2-yl)-6-(4,4-dimethylpiperidin-1-yl)pyridin-2-yl)oxy)-3-azabicyclo[3.1.0]hexan-3-yl)(1-methyl-3-(oxazol-2-yl)-1H-pyrazol-5-yl)methanone

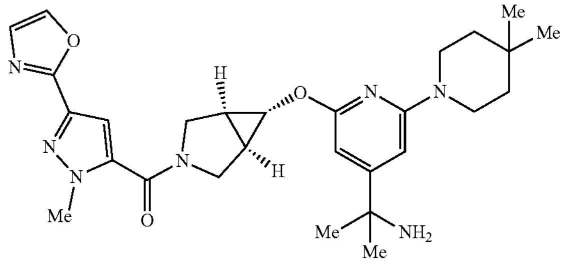 [SMILES: Cn1nc(-c2ncco2)cc1C(=O)N1C[C@@H]2[C@H](C1)[C@H]2Oc1cc(C(C)(C)N)cc(N2CCC(C)(C)CC2)n1]

To a solution of 2-(2-((3-azabicyclo[3.1.0]hexan-6-yl)oxy)-6-(4,4-dimethylpiperidin-1-yl)pyridin-4-yl)propan-2-amine (Int. U, 32 mg, 0.093 mmol) and 1-methyl-3-(oxazol-2-yl)-1H-pyrazole-5-carboxylic acid (Int. N, 18 mg, 0.093 mmol) in DMSO (930 μl) and N-methylmorpholine (31 μl, 0.28 mmol) was added HATU (35 mg, 0.093 mmol). The reaction was stirred at 25° C. for 2 h. The mixture was subjected to reverse phase HPLC (MeCN/water with 0.1% TFA modifier). Fractions containing product were filtered through a SPE plug, rinsed with MeOH (3×2 mL) and eluted with $NH_3$ (2N in MeOH 3×2 mL). The material was dissolved in MeCN/water and lyophilized to afford the title compound. MS m/z $(M+H)^+$: calculated 519.3, observed 520.4. $^1$H NMR (500 MHz, $CD_3OD$) δ 7.99 (d, J=0.7 Hz, 1H), 7.31 (d, J=0.7 Hz, 1H), 7.11 (s, 1H), 6.42 (s, 1H), 6.11 (s, 1H), 4.18 (d, J=12.5 Hz, 1H), 4.05 (s, 3H), 3.97-3.88 (m, 2H), 3.75 (s, 1H), 3.69 (dd, J=12.4, 4.9 Hz, 1H), 3.55-3.50 (m, 4H), 1.96 (s, 2H), 1.42 (s, 6H), 1.40-1.31 (m, 4H), 0.95 (s, 6H).

Example 66A ent-((1R,5S,6s)-6-((4-(2-aminopropan-2-yl)-6-(2-hydroxy-4,4-dimethylcyclohexyl)pyridin-2-yl)oxy)-3-azabicyclo[3.1.0]hexan-3-yl)(1-methyl-3-(thiazol-4-yl)-1H-pyrazol-5-yl)methanone (enantiomer 1) and Example 66B ent-((1R,5S,6s)-6-((4-(2-aminopropan-2-yl)-6-(2-hydroxy-4,4-dimethylcyclohexyl)pyridin-2-yl)oxy)-3-azabicyclo[3.1.0]hexan-3-yl)(1-methyl-3-(thiazol-4-yl)-1H-pyrazol-5-yl)methanone (enantiomer 2) and Example 66C ent-((1R,5S,6s)-6-((4-(2-aminopropan-2-yl)-6-(2-hydroxy-4,4-dimethylcyclohexyl)pyridin-2-yl)oxy)-3-azabicyclo[3.1.0]hexan-3-yl)(1-methyl-3-(thiazol-4-yl)-1H-pyrazol-5-yl)methanone (enantiomer 3) and Example 66D ent-((1R,5S,6s)-6-((4-(2-aminopropan-2-yl)-6-(2-hydroxy-4,4-dimethylcyclohexyl)pyridin-2-yl)oxy)-3-azabicyclo[3.1.0]hexan-3-yl)(1-methyl-3-(thiazol-4-yl)-1H-pyrazol-5-yl)methanone (enantiomer 4)

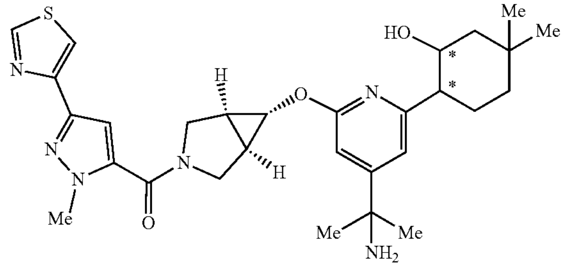 [SMILES: Cn1nc(-c2cscn2)cc1C(=O)N1C[C@@H]2[C@H](C1)[C@H]2Oc1cc(C(C)(C)N)cc(C2CCC(C)(C)CC2O)n1]

Step 1: benzyl (2-(2-chloro-6-(((1R,5S,6s)-3-(3-methyl-1-(thiazol-4-yl)-1H-pyrazole-4-carbonyl)-3-azabicyclo[3.1.0]hexan-6-yl)oxy)pyridin-4-yl)propan-2-yl)carbamate To a solution of 3-methyl-1-(thiazol-4-yl)-1H-pyrazole-4-carboxylic acid (Int.R, 80 mg, 0.38 mmol) in DMF (2 mL) was added DIPEA (0.20 mL, 1.2 mmol) and HATU (220 mg, 0.57 mmol). The mixture was stirred at 25° C. After 15 min, benzyl (2-(2-(((1R,5S,6s)-3-azabicyclo[3.1.0]hexan-6-yl)oxy)-6-chloropyridin-4-yl)propan-2-yl)carbamate (Int. G-01, 150 mg, 0.38 mmol) was added to the mixture and the mixture was stirred at 25° C. After 1 h the reaction mixture was quenched with water (100 mL) and extracted with EtOAc (3×25 mL). The combined organic extracts were washed with brine (50 mL), dried over anhydrous sodium sulfate, filtered and concentrated under reduced pressure. The residue was purified by prep-TLC (60% EtOAc/PE) to afford the title compound.

Step 2: benzyl (2-(2-(4,4-dimethylcyclohex-1-en-1-yl)-6-(((1R,5S,6s)-3-(3-methyl-1-(thiazol-4-yl)-1H-pyrazole-4-carbonyl)-3-azabicyclo[3.1.0]hexan-6-yl)oxy)pyridin-4-yl)propan-2-yl)carbamate To a mixture of benzyl (2-(2-chloro-6-(((1R,5S,6s)-3-(3-methyl-1-(thiazol-4-yl)-1H-pyrazole-4-carbonyl)-3-azabicyclo[3.1.0]hexan-6-yl)oxy)pyridin-4-yl)propan-2-yl)carbamate (250 mg, 0.42 mmol) and 2-(4,4-dimethylcyclohex-1-en-1-yl)-4,4,5,5-tetramethyl-1,3,2-dioxaborolane (120 mg, 0.51 mmol) in water (0.3 mL) and 1,4-dioxane (3 mL) was added $Cs_2CO_3$ (280 mg, 0.84 mmol). The mixture was placed under an atmosphere of $N_2$ and $Pd(dppf)Cl_2$ (61.7 mg, 0.084 mmol) was added and heated to 90° C. After 5 h the reaction was cooled, filtered and concentrated under reduced pressure. The residue was purified by prep-TLC (60% EtOAc/PE) to afford the title compound.

Step 3: dia-benzyl (2-(2-(2-hydroxy-4,4-dimethylcyclohexyl)-6-(((1R,5S,6s)-3-(3-methyl-1-(thiazol-4-yl)-1H-pyrazole-4-carbonyl)-3-azabicyclo[3.1.0]hexan-6-yl)oxy)pyridin-4-yl)propan-2-yl)carbamate (diastereomers 1 and 2)

A mixture of benzyl (2-(2-(4,4-dimethylcyclohex-1-en-1-yl)-6-(((1R,5S,6s)-3-(3-methyl-1-(thiazol-4-yl)-1H-pyrazole-4-carbonyl)-3-azabicyclo[3.1.0]hexan-6-yl)oxy)pyridin-4-yl)propan-2-yl)carbamate (180 mg, 0.27 mmol), 9-Mesityl-10-methylacridinium Perchlorate (3.3 mg, 8.1 μmol) and 1,2-diphenyldisulfane (12 mg, 0.054 mmol) was dissolved in MeCN (5 mL) and water (0.5 mL). The reaction was placed under an atmosphere of $N_2$ irradiated with Blue LED (12 W) at 25° C. After 12 h the reaction was quenched with water (15 mL) and extracted with EtOAc (3×20 mL). The combined organic extracts were washed with brine (15 mL), dried over anhydrous sodium sulfate, filtered and concentrated under reduced pressure. The residue was purified by prep-TLC (60% EtOAc/PE) to afford the title compounds, diastereomer 1 and diastereomer 2.

Step 4-1: ent-benzyl (2-(2-(2-hydroxy-4,4-dimethylcyclohexyl)-6-(((1R,5S,6s)-3-(3-methyl-1-(thiazol-4-yl)-1H-pyrazole-4-carbonyl)-3-azabicyclo[3.1.0]hexan-6-yl)oxy)pyridin-4-yl)propan-2-yl)carbamate (enantiomers 1A and 2A)

A mixture of enantiomers, dia-benzyl (2-(2-(2-hydroxy-4,4-dimethylcyclohexyl)-6-(((1R,5S,6s)-3-(3-methyl-1-(thiazol-4-yl)-1H-pyrazole-4-carbonyl)-3-azabicyclo[3.1.0]hexan-6-yl)oxy)pyridin-4-yl)propan-2-yl)carbamate (diastereomer 1) (40 mg, 0.058 mmol) was subjected to chiral SFC (DAICEL CHIRALPAK AD, 40° C., 40% IPA (with 0.1% $NH_3$—$H_2O$ modifier)/$CO_2$) to give the title compounds, enantiomer 1A (faster eluting enantiomer) and enantiomer 2A (slower eluting enantiomer).

Step 4-2: ent-benzyl (2-(2-(2-hydroxy-4,4-dimethylcyclohexyl)-6-(((1R,5S,6s)-3-(3-methyl-1-(thiazol-4-yl)-1H-pyrazole-4-carbonyl)-3-azabicyclo[3.1.0]hexan-6-yl)oxy)pyridin-4-yl)propan-2-yl)carbamate (enantiomers 3A and 4A)

A mixture of enantiomers, dia-benzyl (2-(2-(2-hydroxy-4,4-dimethylcyclohexyl)-6-(((1R,5S,6s)-3-(3-methyl-1-(thiazol-4-yl)-1H-pyrazole-4-carbonyl)-3-azabicyclo[3.1.0]hexan-6-yl)oxy)pyridin-4-yl)propan-2-yl)carbamate (diastereomer 2) (50 mg, 0.073 mmol) was separated by SFC was subjected to chiral SFC (DAICEL CHIRALPAK OD-H, 40° C., 50% EtOH (with 0.1% $NH_3$—$H_2O$ modifier)/$CO_2$) to give the title compounds, enantiomer 3A (faster eluting enantiomer) and enantiomer 4A (slower eluting enantiomer).

Step 5-1: ent-((1R,5S,6s)-6-((4-(2-aminopropan-2-yl)-6-(2-hydroxy-4,4-dimethylcyclohexyl)pyridin-2-yl)oxy)-3-azabicyclo[3.1.0]hexan-3-yl)(3-methyl-1-(thiazol-4-yl)-1H-pyrazol-4-yl)methanone (enantiomer 1)

A mixture of ent-benzyl (2-(2-(2-hydroxy-4,4-dimethylcyclohexyl)-6-(((1R,5S,6s)-3-(3-methyl-1-(thiazol-4-yl)-1H-pyrazole-4-carbonyl)-3-azabicyclo[3.1.0]hexan-6-yl)oxy)pyridin-4-yl)propan-2-yl)carbamate (enantiomer 1A) (10 mg, 0.015 mmol) in HCl (12 M) (2 mL) was stirred at 80° C. After 10 min the mixture was cooled, filtered and concentrated under reduced pressure. The residue was subjected to reverse phase HPLC (24-44% MeCN/water with 0.04% HCl modifier). The appropriate fractions were lyophilized to afford the title compound as a HCl salt. MS m/z $(M+H)^+$: calculated 551.5, observed 551.2. $^1H$ NMR (400 MHz, $CD_3OD$) δ 9.04 (s, 1H), 8.67 (s, 1H), 7.66 (s, 1H), 7.29 (s, 1H), 7.11 (s, 1H), 4.25 (s, 2H), 4.14 (s, 1H), 4.03 (s, 2H), 3.74 (s, 1H), 2.96-2.93 (m, 1H), 2.45 (s, 3H), 2.31-2.13 (m, 3H), 1.77 (s, 6H), 1.69-1.57 (m, 2H), 1.49 (dd, J=14.0, 3.2 Hz, 1H), 1.38-1.31 (m, 2H), 1.07 (s, 3H), 0.93 (s, 3H).

Step 5-2: ent-((1R,5S,6s)-6-((4-(2-aminopropan-2-yl)-6-(2-hydroxy-4,4-dimethylcyclohexyl)pyridin-2-yl)oxy)-3-azabicyclo[3.1.0]hexan-3-yl)(3-methyl-1-(thiazol-4-yl)-1H-pyrazol-4-yl)methanone (enantiomer 2)

A mixture of ent-benzyl (2-(2-(2-hydroxy-4,4-dimethylcyclohexyl)-6-(((1R,5S,6s)-3-(3-methyl-1-(thiazol-4-yl)-1H-pyrazole-4-carbonyl)-3-azabicyclo[3.1.0]hexan-6-yl)oxy)pyridin-4-yl)propan-2-yl)carbamate (enantiomer 2A) (10 mg, 0.015 mmol) in HCl (12 M) (2 mL) was stirred at 80° C. After 10 min the mixture was cooled, filtered and concentrated under reduced pressure. The residue was subjected to reverse phase HPLC (24-44% MeCN/water with 0.04% HCl modifier). The appropriate fractions were lyophilized to afford the title compound as a HCl salt. MS m/z $(M+H)^+$: calculated 551.5, observed 551.2. $^1H$ NMR (400 MHz, $CD_3OD$) δ 9.02 (s, 1H), 8.65 (s, 1H), 7.64 (d, J=2.1 Hz, 1H), 7.26 (s, 1H), 7.07 (s, 1H), 4.23 (s, 2H), 4.15-1.12 (m, 1H), 4.00 (s, 2H), 3.72 (s, 1H), 2.96-2.89 (m, 1H), 2.45-2.42 (m, 3H), 2.30-2.12 (m, 3H), 1.74 (s, 6H), 1.69-1.59 (m, 2H), 1.47 (dd, J=14.0, 3.2 Hz, 1H), 1.36-1.28 (m, 2H), 1.05 (s, 3H), 0.91 (s, 3H).

Step 5-3: ent-((1R,5S,6s)-6-((4-(2-aminopropan-2-yl)-6-(2-hydroxy-4,4-dimethylcyclohexyl)pyridin-2-yl)oxy)-3-azabicyclo[3.1.0]hexan-3-yl)(3-methyl-1-(thiazol-4-yl)-1H-pyrazol-4-yl)methanone (enantiomer 3)

A mixture of ent-benzyl (2-(2-(2-hydroxy-4,4-dimethylcyclohexyl)-6-(((1R,5S,6s)-3-(3-methyl-1-(thiazol-4-yl)-1H-pyrazole-4-carbonyl)-3-azabicyclo[3.1.0]hexan-6-yl)oxy)pyridin-4-yl)propan-2-yl)carbamate (enantiomer 3A) (20 mg, 0.029 mmol) in HCl (12 M) (2 mL) was stirred at 80° C. After 10 min the mixture was cooled, filtered and concentrated under reduced pressure. The residue was subjected to reverse phase HPLC (24-44% MeCN/water with 0.04% HCl modifier). The appropriate fractions were lyophilized to afford the title compound as a HCl salt. MS m/z $(M+H)^+$: calculated 551.5, observed 551.2. $^1H$ NMR (400 MHz, $CD_3OD$) δ 9.03 (d, J=1.6 Hz, 1H), 8.65 (s, 1H), 7.65 (d, J=2.3 Hz, 1H), 7.40-7.33 (m, 1H), 7.19 (s, 1H), 4.27-4.24 (m, 1H), 4.17-4.01 (m, 4H), 3.73 (s, 1H), 2.63-2.53 (m, 1H), 2.23 (s, 2H), 1.98-1.86 (m, 1H), 1.80-1.73 (m, 8H), 1.49-1.41 (m, 1H), 1.34-1.27 (m, 2H), 0.95 (d, J=8.0 Hz, 6H).

Step 5-4: ent-((1R,5S,6s)-6-((4-(2-aminopropan-2-yl)-6-(2-hydroxy-4,4-dimethylcyclohexyl)pyridin-2-yl)oxy)-3-azabicyclo[3.1.0]hexan-3-yl)(3-methyl-1-(thiazol-4-yl)-1H-pyrazol-4-yl)methanone (enantiomer 4)

A mixture of ent-benzyl (2-(2-(2-hydroxy-4,4-dimethylcyclohexyl)-6-(((1R,5S,6s)-3-(3-methyl-1-(thiazol-4-yl)-1H-pyrazole-4-carbonyl)-3-azabicyclo[3.1.0]hexan-6-yl)oxy)pyridin-4-yl)propan-2-yl)carbamate (enantiomer 4A) (25 mg, 0.037 mmol) in HCl (12 M) (2 mL) was stirred at 80° C. After 10 min the mixture was cooled, filtered and concentrated under reduced pressure. The residue was subjected to reverse phase HPLC (24-44% MeCN/water with 0.04% HCl modifier). The appropriate fractions were lyophilized to afford the title compound as a HCl salt. MS m/z $(M+H)^+$: calculated 551.5, observed 551.2. $^1H$ NMR (400 MHz, $CD_3OD$) δ 9.03 (s, 1H), 8.66 (s, 1H), 7.65 (d, J=2.0 Hz, 1H), 7.42 (d, J=0.8 Hz, 1H), 7.27 (s, 1H), 4.28-4.24 (m, 1H), 4.12 (s, 2H), 4.06-4.02 (m, 2H), 3.73 (s, 1H), 2.64-2.54 (m, 1H), 2.44 (s, 3H), 2.25 (s, 2H), 1.97-1.86 (m, 1H), 1.83-1.74 (m, 8H), 1.51-1.42 (m, 1H), 1.35-1.28 (m, 2H), 0.97 (s, 6H).

Example 67

((1R,5S,6s)-6-((4-(2-aminopropan-2-yl)-6-(4-fluorophenyl)pyridin-2-yl)oxy)-3-azabicyclo[3.1.0]hexan-3-yl)(1'-methyl-1'H-[1,3'-bipyrazol]-5'-yl)methanone

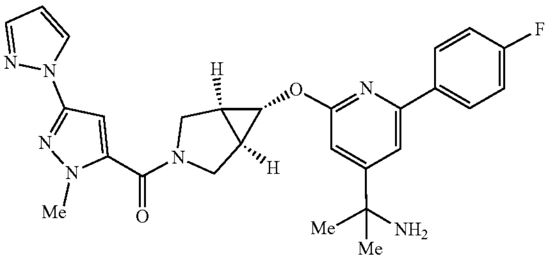 [SMILES: Cn1nc(-n2cccn2)cc1C(=O)N1C[C@@H]2[C@H](C1)[C@H]2Oc1cc(C(C)(C)N)cc(-c2ccc(F)cc2)n1]

Step 1: benzyl (2-(2-(4-fluorophenyl)-6-(((1R,5S,6s)-3-(1'-methyl-1'H-[1,3'-bipyrazole]-5'-carbonyl)-3-azabicyclo[3.1.0]hexan-6-yl)oxy)pyridin-4-yl)propan-2-yl)carbamate To a solution of 1'-methyl-1'H-[1,3'-bipyrazole]-5'-carboxylic acid (Int. V, 30 mg, 0.16 mmol) in DMF (5 mL) was added DIPEA (0.10 mL, 0.47 mmol) and HATU (120 mg, 0.31 mmol). The reaction mixture was stirred at 25° C. for 20 min and benzyl (2-(2-(((1R,5S,6s)-3-azabicyclo[3.1.0]hexan-6-yl)oxy)-6-(4-fluorophenyl)pyridin-4-yl)propan-2-yl)carbamate (Int. H-02, 72 mg, 0.156 mmol) was added. The mixture was stirred at 25° C. After 1 h the reaction mixture was quenched with water (10 mL) and extracted with EtOAc (3×15 mL). The combined organic extracts were washed with brine (15 mL), dried over anhydrous sodium sulfate, filtered and concentrated under reduced pressure. The residue was purified by prep-TLC (30% EtOAc/PE) to afford the title compound.

Step 2: ((1R,5S,6s)-6-((4-(2-aminopropan-2-yl)-6-(4-fluorophenyl)pyridin-2-yl)oxy)-3-azabicyclo[3.1.0]hexan-3-yl)(1'-methyl-1'H-[1,3'-bipyrazol]-5'-yl)methanone A solution of benzyl (2-(2-(4-fluorophenyl)-6-(((1R,5S,6s)-3-(1'-methyl-1'H-[1,3'-bipyrazole]-5'-carbonyl)-3-azabicyclo[3.1.0]hexan-6-yl)oxy)pyridin-4-yl)propan-2-yl) carbamate (75 mg, 0.118 mmol) in HCl (12M) (1 mL) was stirred at 80° C. After 10 min the mixture was concentrated under reduced pressure. The residue was subjected to reverse phase HPLC (25-55% MeCN/water with 0.1% TFA modifier) to afford the title compound as a TFA salt. MS m/z $(M+H)^+$: calculated 502.2, observed 502.2. $^1H$ NMR (400 MHz, $CD_3OD$) δ 8.20 (d, J=2.4 Hz, 1H), 8.17-8.11 (m, 2H), 7.74 (d, J=1.6 Hz, 1H), 7.61 (d, J=1.2 Hz, 1H), 7.24-7.18 (m, 2H), 6.85-6.81 (m, 2H), 6.54-6.50 (m, 1H), 4.23 (d, J=12.4 Hz, 1H), 4.09-4.04 (m, 2H), 3.98 (s, 4H), 3.76 (dd, J=12.4, 3.2 Hz, 1H), 2.09 (d, J=1.6 Hz, 2H), 1.76 (s, 6H).

Utilizing the procedures described in EXAMPLE 67, the following compound (EXAMPLE 68) was prepared substituting the appropriate reagents for 1'-methyl-1'H-[1,3'-bipyrazole]-5'-carboxylic acid.

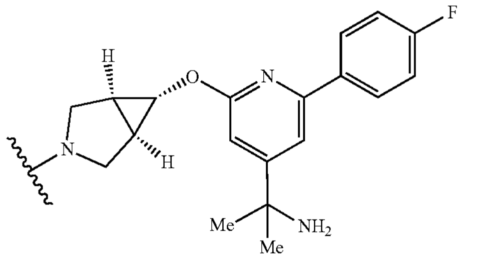 [SMILES: *N1C[C@@H]2[C@H](C1)[C@H]2Oc1cc(C(C)(C)N)cc(-c2ccc(F)cc2)n1]

| Ex # | Structure | Name | Calc'd $[M + H]^+$ | Observed $[M + H]^+$ |
|---|---|---|---|---|
| 68 | 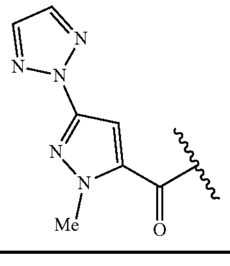 | ((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(2H-1,2,3-triazol-2-yl)-1H-pyrazol-5-yl)methanone | 502.6 | 502.5 |

Assay Descriptions

Sample Corrections:

Wells with DMSO (final concentration of 0.4%) or a compound at a concentration at which viral replication was completely inhibited with a control compound were used as viral replication assay Min_E and Max_E controls, respectively. To set up the assay, ARF vials were thawed in a 37° C. water bath and a control compound was resuspended in assay media DMEM (Dulbecco's Modified Eagle Medium) containing 2% FBS, 100 U/ml Penicillin-Streptomycin.

Generation and Propagation of Recombinant RSV-A2-GFP Virus:

GFP sequence was derived from pJTI™ R4 Dest CMV N-EmGFP pA Vector (Invitrogen) and was cloned into the intergenic sequence between wild-type RSV-A2 P and M genes using standard recombineering techniques. Recombinant RSV-A2-GFP was propagated in Hep2 cells (human cells contain HeLa marker chromosomes and were derived via HeLa contamination, ATCC CCL-23) with a Multiplicity of Infection (MOI) of 0.1. Virus was harvested 3 days after infection by collecting all culture material and then freeze-thawing the mixture for 5 minutes. Working virus stocks were generated by thawing frozen viral cultures in 37° C. water bath, which were centrifuged at 218 g for 15 min at 4° C. 1/10 of 10×SPG (Biological Industries 06-3061-01-5A) were added and then mixed. The supernatant was aliquoted, frozen in liquid nitrogen, and then transferred to a −80° C. freezer for storage. Virus titer was determined by automated plaque assay in HEp-2 cells following methods described previously (Wen Z. et al.; 2019).

Generating Calu-1 Assay Ready Freeze-Down (ARF):

Calu-1 cells were purchased from ATCC (Cat #HTB-54) and were expanded in growth media (DMEM containing 10% FBS, 100 U/ml Penicillin-Streptomycin). To make ARF, cell culture media was removed and discarded and the cell layer was briefly rinsed with PBS to remove serum. 2.5 mL of TrypLE Express solution were added and cells incubated until dislodged, to which growth media was added and the cells were resuspended by gentle pipetting. Cells were counted for concentration and viability as determined by ViCell. Cells were centrifuged at RT, 300 g for 5 minutes to pellet cells. The supernatant was gently aspirated and the pellet was flicked to loosen cells. Cells were resuspended in an appropriate volume of freezing medium (DMEM containing 10% DMSO, 10% FBS, 100 U/ml Penicillin-Streptomycin) to achieve a concentration of $5\times10^6$ cells/mL. 1 mL aliquots of the cell suspension were transferred to freezing vials. The vials were put into an upright container in a −80° C. freezer overnight before transferring vials to liquid nitrogen for storage RSV-A2-GFP Viral Replication Assay:

Assay ready freeze-down (ARF, generation described separately) Calu-1 cells (ATCC HTB-54) were used. Compound plates were prepared by dispensing compounds dissolved in DMSO into the wells of a 384 well Corning® 3985 plate with an ECHO acoustic dispenser and compounds were tested in 10-point serial 3-fold dilution. Wells with DMSO (final concentration of 0.4%) or a compound at a concentration at which viral replication was completely inhibited with a control compound were used as viral replication assay Min_E and Max_E control, respectively. To set up the assay, ARF vial(s) were thawed in a 37° C. water bath and were then resuspended into assay media (DMEM containing 2% FBS, 100 U/ml Penicillin-Streptomycin). Cells were counted using default parameters on ViCell and diluted to 20,000 cells/mL in assay media. RSV-A2-GFP virus was added to cells at 24,000 pfu/ml (MOI=1.2) and mixed by gentle inversion. 10 μL/well of 100% DMSO was dispensed as CellTiter-Glo (CTG) assay Max_E controls wells. The cells were dispensed at 50 μL/well using Bravo with 50 μL filtered tips into compound plates. Plates were covered with MicroClime lids, loaded with 7.5 mL of assay media to minimize evaporation, and were incubated at 37° C. and 5% $CO_2$ for 96 hrs. Following incubation, distinct, GFP-expressing cells were counted using an Acumen imaging system with appropriate settings. A same-well CTG assay was performed by adding 10 μL/well reconstituted CellTiter-Glo reagent (Promega G7573) and plates were read on PerkinElmer Envision according to manufacturer's instructions. Raw data were loaded and analyzed in ActivityBase. Antiviral $IC_{50}$ and cytotoxicity $CC_{50}$ values were determined using a 4 parameter logistic fit based on the Levenberg-Marquardt algorithm. Model: 205-4 Parameter Logistic.

Generation and Propagation of hMPV-GFP Virus:

GFP expressing rgHMPV #3 p3 was generated in Dr. Buchholz's lab (Biacchesi S. et al., *J Virol.* 2007 June; 81(11): 6057-6067) and propagated in VERO cells (ATCC Cat #CCL-81) with a Multiplicity of Infection (MOI) of 0.1. Virus was harvested 4 days after infection by collecting cultured material and was freeze-thaw cycled in liquid nitrogen twice. Working virus stocks were generated from thawing frozen samples in 37° C. water bath, which were centrifuged at 218 g for 15 min at 4° C. 1/10 of 10×SPG (Biological Industries 06-3061-01-5A) were added and then mixed. The supernatant was aliquoted, frozen in liquid nitrogen, and then transferred to a −80° C. freezer for storage. Virus titer was determined by performing titration test in 96-well plates and calculate approximate virus titer using GFP event/well data.

hMPV-GFP Viral Replication Assay:

Compound plates were prepared by dispensing compounds dissolved in DMSO into wells of a 384 well Corning 3985 polystyrene flat clear bottom optical imaging microplate (202.5 nL/well) using an ECHO acoustic dispenser. Each compound was tested in 10-point serial 3-fold dilution (typical final concentrations: 40,300 nM-2 nM). Wells with DMSO (final concentration of 0.4%) or a compound at a concentration at which viral replication was completely inhibited relative to a control compound were used as viral replication assay Min_E and Max_E control, respectively. Continuous culture of VERO cells was maintained in complete culture media (OptiMEM supplemented with 2 mM GlutaMAX™ and 100 U/ml Penicillin-Streptomycin). To set up the assay, VERO cells were trypsinized with 0.25% Trypsin-EDTA until cells were dislodged, then cells were re-suspended with 1 mL FBS. Cells were spundown at 300 g for 5 minutes and cells were washed twice with culture media and counted using default parameters on ViCell. Cells were then diluted to 100,000 cells/mL (5,000 cells/50 μL) in complete culture media+TrypLE Select (80 μL/mL). hMPV-GFP virus was added to cells at 125,000 pfu/mL (MOI=1.25) and were mixed by gentle inversion. 10 μL/well of 100% DMSO was dispensed to CellTiter-Glo (CTG) assay Max_E controls wells. Cells were dispensed at 50 μL/well using Bravo and 50 μL filtered tips into compound plates. Plates were covered with MicroClime lids and loaded with 7.5 mL of assay media to minimize evaporation. Plates were lightly shaken for 10 minutes at room temperature and then incubated at 37° C. and 5% $CO_2$ for 48 hrs. Following incubation, distinct GFP-expressing cells were counted using an Acumen imaging system with appropriate settings. A same-well CTG assay was performed by adding 10 μL/well reconstituted CellTiter-Glo reagent (Promega G7573) and plates were read on PerkinElmer Envision according to manufacturer's instructions. Raw data were loaded and analyzed in ActivityBase. Antiviral $IC_{50}$ and cytotoxicity $CC_{50}$ values were determined using a 4 parameter logistic fit based on the Levenberg-Marquardt algorithm. Model: 205-4 Parameter Logistic.

REFERENCES

Wen Z, Citron M, Bett A J, Espeseth A S, Vora K A, Zhang L, DiStefano D J. Development and application of a higher throughput RSV plaque assay by immunofluorescent imaging. *J Virol Methods.* 2019 January; 263:88-95. doi: 10.1016/j.jviromet.2018.10.022. Epub 2018 Oct. 28. PMID: 30381239.

Biacchesi S, Murphy B R, Collins P L, Buchholz U J. Frequent frameshift and point mutations in the SH gene of human metapneumovirus passaged in vitro. *J Virol.* 2007 June; 81(11):6057-67. doi: 10.1128/JVI.00128-07. Epub 2007 Mar. 21. PMID: 17376897; PMCID: MC1900297.

Assay Data

The $EC_{50}$ of each compound is listed in Table I and $EC_{50}$ ranges are as follows: A≤0.010 μM; B>0.010 μM-≤0.10 μM; C>0.10 μM; ND=Not Determined.

TABLE I

Summary of Activities for RSV

| EX. NO. | RSV $EC_{50}$ | EX. NO. | RSV $EC_{50}$ | EX. NO. | RSV EC50 | EX. NO. | RSV EC50 | EX. NO. | RSV EC50 |
|---|---|---|---|---|---|---|---|---|---|
| 1 | A | 17 | A | 34 | A | 47 | A | 58A | A |
| 2 | B | 18 | A | 35 | A | 48 | A | 58B | A |
| 3 | A | 19 | A | 36 | A | 49A | A | 59 | A |
| 4 | A | 20 | A | 37 | A | 49B | A | 60 | A |
| 5 | A | 21 | A | 38 | A | 50A | A | 61A | A |
| 6 | A | 22 | A | 39 | A | 50B | A | 61B | A |
| 7 | A | 23 | A | 40 | A | 51A | A | 62A | A |
| 8 | A | 24 | A | 41 | A | 51B | A | 62B | A |
| 9 | A | 25 | A | 42 | A | 52 | A | 63 | A |
| 10 | A | 26 | A | 43A | A | 53 | A | 64 | A |
| 11 | A | 27 | B | 43B | A | 54 | A | 65 | A |
| 12 | A | 28 | A | 44A | A | 55A | A | 66A | A |
| 13 | A | 29 | A | 44B | A | 55B | A | 66B | B |
| 14 | A | 30 | A | 45A | A | 56A | A | 66C | B |
| 15 | A | 31 | A | 45B | A | 56B | A | 66D | B |
| 16A | A | 32 | A | 46A | A | 57A | A | 67 | A |
| 16B | A | 33 | A | 46B | A | 57B | A | 68 | A |

The $EC_{50}$ of each compound is listed in Table II and $EC_{50}$ ranges are as follows: A≤0.010 μM; B>0.010 μM-≤0.10 μM; C>0.10 μM; ND=Not Determined.

TABLE II

Summary of Activities for hMPV

| EX. NO. | RSV $EC_{50}$ | EX. NO. | RSV $EC_{50}$ | EX NO. | RSV EC50 | EX NO. | RSV EC50 | EX. NO. | RSV EC50 |
|---|---|---|---|---|---|---|---|---|---|
| 1 | C | 17 | B | 34 | B | 47 | C | 58A | C |
| 2 | C | 18 | B | 35 | C | 48 | C | 58B | C |
| 3 | B | 19 | B | 36 | C | 49A | C | 59 | C |

TABLE II-continued

| Summary of Activities for hMPV | | | | | | | | | |
|---|---|---|---|---|---|---|---|---|---|
| EX. NO. | RSV $EC_{50}$ | EX. NO. | RSV $EC_{50}$ | EX NO. | RSV EC50 | EX NO. | RSV EC50 | EX. NO. | RSV EC50 |
| 4 | B | 20 | B | 37 | C | 49B | C | 60 | C |
| 5 | B | 21 | C | 38 | C | 50A | C | 61A | C |
| 6 | C | 22 | B | 39 | C | 50B | C | 61B | C |
| 7 | B | 23 | C | 40 | C | 51A | C | 62A | C |
| 8 | B | 24 | C | 41 | C | 51B | C | 62B | C |
| 9 | C | 25 | B | 42 | C | 52 | C | 63 | C |
| 10 | C | 26 | C | 43A | B | 53 | C | 64 | C |
| 11 | C | 27 | C | 43B | C | 54 | B | 65 | C |
| 12 | C | 28 | C | 44A | B | 55A | B | 66A | C |
| 13 | B | 29 | C | 44B | B | 55B | C | 66B | C |
| 14 | C | 30 | C | 45A | C | 56A | C | 66C | C |
| 15 | C | 31 | B | 45B | C | 56B | C | 66D | C |
| 16A | B | 32 | C | 46A | C | 57A | C | 67 | C |
| 16B | C | 33 | C | 46B | C | 57B | C | 68 | B |

What is claimed is:

1. A compound of Formula I,

I

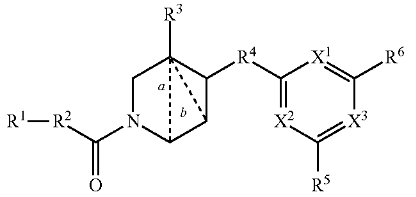

or a pharmaceutically acceptable salt thereof, wherein:

$R^1$ is a 5-member aromatic heterocyclyl ring comprised of:

(1) two carbon atoms and (ii) two of N and one of NH or (i) three of N, (2) three carbon atoms and (i) two of N, (ii) N and NH, or (iii) N and one of S or O, or (3) four carbon atoms and one of S or O, wherein the heterocyclyl ring is unsubstituted or substituted with 1 or 4 substituents, as valence will allow, independently selected at each occurrence from halo and $C_{1-6}$alkyl;

$R^2$ is 5-member aromatic heterocyclyl ring comprised of:

(1) three carbon atoms and (i) two of N, (ii) N and NH, or (iii) N and one of S or O, or (2) two carbon atoms and (i) three of N, (ii) two of N and one of NH or (iii) two of N and one of S or O, wherein the heterocyclyl ring is unsubstituted or substituted with 1, 2 or 3 substituents, as valence will allow, independently selected at each occurrence from:

(a) halo, (b) —$NH_2$, (c) —$C_{3-6}$cycloalkyl, (d) —$C_{1-6}$alkyl unsubstituted or substituted with 1 to 6 substituents independently selected at each occurrence from halo, —OH, and —$NH_2$, and (e) —$OC_{1-6}$alkyl unsubstituted or substituted with 1 to 6 substituents independently selected at each occurrence from halo, —OH, and —$NH_2$;

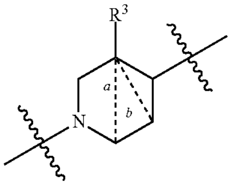

represents a bicyclic ring that is:

(i)

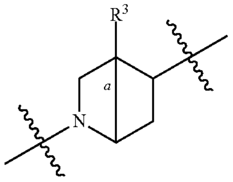

or (ii)

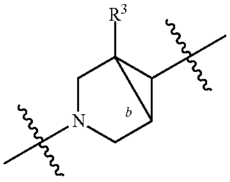

2-azabicyclo[2.2.0]hexane 3-azabicyclo[3.1.0]hexane;

$R^3$ is —H, halo or —$C_{1-6}$alkyl;

$R^4$ is —O— or —NH—;

One of $X^1$, $X^2$ and $X^3$ is N and the others are each CH;

$R^5$ is selected from:

(1) —$C_{1-6}$alkyl unsubstituted or substituted with 1 to 6 substituents independently selected at each occurrence from halo, —OH, —$NR^XR^Y$ and —C(O)$NR^XR^Y$, (2) —C(O)$NR^XR^Y$, (3)

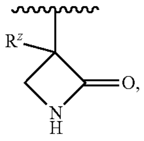

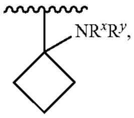

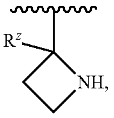

and (4)

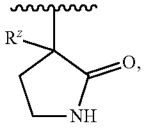

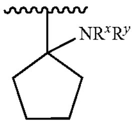

and

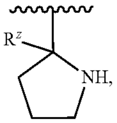

wherein $R^X$ and $R^Y$ are independently selected from —H, —$C_{1-6}$alkyl, and $R^Z$ is —$C_{1-6}$alkyl; and $R^6$ is selected from:

(1) phenyl, unsubstituted or substituted with 1 to 5 substituents independently selected at each occurrence from:

(a) halo, (b) —CN, (c) —$C_{1-6}$alkyl unsubstituted or substituted with 1 to 6 substituents independently selected at each occurrence from halo and —OH;

(d) —$OC_{1-6}$alkyl unsubstituted or substituted with 1 to 6 substituents independently selected at each occurrence from halo and —OH, and (e) —$C_{3-6}$cycloalkyl unsubstituted or substituted with 1 to 5 substituents independently selected at each occurrence from halo, —OH, —$C_{1-6}$alkyl and —$OC_{1-6}$alkyl;

(2) pyridinyl, unsubstituted or substitituted with 1 to 5 substituents independently selected at each occurrence from (i) halo, (ii) CN, and (iii) —$C_{1-6}$alkyl unsubstituted or substituted with 1 to 6 of —F and/or —Cl;

(3)

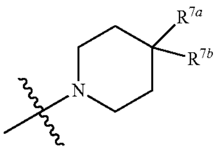

wherein $R^{7a}$ and $R^{7b}$ are each selected from —H, —$C_{1-6}$alkyl unsubstituted or substituted with 1 to 6 of —F and/or —Cl;

(4)

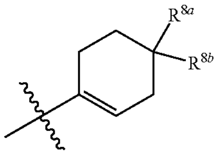

and

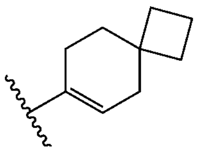

wherein $R^{8a}$ and $R^{8b}$ are each selected from —H, —$C_{1-3}$alkyl and —$CF_3$;

(5) A bicyclic ring system selected from:

(a)

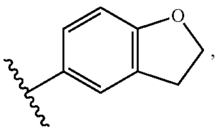

(b)

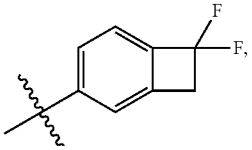

(c)

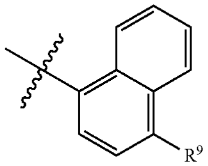

-continued (d)

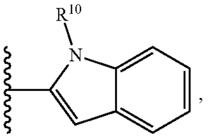

(e)

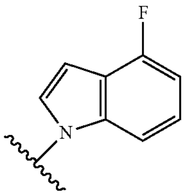

and (f)

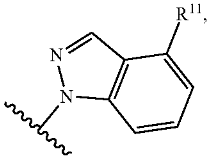

wherein $R^9$, $R^{10}$ and $R^{11}$ are independently selected at each occurrence from —H, —$C_{1-6}$alkyl, —$CF_3$ and 1, 2 or 3 of halo;

(6) —$C_{3-6}$cycloalkyl unsubstituted or substituted with 1 to 5 substituents independently selected at each occurrence from halo, —OH, —$C_{1-6}$alkyl, and —$OC_{1-6}$alkyl; and (7) pyrazolyl, unsubstituted or substituted with one or more substituents independently selected at each occurrence from:

(a) 1 to 3 of halo, (b) CN, (c) —$C_{1-6}$alkyl unsubstituted or substituted with 1 to 6 substituents independently selected at each occurrence from halo, —OH, and —$OC_{1-6}$alkyl;

(d) —$OC_{1-6}$alkyl unsubstituted or substituted with 1 to 6 substituents independently selected at each occurrence from halo, —OH, and $OC_{1-6}$alkyl, and (e) —$C_{3-6}$cycloalkyl unsubstituted or substituted with 1 to 5 substituents independently selected at each occurrence from halo, —OH, and —$OC_{1-6}$alkyl; and (8)

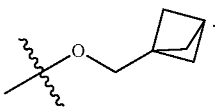 [SMILES: *OCC12CC(C1)C2]

2. The compound of claim 1, or a pharmaceutically acceptable salt thereof, wherein $R^1$ is 5-member aromatic heterocyclyl ring selected from thiazolyl, imidazolyl, oxazolyl, isoxazolyl, triazolyl, thiophenyl and furanyl, wherein each ring is unsubstituted or substituted with 1 to 4 substituents as valence will allow, independently selected at each occurrence from halo and $C_{1-6}$alkyl.

3. The compound of claim 1, or a pharmaceutically acceptable salt thereof, wherein $R^1$ is selected from:

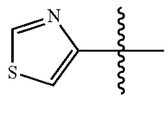,

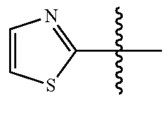,

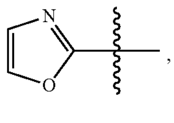,

-continued

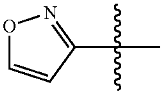, 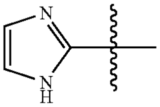, 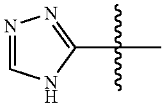,

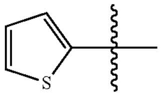 and 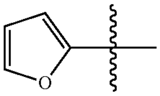, wherein the heterocyclyl ring is unsubstituted or substituted with 1, 2, 3 or 4 substituents, as valence will allow, independently selected at each occurrence from halo and $C_{1-6}$alkyl.

4. The compound of claim 1, or a pharmaceutically acceptable salt thereof, wherein $R^1$ is substituted with 1 or 2 substituents selected at each occurrence from —F, —Cl and $C_{1-3}$alkyl.

5. The compound of claim 1, or a pharmaceutically acceptable salt thereof, wherein $R^2$ is selected from thiadiazolyl, triazolyl, pyrazolyl, thiazolyl and isothiazolyl, wherein each is unsubstituted or substituted with a 1, 2 or 3 substituents selected from (i) halo, (ii) —$NH_2$, (iii) $C_{1-3}$alkyl unsubstituted or substituted with 1 to 5 substituents selected from halo, —OH, and $C_{3-6}$cycloalkyl.

6. The compound of claim 1, or a pharmaceutically acceptable salt thereof, wherein $R^2$ is selected from:

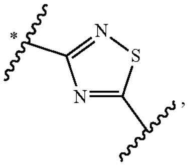, 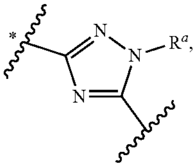

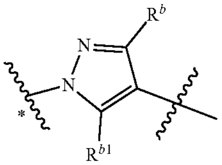, 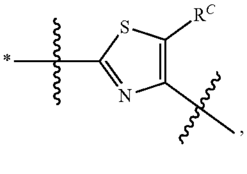,

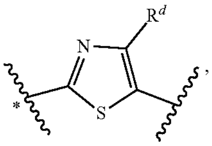, 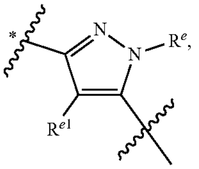

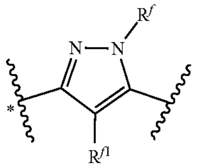 and 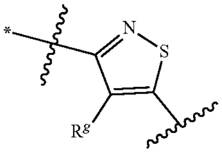

wherein * is the point of attachment to $R^1$, and each of $R^a$, $R^b$, $R^{b1}$, $R^c$, $R^d$, $R^e$, $R^{e1}$, $R^f$, $R^{f1}$ and $R^g$ is independently selected from:

(a) —H, (b) halo, (c) —$NH_2$, (d) —$C_{3-6}$cycloalkyl, (e) —$C_{1-6}$alkyl unsubstituted or substituted with 1 to 6 substituents independently selected at each occurrence from halo, —OH, and —$NH_2$, and (f) —$OC_{1-6}$alkyl unsubstituted or substituted with 1 to 6 substituents independently selected at each occurrence from halo, —OH, and —$NH_2$.

7. The compound of claim 1, or a pharmaceutically acceptable salt thereof, wherein:

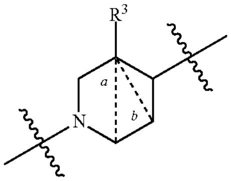 is 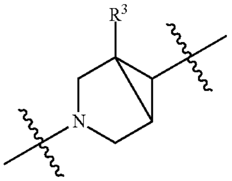.

8. The compound of claim 1, or a pharmaceutically acceptable salt thereof, wherein:

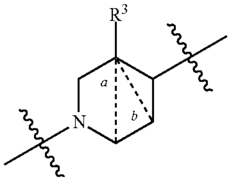 is 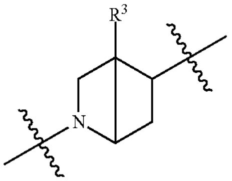.

9. The compound of claim 1, or a pharmaceutically acceptable salt thereof, wherein $R^3$ is selected from —H, halo or —$C_{1-3}$alkyl.

10. The compound of claim 1, or a pharmaceutically acceptable salt thereof, wherein $R^4$ is —O—.

11. The compound of claim 1, or a pharmaceutically acceptable salt thereof, wherein $R^4$ is —NH—.

12. The compound of claim 1, or a pharmaceutically acceptable salt thereof, wherein $X^1$ is N, and $X^2$ and $X^3$ are each CH; $X^2$ is N, and $X^1$ and $X^3$ are each CH; or $X^3$ is N and $X^1$ and $X^2$ are each CH.

13. The compound of claim 1, or a pharmaceutically acceptable salt thereof, wherein $R^5$ is is selected from:

(a) —$C_{1-6}$alkyl unsubstituted or substituted with 1 to 6 substituents independently selected at each occurrence from halo, —OH, —$NH_2$ and —C(O)$NH_2$, (b) —C(O)$NH_2$, (c)

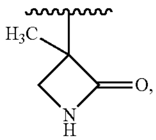, 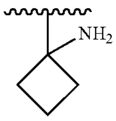, 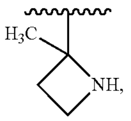, and (d)

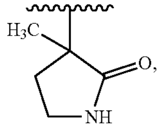, 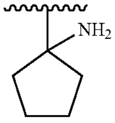 and 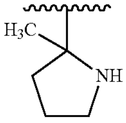.

14. The compound of claim 1, or a pharmaceutically acceptable salt thereof, wherein $R^6$ is (1) phenyl, unsubstituted or substituted with 1 to 5 substituents independently selected at each occurrence from:

(a) —F and —Cl, (b) —CN, (c) —$C_{1-3}$alkyl unsubstituted or substituted with 1 to 4 substituents independently selected at each occurrence from —F, —Cl, and —OH, (d) —$OC_{1-3}$alkyl unsubstituted or substituted with 1 to 4 substituents independently selected at each occurrence from —F, —Cl, and —OH, and (e) —$C_{3-6}$cycloalkyl, unsubstituted or substituted with 1 to 3 substituents independently selected at each occurrence from —F, —Cl, —OH and —$C_{1-3}$alkyl and —$OC_{1-3}$alkyl;

(2) pyridinyl, unsubstituted or substitituted with 1, 2 or 3 substituents independently selected at each occurrence from (i) —F and —Cl, (ii) CN and (iii) $C_{1-3}$alkyl unsubstituted or substituted with 1 to 6 of —F and/or —Cl;

(3)

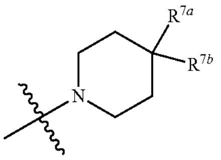

wherein $R^{7a}$ and $R^{7b}$ are each selected from —H and —$C_{1-3}$alkyl unsubstituted or substituted with 1 to 6 of —F and/or —Cl;

(4)

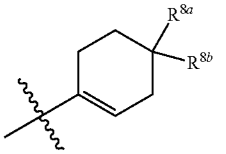

and

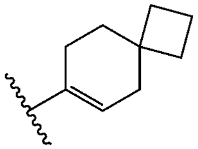

wherein $R^{8a}$ and $R^{8b}$ are each selected from —H, —$C_{1-3}$alkyl unsubstituted or substituted with 1 to 6 of —F and/or —Cl;

(5) A bicyclic ring system selected from:

(a)

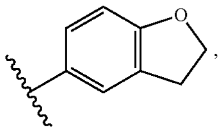, (b)

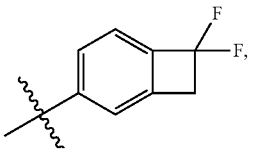

-continued (c)

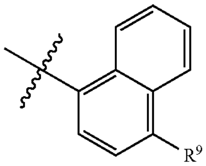

(d)

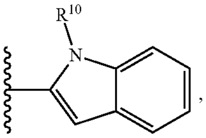, (e)

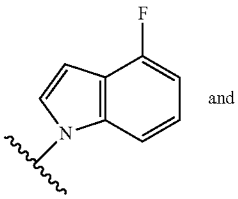

and (f)

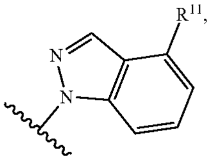

wherein $R^9$, $R^{10}$ and $R^{11}$ are independently selected at each occurrence from —H, 1, 2 or 3 of halo, and —$C_{1-3}$alkyl unsubstituted or substituted with 1 to 6 of —F and/or —Cl;

(6) —$C_{3-6}$cycloalkyl unsubstituted or substituted with 1 to 5 substituents independently selected at each occurrence from halo, —OH, —$C_{1-6}$alkyl, and —$OC_{1-6}$alkyl;

(7)

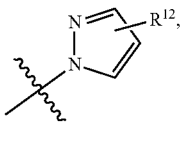

wherein $R^{12}$ is selected from (a) —H, (b) halo, (c) CN, (d) —$C_{1-3}$alkyl unsubstituted or substituted with 1 to 6 of —F and/or —Cl and (e) —$C_{3-6}$cycloalkyl; and (8)

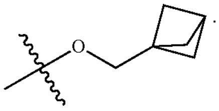 [SMILES: *OCC12CC(C1)C2].

15. The compound of claim 1 that is:

rel-((1R,4R,5R)-5-((4-(2-aminopropan-2-yl)-6-(4-fluorophenyl)pyridin-2-yl)oxy)-2-azabicyclo[2.2.0]hexan-2-yl)(1-methyl-3-(thiazol-4-yl)-1H-pyrazol-5-yl)methanone (enantiomer 2)

-continued rel-((1R,4R,5R)-5-((4-(2-aminopropan-2-yl)-6-(4-fluorophenyl)pyridin-2-yl)oxy)-2-azabicyclo[2.2.0]hexan-2-yl)(1-methyl-3-(oxazol-2-yl)-1H-pyrazol-5-yl)methanone (enantiomer 2)

((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(oxazol-2-yl)thiazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(5-methyloxazol-2-yl)thiazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(2-(isoxazol-3-yl)-4-methylthiazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-[2,2'-bithiazol]-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-[2,4'-bithiazol]-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(4-cyclopropy]-[2,4'-bithiazol]-5-yl)methanone (2-(1H-imidazol-2-yl)-4-methylthiazol-5-yl)((1R,5S,6s)-6-((4-(2-aminopropan-2-yl)-6-(4-fluorophenyl)pyridin-2-yl)oxy)-3-azabicyclo[3.1.0]hexan-3-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(1H-1,2,4-triazol-5-yl)thiazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(4-ethyl-2-(1H-1,2,4-triazol-3-yl)thiazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(thiophen-2-yl)thiazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(2-(furan-2-yl)-4-methylthiazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(4-(difluoromethyl)-[2,4'-bithiazol]-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(4-(difluoromethyl)-2-(oxazol-2-yl)thiazol-5-yl)methanone ent-((1R,5S,6S)-6-((4-(2-aminopropan-2-yl)-6-(4-fluorophenyl)pyridin-2-yl)oxy)-3-azabicyclo[3.1.0]hexan-3-yl)(4-(1-hydroxyethyl)-[2,4'-bithiazol]-5-yl)methanone (enantiomer 1)

ent-((1R,5S,6S)-6-((4-(2-aminopropan-2-yl)-6-(4-fluorophenyl)pyridin-2-yl)oxy)-3-azabicyclo[3.1.0]hexan-3-yl)(4-(1-hydroxyethyl)-[2,4'-bithiazol]-5-yl)methanone (enantiomer 2)

((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(oxazol-2-yl)-1H-pyrazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(1-ethyl-3-(thiazol-4-yl)-1H-pyrazol-5-yl)methanone -continued ((1R,5S,6s)-6-((4-(2-aminopropan-2-yl)-6-(4-fluorophenyl)pyridin-2-yl)oxy)-3-azabicyclo[3.1.0]hexan-3-yl)(3-(5-fluorothiazol-4-yl)-1-methyl-1H-pyrazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(3-(isoxazol-3-yl)-1-methyl-1H-pyrazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(5-methyloxazol-2-yl)-1H-pyrazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(thiazol-2-yl)-1H-pyrazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(2-methylthiazol-4-yl)-1H-pyrazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(4-fluoro-1-methyl-3-(thiazol-4-yl)-1H-pyrazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(4-fluoro-1-methyl-3-(oxazol-2-yl)-1H-pyrazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(3-(thiazol-4-yl)-1,2,4-thiadiazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(3-methyl-1-(thiazol-4-yl)-1H-pyrazol-4-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(3-(thiazol-4-yl)isothiazol-5-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(thiazol-4-yl)-1H-1,2,4-triazol-5-yl)methanone ((1R,5S,6s)-6-((4-(2-aminopropan-2-yl)-6-(2,4-difluorophenyl)pyridin-2-yl)oxy)-3-azabicyclo[3.1.0]hexan-3-yl)(4-methyl-2-(oxazol-2-yl)thiazol-5-yl)

((1R,5S,6s)-6-((4-(2-aminopropan-2-yl)-6-(2,4-difluorophenyl)pyridin-2-yl)oxy)-3-azabicyclo[3.1.0]hexan-3-yl)(2-(isoxazol-3-yl)-4-methylthiazol-5-yl)methanone ((1R,5S,6s)-6-((4-(2-aminopropan-2-yl)-6-(2,4-difluorophenyl)pyridin-2-yl)oxy)-3-azabicyclo[3.1.0]hexan-3-yl)(4-methyl-[2,4'-bithiazol]-5-yl)methanone ((1R,5S,6s)-6-((4-(2-aminopropan-2-yl)-6-(2,4-difluorophenyl)pyridin-2-yl)oxy)-3-azabicyclo[3.1.0]hexan-3-yl)(4-cyclopropy]-[2,4'-bithiazol]-5-yl)methanone ((1R,5S,6s)-6-((4-(2-aminopropan-2-yl)-6-(7,7-difluorobicyclo[4.2.0]octa-1(6),2,4-trien-3-yl)pyridin-2-yl)oxy)-3-azabicyclo[3.1.0]hexan-3-yl)(1-methyl-3-(oxazol-2-yl)-1H-pyrazol-5-yl)methanone ((1R,5S,6s)-6-((4-(2-aminopropan-2-yl)-6-(7,7-difluorobicyclo[4.2.0]octa-1(6),2,4-trien-3-yl)pyridin-2-yl)oxy)-3-azabicyclo[3.1.0]hexan-3-yl)(3-(isoxazol-3-yl)-1-methyl-1H-pyrazol-5-yl)methanone ((1R,5S,6s)-6-((4-(2-aminopropan-2-yl)-6-(4-cyclopropyl-1H-pyrazol-1-yl)pyridin-2-yl)oxy)-3-azabicyclo[3.1.0]hexan-3-yl)(4-methyl-2-(oxazol-2-yl)thiazol-5-yl)methanone -continued ((1R,5S,6s)-6-((4-(2-aminopropan-2-yl)-6-(4-cyclopropyl-1H-pyrazol-1-yl)pyridin-2-yl)oxy)-3-azabicyclo[3.1.0]hexan-3-yl)(1-methyl-3-(thiazol-4-yl)-1H-pyrazol-5-yl)methanone ((1R,5S,6s)-6-((4-(2-aminopropan-2-yl)-6-(4,4-dimethylpiperidin-1-yl)pyridin-2-yl)oxy)-3-azabicyclo[3.1.0]hexan-3-yl)(1-methyl-3-(thiazol-4-yl)-1H-pyrazol-5-yl)methanone ((1R,5S,6s)-6-((4-(2-aminopropan-2-yl)-6-(4-(trifluoromethyl)piperidin-1-yl)pyridin-2-yl)oxy)-3-azabicyclo[3.1.0]hexan-3-yl)(1-methyl-3-(oxazol-2-yl)-1H-pyrazol-5-yl)methanone ((1R,5S,6s)-6-((4-(2-aminopropan-2-yl)-6-(4-(trifluoromethyl)piperidin-1-yl)pyridin-2-yl)oxy)-3-azabicyclo[3.1.0]hexan-3-yl)(1-methyl-3-(thiazol-4-yl)-1H-pyrazol-5-yl)methanone ((1R,5S,6s)-6-((4-(2-aminopropan-2-yl)-6-(bicyclo[1.1.1]pentan-1-ylmethoxy)pyridin-2-yl)oxy)-3-azabicyclo[3.1.0]hexan-3-yl)(1-methyl-3-(thiazol-4-yl)-1H-pyrazol-5-yl)methanone rel-((1R,5S,6S)-6-((4-(2-aminopropan-2-yl)-6-(4-fluorophenyl)pyridin-2-yl)oxy)-1-methyl-3-azabicyclo[3.1.0]hexan-3-yl)(1-methyl-3-(thiazol-4-yl)-1H-pyrazol-5-yl)methanone (enantiomer 1)

rel-((1R,5S,6S)-6-((4-(2-aminopropan-2-yl)-6-(4-fluorophenyl)pyridin-2-yl)oxy)-1-methyl-3-azabicyclo[3.1.0]hexan-3-yl)(1-methyl-3-(thiazol-4-yl)-1H-pyrazol-5-yl)methanone (enantiomer 2)

rel-((1R,5S,6S)-6-((4-(2-aminopropan-2-yl)-6-(4-fluorophenyl)pyridin-2-yl)oxy)-1-methyl-3-azabicyclo[3.1.0]hexan-3-yl)(1-methyl-3-(oxazol-2-yl)-1H-pyrazol-5-yl)methanone (enantiomer 1)

rel-((1R,5S,6S)-6-((4-(2-aminopropan-2-yl)-6-(4-fluorophenyl)pyridin-2-yl)oxy)-1-methyl-3-azabicyclo[3.1.0]hexan-3-yl)(1-methyl-3-(oxazol-2-yl)-1H-pyrazol-5-yl)methanone (enantiomer 2)

rel-((1R,5S,6S)-6-((4-(2-aminopropan-2-yl)-6-(4-fluorophenyl)pyridin-2-yl)oxy)-1-methyl-3-azabicyclo[3.1.0]hexan-3-yl)(3-(isoxazol-3-yl)-1-methyl-1H-pyrazol-5-yl)methanone (enantiomer 1)

rel-((1R,5S,6S)-6-((4-(2-aminopropan-2-yl)-6-(4-fluorophenyl)pyridin-2-yl)oxy)-1-methyl-3-azabicyclo[3.1.0]hexan-3-yl)(3-(isoxazol-3-yl)-1-methyl-1H-pyrazol-5-yl)methanone (enantiomer 2)

rel-((1R,5S,6S)-6-((4-(2-aminopropan-2-yl)-6-(4,4-dimethylpiperidin-1-yl)pyridin-2-yl)oxy)-1-methyl-3-azabicyclo[3.1.0]hexan-3-yl)(1-methyl-3-(thiazol-4-yl)-1H-pyrazol-5-yl)methanone (enantiomer 1)

rel-((1R,5S,6S)-6-((4-(2-aminopropan-2-yl)-6-(4,4-dimethylpiperidin-1-yl)pyridin-2-yl)oxy)-1-methyl-3-azabicyclo[3.1.0]hexan-3-yl)(1-methyl-3-(thiazol-4-yl)-1H-pyrazol-5-yl)methanone (enantiomer 2)

2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)isonicotinamide 2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-2-methylpropanamide ent-2-amino-2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)propanamide (enantiomer 1)

ent-2-amino-2-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)propanamide (enantiomer 2)

ent-3-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-3-methylazetidin-2-one (enantiomer 1)

ent-3-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-3-methylazetidin-2-one (enantiomer 2)

ent-3-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-3-methylpyrrolidin-2-one (enantiomer 1)

ent-3-(2-(4-fluorophenyl)-6-(((1R,5S,6s)-3-(1-methyl-3-(thiazol-4-yl)-1H-pyrazole-5-carbonyl)-3-azabicyclo[3.1.0]hexan-6-yl)oxy)pyridin-4-yl)-3-methylpyrrolidin-2-one (enantiomer 2)

((1R,5S,6s)-6-((4-(1-aminocyclobutyl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone ((1R,5S,6s)-6-((4-(1-aminocyclopentyl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone ((1R,5S,6s)-6-((4-(1-amino-2-methylpropan-2-yl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone ent-((1R,5S,6s)-6-((6-(4-fluorophenyl)-4-(2-methylazetidin-2-yl)pyridin-2-yl)oxy)-3-azabicyclo[3.1.0]hexan-3-yl)(1-methyl-3-(thiazol-4-yl)-1H-pyrazol-5-yl)methanone (enantiomer 1)

ent-((1R,5S,6s)-6-((6-(4-fluorophenyl)-4-(2-methylazetidin-2-yl)pyridin-2-yl)oxy)-3-azabicyclo[3.1.0]hexan-3-yl)(1-methyl-3-(thiazol-4-yl)-1H-pyrazol-5-yl)methanone (enantiomer 2)

ent-((1R,5S,6s)-6-((6-(4-fluorophenyl)-4-(2-methylpyrrolidin-2-yl)pyridin-2-yl)oxy)-3-azabicyclo[3.1.0]hexan-3-yl)(1-methyl-3-(thiazol-4-yl)-1H-pyrazol-5-yl)methanone (enantiomer 1)

ent-((1R,5S,6s)-6-((6-(4-fluorophenyl)-4-(2-methylpyrrolidin-2-yl)pyridin-2-yl)oxy)-3-azabicyclo[3.1.0]hexan-3-yl)(1-methyl-3-(thiazol-4-yl)-1H-pyrazol-5-yl)methanone (enantiomer 2)

ent-((1R,5S,6s)-6-((4-(2-amino-1-hydroxypropan-2-yl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone (enantiomer 1)

ent-((1R,5S,6s)-6-((4-(2-amino-1-hydroxypropan-2-yl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone (enantiomer 2)

ent-((1R,5S,6s)-6-((4-(2-amino-1-hydroxypropan-2-yl)-6-(4-fluorophenyl)pyridin-2-yl)oxy)-3-azabicyclo[3.1.0]hexan-3-yl)(1-methyl-3-(oxazol-2-yl)-1H-pyrazol-5-yl)methanone (enantiomer 1)

ent-((1R,5S,6s)-6-((4-(2-amino-1-hydroxypropan-2-yl)-6-(4-fluorophenyl)pyridin-2-yl)oxy)-3-azabicyclo[3.1.0]hexan-3-yl)(1-methyl-3-(oxazol-2-yl)-1H-pyrazol-5-yl)methanone (enantiomer 2)

((1R,5S,6s)-6-((6-(2-aminopropan-2-yl)-4-(4-fluorophenyl)pyridin-2-yl)oxy)-3-azabicyclo[3.1.0]hexan-3-yl)(1-methyl-3-(thiazol-4-yl)-1H-pyrazol-5-yl)methanone -continued ((1R,5S,6s)-6-((6-(2-aminopropan-2-yl)-4-(4-fluorophenyl)pyridin-2-yl)oxy)-3-azabicyclo[3.1.0]hexan-3-yl)(1-methyl-3-(oxazol-2-yl)-1H-pyrazol-5-yl)methanone ent-((1R,5S,6s)-6-((4-(1-aminoethyl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone (enantiomer 1)

ent-((1R,5S,6s)-6-((4-(1-aminoethyl)-6-(4-fluorophenyl)pyridin-2-yl)oxy)-3-azabicyclo[3.1.0]hexan-3-yl)(1-methyl-3-(thiazol-4-yl)-1H-pyrazol-5-yl)methanone (enantiomer 2)

ent-((1R,5S,6s)-6-((4-(1-aminoethyl)-6-(4-fluorophenyl)pyridin-2-yl)oxy)-3-azabicyclo[3.1.0]hexan-3-yl)(3-(isoxazol-3-yl)-1-methyl-1H-pyrazol-5-yl)methanone (enantiomer 1)

ent-((1R,5S,6s)-6-((4-(1-aminoethyl)-6-(4-fluorophenyl)pyridin-2-yl)oxy)-3-azabicyclo[3.1.0]hexan-3-yl)(3-(isoxazol-3-yl)-1-methyl-1H-pyrazol-5-yl)methanone (enantiomer 2)

((1R,5S,6s)-6-((4-(2-aminopropan-2-yl)-6-(4-fluorophenyl)pyridin-2-yl)oxy)-3-azabicyclo[3.1.0]hexan-3-yl)(1'-methyl-1'H-[1,3'-bipyrazol]-5'-yl)methanone ((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(2H-1,2,3-triazol-2-yl)-1H-pyrazol-5-yl)methanone ent-((1R,5S,6s)-6-((4-(2-aminopropan-2-yl)-6-(2-hydroxy-4,4-dimethylcyclohexyl)pyridin-2-yl)oxy)-3-azabicyclo[3.1.0]hexan-3-yl)(1-methyl-3-(thiazol-4-yl)-1H-pyrazol-5-yl)methanone (enantiomer 1)

ent-((1R,5S,6s)-6-((4-(2-aminopropan-2-yl)-6-(2-hydroxy-4,4-dimethylcyclohexyl)pyridin-2-yl)oxy)-3-azabicyclo[3.1.0]hexan-3-yl)(1-methyl-3-(thiazol-4-yl)-1H-pyrazol-5-yl)methanone (enantiomer 2)

ent-((1R,5S,6s)-6-((4-(2-aminopropan-2-yl)-6-(2-hydroxy-4,4-dimethylcyclohexyl)pyridin-2-yl)oxy)-3-azabicyclo[3.1.0]hexan-3-yl)(1-methyl-3-(thiazol-4-yl)-1H-pyrazol-5-yl)methanone (enantiomer 3)

ent-((1R,5S,6s)-6-((4-(2-aminopropan-2-yl)-6-(2-hydroxy-4,4-dimethylcyclohexyl)pyridin-2-yl)oxy)-3-azabicyclo[3.1.0]hexan-3-yl)(1-methyl-3-(thiazol-4-yl)-1H-pyrazol-5-yl)methanone (enantiomer 4)

((1R,5S,6s)-6-((4-(2-aminopropan-2-yl)-6-(4,4-dimethylpiperidin-1-yl)pyridin-2-yl)oxy)-3-

-continued azabicyclo[3.1.0]hexan-3-yl)(1-methyl-3-(oxazol-2-yl)-1H-pyrazol-5-yl)methanone ((1R,5S,6s)-6-((4-(2-aminopropan-2-yl)-6-(4-(trifluoromethyl)piperidin-1-yl)pyridin-2-yl)oxy)-3-azabicyclo[3.1.0]hexan-3-yl)(3-(isoxazol-3-yl)-1-methyl-1H-pyrazol-5-yl)methanone, or ((1R,5S,6s)-6-((4-(2-aminopropan-2-yl)-6-(1-methylcyclopentyl)pyridin-2-yl)oxy)-3-azabicyclo[3.1.0]hexan-3-yl)(1-methyl-3-(thiazol-4-yl)-1H-pyrazol-5-yl)methanone, or a pharmaceutically acceptable salt thereof.

16. A pharmaceutical composition comprising an effective amount of the compound according to claim 1, or a pharmaceutically acceptable salt thereof, and a pharmaceutically acceptable carrier.

17. A method for the inhibition of replication of hRSV in a human subject in need thereof which comprises administering to the subject an effective amount of the compound according to claim 1, or a pharmaceutically acceptable salt thereof.

18. A method for the treatment of hRSV infection in a human subject in need thereof which comprises administering to the subject an effective amount of the compound according to claim 1, or a pharmaceutically acceptable salt thereof.

19. A method for the prophylaxis of hRSV infection in a human subject which comprises administering to the subject an effective amount of the compound according to according to claim 1, or a pharmaceutically acceptable salt thereof.

20. A method for the inhibition of replication of hMPV in a human subject in need thereof which comprises administering to the subject an effective amount of the compound according to claim 1, or a pharmaceutically acceptable salt thereof.

21. A method for the treatment of hMPV infection in a human subject in need thereof which comprises administering to the subject an effective amount of the compound according to claim 1, or a pharmaceutically acceptable salt thereof.

22. A method for prophylaxis of hMPV infection in a human subject which comprises administering to the subject an effective amount of the compound according to claim 1, or a pharmaceutically acceptable salt thereof.

* * * * *